(12) United States Patent
van der Walt et al.

(10) Patent No.: US 12,376,972 B2
(45) Date of Patent: Aug. 5, 2025

(54) HIP REPLACEMENT NAVIGATION SYSTEM AND METHOD

(71) Applicant: OrthAlign, Inc., Aliso Viejo, CA (US)

(72) Inventors: Nicholas van der Walt, Laguna Hills, CA (US); Jonathan Nielsen, Aliso Viejo, CA (US)

(73) Assignee: OrthAlign, Inc., Irvine, CA (US)

( * ) Notice: Subject to any disclaimer, the term of this patent is extended or adjusted under 35 U.S.C. 154(b) by 984 days.

(21) Appl. No.: 17/244,101

(22) Filed: Apr. 29, 2021

(65) Prior Publication Data

US 2021/0315716 A1   Oct. 14, 2021

Related U.S. Application Data

(63) Continuation of application No. 15/550,564, filed as application No. PCT/US2016/018508 on Feb. 18, (Continued)

(51) Int. Cl.
*A61B 5/00* (2006.01)
*A61B 17/17* (2006.01)
(Continued)

(52) U.S. Cl.
CPC ........ *A61F 2/4657* (2013.01); *A61B 17/1746* (2013.01); *A61B 34/20* (2016.02);
(Continued)

(58) Field of Classification Search
None
See application file for complete search history.

(56) References Cited

U.S. PATENT DOCUMENTS 3,174,080 A   3/1965   Eldon
3,670,324 A   6/1972   Trevor, III
(Continued)

FOREIGN PATENT DOCUMENTS

CA   2241359   12/1999
CA   2 594 874   7/2006
(Continued)

OTHER PUBLICATIONS

Shah et al., "Is the pelvis stable during supine total hip arthroplasty?", Acta Orthop Belg., Mar. 1, 2017, vol. 83, No. 1, pp. 81-86.
(Continued)

*Primary Examiner* — Joel F Brutus
(74) *Attorney, Agent, or Firm* — Knobbe, Martens, Olson & Bear, LLP

(57) ABSTRACT

A hip joint navigation system is provided that includes a base having at least one channel disposed therethrough for receiving a pin for mounting the base to the pelvis. A mount feature is disposed on a top surface. A registration jig is configured to couple with the base and to engage anatomical landmarks. In some aspects, a patient specific jig system for hip replacement is provided including an engagement surface formed to closely mate to acetabular bone contours of a specific patient and a registration feature configured to be in a pre-determined orientation relative to an acetabulum the patient when the jig is coupled with acetabular bone contours of the specific patient. In other aspects, methods of using the systems are provided.

20 Claims, 111 Drawing Sheets

Related U.S. Application Data 2016, now Pat. No. 11,020,245, which is a continuation-in-part of application No. 14/643,864, filed on Mar. 10, 2015, now Pat. No. 10,363,149.

(60) Provisional application No. 62/118,987, filed on Feb. 20, 2015.

(51) Int. Cl.
| | |
|---|---|
| *A61B 34/20* | (2016.01) |
| *A61F 2/46* | (2006.01) |
| *A61B 17/00* | (2006.01) |
| *A61B 17/56* | (2006.01) |
| *A61B 90/00* | (2016.01) |
| *A61B 90/30* | (2016.01) |
| *A61F 2/34* | (2006.01) |
| *A61F 2/36* | (2006.01) |

(52) U.S. Cl.
CPC .. *A61F 2/4684* (2013.01); *A61B 2017/00477* (2013.01); *A61B 2017/568* (2013.01); *A61B 2034/2048* (2016.02); *A61B 2034/2068* (2016.02); *A61B 2090/061* (2016.02); *A61B 2090/067* (2016.02); *A61B 2090/0811* (2016.02); *A61B 90/30* (2016.02); *A61F 2/34* (2013.01); *A61F 2/3601* (2013.01); *A61F 2/4609* (2013.01); *A61F 2002/4658* (2013.01); *A61F 2002/4668* (2013.01); *A61F 2002/4681* (2013.01)

(56) References Cited

U.S. PATENT DOCUMENTS

| | | |
|---|---|---|
| 4,349,018 A | 9/1982 | Chambers |
| 4,421,112 A | 12/1983 | Mains et al. |
| 4,436,099 A | 3/1984 | Raftopoulos |
| 4,459,985 A | 7/1984 | McKay et al. |
| 4,475,549 A | 10/1984 | Oh |
| 4,501,266 A | 2/1985 | McDaniel |
| 4,509,393 A | 4/1985 | Castiglione |
| 4,518,855 A | 5/1985 | Malak |
| 4,524,766 A | 6/1985 | Petersen |
| 4,529,348 A | 7/1985 | Johnson et al. |
| 4,567,885 A | 2/1986 | Androphy |
| 4,567,886 A | 2/1986 | Petersen |
| 4,621,630 A | 11/1986 | Kenna |
| 4,646,729 A | 3/1987 | Kenna |
| 4,716,894 A | 1/1988 | Lazzeri et al. |
| 4,718,078 A | 1/1988 | Bleidorn et al. |
| 4,738,253 A | 4/1988 | Buechel et al. |
| 4,759,350 A | 7/1988 | Dunn et al. |
| 4,823,807 A | 4/1989 | Russell et al. |
| 4,938,762 A | 7/1990 | Wehrli |
| 4,944,760 A | 7/1990 | Kenna |
| 4,945,799 A | 8/1990 | Knetzer |
| 4,952,213 A | 8/1990 | Bowman et al. |
| 5,002,547 A | 3/1991 | Poggie et al. |
| 5,053,037 A | 10/1991 | Lackey |
| 5,065,612 A | 11/1991 | Ooka et al. |
| 5,067,821 A | 11/1991 | Young |
| 5,116,338 A | 5/1992 | Poggie et al. |
| 5,122,146 A | 6/1992 | Chapman et al. |
| 5,129,908 A | 7/1992 | Petersen |
| 5,141,512 A | 8/1992 | Farmer et al. |
| 5,171,244 A | 12/1992 | Caspari et al. |
| 5,213,112 A | 5/1993 | Niwa et al. |
| 5,249,581 A | 10/1993 | Horbal et al. |
| 5,251,127 A | 10/1993 | Raab |
| 5,279,309 A | 1/1994 | Taylor et al. |
| 5,296,855 A | 3/1994 | Matsuzaki et al. |
| 5,306,276 A | 4/1994 | Johnson et al. |
| 5,320,625 A | 6/1994 | Bertin |
| 5,324,293 A | 6/1994 | Rehmann |
| 5,325,029 A | 6/1994 | Janecke et al. |
| 5,329,933 A | 7/1994 | Graf |
| 5,342,367 A | 8/1994 | Ferrante et al. |
| 5,343,391 A | 8/1994 | Mushabac |
| 5,358,526 A | 10/1994 | Tornier |
| 5,376,093 A | 12/1994 | Newman |
| 5,395,377 A | 3/1995 | Petersen et al. |
| 5,417,694 A | 5/1995 | Marik et al. |
| 5,423,827 A | 6/1995 | Mumme |
| 5,431,653 A | 7/1995 | Callaway |
| 5,462,548 A | 10/1995 | Pappas et al. |
| 5,468,244 A | 11/1995 | Attfield et al. |
| 5,474,088 A | 12/1995 | Zaharkin et al. |
| 5,486,177 A | 1/1996 | Mumme et al. |
| 5,514,143 A | 5/1996 | Bonutti et al. |
| 5,529,070 A | 6/1996 | Augustine et al. |
| 5,540,696 A | 7/1996 | Booth, Jr. et al. |
| 5,540,697 A | 7/1996 | Rehmann et al. |
| 5,553,198 A | 9/1996 | Wang et al. |
| 5,576,727 A | 11/1996 | Rosenberg et al. |
| 5,584,837 A | 12/1996 | Peterson |
| 5,597,379 A | 1/1997 | Haines et al. |
| 5,611,353 A | 3/1997 | Dance et al. |
| 5,624,444 A | 4/1997 | Wixson et al. |
| 5,628,750 A | 5/1997 | Whitlock et al. |
| 5,645,077 A | 7/1997 | Foxlin |
| 5,653,764 A | 8/1997 | Murphy |
| 5,681,316 A | 10/1997 | DeOrio et al. |
| 5,683,398 A | 11/1997 | Carls et al. |
| 5,688,282 A | 11/1997 | Baron et al. |
| 5,720,752 A | 2/1998 | Elliot et al. |
| 5,724,264 A | 3/1998 | Rosenberg et al. |
| 5,748,767 A | 5/1998 | Raab |
| 5,769,861 A | 6/1998 | Vilsmeier |
| 5,776,137 A | 7/1998 | Katz |
| 5,788,700 A | 8/1998 | Morawa et al. |
| 5,824,085 A | 10/1998 | Sahay et al. |
| 5,840,047 A | 11/1998 | Stedham |
| 5,880,714 A | 3/1999 | Rosenberg et al. |
| 5,916,219 A | 6/1999 | Matsuno et al. |
| 5,919,149 A | 7/1999 | Allum |
| 5,935,086 A | 8/1999 | Beacon et al. |
| 5,976,156 A | 11/1999 | Taylor et al. |
| 6,027,507 A | 2/2000 | Anderson et al. |
| 6,036,696 A | 3/2000 | Lambrecht et al. |
| 6,056,756 A | 5/2000 | Eng et al. |
| 6,090,114 A | 7/2000 | Matsuno et al. |
| 6,094,019 A | 7/2000 | Saiki |
| 6,120,509 A | 9/2000 | Wheeler |
| 6,122,538 A | 9/2000 | Sliwa, Jr. et al. |
| 6,126,608 A | 10/2000 | Kemme et al. |
| 6,162,191 A | 12/2000 | Foxin |
| 6,167,292 A | 12/2000 | Badano et al. |
| 6,171,310 B1 | 1/2001 | Giordano |
| 6,195,615 B1 | 2/2001 | Lysen |
| 6,197,032 B1 | 3/2001 | Lawes et al. |
| 6,214,013 B1 | 4/2001 | Lambrech et al. |
| 6,214,014 B1 | 4/2001 | McGann |
| 6,216,029 B1 | 4/2001 | Paltieli |
| 6,246,898 B1 | 6/2001 | Vesely et al. |
| 6,258,095 B1 | 7/2001 | Lombardo et al. |
| 6,261,247 B1 | 7/2001 | Ishikawa et al. |
| 6,299,646 B1 | 10/2001 | Chambat et al. |
| 6,332,089 B1 | 12/2001 | Acker |
| 6,348,058 B1 | 2/2002 | Melken et al. |
| 6,354,011 B1 | 3/2002 | Albrecht |
| 6,361,506 B1 | 3/2002 | Saenger et al. |
| 6,361,507 B1 | 3/2002 | Foxlin |
| 6,361,508 B1 | 3/2002 | Johnson et al. |
| 6,377,839 B1 | 4/2002 | Kalfas et al. |
| 6,381,485 B1 | 4/2002 | Hunter et al. |
| 6,383,149 B1 | 5/2002 | DeMayo |
| 6,395,005 B1 | 5/2002 | Lovell |
| 6,447,448 B1 | 9/2002 | Ishikawa et al. |
| 6,468,280 B1 | 10/2002 | Saenger et al. |
| 6,470,207 B1 | 10/2002 | Simon et al. |
| 6,471,637 B1 | 10/2002 | Green et al. |
| 6,473,635 B1 | 10/2002 | Rasche |
| 6,477,400 B1 | 11/2002 | Barrick |

(56) References Cited

U.S. PATENT DOCUMENTS

| | | |
|---|---|---|
| 6,477,421 B1 | 11/2002 | Andersen et al. |
| 6,478,799 B1 | 11/2002 | Williamson |
| 6,488,713 B1 | 12/2002 | Hershnerger |
| 6,499,488 B1 | 12/2002 | Hunter et al. |
| 6,514,259 B2 | 2/2003 | Picard et al. |
| 6,527,443 B1 | 3/2003 | Vilsmeier |
| 6,551,325 B2 | 4/2003 | Neubauer et al. |
| 6,585,666 B2 | 7/2003 | Suh et al. |
| 6,595,997 B2 | 7/2003 | Axelson, Jr. et al. |
| 6,595,999 B2 | 7/2003 | Marchione et al. |
| 6,607,487 B2 | 8/2003 | Chang et al. |
| 6,640,128 B2 | 10/2003 | Vilsmeier et al. |
| 6,648,896 B2 | 11/2003 | Overes et al. |
| 6,679,916 B1 | 1/2004 | Frankie et al. |
| 6,685,655 B2 | 2/2004 | DeMayo |
| 6,685,711 B2 | 2/2004 | Axelson et al. |
| 6,711,431 B2 | 3/2004 | Sarin et al. |
| 6,712,824 B2 | 3/2004 | Millard et al. |
| 6,715,213 B2 | 4/2004 | Richter |
| 6,725,080 B2 | 4/2004 | Melkent et al. |
| 6,725,173 B2 | 4/2004 | An |
| 6,743,235 B2 | 6/2004 | Rao |
| 6,770,078 B2 | 8/2004 | Bonutti |
| 6,786,877 B2 | 9/2004 | Foxlin |
| 6,802,864 B2 | 10/2004 | Tornier |
| 6,817,470 B1 | 11/2004 | Goldberg |
| 6,820,025 B2 | 11/2004 | Bachmann et al. |
| 6,827,723 B2 | 12/2004 | Carson |
| 6,917,827 B2 | 7/2005 | Kienzle, III |
| 6,923,817 B2 | 8/2005 | Carson et al. |
| 6,928,742 B2 | 8/2005 | Broers et al. |
| 6,947,783 B2 | 9/2005 | Immerz |
| 6,986,181 B2 | 1/2006 | Murphy et al. |
| 6,997,882 B1 | 2/2006 | Parker et al. |
| 7,007,699 B2 | 3/2006 | Martinelli et al. |
| 7,021,140 B2 | 4/2006 | Perkins |
| 7,027,477 B2 | 4/2006 | Sutter et al. |
| 7,037,310 B2 | 5/2006 | Murphy |
| 7,048,741 B2 | 5/2006 | Swanson |
| 7,089,148 B1 | 8/2006 | Bachmann et al. |
| 7,094,241 B2 | 8/2006 | Hodorek et al. |
| 7,104,998 B2 | 9/2006 | Yoon et al. |
| 7,105,028 B2 | 9/2006 | Murphy |
| 7,194,295 B2 | 3/2007 | Vilsmeier |
| 7,209,776 B2 | 4/2007 | Leitner |
| 7,219,033 B2 | 5/2007 | Kolen |
| 7,273,500 B2 | 9/2007 | Williamson |
| 7,311,441 B2 | 12/2007 | Weaver et al. |
| 7,331,932 B2 | 2/2008 | Leitner |
| 7,344,541 B2 | 3/2008 | Haines et al. |
| 7,392,076 B2 | 6/2008 | Moctezuma de la Barrera |
| 7,396,357 B2 | 7/2008 | Tornier et al. |
| 7,444,178 B2 | 10/2008 | Goldbach |
| 7,468,075 B2 | 12/2008 | Lang et al. |
| 7,468,077 B2 | 12/2008 | Rochetin |
| 7,497,029 B2 | 3/2009 | Plassky et al. |
| 7,520,880 B2 | 4/2009 | Claypool et al. |
| 7,547,307 B2 | 6/2009 | Carson et al. |
| 7,559,931 B2 | 7/2009 | Stone |
| 7,578,821 B2 | 8/2009 | Fisher et al. |
| 7,594,933 B2 | 9/2009 | Kammerzell et al. |
| 7,611,520 B2 | 11/2009 | Broers et al. |
| 7,611,522 B2 | 11/2009 | Gorek |
| 7,621,920 B2 | 11/2009 | Claypool et al. |
| 7,623,902 B2 | 11/2009 | Pacheco |
| 7,726,564 B2 | 6/2010 | Goldbach |
| 7,776,098 B2 | 8/2010 | Murphy |
| 7,815,644 B2 | 10/2010 | Masini |
| 7,831,292 B2 | 11/2010 | Quaid et al. |
| 7,834,847 B2 | 11/2010 | Boillot et al. |
| 7,840,256 B2 | 11/2010 | Lakin et al. |
| 7,846,092 B2 | 12/2010 | Murphy |
| 7,857,821 B2 | 12/2010 | Couture et al. |
| 7,885,705 B2 | 2/2011 | Murphy |
| 7,970,174 B2 | 6/2011 | Goldbach |
| 8,057,479 B2 | 11/2011 | Stone |
| 8,057,482 B2 | 11/2011 | Stone |
| 8,078,254 B2 | 12/2011 | Murphy |
| 8,104,960 B2 | 1/2012 | Gill et al. |
| 8,118,815 B2 | 2/2012 | van der Walt |
| 8,241,296 B2 | 8/2012 | Wasielewski |
| 8,265,790 B2 | 9/2012 | Amiot et al. |
| 8,267,938 B2 | 9/2012 | Murphy |
| 8,277,455 B2 | 10/2012 | Couture et al. |
| 8,282,685 B2 | 10/2012 | Rochetin et al. |
| 8,355,773 B2 | 1/2013 | Leitner et al. |
| 8,412,308 B2 | 4/2013 | Goldbach |
| 8,421,854 B2 | 4/2013 | Zerkin |
| 8,446,473 B2 | 5/2013 | Goldbach |
| 8,512,346 B2 | 8/2013 | Couture |
| 8,551,108 B2 | 10/2013 | Pelletier et al. |
| 8,588,892 B2 | 11/2013 | Hladio et al. |
| 8,690,888 B2 | 4/2014 | Stein et al. |
| 8,718,820 B2 | 5/2014 | Amiot et al. |
| 8,734,432 B2 | 5/2014 | Tuma et al. |
| 8,764,758 B2 | 7/2014 | Echeverri |
| 8,867,198 B2 | 10/2014 | Steele |
| 8,888,786 B2 | 11/2014 | Stone |
| 8,911,447 B2 | 12/2014 | van der Walt et al. |
| 8,974,467 B2 | 3/2015 | Stone |
| 8,974,468 B2 | 3/2015 | Borja |
| 8,998,910 B2 | 4/2015 | Borja et al. |
| 9,044,218 B2 | 6/2015 | Young |
| 9,138,319 B2 | 9/2015 | Fanson et al. |
| 9,192,392 B2 | 11/2015 | van der Walt et al. |
| 9,262,802 B2 | 2/2016 | Aghazadeh |
| 9,271,756 B2 | 3/2016 | van der Walt et al. |
| 9,339,226 B2 | 5/2016 | van der Walt et al. |
| 9,375,178 B2 | 6/2016 | Aghazadeh |
| 9,456,769 B2 | 10/2016 | Stein et al. |
| 9,549,742 B2 | 1/2017 | Berend et al. |
| 9,572,586 B2 | 2/2017 | van der Walt et al. |
| 9,642,572 B2 | 5/2017 | Mahfouz et al. |
| 9,649,160 B2 | 5/2017 | van der Walt et al. |
| 9,775,725 B2 | 10/2017 | van der Walt et al. |
| 9,855,075 B2 | 1/2018 | van der Walt et al. |
| 9,930,946 B2 | 4/2018 | Zondervan |
| 9,931,059 B2 | 4/2018 | Borja |
| 10,206,714 B2 | 2/2019 | van der Walt et al. |
| 10,238,510 B2 | 3/2019 | van der Walt et al. |
| 10,321,852 B2 | 6/2019 | Borja |
| 10,363,149 B2 | 7/2019 | van der Walt et al. |
| 10,597,178 B2 | 3/2020 | Ryterski et al. |
| 10,603,115 B2 | 3/2020 | van der Walt et al. |
| 10,716,580 B2 | 7/2020 | Berend et al. |
| 10,863,995 B2 | 12/2020 | Nielsen et al. |
| 10,864,019 B2 | 12/2020 | van der Walt et al. |
| 10,869,771 B2 | 12/2020 | van der Walt et al. |
| 10,918,499 B2 | 2/2021 | Nielsen et al. |
| 11,020,245 B2 | 6/2021 | van der Walt et al. |
| 11,179,062 B2 | 11/2021 | Borja et al. |
| 11,179,167 B2 | 11/2021 | Stone |
| 11,191,334 B2 | 12/2021 | Aghazadeh et al. |
| 11,273,232 B2 | 3/2022 | Placik |
| 11,540,746 B2 | 1/2023 | Borja et al. |
| 11,547,451 B2 | 1/2023 | van der Walt et al. |
| 11,547,580 B2 | 1/2023 | Nielsen et al. |
| 11,633,293 B2 | 4/2023 | van der Walt et al. |
| 11,653,981 B2 | 5/2023 | van der Walt et al. |
| 11,684,392 B2 | 6/2023 | van der Walt et al. |
| 11,786,261 B2 | 10/2023 | Nielsen et al. |
| 11,871,965 B2 | 1/2024 | van der Walt et al. |
| 11,903,597 B2 | 2/2024 | Stone |
| 11,911,119 B2 | 2/2024 | van der Walt et al. |
| 12,144,567 B2 | 11/2024 | van der Walt et al. |
| 2002/0077540 A1 | 6/2002 | Kienzie, III |
| 2002/0103610 A1 | 8/2002 | Bachmann et al. |
| 2002/0107522 A1 | 8/2002 | Picard et al. |
| 2002/0133175 A1 | 9/2002 | Carson |
| 2002/0198451 A1 | 12/2002 | Carson |
| 2003/0019294 A1 | 1/2003 | Richter |
| 2003/0069591 A1 | 4/2003 | Carson et al. |
| 2003/0093080 A1 | 5/2003 | Brown et al. |
| 2003/0105470 A1 | 6/2003 | White |

(56) References Cited

U.S. PATENT DOCUMENTS

| | | |
|---|---|---|
| 2003/0120282 A1 | 6/2003 | Scouten et al. |
| 2003/0163142 A1 | 8/2003 | Paltieli et al. |
| 2003/0181919 A1 | 9/2003 | Gorek |
| 2003/0184297 A1 | 10/2003 | Jakab |
| 2003/0199882 A1 | 10/2003 | Gorek |
| 2003/0204965 A1 | 11/2003 | Hennessey |
| 2003/0229356 A1 | 12/2003 | Dye |
| 2004/0006393 A1 | 1/2004 | Burkinshaw |
| 2004/0019382 A1 | 1/2004 | Amirouche et al. |
| 2004/0034313 A1 | 2/2004 | Leitner |
| 2004/0039396 A1 | 2/2004 | Couture et al. |
| 2004/0068260 A1 | 4/2004 | Cossette et al. |
| 2004/0073225 A1 | 4/2004 | Subba Rao |
| 2004/0087958 A1 | 5/2004 | Myers et al. |
| 2004/0087962 A1 | 5/2004 | Gorek |
| 2004/0097952 A1 | 5/2004 | Sarin et al. |
| 2004/0102792 A1 | 5/2004 | Sarin et al. |
| 2004/0106916 A1 | 6/2004 | Quaid et al. |
| 2004/0122441 A1 | 6/2004 | Muratsu |
| 2004/0147926 A1 | 7/2004 | Iversen |
| 2004/0149036 A1 | 8/2004 | Foxlin et al. |
| 2004/0152955 A1 | 8/2004 | McGinley et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0181144 A1 | 9/2004 | Cinquin et al. |
| 2004/0201857 A1 | 10/2004 | Foxlin |
| 2004/0230197 A1 | 11/2004 | Tornier et al. |
| 2004/0243148 A1 | 12/2004 | Wasielewski |
| 2005/0021037 A1 | 1/2005 | McCombs et al. |
| 2005/0021044 A1 | 1/2005 | Stone et al. |
| 2005/0070864 A1 | 3/2005 | Fellion |
| 2005/0107799 A1 | 5/2005 | Graf et al. |
| 2005/0113846 A1 | 5/2005 | Carson |
| 2005/0149040 A1 | 7/2005 | Haines et al. |
| 2005/0149054 A1 | 7/2005 | Gorek |
| 2005/0197814 A1 | 9/2005 | Aram et al. |
| 2005/0209605 A1 | 9/2005 | Grimm et al. |
| 2005/0222574 A1 | 10/2005 | Giordano et al. |
| 2005/0234332 A1 | 10/2005 | Murphy |
| 2005/0251026 A1 | 11/2005 | Stone |
| 2005/0251148 A1 | 11/2005 | Friedrich |
| 2006/0009780 A1 | 1/2006 | Foley et al. |
| 2006/0015018 A1 | 1/2006 | Jutras et al. |
| 2006/0015120 A1 | 1/2006 | Richard et al. |
| 2006/0020177 A1 | 1/2006 | Seo et al. |
| 2006/0064105 A1 | 3/2006 | Raistrick et al. |
| 2006/0084977 A1 | 4/2006 | Lieberman |
| 2006/0089657 A1 | 4/2006 | Broers et al. |
| 2006/0094958 A1 | 5/2006 | Marquart et al. |
| 2006/0122491 A1 | 6/2006 | Murray et al. |
| 2006/0142656 A1 | 6/2006 | Malackowski et al. |
| 2006/0142657 A1 | 6/2006 | Quaid et al. |
| 2006/0149276 A1 | 7/2006 | Grimm |
| 2006/0161051 A1 | 7/2006 | Terrill-Grisoni et al. |
| 2006/0217733 A1 | 9/2006 | Plassky et al. |
| 2006/0217734 A1 | 9/2006 | Sanford et al. |
| 2006/0241639 A1 | 10/2006 | Kuczynski et al. |
| 2006/0270949 A1 | 11/2006 | Mathie et al. |
| 2006/0282023 A1 | 12/2006 | Leitner |
| 2007/0016009 A1 | 1/2007 | Lakin et al. |
| 2007/0032748 A1 | 2/2007 | McNeil et al. |
| 2007/0043287 A1 | 2/2007 | Degraaf |
| 2007/0043375 A1 | 2/2007 | Anissian |
| 2007/0073296 A1 | 3/2007 | Panchbhavi |
| 2007/0100346 A1 | 5/2007 | Wyss et al. |
| 2007/0162142 A1 | 7/2007 | Stone |
| 2007/0179626 A1 | 8/2007 | de la Barrera et al. |
| 2007/0179628 A1 | 8/2007 | Rochetin |
| 2007/0219559 A1 | 9/2007 | Heavener et al. |
| 2007/0219561 A1 | 9/2007 | Lavallee et al. |
| 2007/0226986 A1 | 10/2007 | Park et al. |
| 2007/0244488 A1 | 10/2007 | Metzger et al. |
| 2007/0249967 A1 | 10/2007 | Buly et al. |
| 2007/0270718 A1 | 11/2007 | Rochetin et al. |
| 2007/0270973 A1 | 11/2007 | Johnson et al. |
| 2007/0287911 A1 | 12/2007 | Haid et al. |
| 2008/0058945 A1 | 3/2008 | Hajaj et al. |
| 2008/0071195 A1 | 3/2008 | Cuellar et al. |
| 2008/0103509 A1 | 5/2008 | Goldbach |
| 2008/0108912 A1 | 5/2008 | Node-Langlois |
| 2008/0162074 A1 | 7/2008 | Schneider |
| 2008/0183179 A1 | 7/2008 | Siebel et al. |
| 2008/0195109 A1 | 8/2008 | Hunter et al. |
| 2008/0202200 A1 | 8/2008 | West |
| 2008/0211768 A1 | 9/2008 | Breen et al. |
| 2008/0243127 A1 | 10/2008 | Lang et al. |
| 2008/0249394 A1 | 10/2008 | Giori et al. |
| 2008/0262812 A1 | 10/2008 | Arata et al. |
| 2008/0275451 A1 | 11/2008 | McAllister et al. |
| 2008/0281328 A1 | 11/2008 | Lang et al. |
| 2008/0285805 A1 | 11/2008 | Luinge et al. |
| 2009/0000626 A1 | 1/2009 | Quaid et al. |
| 2009/0000627 A1 | 1/2009 | Quaid et al. |
| 2009/0012532 A1 | 1/2009 | Quaid et al. |
| 2009/0040224 A1 | 2/2009 | Igarashi et al. |
| 2009/0070038 A1 | 3/2009 | Geelen et al. |
| 2009/0076507 A1 | 3/2009 | Claypool et al. |
| 2009/0076519 A1 | 3/2009 | Iversen |
| 2009/0088753 A1 | 4/2009 | Aram et al. |
| 2009/0099665 A1 | 4/2009 | Taylor et al. |
| 2009/0171370 A1 | 7/2009 | Yoon et al. |
| 2009/0209884 A1 | 8/2009 | Van Vorhis et al. |
| 2009/0216247 A1 | 8/2009 | Collette |
| 2009/0216285 A1 | 8/2009 | Ek |
| 2009/0234360 A1 | 9/2009 | Alexander |
| 2009/0247863 A1 | 10/2009 | Proulx et al. |
| 2009/0248044 A1 | 10/2009 | Amiot et al. |
| 2009/0264737 A1 | 10/2009 | Haechler et al. |
| 2009/0270864 A1 | 10/2009 | Poncet |
| 2009/0270865 A1 | 10/2009 | Poncet et al. |
| 2009/0270868 A1 | 10/2009 | Park et al. |
| 2009/0270869 A1 | 10/2009 | Colquhoun et al. |
| 2009/0270874 A1 | 10/2009 | Santarella et al. |
| 2009/0270875 A1 | 10/2009 | Poncet |
| 2009/0270928 A1 | 10/2009 | Stone et al. |
| 2009/0276054 A1 | 11/2009 | Clifford et al. |
| 2009/0281545 A1 | 11/2009 | Stubbs |
| 2009/0289806 A1 | 11/2009 | Thornberry |
| 2009/0292227 A1 | 11/2009 | Scholten et al. |
| 2009/0299416 A1 | 12/2009 | Haenni et al. |
| 2009/0299483 A1 | 12/2009 | Amirouche et al. |
| 2009/0306679 A1 | 12/2009 | Murphy |
| 2009/0312973 A1 | 12/2009 | Hatlestad et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0324078 A1 | 12/2009 | Wu et al. |
| 2010/0016705 A1 | 1/2010 | Stone |
| 2010/0023018 A1 | 1/2010 | Theofilos |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0087829 A1 | 4/2010 | Metzger et al. |
| 2010/0100011 A1 | 4/2010 | Roche |
| 2010/0100154 A1 | 4/2010 | Roche |
| 2010/0113980 A1 | 5/2010 | Herr et al. |
| 2010/0121334 A1 | 5/2010 | Couture et al. |
| 2010/0137871 A1 | 6/2010 | Borja |
| 2010/0153081 A1 | 6/2010 | Bellettre et al. |
| 2010/0179605 A1 | 7/2010 | Branch et al. |
| 2010/0182914 A1 | 7/2010 | DelRegno et al. |
| 2010/0192662 A1 | 8/2010 | Yanni |
| 2010/0198067 A1 | 8/2010 | Mahfouz et al. |
| 2010/0198275 A1 | 8/2010 | Chana et al. |
| 2010/0204551 A1 | 8/2010 | Roche |
| 2010/0204575 A1 | 8/2010 | Roche et al. |
| 2010/0204955 A1 | 8/2010 | Roche et al. |
| 2010/0211077 A1 | 8/2010 | Couture et al. |
| 2010/0239996 A1 | 9/2010 | Ertl |
| 2010/0241126 A1 | 9/2010 | Ghijselings |
| 2010/0249533 A1 | 9/2010 | Pierce et al. |
| 2010/0249534 A1 | 9/2010 | Pierce et al. |

(56) References Cited

U.S. PATENT DOCUMENTS

| | | |
|---|---|---|
| 2010/0249535 A1 | 9/2010 | Pierce et al. |
| 2010/0249659 A1 | 9/2010 | Sherman et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250276 A1 | 9/2010 | Pierce et al. |
| 2010/0250284 A1 | 9/2010 | Roche et al. |
| 2010/0250571 A1 | 9/2010 | Pierce et al. |
| 2010/0256504 A1 | 10/2010 | Moreau-Gaudry et al. |
| 2010/0261998 A1 | 10/2010 | Stiehl |
| 2010/0268067 A1 | 10/2010 | Razzaque et al. |
| 2010/0298661 A1 | 11/2010 | McCombie et al. |
| 2010/0324457 A1 | 12/2010 | Bean et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331633 A1 | 12/2010 | Stein |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331683 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2010/0331894 A1 | 12/2010 | Stein |
| 2010/0332152 A1 | 12/2010 | Stein |
| 2011/0028865 A1 | 2/2011 | Luinge et al. |
| 2011/0032184 A1 | 2/2011 | Roche et al. |
| 2011/0093081 A1 | 4/2011 | Chana et al. |
| 2011/0213275 A1 | 9/2011 | Boos et al. |
| 2011/0218458 A1 | 9/2011 | Valin et al. |
| 2011/0218546 A1 | 9/2011 | De La Fuente Klein et al. |
| 2011/0275957 A1 | 11/2011 | Bhandari |
| 2012/0029389 A1 | 2/2012 | Amiot et al. |
| 2012/0053488 A1 | 3/2012 | Boutin et al. |
| 2012/0053594 A1 | 3/2012 | Pelletier et al. |
| 2012/0093377 A1 | 4/2012 | Tsougarakis et al. |
| 2012/0157887 A1 | 6/2012 | Fanson et al. |
| 2012/0172712 A1 | 7/2012 | Bar-Tal |
| 2012/0172884 A1 | 7/2012 | Zheng et al. |
| 2012/0203140 A1 | 8/2012 | Malchau et al. |
| 2012/0283599 A1* | 11/2012 | Borja .......... A61B 5/1072 600/587 |
| 2013/0053859 A1 | 2/2013 | Penenberg |
| 2013/0064478 A1 | 3/2013 | Sold et al. |
| 2013/0066323 A1 | 3/2013 | Nycz et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079790 A1 | 3/2013 | Stein et al. |
| 2013/0079791 A1 | 3/2013 | Stein et al. |
| 2013/0079793 A1 | 3/2013 | Stein et al. |
| 2013/0190887 A1 | 7/2013 | Fanson et al. |
| 2013/0274633 A1 | 10/2013 | Hladio et al. |
| 2014/0005673 A1 | 1/2014 | Pelletier et al. |
| 2014/0031672 A1 | 1/2014 | McCaulley et al. |
| 2014/0114179 A1 | 4/2014 | Muller et al. |
| 2014/0134586 A1 | 5/2014 | Stein et al. |
| 2014/0135658 A1 | 5/2014 | Hladio et al. |
| 2014/0135744 A1 | 5/2014 | Stein et al. |
| 2014/0135773 A1 | 5/2014 | Stein et al. |
| 2014/0136143 A1 | 5/2014 | Stein et al. |
| 2014/0182062 A1 | 7/2014 | Aghazadeh |
| 2014/0224685 A1 | 8/2014 | Carnevali |
| 2014/0270583 A1 | 9/2014 | Anderson |
| 2014/0275940 A1 | 9/2014 | Hladio et al. |
| 2014/0276000 A1 | 9/2014 | Mullaney et al. |
| 2014/0276864 A1 | 9/2014 | Aghazadeh |
| 2014/0303631 A1 | 10/2014 | Thornberry |
| 2014/0330281 A1 | 11/2014 | Aghazadeh |
| 2014/0364858 A1 | 12/2014 | Li et al. |
| 2015/0018718 A1 | 1/2015 | Aghazadeh |
| 2015/0142372 A1 | 5/2015 | Singh |
| 2015/0143781 A1 | 5/2015 | Agnihotri |
| 2015/0150569 A1 | 6/2015 | van der Walt et al. |
| 2015/0164657 A1 | 6/2015 | Miles et al. |
| 2015/0238204 A1 | 8/2015 | Stone |
| 2015/0245914 A1 | 9/2015 | Langton |
| 2015/0313723 A1 | 11/2015 | Jansen |
| 2015/0342516 A1 | 12/2015 | Nguyen et al. |
| 2016/0038242 A1 | 2/2016 | Lo Iacono et al. |
| 2016/0175055 A1 | 6/2016 | Hook et al. |
| 2016/0206378 A1 | 7/2016 | Flett et al. |
| 2016/0220315 A1 | 8/2016 | Falardeau |
| 2016/0220318 A1 | 8/2016 | Falardeau et al. |
| 2016/0220385 A1 | 8/2016 | Falardeau et al. |
| 2016/0346044 A1 | 12/2016 | Brown et al. |
| 2017/0296203 A1 | 10/2017 | Stone |
| 2017/0325892 A1 | 11/2017 | Aghazadeh |
| 2018/0064496 A1 | 3/2018 | Hladio et al. |
| 2018/0177509 A1 | 6/2018 | Trabish et al. |
| 2018/0206860 A1 | 7/2018 | van der Walt et al. |
| 2018/0235762 A1 | 8/2018 | Radermacher et al. |
| 2019/0350728 A1 | 11/2019 | van der Walt et al. |
| 2019/0357809 A1 | 11/2019 | Borja et al. |
| 2020/0352654 A1 | 11/2020 | van der Walt et al. |
| 2020/0390501 A1 | 12/2020 | Brown et al. |
| 2021/0153880 A1 | 5/2021 | Nielsen et al. |
| 2021/0153908 A1 | 5/2021 | van der Walt et al. |
| 2021/0186711 A1 | 6/2021 | van der Walt et al. |
| 2021/0220152 A1 | 7/2021 | Nielsen et al. |
| 2022/0071509 A1 | 3/2022 | Borja et al. |
| 2022/0240953 A1 | 8/2022 | Stone |
| 2022/0313455 A1 | 10/2022 | van der Walt et al. |
| 2022/0378516 A1 | 12/2022 | Sierra et al. |
| 2023/0059247 A1 | 2/2023 | Gannoe |
| 2023/0135541 A1 | 5/2023 | Borja et al. |
| 2023/0149185 A1 | 5/2023 | Nielsen et al. |
| 2023/0157727 A1 | 5/2023 | van der Walt et al. |
| 2023/0248447 A1 | 8/2023 | van der Walt et al. |
| 2023/0277335 A1 | 9/2023 | van der Walt et al. |
| 2023/0301685 A1 | 9/2023 | van der Walt et al. |
| 2024/0099731 A1 | 3/2024 | Nielsen et al. |
| 2024/0099744 A1 | 3/2024 | van der Walt et al. |
| 2024/0197406 A1 | 6/2024 | van der Walt et al. |

FOREIGN PATENT DOCUMENTS

| | | |
|---|---|---|
| CA | 2 537 711 | 8/2007 |
| CN | 109846528 | 6/2019 |
| DE | 4 225 112 | 12/1993 |
| DE | 29704393 | 8/1997 |
| DE | 198 30 359 | 1/2000 |
| DE | 20116368 | 12/2001 |
| EP | 0 557 591 | 9/1993 |
| EP | 0 651 968 | 5/1995 |
| EP | 1 635 705 | 3/2006 |
| EP | 1 817 547 | 4/2012 |
| EP | 2 957 249 | 12/2015 |
| EP | 3 395 281 | 10/2018 |
| GB | 2 197 790 | 6/1988 |
| GB | 2 511 885 | 9/2014 |
| JP | 07-184929 | 7/1995 |
| JP | H08-240611 | 9/1996 |
| JP | 2004-237064 | 8/2004 |
| JP | 2006-314775 | 11/2006 |
| JP | 2006-528496 | 12/2006 |
| JP | 2007-503289 | 2/2007 |

(56) References Cited

FOREIGN PATENT DOCUMENTS

| | | |
|---|---|---|
| JP | 2007-534351 | 11/2007 |
| JP | 2008-521574 | 6/2008 |
| JP | 2008-537496 | 9/2008 |
| JP | 2009-511136 | 3/2009 |
| JP | 2011-502626 | 1/2011 |
| JP | 2013-000230 | 1/2013 |
| JP | 2014-524815 | 9/2014 |
| JP | 2015-524733 | 8/2015 |
| JP | 2015-226613 | 12/2015 |
| JP | 6980248 | 11/2021 |
| JP | 7180159 | 11/2022 |
| WO | WO 99/60939 | 12/1999 |
| WO | WO 2001/030247 | 5/2001 |
| WO | WO 02/000131 | 1/2002 |
| WO | WO 02/17798 | 3/2002 |
| WO | WO 2004/080323 | 9/2004 |
| WO | WO 2004/112610 | 12/2004 |
| WO | WO 2005/006993 | 1/2005 |
| WO | WO 2006/119387 | 11/2006 |
| WO | WO 2007/136784 | 11/2007 |
| WO | WO 2008/073999 | 6/2008 |
| WO | WO 2008/129414 | 10/2008 |
| WO | WO 2009/117833 | 10/2009 |
| WO | WO 2010/011978 | 1/2010 |
| WO | WO 2010/030809 | 3/2010 |
| WO | WO 2010/063117 | 6/2010 |
| WO | WO 2011/044273 | 4/2011 |
| WO | WO 2012/006172 | 1/2012 |
| WO | WO 2012/027815 | 3/2012 |
| WO | WO 2012/027816 | 3/2012 |
| WO | WO 2012/082164 | 6/2012 |
| WO | WO 2012/109361 | 8/2012 |
| WO | WO 2012/113054 | 8/2012 |
| WO | WO 2013/012561 | 1/2013 |
| WO | WO 2013/013094 | 1/2013 |
| WO | WO 2013/049534 | 4/2013 |
| WO | WO 2013/169674 | 11/2013 |
| WO | WO 2013/173700 | 11/2013 |
| WO | WO 2013/188960 | 12/2013 |
| WO | WO 2014/028227 | 2/2014 |
| WO | WO 2014/063181 | 5/2014 |
| WO | WO 2014/197988 | 12/2014 |
| WO | WO 2015/054745 | 4/2015 |
| WO | WO 2016/070288 | 5/2016 |
| WO | WO 2016/134168 | 8/2016 |
| WO | WO 2016/147153 | 9/2016 |
| WO | WO 2016/154489 | 9/2016 |
| WO | WO 2017/093769 | 6/2017 |
| WO | WO 2018/085900 | 5/2018 |
| WO | WO 2018/119360 | 6/2018 |
| WO | WO 2018/169980 | 9/2018 |
| WO | WO 2018/169995 | 9/2018 |
| WO | WO 2019/036752 | 2/2019 |
| WO | WO 2021/119001 | 6/2021 |
| WO | WO 2021/188798 | 9/2021 |
| WO | WO 2022/165561 | 8/2022 |

OTHER PUBLICATIONS 510 (k) Summary for Total Knee Surgetics Navigation System, in 5 pages.
510 (k) Summary of Safety and Effectiveness for BrainLAB knee, in 5 pages.
Anderson MD., Kevin, et al., "Computer Assisted Navigation in Total Knee Arthroplasty", The Journal of Arthroplasty, 2005, vol. 20, No. 7, Suppl. 3, in 7 pages.
Ang, et al., An Active Hand-Held Instrument for Enhanced Microsurgical Accuracy, Medical Image Computing and Computer-Assisted Intervention, 2000, vol. 1935, pp. 878-887.
Arnold-Moore, et. al., Architecture of a Content Management Server for XML Document Applications, RMIT Multimedia Database Systems, Royal Melbourne Institute of Technology, Victoria Australia, in 12 pages.
ArthroCAD, Enhancing orthopedic outcomes through optimal alignment, 2012, Pages in 2 pages.
Bae et al., "Computer Assisted Navigation in Knee Arthroplasty", Clinics in Orthopedic Surgery, 2011, vol. 3, pp. 259-267.
Bargren, MD., et al,, Alignment in Total Knee Arthroplasty, Correlated Biomechanicaland Clinical Observations, Clinical Orthopaedics and Related Research, Mar. 1, 1983, Issue 173, pp. 178-183, Philadelphia.
Bathis, H. et al., "Alignment in total knee arthroplasty", The Journal of Bone & Joint Surgery (Br), 2004, 86-B, pp. 682-687, British Editorial.
Bhandari, Design and Prototype of a Computer Assisted Surgical Navigation System for Total Knee Replacement Surgery, May 12, 2009, Pages in 294 pages.
Biomet Orthopedics, Inc, Vision Acetabular Surgical Techniques, website brochure, pp. 16 pages.
Biomet Orthopedics, Inc., Universal Ringlock® Acetabular Series, vol. website brochure, pp. 13 pages.
Brainlab, "Position Determination and Calibration in optical tracking systems", FLORENUS the technology merchants, in 2 pages.
Brainlab, "Tracking and imaging in Navigation", FLORENUS, in 2 pages.
Brennan, et al., Quantification of Inertial Sensor-Based 3D Joint Angle Measurement Accuracy Using and Instrumented Gimbal, Gait & Posture, May 23, 2011, vol. 34, pp. 320-323.
Chauhan, et al., Computer-Assisted Knee Arthroplasty Versus a Conventional Jig-Based Technique, The Journal of Bone & Joint Surgery, 2004, vol. 86-B, pp. 372-377.
Cutti, et al., Motion Analysis of the Upper-Limb Based on Inertial Sensors: Part 1—Protocol Description, Journal of Biomechanics, Jan. 1, 2007, vol. 40, pp. S250.
Decking, MD., et al., Leg Axis After Computer-Navigated Total Knee Arthroplasty, The Journal of Arthroplasty, 2005, vol. 20, Issue 3, pp. 282-288.
Depuy, Johnson & Johnson, Co.,, Summit Cemented Hip System, website brochure, pp. 21 pages.
De Momi, et al., "In-vitro experimental assessment of a new robust algorithm for hip joint centre estimation", Journal of Biomechanics, Feb. 26, 2009, vol. 42, pp. 989-995.
Digioia III, MD., et al., "Comparison of a Mechanical Acetabular Alignment Guide with Computer Placement of the Socket", The Journal of Arthroplasty, Apr. 2002, vol. 17, No. 3, in 6 pages.
Eric Foxlin, Chapter 7. Motion Tracking Requirements and Technologies, Handbook of Virtual Environment Technology, 2002, vol. Kay Stanney, Ed., Issue Lawrence Erlbaum Ass.
Favre, et al., 3D Evaluation of the Knee Joint Using Ambulatory System: Application to ACL-Deficient Knees, Journal of Biomechanics, Jan. 1, 2007, vol. 40, pp. S251.
Favre, et al., A New Ambulatory System for Comparative Evaluation of the Three-Dimensional Knee Kinematics, Applied to Anterior Cruciate Ligament Injuries, Knee Surgery, Sports Traumatology, Arthroscopy, Jan. 19, 2006, vol. 14, pp. 592-604.
Favre, et al., Ambulatory Measurement of 3D Knee Joint Angle, Journal of Biomechanics, Jan. 28, 2008, vol. 41, Issue 1029-1035.
Fixed Reference Surgical Technique, SIGMA High Performance Instruments, DePuy Orthopaedics, Inc., 2008, Warsaw, IN, in 52pages.
Ganapathi et al., "Limb Length and Femoral Offset Reconstruction During THA Using CT-Free Computer Navigation", The Journal of Bone and Joint Surgery, 2009, vol. 91-B, Supplement III, p. 399.
Goniometer, AllHeart.com, 2004, website: http://allheart.com/allheart, (1 page).
Haaker et al., "Computer-Assisted Navigation Increases Precision of Component Placement in Total Knee Arthroplasty", Clinical Orthopaedics and Related Research, Apr. 2005, vol. 433, pp. 152-159.
Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.
Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.
IAssist Knee, Surgical Technique, Zimmer, Inc., 2012.

(56) References Cited

OTHER PUBLICATIONS

International Preliminary Report for Application No. PCT/US2004/018244, dated Dec. 13, 2005, in 11 pages.
International Search Report and Written Opinion issued in PCT Application No. PCT/US2013/039770, dated Sep. 25, 2013.
International Preliminary Report on Patentability issued in PCT Application No. PCT/US2013/039770, dated Nov. 11, 2014.
International Search Report and Written Opinion issued in PCT Application No. PCT/US2013/041556, dated Sep. 13, 2013.
International Preliminary Report on Patentability issued in PCT Application No. PCT/US2013/041556, dated Nov. 18, 2014.
International Search Report and Written Opinion issued in PCT Application No. PCT/US2013/053182, dated Nov. 11, 2013.
International Search Report for Application No. PCT/US2004/018244, dated Feb. 15, 2005, in 4 pages.
International Search Report for International Application No. PCT/US2009/051769 dated Nov. 19, 2009, in 11 pages.
International Search Report for International Application No. PCT/US2009/051769 dated Nov. 19, 2009, in 3 pages.
International Search Report for International Application No. PCT/US2011/022162, dated Jun. 16, 2011, in 4 pages.
International Search Report for International Application No. PCT/US2009/056553, dated Nov. 4, 2009, in 12 pages.
International Preliminary Report on Patentability issued in PCT Application No. PCT/US2013/053182, dated Feb. 17, 2015, in 10 pages.
International Search Report and Written Opinion issued in International Application No. PCT/US2016/018508, dated Jun. 22, 2016, in 19 pages.
Jenny, et al., Computer-Assisted Implantation of Total Knee Prosthesis: A Case-Control Comparative Study with Classical Instrumentation, Computer Aided Surgery, 2001, vol. 6, pp. 217-220.
Konyves et al., "The importance of leg length discrepancy after total hip arthroplasty", The Journal of Bone & Joint Surgery (Br), Feb. 2005, vol. 87-B, No. 2, pp. 155-157.
Leenders, MD., et al., "Reduction in Variability of Acetabular Cup Abduction Using Computer Assisted Surgery: A Prospective and Randomized Study", Computer Aided Surgery, 2002, vol. 7, pp. 99-106.
Leung, et al., Intraobserver Errors in Obtaining Visually Selected Anatomic Landmarks During Registration Process in Nonimage-based Navigation-assisted Total Knee Arthroplasty, The Journal of Arthroplasty, 2005, vol. 20, Issue 5, pp. 591-601.
Liebergall, Meir, et al., "Computerized Navigation for the Internal Fixation of Femoral Neck Fractures", The Journal of Bone & Joint Surgery Am, 2006, vol. 88, pp. 1748-1754.
Longo, et al., MIKA Surgical Technique, DJO Surgical, 2008, Austin Texas in 14 pages.
Luinge, Inertial Sensing of Human Movement, Twente University Press, Feb. 15, 1973, Pages in 88 pages.
MacKenzie, et al., A Two-Ball Mouse Affords Three Degrees of Freedom, Extended Abstracts of the CHI '97 Conference on Human Factors in Compounding Systems (as printed from the internet on Jun. 13, 2012 URL: http://www.yorku.ca/mack/CHI97a.htm), 1997, pp. 303-304.
Medical Research Ltd, Clinical Goniometer, http://www.mie-uk.com/Gonio, 1997, pp. 1 page.
Minimally Invasive TKA Genesis II Anterior Cut First, Surgical Technique, Smith & Nephew, Nov. 2003, Memphis TN, in 16 pages.
Noble et al., "Computer Simulation: How Can it Help the Surgeon Optimize Implant Position?", Clinical Orthopaedics and Related Research, Dec. 2003, vol. 417, pp. 242-252.
Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.
Perseus Intelligent Cutting Guide, Orthokey, Product Guide, in 8 pages.
Perseus Intelligent Cutting Guide, Smart Instruments for Knee Arthroplasty, Orthokey, in 2 pages.
Ritter, M.D., et al., Postoperative Alignment of Total Knee Replacement, Its Effect onSurvival, Clinical Orthopaedics and Related Research, Feb. 1, 1994, Issue 299, pp. 153-156, Philadelphia.
Rocon, et al., Application of Inertial Sensors and Rehabilitation Robotics, Rehabilitation Robotics 2007, Jun. 1, 2007, pp. 145-150.
Sacks-Davis et. Al., Atlas: A nested Relational Database System for Text Applications, IEEE Transations on Knowledge and Data Engineering, v.7, n.3, Jun. 1995, pp. 454-470.
Schep, et al., "Computer assisted orthopaedic and trauma surgery State of the art and future perspectives", Injury Int. J. Care Injured 34, (website: www.elsevier.com/locate/injury), 2003 pp. 299-306.
Scott, M.S., et al., P.F.C. Sigma Knee System, Primary Surgical Technique Part 1 of 2, DePuy International Ltd., 2003, England, (up to p. 44), in 48 pages.
Scott, M.S., et al., P.F.C. Sigma Knee System, Primary Surgical Technique Part 2 of 2, DePuy International Ltd., 2003, England, Part A (up to p. 74), in 31 pages. (This reference was split in two due to size exceeding over 25MB).
Scott, M.S., et al., P.F.C. Sigma Knee System, Primary Surgical Technique Part 2 of 2, DePuy International Ltd., 2003, England, Part B (up to p. 104), in 31 pages. (This reference was split in two due to size exceeding over 25MB).
Sikorski et al., "Computer-Assisted Orthopaedic Surgery: Do We Need CAOS?", The Journal of Bone & Joint Surgery (Br), Apr. 2003, vol. 85-B, No. 3, pp. 319-323.
Slomczykowski, et al., "Novel Computer-Assisted Fluoroscopy System for Intraoperative Guidance: Feasibility Study for Distal Locking of Femoral Nails", Journal of Orthopaedic Trauma, 2001, vol. 15, No. 2, pp. 122-131, Lippincott Williams & Wilkins, Inc., Philadelphia.
Stulberg, et al., Computer-Assisted Total Knee Replacement Arthroplasty, Operative Techniques in Orthopaedics, Jan. 2000, vol. 10, Issue 1, pp. 25-39.
The Academy of Orthopaedic Surgeons, Academy News, http://www.aaos.org/wordhtml/2001news/b6-01.htm, Mar. 1, 2001, pp. 1 page.
Tilt Sensors: High Accuracy, Digital Series, Crossbow Technology, Inc., pp. 32-35.
Upadhyay et al., "Medical Malpractice in Hip and Knee Arthroplasty", The Journal of Arthroplasty, 2007, vol. 22, No. 6, Suppl. 2, pp. 2-7.
Visser, et al., 3D Analysis of Upper Body Movements in Bilateral Amputee Gait Using Inertial Sensors, Journal of Biomechanics, Jan. 1, 2007, vol. 40, Issue S509.
Wentzensen et al., "Image-based hip navigation", International Orthopaedics (SICOT), 2003, vol. 27 (Suppl. 1), pp. S43-S46.
Wolfstadt et al., "An intelligent instrument for improved leg length and hip offset accuracy in total hip arthroplasty", Abstract Only.
Written Opinion for International Application No. PCT/US2009/051769, dated Nov. 19, 2009, in 7 pages.
Written Opinion for International Application No. PCT/US2011/022162, dated Jun. 16, 2011, in 9 pages.
Written Opinion of the ISR for Application No. PCT/US2004/018244, in 10 pages.
Wylde et al., "Prevalence and functional impact of patient-perceived leg length discrepancy after hip replacement", International Orthopaedics, 2009, vol. 33, pp. 905-909.
Wylde et al., "Patient-perceived leg length discrepancy after total hip replacement: prevalence and impact on functional outcome", International Orthopaedics, 2008, vol. 24, No. 2, pp. 210-216.
Zheng et al., "Technical Principles of Computer Assisted Orthopaedic Surgery", Suomen Ortopedia ja Traumatologia, Feb. 2008, vol. 31, pp. 135-147.
Zhou, et al., Use of Multiple Wearable Inertial Sensors in Upper Limb Motion Tracking, Medical Engineering & Physics, Jan. 1, 2008, vol. 30, pp. 123-133.
Zimmer NexGen Flexion Balancing Instruments, Surgical Technique, 2007, www.zimmer.com, in 44 pages.
Zorman, David, et al., "Computer-assisted total knee arthroplasty: comparative results in a preliminary series of 72 cases", ActaOrthop. Belg., 2005, 71, pp. 696-702.

* cited by examiner

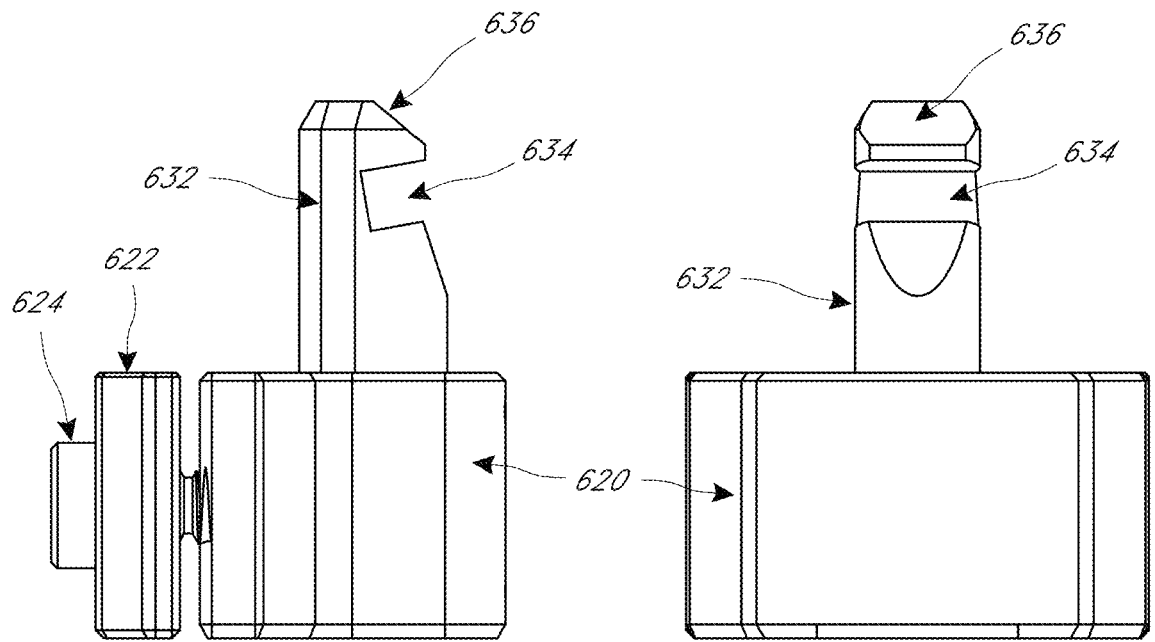
FIG. 20B                    FIG. 20D
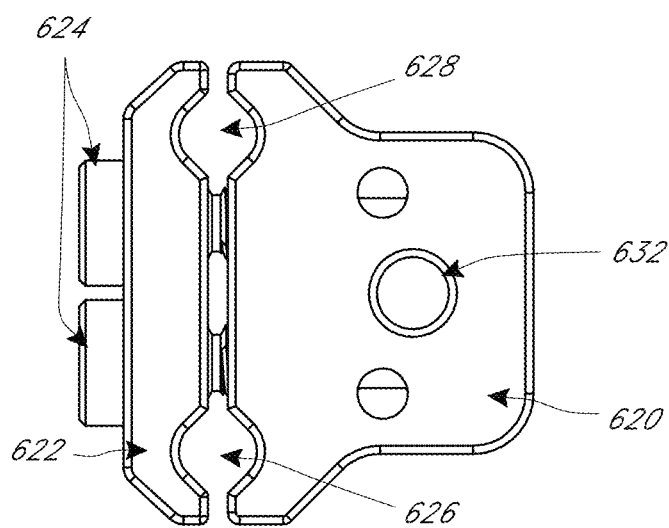
FIG. 20C

View A-A

Detail A

Detail B

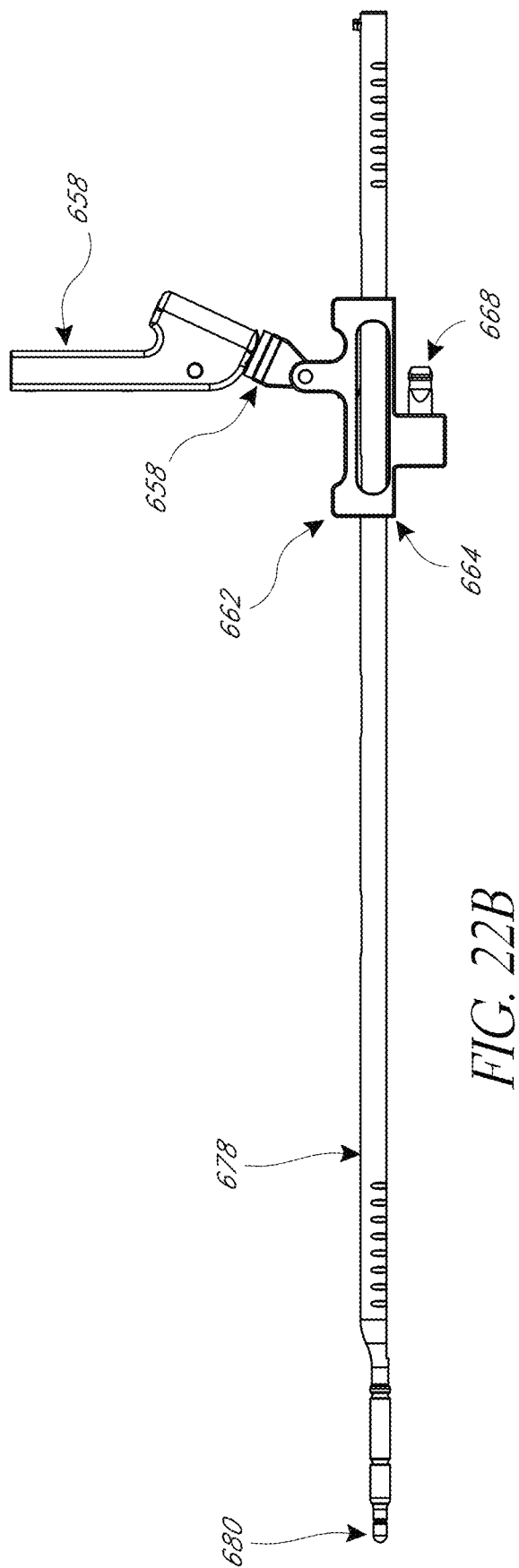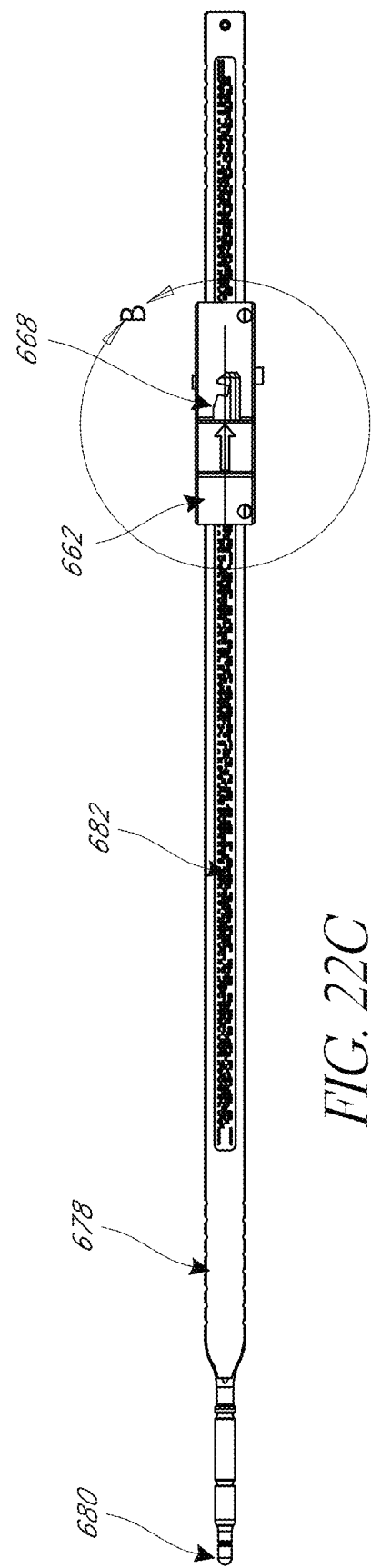

DETAIL A
SCALE 2 : 1

DETAIL B
SCALE 1 : 1

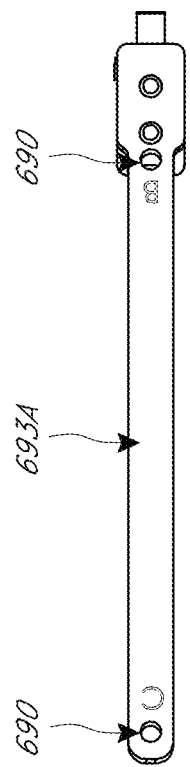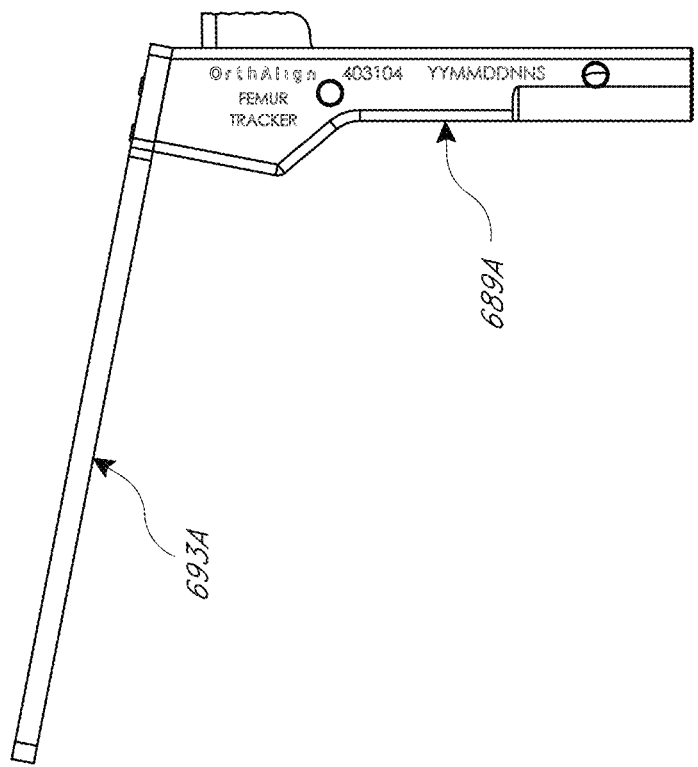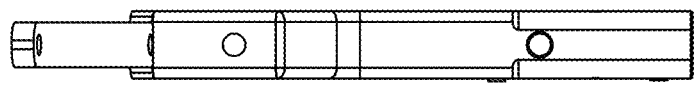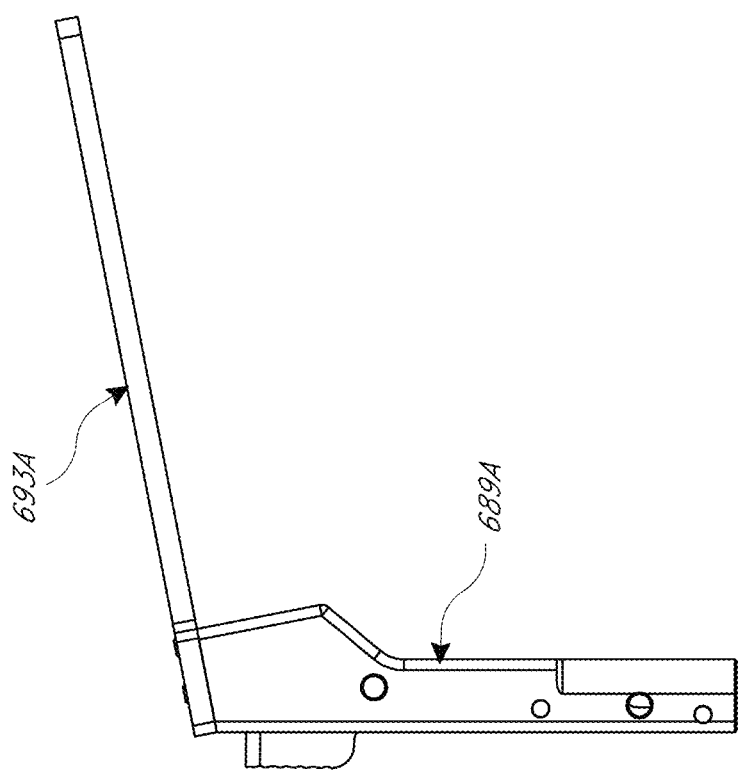

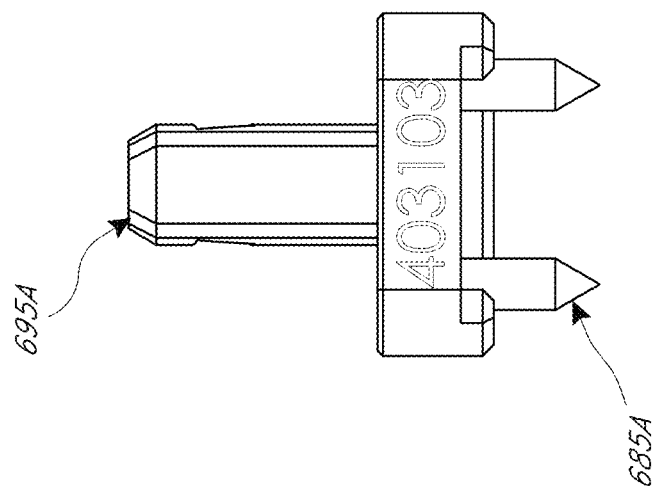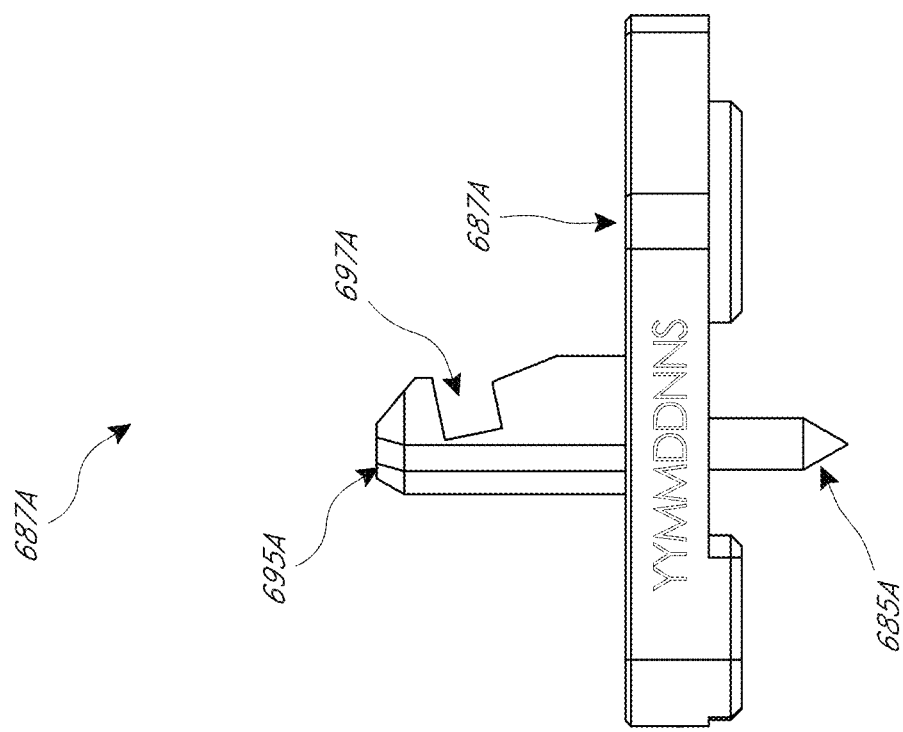

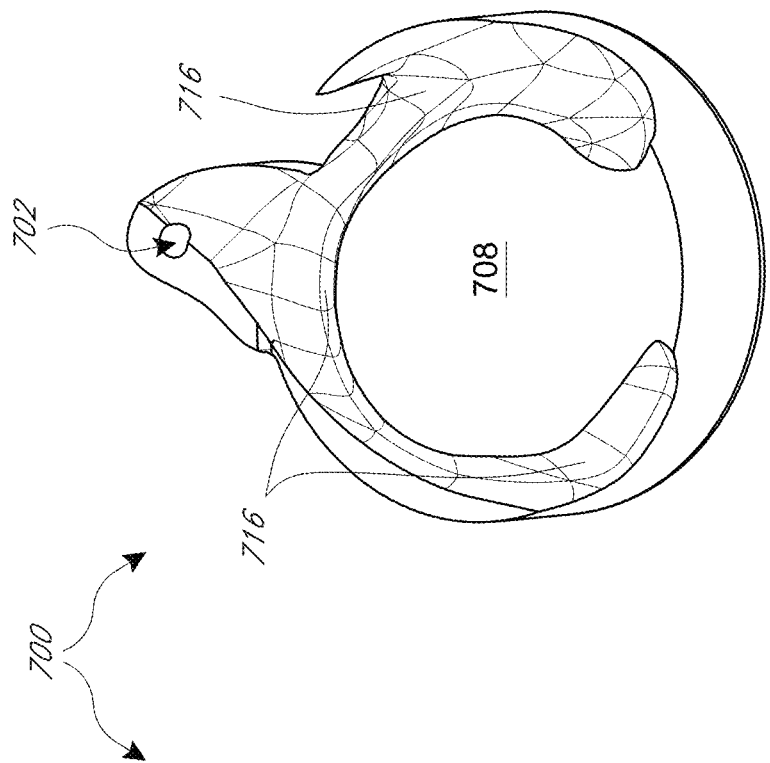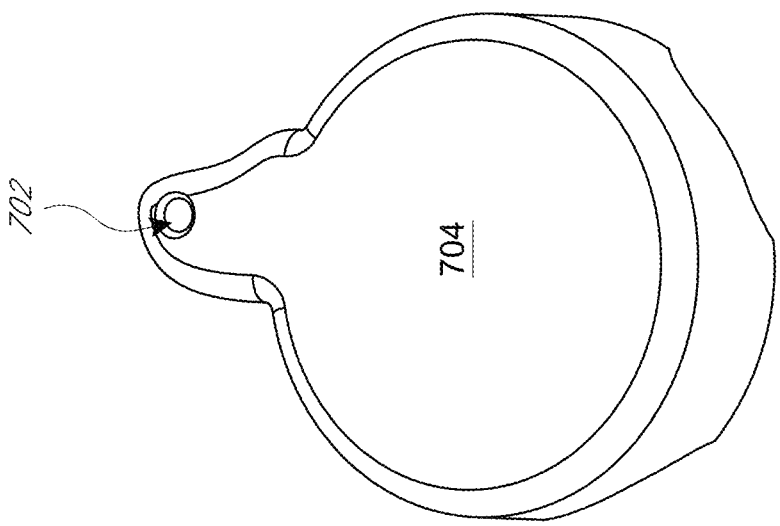
FIG. 44

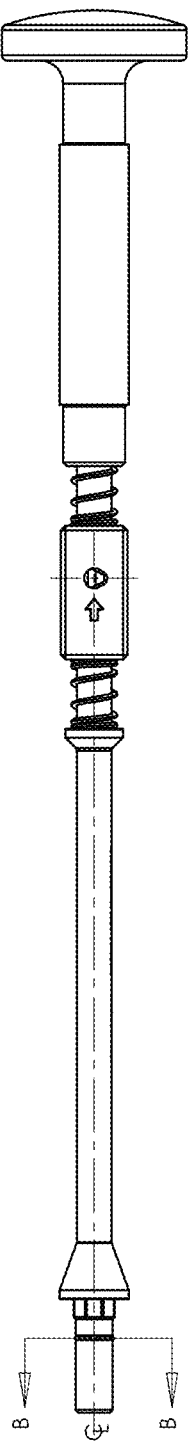
FIG. 56B
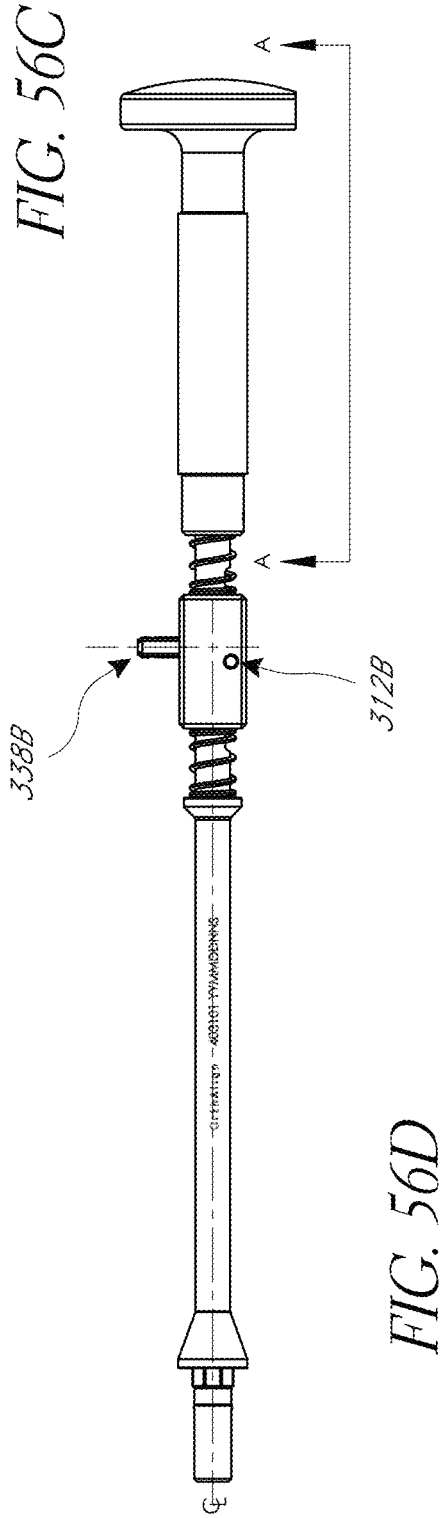
FIG. 56C
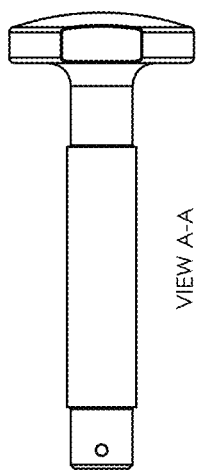
FIG. 56E
FIG. 56D
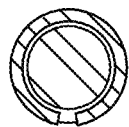

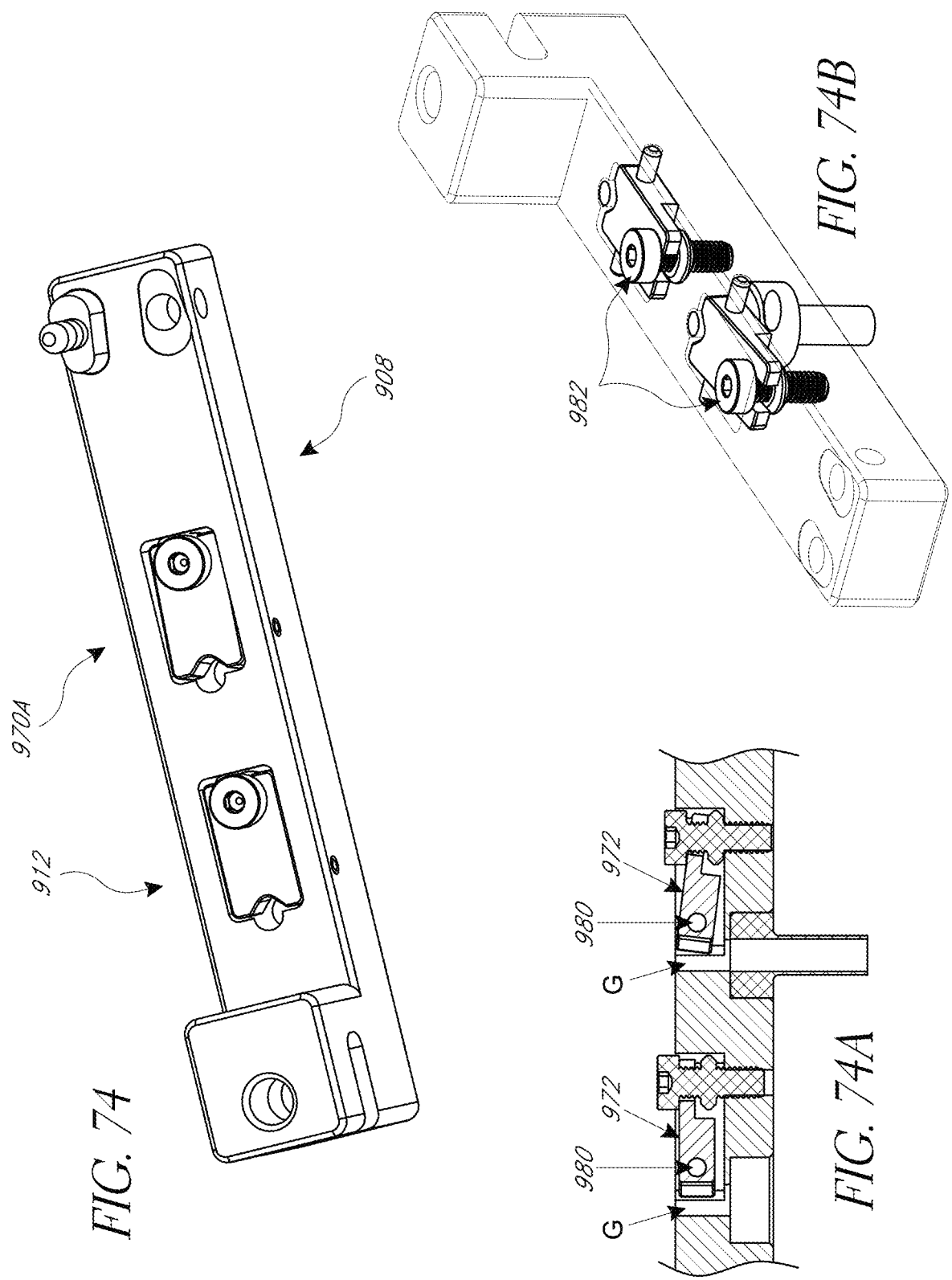

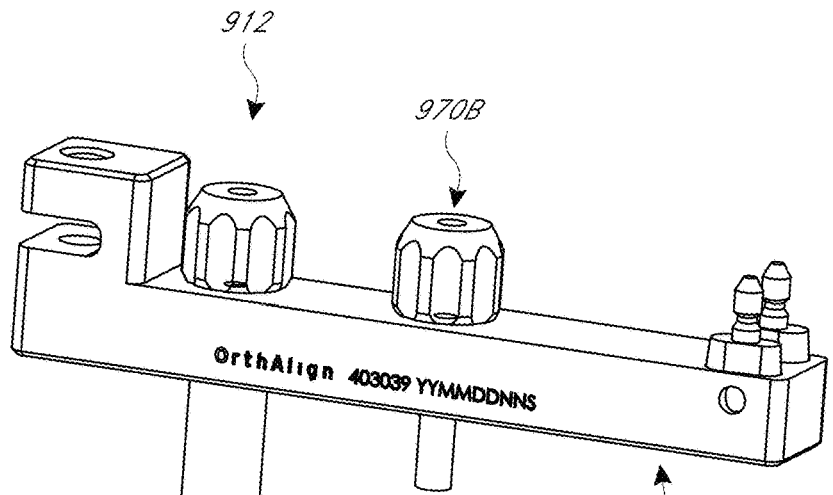
FIG. 75
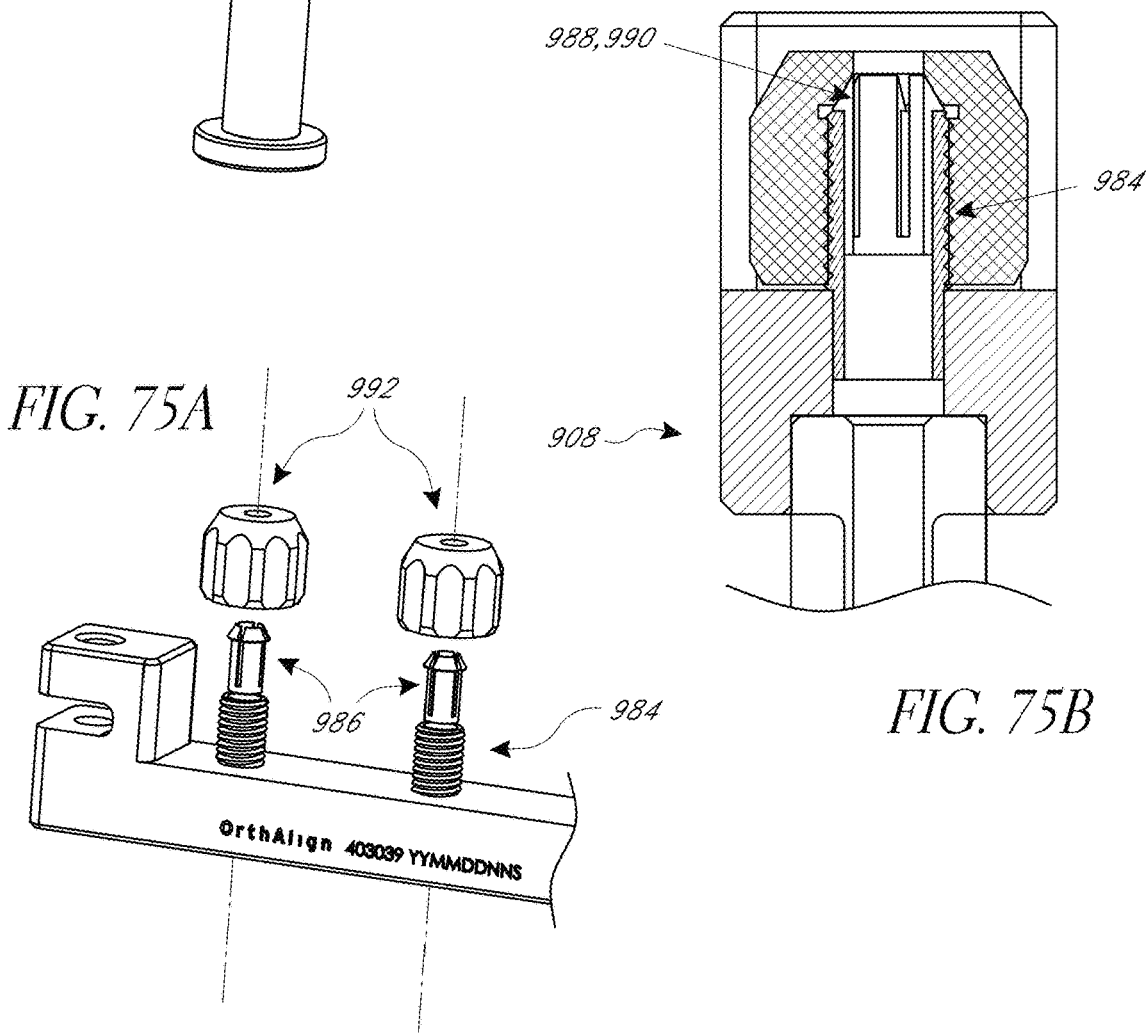
FIG. 75A
FIG. 75B

HIP REPLACEMENT NAVIGATION SYSTEM AND METHOD

INCORPORATION BY REFERENCE TO ANY PRIORITY APPLICATIONS

This application is a continuation of U.S. patent application Ser. No. 15/550,564, filed Aug. 11, 2017, which is the U.S. National Phase under 35 U.S.C. § 371 of International Application No. PCT/US2016/018508, filed Feb. 18, 2016, which is a continuation-in-part of U.S. patent application Ser. No. 14/643,864, filed Mar. 10, 2015 and claims priority benefit to U.S. Provisional Patent Application No. 62/118,987 filed Feb. 20, 2015 the entire contents of each is incorporated in its entirety by reference herein. Any and all applications for which a foreign or domestic priority claim is identified in the Application Data Sheet as filed with the present application including U.S. provisional application No. 62/118,987, filed Feb. 20, 2015, and U.S. nonprovisional application Ser. No. 14/643,864, filed Mar. 10, 2015, are hereby incorporated by reference under 37 CFR 1.57.

BACKGROUND OF THE INVENTION

Field of the Invention

This application is directed to the field of hip replacement, and particularly to surgical tools and methods for guiding the preparation of the bones in connection therewith.

Description of the Related Art

Hip replacement surgery is common and getting more common by the year. One persistent issue with hip replacement is the relatively high incidence of poor placement of the cup and ball components of the prosthetic hip joint. For example, the cup is optimally placed in a specific alignment with a plane including a rim of the acetabulum of the pelvis. For several reasons an unacceptably high percentage of patients have the cup of the artificial hip joint out of alignment with this plane.

Unfortunately, misalignment can lead to dislocation of the hip as soon as within one year of the implantation procedure. This is particularly problematic because recovery from a hip procedure can take many months. Patients undergoing a revision so soon after the initial implantation will certainly be dissatisfied with their care, being subject to addition redundant surgery. Of course, all surgery carries some degree of risk. These poor outcomes are unsatisfactory for patients and surgeons and are inefficient for the healthcare system as a whole.

Also, in cup placement in total hip arthroplasty, the inclination and anteversion angles are with respect to the Anterior Pelvic Plane (defined as a plane created by the two anterior superior iliac spines (ASIS) and the pubic symphysis). While these anatomical features are visible/palpable while the patient is in a supine position, the majority of total hip replacements are accomplished via a posterolateral approach with the patient in some variation of a lateral position, in which most of these landmarks are not accessible or visible. Historically, navigation for posterior approach hip replacement has been accomplished by registering the anatomical features of the Anterior Pelvic Plane with the patient first in a supine position and, once this plane is recorded by the navigation computer, moving the patient to a lateral position in order to perform hip surgery—with navigation performed with respect to the directly registered Anterior Pelvic Plane. This approach to hip navigation is sub-optimal for surgical workflow because the extra movement of the patient from supine to lateral position takes more surgeon and staff time and requires breaking sterility and re-draping. This is one of the key reasons why hip navigation has failed to be adopted by most of the market.

Additionally, altered leg length is a common patient complaint arising from hip replacement surgery and has been a common cause of medical malpractice lawsuits that arise from hip replacement. Because part of the hip replacement procedure requires precise measurements of patient leg length and joint off-set that are frequently difficult to visualize utilizing conventional instrumentation, there are opportunities to improve the surgeon's performance of these measurements using computer technology.

SUMMARY OF THE INVENTION

There is a need for improved systems and methods for providing for proper alignment of hip components with a patient's anatomy during a hip replacement procedure. This can involve modular systems with low profile components. This can involve a camera component designed to read a length measurement. This can involve techniques for measuring leg length and joint offset. This can involve techniques for locating one or more points on a fixed femur tracker.

In some embodiments, a hip joint navigation system is provided. The hip joint navigation system can include a jig comprising a fixation base configured to be secured to a pelvis of a patient. The hip joint navigation system can include an optical component coupled to the jig and having at least one degree of freedom relative to the fixation base. In some embodiments, the optical component is configured to project light toward a portion of a extremity of the patient. In some embodiments, the optical component is configured to determine the orientation of the extremity pre-operatively and/or post-operatively.

The hip joint navigation system can include an inertial sensor coupled to the jig and having at least one degree of freedom relative to the fixation base. In some embodiments, the optical component and the inertial sensor are separate components. In some embodiments, the optical component and the inertial sensor are integrated into a single housing. In some embodiments, the inertial sensor is coupled to the jig to allow polyaxial movement between the inertial sensor and the fixation base. In some embodiments, the optical component is coupled to the jig to allow polyaxial movement between the optical sensor and the fixation base. In some embodiments, the optical component is rotatable about an axle in addition to the polyaxial movement. In some embodiments, the optical component is configured to be positioned independently of the inertial sensor.

In some embodiments, the optical component is coupled to the jig to allow polyaxial movement between the optical sensor and the fixation base. In some embodiments, the optical component is rotatable about an axle in addition to the polyaxial movement. In some embodiments, the optical component comprises a laser. In some embodiments, the optical component is configured to move up and down in pitch to adjust the position of light along the extremity. In some embodiments, the optical component is configured to tilt toward and away from the pelvis to sweep light along the extremity. In some embodiments, the optical component is configured to swivel right and left to sweep light across the extremity. In some embodiments, the optical component is configured to roll to change the orientation of a plane relative to the extremity. The hip joint navigation system can include a probe coupled to the jig.

In some embodiments, a method of performing a hip joint replacement procedure is provided. The method can include the step of placing an extremity of a patient in an extended position. The method can include the step of mounting an optical component to the pelvis adjacent to the hip joint. The method can include the step of projecting a light onto the extremity to illuminate a portion of the extremity away from the hip joint. The method can include the step of recording the position of incidence of the light. The method can include the step of replacing the hip joint, or a portion thereof, with an artificial hip joint. The method can include the step of projecting the light onto the extremity to confirm orientation of the femur relative to the pelvis.

The method can include the step of registering a portion of the proximal femur adjacent to the hip joint. The method can include the step of registering the portion of the proximal femur adjacent to the hip joint to confirm leg length and/or joint off-set. In some embodiments, the step of registering the portion of the proximal femur comprises registering the femur at the greater trochanter. The method can include the step of mounting an articulated member to the pelvis and coupling the optical component with the articulated member. In some embodiments, the articulated member comprises a ball joint. The method can include the step of articulating the optical component to direct the laser light onto a portion of the extremity. The method can include the step of locking the articulating member into a fixed configuration and maintaining the fixed configuration while replacing the hip joint. In some embodiments, the step of recording comprises marking points on the surface of the extremity coincident with the light. In some embodiments, the step of recording comprises capturing a photographic image of the light and the extremity. In some embodiments, the step of projecting the light onto the extremity to confirm orientation of the femur relative to the pelvis comprises recreating the recorded position by lining up the extremity with the incidence of light. The method can include the step of constraining the motion of the foot relative to the lower extremity during projecting the light. In some embodiments, the optical component is disposed in a housing including an inertial measurement unit. The method can include the step of coupling the optical component and an inertial measurement unit to a jig. The method can include the step of independently adjusting the optical component relative to the inertial measurement unit. In some embodiments, the optical component and the inertial measurement unit are separate components. The method can include the step of coupling the jig to the pelvis, wherein the inertial measurement unit has at least one degree of freedom relative to the pelvis. In some embodiments, the optical component has an additional degree of freedom relative to the pelvis. The method can include the step of coupling the jig to the pelvis, wherein the optical component has at least one degree of freedom relative to the pelvis.

In some embodiments, a method of performing a hip joint replacement procedure is provided. The method can include the step of mounting an optical component to the pelvis adjacent to the hip joint. The method can include the step of registering a portion of the proximal femur adjacent to the hip joint. The method can include the step of projecting light from the optical component onto the extremity to confirm correspondence between pre-operative orientation of the femur and pelvis and the post-operative orientation of the femur and pelvis. The method can include the step of registering the portion of the proximal femur adjacent to the hip joint to confirm post-operative leg length and/or joint off-set.

The method can include the step of coupling the optical component and an inertial measurement unit to a jig. The method can include the step of independently adjusting the optical component relative to the inertial measurement unit. In some embodiments, the optical component and the inertial measurement unit are separate components. The method can include the step of coupling the jig to the pelvis, wherein the inertial measurement unit has at least one degree of freedom relative to the pelvis. In some embodiments, the optical component has an additional degree of freedom relative to the pelvis. The method can include the step of coupling the jig to the pelvis, wherein the optical component has at least one degree of freedom relative to the pelvis.

In some embodiments, a hip joint navigation system is provided. The hip joint navigation system can include a base comprising at least one channel disposed therethrough for receiving a pin for mounting the base to the pelvis and a mount feature disposed on a top surface. The hip joint navigation system can include a registration jig configured to couple with the base and to engage anatomical landmarks. In some embodiments, a hip joint navigation system is provided. The hip joint navigation system can include a base comprising at least one channel disposed therethrough for receiving a fastener for mounting the base to a pelvis, the base comprising a mount feature disposed on a surface thereof. The hip joint navigation system can include a registration jig configured to couple with the base and to engage anatomical landmarks.

In some embodiments, the base has a lower surface configured to be placed on the pelvis and where the at least one channel comprises two channels for receiving threaded members to engage with the pelvis. In some embodiments, wherein the base has a lower surface configured to be placed on the pelvis and where the at least one channel comprises two channels for receiving fastener to engage with the pelvis. In some embodiments, the mount comprises a latch feature for removably securing a tower to the base. In some embodiments, the mount feature comprises a latch feature for removably securing a tower to the base. In some embodiments, the tower comprises a lower end configured to secure to the mount and an upper end configured to secure to an inertial sensor assembly. In some embodiments, the upper end is disposed at an angle (e.g., 35 degrees) to the lower end of the tower. In some embodiments, the upper end is disposed at an angle about 35 degrees to the lower end of the tower. In some embodiments, a mount feature is disposed between the lower end and the upper end of the tower, the mount feature configured to be coupled with the registration jig. In some embodiments, a secondary mount feature is disposed between the lower end and the upper end of the tower, the secondary mount feature configured to be coupled with the registration jig. In some embodiments, the mount feature comprises a ball joint for removably securing a tower to the base. In some embodiments, the tower comprises a lower end configured to secure to the mount and an upper end configured to secure to an inertial sensor assembly. In some embodiments, the upper end is disposed at an angle about 35 degrees to the lower end of the tower. In some embodiments, a secondary mount feature is disposed between the lower end and the upper end of the tower, the secondary mount feature configured to be coupled with the registration jig. In some embodiments, the registration jig includes an elongate member configured to be coupled with the base, a housing having at least two degrees of freedom relative to the elongate member, and a probe being slideably disposed through the housing. In some embodiments, the probe comprises a distal portion angled relative to a proximal portion thereof. In some embodiments, the probe is substantially straight along its length. In some embodiments, the probe includes a machine readable feature disposed on a side surface thereof. In some embodiments, the machine readable feature comprises a binary code or other symbol. In some embodiments, the housing of the registration jig includes a sensor mount configured to releasably attach to a sensor unit to position the sensor unit to read the readable feature. The hip joint navigation system can include a sensor unit adapted to optically detect the machine readable feature on the probe when coupled with the sensor mount.

In some embodiments, a femur jig is provided. The femur jig can include a base configured to securely couple with a proximal aspect of a femur. The femur jig can include a reference frame member configured to be disposed above the base having a plurality of reference frame targets. In some embodiments, a femur jig is provided. The femur jig can include a base configured to securely couple with a proximal aspect of a femur, the base comprising a plurality of registration points. The femur jig can include a reference frame member configured to contact the plurality of registration points. In some embodiments, the base has at least one aperture therethrough configured to receive threaded pins to secure the base to the femur. In some embodiments, the base has at least one aperture therethrough configured to receive one or more fasteners to secure the base to the femur. In some embodiments, the member is removably mountable to the base and comprises an elongate upright member and an angled portion configures to be oriented generally along the long axis of the femur. In some embodiments, the reference frame member comprises an elongate upright member and an angled portion configures to be oriented generally along the long axis of the femur. In some embodiments, the base is configured to be attached to the proximal femur within an incision prior to dislocation of the hip. In some embodiments, the reference frame member is accessible by a reference probe coupled with the pelvis in use. In some embodiments, wherein the reference frame member is coupled with the pelvis in use.

In some embodiments, a system includes the femur jig and a module for comparing pre- and post-operative anatomical arrangement of the hip joint is provided. In some embodiments, the module is adapted to compare pre- and post-operative anatomical arrangement of the hip joint using anatomical landmark information derived from the acetabular rim. In some embodiments, the module is adapted include registration of a plurality points on a rim of an acetabular shell implant to calculate the center of rotation (COR) of the hip. In some embodiments, the module is adapted to calculate at least one of a change in angle between the pelvis and femur, a change in leg length, and joint offset. In some embodiments, the system displays an error message with guidance on re-positioning the femur if a threshold value of joint angle, leg length or offset is exceeded. In some embodiments, the guidance advises the user to abduct/adduct, flex/extend, and/or internally rotate/externally rotate the femur. In some embodiments, the base and reference frame member are disposed on opposite sides of the same member. In some embodiments, the same member comprises a thin plate structure. In some embodiments, the member is configured to conform to the femur to be low profile.

In some embodiments, a sensor unit for orthopedic navigation is provided. The sensor unit can include a housing having an elongate structure. The sensor unit can include an inertial sensor disposed at least partially disposed within the housing. The sensor unit can include a camera at least partially disposed within the housing, the camera oriented transverse to a longitudinal axis of the housing. In one embodiment, the sensor unit has a transparent area on a side surface thereof.

The sensor unit with a camera disposed in the housing can be combined with one or more other components in one or more systems. A system that includes the sensor unit can be coupled with a jig that includes a coupler that holds the sensor unit fixed relative to a device to be observed by the camera. The sensor unit can be oriented with its width or height extending along an extendable probe. The jig can include a sliding bearing for allowing the probe to be moved along a range and while being moved to pass through a viewing area toward which the camera is directed. The probe can include a binary code or other symbol that the camera can read. In another system the sensor unit is coupled with a user interface device. The user interface device can be located inside the surgical field in use. The user interface device can be coupled with a jig configured to mount to a bone, e.g., a pelvis, in use.

In some embodiments, a method of orthopedic navigation is provided. The method can include the step of detecting the orientation or positioning of a probe using inertial sensor. The method can include the step of detecting the extension of a probe using a camera. In some embodiments, the camera is positioned directly above the probe.

In some embodiments, a patient specific jig system for hip replacement is provided. The patient specific jig system can include an engagement surface formed to closely mate to acetabular bone contours of a specific patient. The patient specific jig system can include a registration feature configured to be in a pre-determined orientation relative to an acetabulum the patient when the jig is coupled with acetabular bone contours of the specific patient.

The patient specific jig system can include an anatomical engagement portion. The patient specific jig system can include a registration portion disposed laterally of the anatomical engagement portion such that the registration portion is disposed in a zone outside the acetabular rim. The patient specific jig system can include a registration channel extending from an anterior surface of the registration portion toward a posterior surface of the registration portion.

The patient specific jig system can include a mount base configured to be coupled with the pelvis adjacent to the acetabulum but spaced apart from a closest portion of the jig when the engagement surface is in engagement with acetabular bone contours. The patient specific jig system can include an inertial sensor device. In some embodiments, the registration feature comprises a recess extending from an exposed face of the jig. The patient specific jig system can include a channel extending posteriorly from an anterior side of the jig, the channel configured to receive a mounting pin of a navigation system. The patient specific jig system can include at least two channels extending posteriorly from an anterior side of the jig, the channel configured to receive a mounting pin of a navigation system. In some embodiments, the channels are disposed at an orientation related to a plane of the acetabulum.

In some embodiments, a patient specific method is provided. The method can include the step of coupling a patient specific jig to a rim of the acetabulum. The method can include the step of registering the orientation of a proxy for the plane of the acetabular rim using an inertial sensor device coupled with the patient specific jig. The method can include the step of removing the patient specific jig from the acetabulum. The method can include the step of orienting an acetabular shell in the acetabulum using an impactor and an inertial sensor device, wherein during orienting, inertial data from the inertial sensor device is used to confirm a proper orientation of the acetabular shell.

In some embodiments, the inertial sensor device is a first inertial sensing device and further comprising mounting a base on the pelvis adjacent to the acetabulum and coupling a second inertial sensing device to the base, the second inertial sensing device being fixed relative to the pelvis. In some embodiments, the base is mounted at a location that is independent of the patient specific jig. In some embodiments, the second inertial sensing device is configured to track motion of the pelvis and to generate an output that eliminates error due to the movement of the pelvis. In some embodiments, the second inertial sensing device includes a display providing a user interface. The method can include the step of coupling the first inertial sensing device with the base to relate the orientation data of the first inertial sensing device to a reference frame of the second inertial sensing. In some embodiments, mounting the base comprises inserting at least a fixation pin through the patient specific jig along an axis disposed at a pre-defined angle corresponding to the reference frame of the second inertial sensing device. In some embodiments, mounting the base comprises inserting at least two fixation pins through the patient specific jig along an axis disposed at a pre-defined angle corresponding to the reference frame of the second inertial sensing device. In some embodiments, registering includes coupling the inertial sensor device with an impactor and coupling the impactor with the patient specific jig. In some embodiments, registering includes coupling a distal portion of the impactor with a registration feature of the jig at a specific pre-defined angular position. In some embodiments, registering includes aligning the inertial sensing device with an orientation symbol on the patient specific jig prior to coupling the impactor with the patient specific jig. The method can include the step of coupling the inertial sensor device with the impactor. The method can include the step of changing the orientation of the impactor in response to an output reflecting the inertial data generated by the inertial sensing device. The method can include the step of aligning the acetabular shell to a target anteversion angle. The method can include the step of aligning the acetabular shell to a target inclination angle. The method can include the step of aligning the acetabular shell to a target anteversion angle.

In some embodiments, a method of performing a hip joint replacement procedure is provided. The method can include the step of placing a patient in a supine position, with a leg of the hip joint in an extended position. The method can include the step of mounting a laser projecting device to the pelvis adjacent to the hip joint. The method can include the step of projecting a laser light onto the leg to illuminate a portion of the leg away from the hip joint. The method can include the step of recording the position of incidence of the laser light. The method can include the step of registering a portion of the proximal femur adjacent to the hip joint. The method can include the step of replacing the hip joint with an artificial hip joint. The method can include the step of projecting the laser light onto the leg and/or foot to confirm orientation of the femur relative to the pelvis. The method can include the step of registering the portion of the proximal femur adjacent to the hip joint to confirm leg length and/or off-set.

The method can include the step of mounting an articulated member to the pelvis and coupling the laser projecting device to the articulated member. In some embodiments, the articulated member comprises a ball joint. The method can include the step of articulating the laser projecting device to direct the laser light onto a portion of a foot of the leg. The method can include the step of locking the articulating member into a fixed configuration and maintaining the fixed configuration from at least step projecting a laser light onto the leg to illuminate a portion of the leg away from the hip joint to step projecting the laser light onto the leg and/or foot to confirm orientation of the femur relative to the pelvis. In some embodiments, recording comprises marking three points on the surface of the leg and foot coincident with the laser light. In some embodiments, recording comprises capturing a photographic image of the laser light and the leg and/or foot. In some embodiments, registering the portion of the proximal femur comprises registering the femur at the greater trochanter. In some embodiments, the step of projecting the laser light onto the leg and/or foot to confirm orientation of the femur relative to the pelvis includes recreating the recorded position by lining up the incidence of light with the leg and or foot. The method can include the step of constraining the motion of the foot relative to the lower in leg in at least one of step of recording the position of incidence of the laser light and projecting the laser light onto the leg and/or foot to confirm orientation of the femur relative to the pelvis. In some embodiments, the laser projecting device is disposed in a housing including an inertial measurement unit.

In some embodiments, a method of performing a hip joint replacement procedure is provided. The method can include the step of mounting a laser projecting device to the pelvis adjacent to the hip joint. The method can include the step of registering a portion of the proximal femur adjacent to the hip joint. The method can include the step of projecting laser light from the laser projecting device onto the leg and/or foot to confirm correspondence between pre-operative orientation of the femur and pelvis and the post-operative orientation of the femur and pelvis. The method can include the step of registering the portion of the proximal femur adjacent to the hip joint to confirm leg length and/or off-set.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments.

FIGS. 17-17C-2 illustrate modified systems configured for navigating a posterior approach hip replacement procedure.

FIG. 20A-20H illustrate various view of embodiments of a fixation base of FIG. 18.

FIG. 22A-22F illustrate various view of embodiments of a second assembly of FIG. 18.

FIG. 27A-28C illustrate various view of embodiments of a femur tracker of FIG. 25C.

FIGS. 43-52 illustrate various aspects of methods involving patient-specific positioning jigs.

FIGS. 61A-63 illustrate various aspects of methods involving patient-specific positioning jigs.

FIGS. 74-74B illustrate a second embodiment of pin securement devices.

FIGS. 75-75B illustrate a third embodiment of pin securement devices.

DETAILED DESCRIPTION OF THE PREFERRED EMBODIMENTS

A variety of systems and methods are discussed below that can be used to improve outcomes for patients by increasing the likelihood of proper placement of a hip joint. These systems can be focused on inertial navigation techniques, close range optical navigation, or a combination of inertial and optical navigation.

I. Hip Navigation Using Inertial Sensors

Systems and methods described below can improve prosthetic hip joint placement using navigation in connection with referencing anatomical landmarks, incorporating pre-operative custom fit jigs based on imaging, and a combination of pre-operative imaging and landmark referencing. These hip procedures generally guide a prosthetic hip to an orientation within the acetabulum that minimizes the chance of dislocation due to impingement of the femoral neck on the cup or on bones around the acetabulum or other reasons related to suboptimal orientation of the prosthetic. Various techniques leverage population averages of proper placement while others are amenable to patient specific refinements. Also various techniques for registering and confirming the position and/or orientation of the femur pre- and post-implantation are discussed herein, which are useful to control leg length and joint offset at the end of the procedure.

A. Navigation Using Inertial Sensors and Jigs for Referencing Anatomical Landmarks with Posterior Approach Most hip replacement procedures presently are performed from a posterior approach. In this approach, the patient is positioned on his/her side and the anterior pelvic plane is oriented vertically, e.g., perpendicular to the plane of the table on which the patient is positioned. Most surgeons performing hip replacement are very familiar with this approach and will immediately recognize the benefit of enhanced certainty about the orientation of the relevant anatomy when the patient is in this position.

Figure 1:
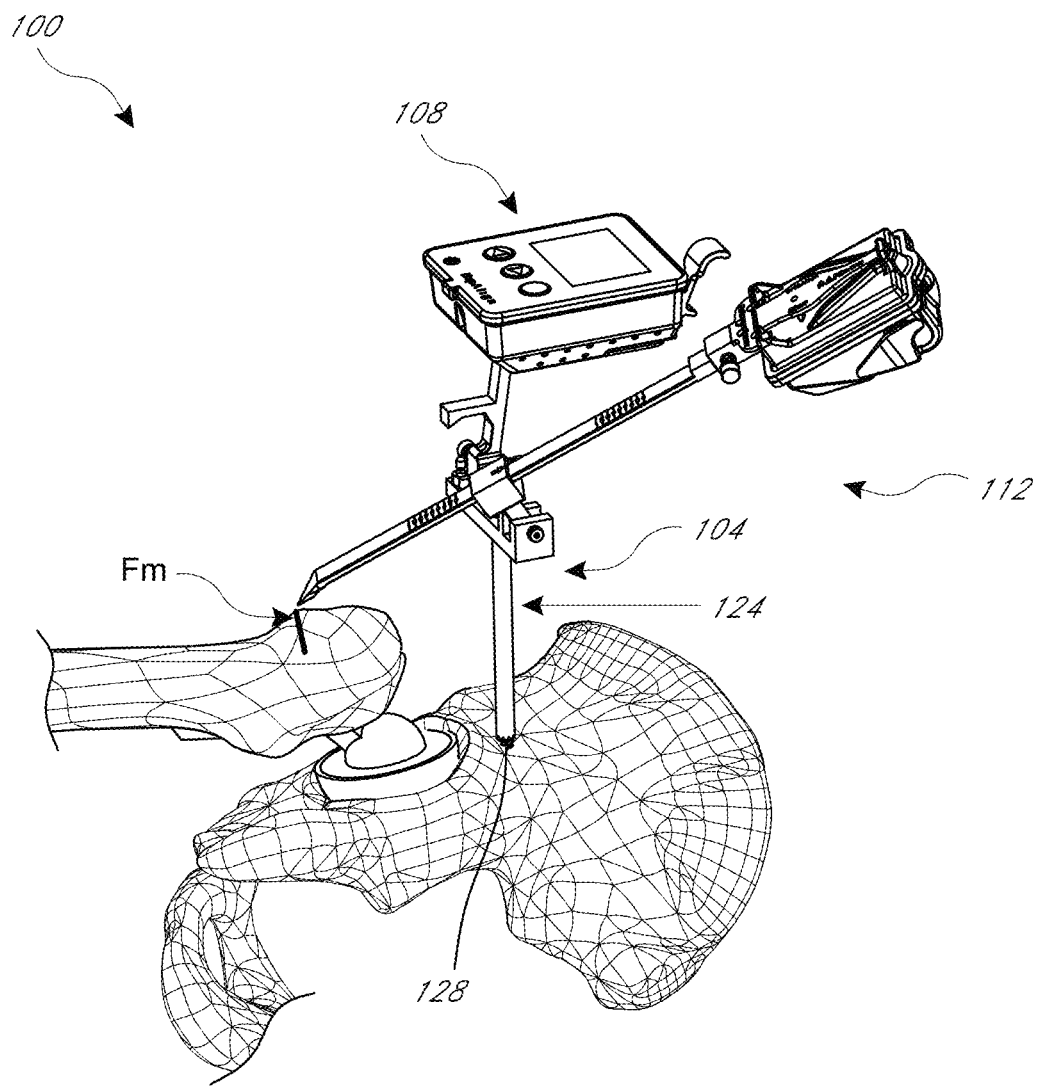
FIG. 1 is a perspective view of a hip navigation system applied to a patient illustrating a measurement of leg length and/or joint offset after implantation of the prosthetic hip joint.
Figure 4:
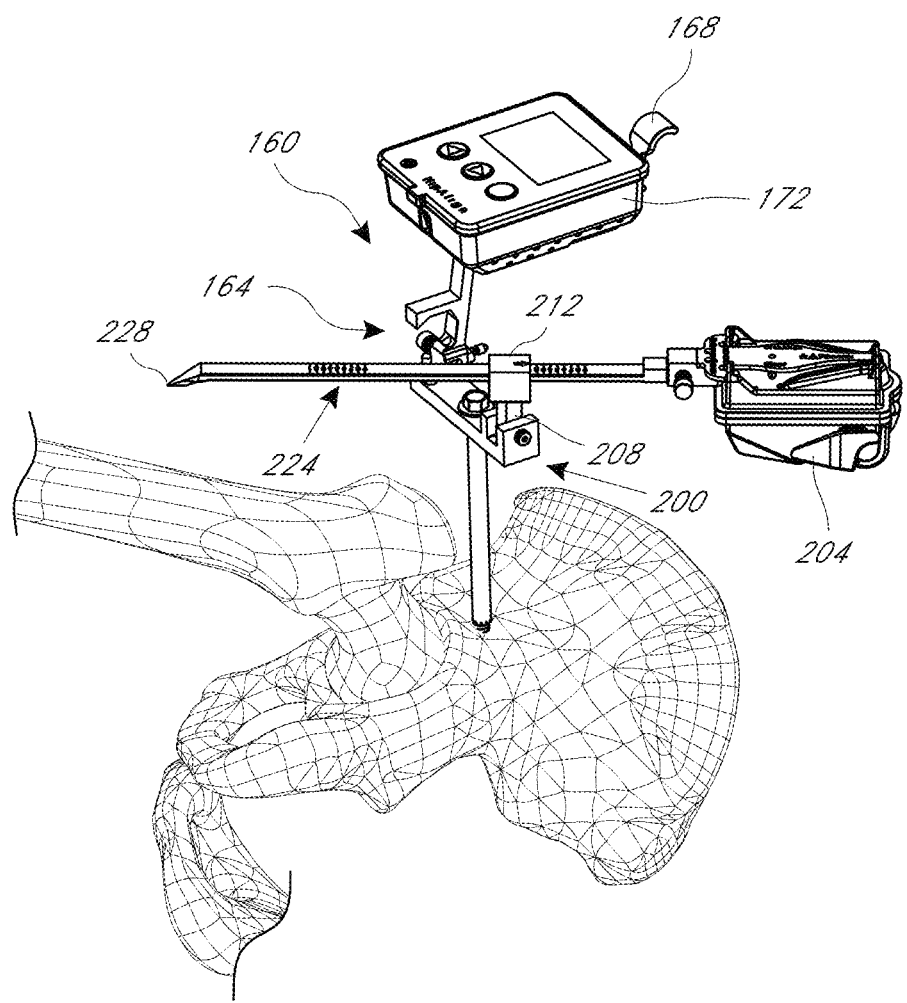
FIG. 4 is a perspective view illustrating first and second orientation detecting devices coupled with the base of FIG. 3.

1. Posterior Approach: Systems with an Orientation Sensing Device Coupled to a Probe FIGS. 1 and 4 show a hip navigation system 100 adapted to navigate a hip joint procedure with reference to anatomical landmarks without requiring, but not necessarily excluding, pre-operative imaging or other inputs apart from those discussed below. The system 100 is shown mounted on a pelvis in a posterior approach in FIG. 1. FIG. 4 shows an early phase of a procedure prior to the joint being dislocated but after the system 10 is mounted to the pelvis. FIG. 1 shows a late phase of some variations of techniques for which the system 100 is adapted. As discussed further below, such variations involve registering the femur prior to and after the joint is replaced to confirm an aspect of the relative position and/or orientation of the femur, e.g., leg length, joint offset, and rotational orientation of the femoral neck.

The system 100 includes a registration jig 104, an alignment assembly 108 and a landmark acquisition assembly 112. The alignment assembly 108 is rigidly connected to the hip in the illustrated configuration so that motion of the hip cause corresponding motion of sensor(s) in the assembly 108 as discussed below. Sensing this motion enables the system 100 to eliminate movement of the patient as a source of error in the navigation. The landmark acquisition assembly 112 provides a full range of controlled motion and sensor(s) that are able to track the motion, in concert with sensor(s) in the assembly 108. Additional details of systems, devices, sensors, and methods are set forth in U.S. Pat. No. 8,118,815; US US2010/0076505; and U.S. Pat. No. 8,057,479 which are all incorporated by reference herein in their entireties for all purposes. The sensors in assemblies 108, 112 preferably transfer data among themselves and in some cases with external devices and monitors wirelessly, using Bluetooth, Wifi® or other standard wireless telemetry protocol.

The registration jig 104 includes a fixation cannula 124 that has a distal end that can be advanced to a pelvic bone at an anatomical location or landmark or other selected location. In the illustrated technique, the cannula 124 is secured by a pin 132 (see FIG. 3) that is driven into the ilium on the pelvis through the cannula 124. A distal end 128 of the pin 132 is shown in FIG. 1.

Figure 2:
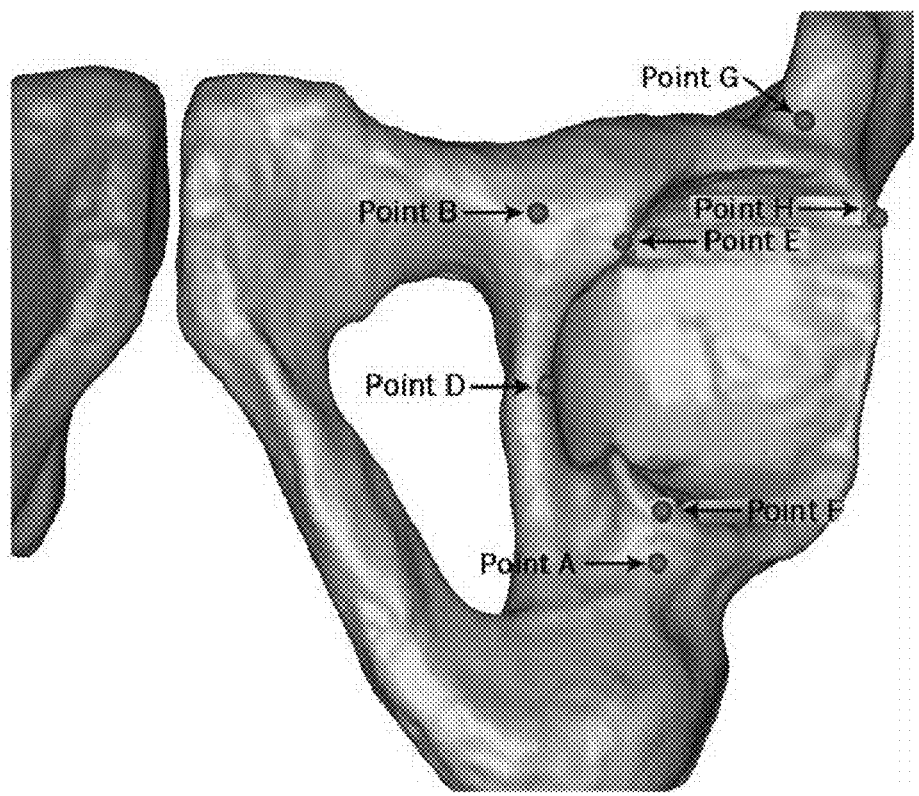
FIG. 2 is an image of hip anatomy illustrating some examples of anatomical landmarks that can be used in a method of navigating a hip prosthesis with the navigation system of FIG. 1.

As discussed further below, the cannula 124 can be coupled with other bones in other techniques with a posterior approach. For example, the cannula 124 can be coupled with the ischium or the pubis in other techniques. In some techniques, the cannula 124 is mounted to a pelvic bone but not at a landmark. The hip navigation system 450 discussed below in connection with FIG. 17-17C-2 can be used such that the fixation member 466 is coupled at a point superior to the superior-most point on the acetabular rim. In a specific technique, the member 466 is about 10 mm above the superior-most point on the acetabular rim. In such techniques, three or more anatomical landmarks disposed about the acetabulum can be acquired, as discussed below. When the cannula 124 is coupled with a landmark, only two additional landmarks are acquired in some embodiments as discussed below. In another variation, a clamp can be used to couple with a bone without requiring that the pin 132 be driven through the cannula 124 into the bone. For example, if the bone is thinner in the region where the system 100 is to be anchored, placing the pin may be disadvantageous. FIG. 2 shows a region where a clamp may be used beneath the point "A" on the ischium. One reason for mounting or clamping the cannula 124 away from the landmarks is that the landmarks may not be visible or accessible before dislocating the hip joint. If the clinician wishes to use the system 100 to reference the femur (as discussed below), it may be required to mount or clamp the cannula 124 away from the landmarks.

FIG. 1 illustrates a step toward the end of a navigated hip joint implant procedure discussed in detail below. Some of the preceding steps involve removing the to-be-replaced joint, navigating the hip joint, preparing the implant location for the artificial joint, and placing the joint, as elaborated below. As discussed further below, FIG. 1 illustrates a technique for confirming that these steps were properly performed.

FIG. 2 shows some of the anatomy that is relevant to various methods and systems herein. In some embodiments, the navigation system 100 is configured to locate a relevant anatomical feature to aid in proper placement of a prosthetic hip joint. For example, a plane can be located using the system 100 that includes at least a portion of a patient's acetabular rim. In practice, the acetabular rim may be uneven due to development of ostephytes. So, in the context of this application locating the anatomical plane can be an approximation of the actual topography, for example an estimate of the plane, a plane including a substantial fraction, e.g., a majority of the surface of the acetabular rim, or some other manner of estimating a relevant anatomical feature. Preferably the anatomical landmark being located is used to confirm accurate placement of at least the cup and preferably the complete artificial hip joint.

FIG. 2 also shows an example of anatomical landmarks that can be used to approximate the acetabular rim or another plane relevant anatomical landmark. In many patients the acetabular rim is not well defined, due to injury, advanced stages of arthritis or other conditions. Accordingly, approximating the acetabular rim for these patients includes calculating in the system 100 a plane that references but may not include most or any of the actual acetabular rim. The plane that is defined is located near the rim but more importantly has a known anteversion and abduction angle relative to the anterior pelvic plane. For example, three points can be used to estimate the plane of the acetabular rim. In one technique, some or all of the points illustrated in FIG. 2 are used.

Figure 66:
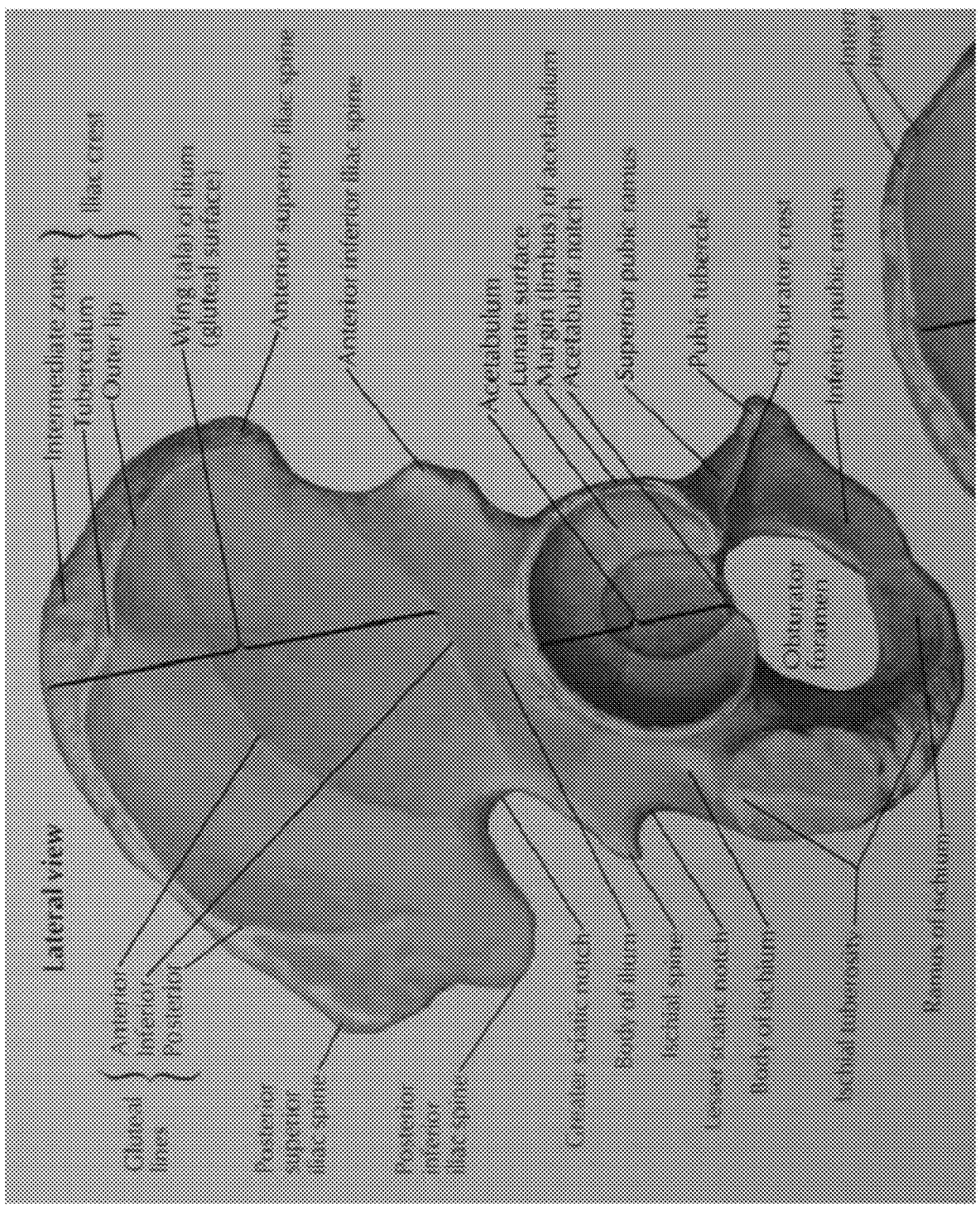
FIGS. 66-67 illustrate various anatomical landmarks that can be used in various methods involving navigating with landmarks.
Figure 67:
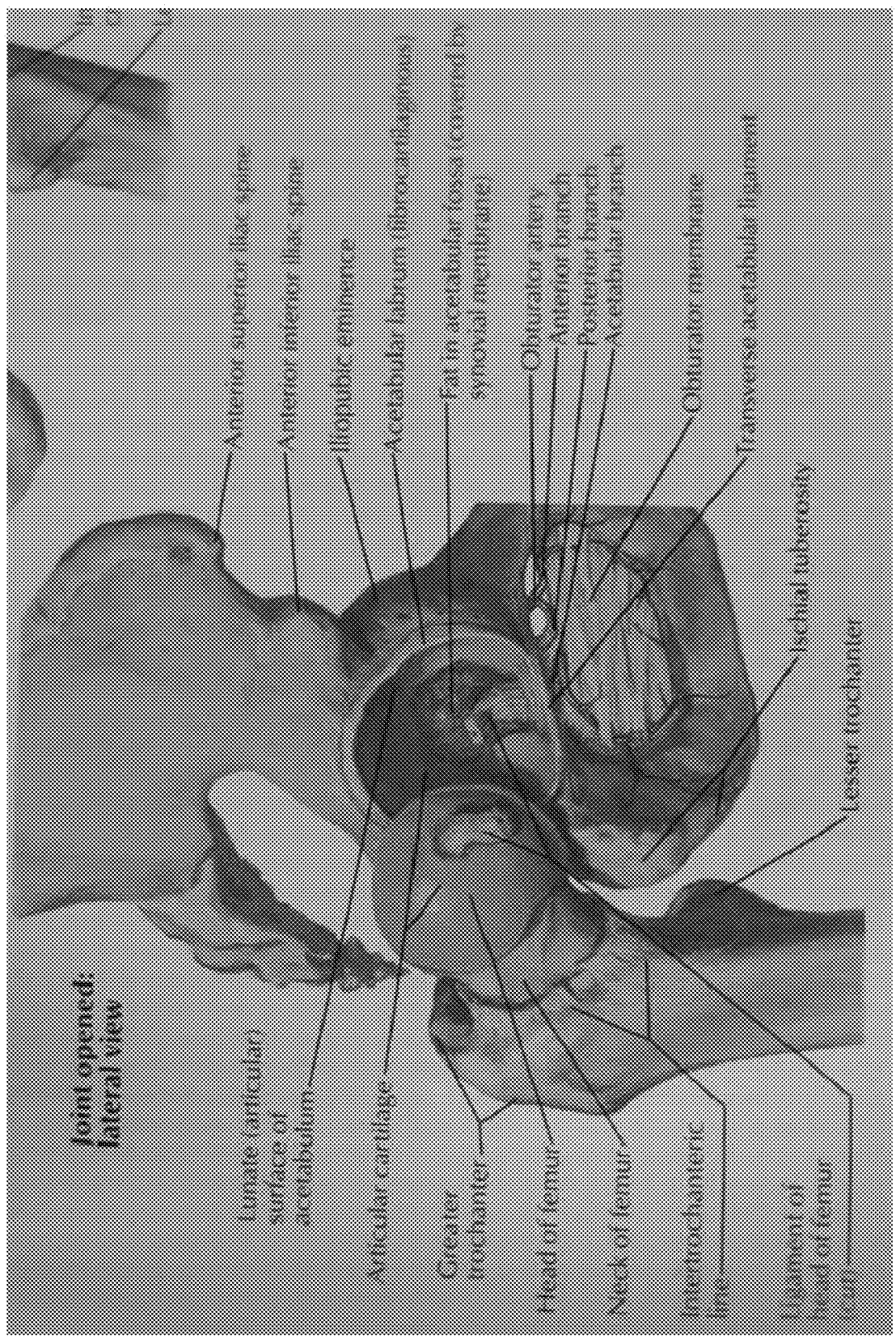

As illustrated by FIG. 2, three landmarks are defined at "A", "B", and "H". The landmark "H" is located on the ilium at a location that is spaced away from the rim by an amount sufficient to avoid irregular bony growth due to injury, advanced stages of arthritis or other conditions, for example 1 cm superior to the most superior point on the acetabular rim. The landmarks "A" and "B" can be located on the ischium and pubis respectively and can be similarly spaced from the rim to avoid damaged/diseased areas. Each of these landmarks preferably is close enough to the rim, however, to be within the standard open area, e.g., the area exposed by the surgical cut down. Other landmarks that could be used include: anterior insertion point of trans-acetabular ligament to the ischium, mid-point of the inferior aspect of the acetabular notch, the anterior superior iliac spine, anterior inferior iliac spine, convergence of the acetabulum and anterior inferior iliac spine, as well as the other landmarks illustrate on FIGS. 66 and 67. In the techniques discussed below all of the ilium, the pubis, and the ischium are used to locate the acetabular rim. The navigation system 100 has one or more processors that receive(s) data and determines the relative position of these (or other) anatomical landmarks from these points. The data can be generated by inertial sensors, as discussed elsewhere herein, or other types of sensors. Preferably the sensors are small enough to be mounted on or in handheld housings or embedded in the instruments. The navigation system 100 preferably also has a memory device to at least temporarily store the position of these points or relevant orientation data.

Figure 3:
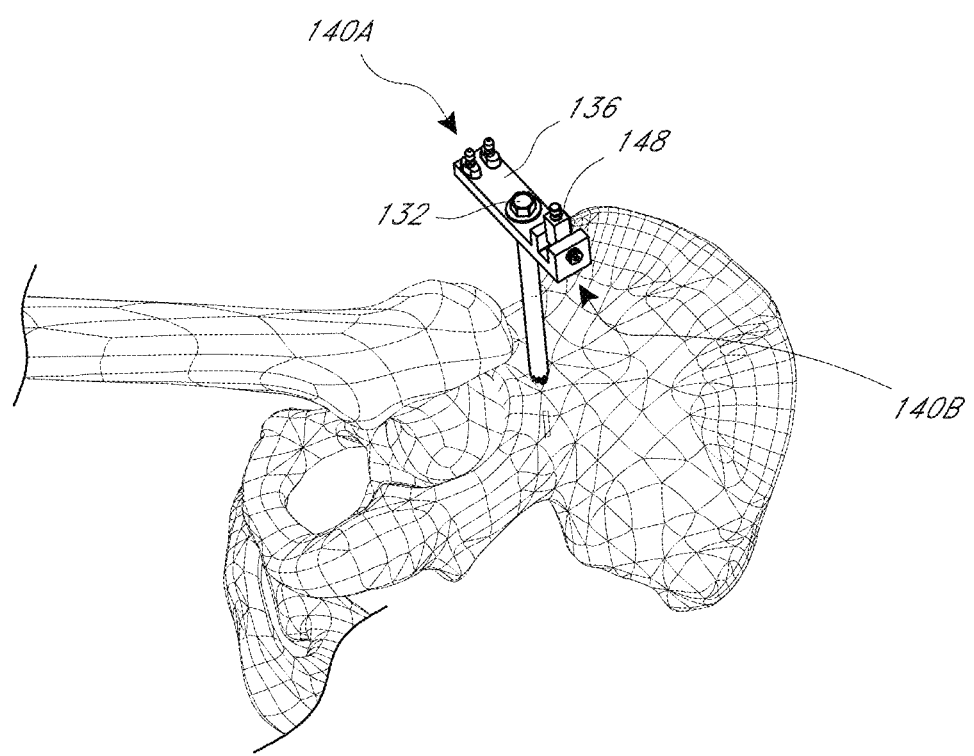
FIG. 3 shows a navigation base assembly coupled with a first anatomical landmark, in this case the ilium on the pelvis of the patient.

FIG. 3 shows further details of the registration jig 104 and further aspects of methods of navigating an artificial hip joint. A proximal end of the pin 132 is coupled with or disposed above a platform 136 that is configured to couple with the alignment assembly 108 and/or the landmark acquisition assembly 112. As shown in FIG. 1, the platform 136 can be connected to both of the alignment assembly 108 and the landmark acquisition assembly 112 at the same time. The platform 136 comprises a rigid bar fixed to the proximal end of the pin 132 and/or the cannula 124 in the illustrated embodiment. The platform 136 includes a plurality of mount features 140A, 140B, e.g., a mount feature on each of two lateral ends 144A, 144B of the platform. The mount feature 140A is configured to permit non-rotational attachment to the alignment assembly 108.

Figure 5:
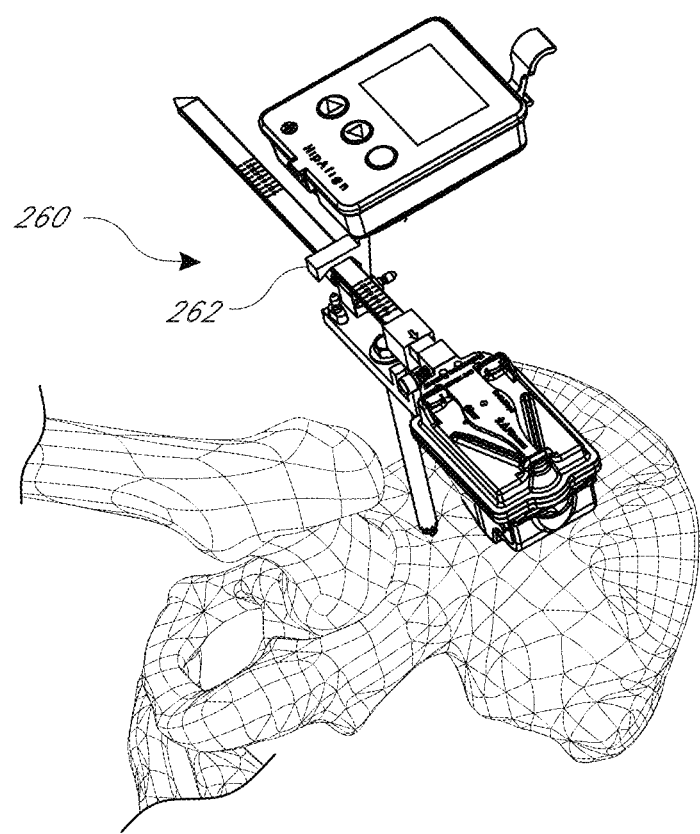
FIG. 5 is a perspective view of the navigating system, illustrating one technique for synchronizing a plurality of orientation and/or position detecting devices of the navigating system of FIG. 1.

FIG. 3 illustrates that the registration jig 104 is configured to be used in left and right hip procedures, for example having a dedicated mount feature 140A for each hip. Preferably the mount feature 140A provides a post spaced away from the joint being treated so that the alignment assembly 108 can be mounted as far away from the hip joint as possible. FIG. 5 shows the alignment assembly 108 on this post and another post exposed. The exposed post is not used during the procedure on the hip joint illustrated in FIG. 5. However, if the other hip of the patient is being treated, the platform 136 is in the opposite orientation and the posted exposed in FIG. 5 will be coupled with the alignment assembly 108. Stated another way, a longitudinal axis of the platform 136 extends between two mount posts, each of which can be dedicated to a hip on one side of the medial-lateral mid-plane of the patient.

The mount feature 140B enables rotational mounting of the landmark acquisition assembly 112. For example, the mount feature 140B can include a pivotally mounted jig 148 that projects upward to a free end that is adapted to mate with an orientation sensing device as discussed below. The joint 148 permits a registration arm, such as the elongate member 224 discussed below to be tilted downward to touch landmarks at different elevations.

In one technique, the registration jig 104 is preassembled and is driven into a suitable anatomical landmark, such as the ilium. In other techniques, an anchor jig can be mounted off-set from a landmark to be acquired. The ilium will have been previously identified by conventional means, such as by X-ray examination, palpation, or by making an incision and visually inspecting the pelvis. In one technique, the cannula 124, the pin 132, and the platform 136 are separable so that the pin can be placed and the platform 136 coupled to the pin at a later time. The cannula 124 can be coupled with other landmarks in some variations.

FIG. 4 illustrates further steps of various techniques. For example, the alignment assembly 108 can be coupled with the mount feature 140A. In one embodiment, the alignment assembly 108 includes a rigid extension 160 that is adapted to be mounted detachably to the mount feature 140A. The extension 160 has a first end 164 and a second end 168. The second end 168 is detachably mountable to a surgical orientation device 172 that detects orientation and rotation of the device 172 relative to a reference frame. The orientation device 172 preferably comprises at least one sourceless sensor, such as an accelerometer, a gyroscope, or a combination of these sensors and other sensors. In one preferred embodiment, the orientation device includes a three axis accelerometer to detect orientation relative to gravity and a plurality of gyroscopes to detect rotation. Other sensors could be used in various modifications. Examples of specific sensor combinations include Analog Devices ADIS 16445 and Invensense MPU-6050 or MPU-9150 among others. In some approaches, the orientation device 172 can be disposable and so the sensors preferably are less expensive sensors. Sensors on the landmark acquisition assembly 112 may be reusable in some configurations and thus may incorporate more expensive, more rugged or more accurate sensors.

The first end 164 of the detachable extension provides several functions. The first end 164 has a device to engage the mount 140A in a secure but releasable manner. The engagement between the extension 160 and the platform 136 minimizes or prevents relative movement therebetween to avoid any mechanical relative movement during navigation procedures so that movement of the orientation device 172 corresponds to movement of the hip. The first end 164 also has a docking device that, as discussed further below, provides a stable and controlled manner to position the landmark acquisition assembly 112 relative to the orientation device 172.

FIG. 4 also illustrates that the landmark acquisition assembly 112 can be securely coupled to the platform 136, e.g., at the mount 140B. In one embodiment, the landmark acquisition assembly 112 includes a gimbaled jig 200 and an orientation sensing device 204. The jig 200 includes a coupler 208 for detachably coupling with the mount feature 140B of the platform 136. The coupler 208 is pivotally connected to a sliding support 212. The sliding support 212 includes a slot that permits slideable extension of an elongate member 224. The slideable extension permits a range of motion of a distal end 228 of the elongate member to facilitate acquiring a plurality of landmarks that are different distances from the attachment location of the cannula 124, as discussed further below. In other words, the distal end 228 can be extended away from the axis of the sliding support 212 or can be retracted to a position closer to the axis of the sliding support 212.

Figure 6:
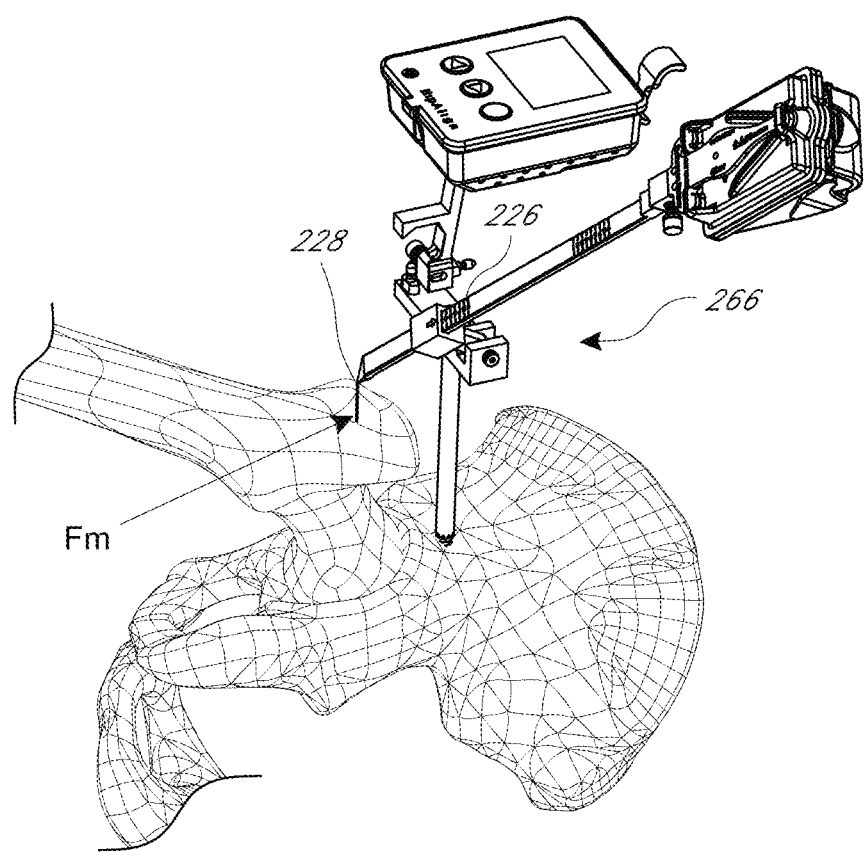
FIG. 6 is a perspective view of the navigation system of FIG. 1 coupled with the pelvis and illustrating a step of registering a landmark of a femur prior to resecting the femur.

FIGS. 4 and 6 illustrate the moveability of the landmark acquisition assembly 112 relative to the platform 136 between two positions. In FIG. 4, the elongate member 224 is swung about an axis that may be parallel to a longitudinal axis of the cannula 124 to move the distal end 228 away from the first end 164 of the extension 160. This is a moving configuration of the gimbaled jig 200. In addition to rotation enabled by the pivotal coupling between the coupler 208 and sliding support 212, the pivotally mounted joint 148 can enable the elongate member 224 to pivot about an axis that is not parallel to the axis of the cannula 124. The axis of rotation of the joint 148 can be perpendicular to the axis of rotation of the sliding support 212. This rotatability enables the distal end 228 of the elongate member 224 to pivot down to contact anatomical landmarks, as discussed above. Additionally, the slideability of the elongate member 224 within the sliding support 212, discussed above, enables the distal end 228 to move to reach anatomical landmarks in the same plane but closer to or farther from the distal end of the cannula 124 or pin 132. FIG. 6 shows the distal end 228 of the elongate member 224 positioned closer to the platform 136 for referencing landmarks at higher elevation or closer positions, e.g. on the lateral side of the femur.

FIG. 4 also shows that the distal end 228 can include an angled length that enables the elongate member 224 to avoid minor irregularities in height adjacent to the anatomical landmarks being registered. Such irregularities may be normal anatomy, osteophytes or irregular bone growth of various types.

FIG. 5 illustrates a parked configuration 260 of the landmark acquisition assembly 112. In particular, a portion of the elongate member 224 is moved into a latch 262 disposed at the first end 164 of the upright extension 160. The parked configuration 260 enables the navigation system 100 to manage errors that can compound in some inertial sensors. For example, in one embodiment, gyroscopic sensors in the orientation device 172 and in the orientation sensing device 204 can be synchronized when a stable and known orientation is detected and one or more of the gyroscopes, e.g., the gyroscope in the device 204, can be zeroed after that condition is met. Further techniques employing the parked configuration 260 will be discussed further below. As discussed below in connection with the system 450, some jigs have a registration point adjacent to the distal end of the anchor jig or bone connection site. The system 450 is capable of accurately acquiring landmarks based on only accelerometers operating in the device 204 in one mode. In such a mode, a registration feature can provide an analogous function to the parked configuration, e.g., to enhance accuracy of the sensing devices in the system.

Another example of a parked configuration of the system 100 can be provided. For example, the parked configuration advantageously includes the ability to stably position and hold the devices 172, 204 for substantially no relative movement. In one approach, the orientation sensing device 204 is mounted on the rigid extension 160. Other arrangements could include a mounting post on the platform 136 adjacent to the rigid extension 160.

Where error management is less an issue, the parked configuration 260 can still be useful in that it prevents unwanted swinging or other movement in the surgical field.

In one basic method, the jigs discussed above are connected to the pelvic bone, the system 100 is put into the parked configuration 260, and the sensors are initialized. The initializing can include synchronizing at least two sensors. In some cases, the initializing can include zeroing one or more sensors. In this context, "zeroing" is a broad term that includes any method of eliminating accumulated error in the system, including any form of resetting of the sensors, and/or confirming in one device that the data from the other device is reliable for at least a fixed period.

FIG. 6 illustrates an optional step of acquiring a landmark of a femur in connection with a hip replacement procedure. The hip is positioned in a neutral flexion/abduction position. The landmark acquisition assembly 112 is in a withdrawn configuration 266 with the elongate member 224 moved, such as by sliding in the sliding support 212, to accommodate the relatively short distance from the platform 136 and a landmark of the proximal femur. In one technique the tip of the distal end 228 is brought into contact with a part of the greater trochanter or elsewhere on the proximal femur. After the landmark is found and/or contacted, the clinician can make a mark Fm on the femur, such as a bovie mark, a pen mark, a stitch or other durable indication. Once the tip of the distal end 228 is in contact with the desired landmark, the navigation system 100 processes data from and stores the orientation of one or more sensor(s) in the orientation sensing device 204. Additionally, in some embodiments, the elongate member 224 is provided with a scale 226 indicating position of the tip of the elongate member 224, e.g., relative to the cannula 124 or some other relevant fixed feature of the patient or the system 100. By providing the scale 226 to be read by the clinician, the system is made simple and cost effective.

After the optional step illustrated in FIG. 6, the proximal femur can be resected to remove the natural ball thereon.

Figure 7:
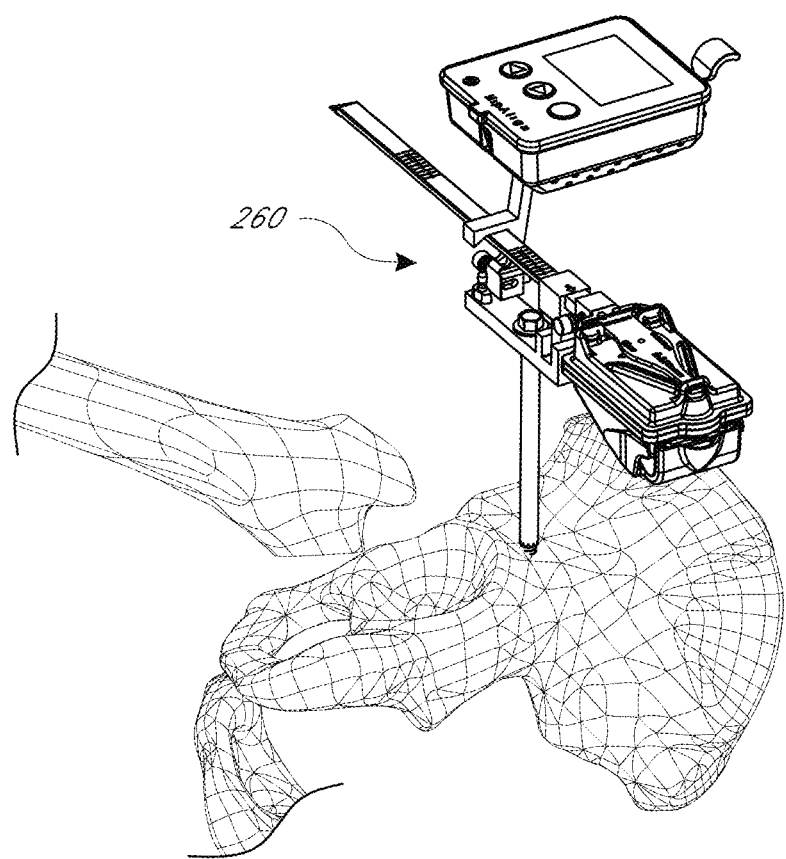
FIG. 7 shows the anatomy after the femoral head has been resected and an optional step of synchronizing a plurality of inertial sensors of the navigation system.

FIG. 7 illustrates that in one advantageous technique, the user returns the system 100 to the parked configuration 260. This step may be optional depending on the sensor(s) and the timing of the resecting of the femur. In this position, the sensor(s) in the orientation devices 172, 204 can be initialized again, e.g., zeroed. As discussed above, this is one technique for minimizing accumulation of error in some inertial sensors. By providing this optional step, less costly sensors can be used enabling the system 100 to deliver highly accurate hip replacement while helping to manage cost for the patient, medical provider and healthcare system generally.

Figure 8:
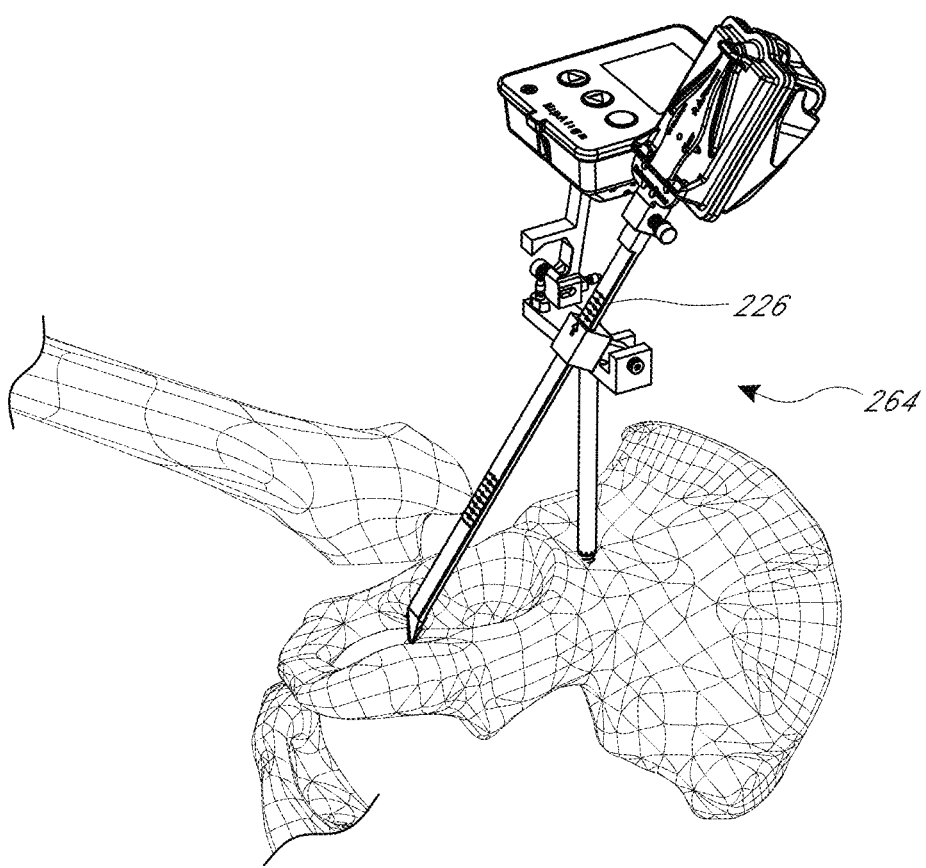
FIG. 8 illustrates a step of registering an anatomical landmark disposed about the acetabular rim on the pelvis.

FIG. 8 illustrates a first extended configuration 264 provided in a step after the resecting of the proximal femur in which a second anatomical landmark is acquired or referenced. In particular, the elongate member 224 can be extended and can be rotated by the jigs 148, 200 to be in contact with any suitable landmark. In one technique, contact is made between the distal end 228 and the ischium. To provide maximum accuracy, this contact may be provided within a short period, e.g., within about 20 seconds of being disengaged from the parked configuration 260. Once contact is made, the system 100 is configured to store the orientation of the sensing device 204. In one configuration, the orientation is stored after a button or other indirect means is pressed on the orientation device 172. In addition to acquiring the orientation, a position value is input to the system. For example, the scale 226 on the elongate member 224 can be read by the user and the value of the scale input into the system. In one technique where the scale 226 is read and input by the user, the orientation device 172 has a user interface with an input device for inputting such variables. As can be seen in the drawings, the scale 226 can in fact be two different scales, one for each of the retracted configuration 266 and the extended configuration 264. Alternatively, the scale 226 can extend the entire length of the elongate member 224 to provide a greater range of positions that can be read by the clinician or by the system as in FIGS. 13 and 14.

The extended configuration 264 is one in which the distal end 228 of the elongate member 224 is adapted to touch an anatomical landmark located between the medial cephaladcaudal plane of the patient and the acetabulum of the pelvis.

Depending on the sensors used and the timing of landmark acquiring step of FIG. 8, the user may return the system 100 to the parked configuration 260 and also may initialize, e.g., zero, the system 100 again.

Figure 9:
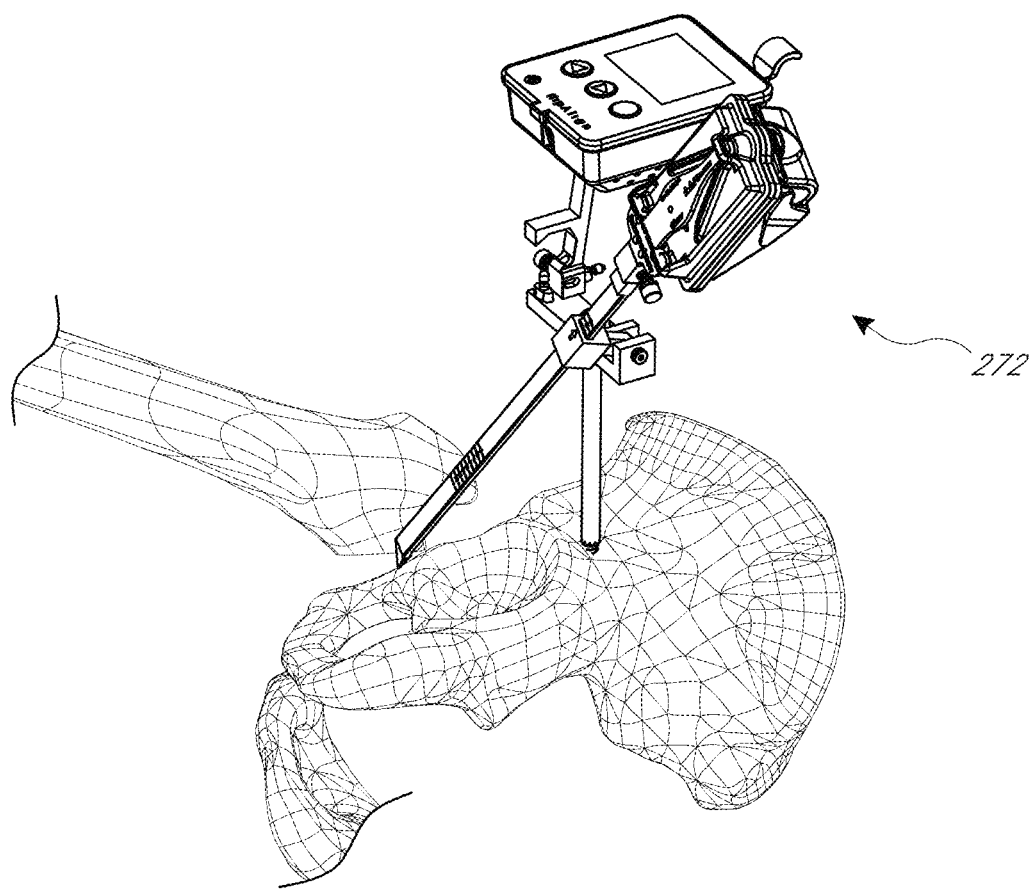
FIG. 9 illustrates a step of registering another anatomical landmark disposed about the acetabular rim of the pelvis.

FIG. 9 illustrates a second extended configuration 272 provided in a step after the resecting of the proximal femur in which a third anatomical landmark is acquired or referenced. The third anatomical landmark can be acquired before the second anatomical landmark in some techniques. In the second extended configuration the distal end 228 of the elongate member 224 moved to contact a landmark, such as the pubis. To provide maximum accuracy, this contact may be provided within a short period, e.g., within about 20 seconds of being disengaged from the parked configuration 260. Once contact is made, the system 100 can store the orientation of the sensing device 204. The orientation can be stored by pushing a button or other user interface device. In some techniques orientation and position are input into the system. For example, the scale 226 on the elongate member 224 can be read by the user and the value of the scale input into the system. In one technique where the scale is read and input by the user, the orientation device 172 has an input device, such as a user interface for inputting such variables.

The extended configuration 272 is one in which the distal end 228 of the elongate member 224 is adapted to touch an anatomical landmark located anteriorly of the acetabulum.

Once landmarks have been acquired, the system 100 can determine the bearing of three landmarks including that of the attachment location of the cannula 124, if the pin is attached to a relevant landmark. The system can calculate the orientation of the orientation device 172 relative the plane containing these three (or in other methods another group of three or more) landmarks. From this, a variety of post processing can be performed. For example, the orientation (anteversion and/or abduction) can be adjusted based on the known mean orientation of the plane containing these three (or another three or more, if used) landmarks from the pelvic anatomic reference planes.

One variant of the system 100 enables a user to select between multiple sets of landmarks for use in the above calculations. The method discussed above exploits the use of three points that are off of the acetabular rim. These points are less impacted by local prominences at the rim that may be due to disease or deformity. Thus, they have a lower likelihood of requiring intra-operative improvisation. On the other hand, another set of landmarks can be selected where the rim is free of deformities, which might be confirmed pre-operatively. For example, two or three points can be selected on the acetabular rim for landmark acquisition. The on-rim landmarks are advantageous in that they are easier to access through a smaller incision. For example, on-rim points can include the center of the posterior insertion of the transacetabular ligament, the center of the anterior insertion of the transacetabular ligament and the most superior point on the rim. A group of anatomical landmarks including one or more extra-acetabular landmarks can include the ilium (where the registration jig 104 or other anchor member can be inserted), the lowest point of the acetabular sulcus of the ischium, and the prominence of the superior pelvis ramus.

Some techniques involve referencing a fourth point. The fourth point can be used in connection with some forms of patient specific registration. The fourth point can be extra-acetabular or can be disposed on the acetabular rim. An example of an acetabular landmark is the acetabular notch. Other landmarks are discussed herein, for example in connection with FIGS. 34 and 35.

The posterior approach systems are advantageously configured to allow intra-operative selection between on-rim and off-rim points. For example, if the rim looks free of deformities pre-operatively but when exposed presents differently, the surgeon can select an off-rim landmark set.

Several techniques for enhancing the accuracy of the relationship between the sensed landmarks and the location of calculated anatomical features, such as the anterior pelvic plane or angle of the acetabulum can be employed. For example, user input can be collected indicating whether the hip being treated is on the left or the right side of the patient and whether the patient is male or female. A more refined estimation of the model can be provided based on a characterization of a study group. For example, hip joints of a group of 30 or more patients can be studied to identify the correspondence between a feature that can be accessed in one approach and an anatomical feature of more surgical relevance that cannot. A group of subjects can be studied for any number of demographic characteristics such as gender, age, weight, height or any other variable in a relevant population. For those sub-groups, a correlation or transformation between a measured parameter and a parameter that cannot be measured but is desirable to know can be generated. Once such a correlation or transformation is established, transforming a measured feature into the unmeasurable but useful to have feature can be achieved by operating software on a processor. The software can be programmed to calculate one or two angles, e.g., inclination and anteversion based on a registered pelvic plane, such as a proxy acetabular plane. Such a system can be used to generate in real time the angles of a free hand instrument relative to the anatomy, e.g., relative to an acetabulum in placing a hip socket component.

Additionally, data from the use of pre-operative imaging or positioning (discussed below) can be used to enhance the accuracy of these calculations. Thus, the posterior approach systems preferably are configured to take user input directly by actuating buttons on the orientation device 172 or by connecting an auxiliary data storage device, such as a flash memory device, to the system or by any means of other communication with the system, including wifi connection, Bluetooth, Internet connection among others.

In some techniques, the posterior approach systems described herein are adapted to determine, monitor, and confirm proper leg length and joint offset outcome in a hip replacement. For example, the system 100 can calculate and store components of a leg length metric, e.g., a vector along the superior-inferior axis (leg length) and/or along the medial-lateral axis (offset). In one approach, the device 172 has a display that indicates when the femur is in the same position pre- and post-operatively. For example, it can indicate "0" meaning no displacement causing a leg length change and "0" indicating no movement of the femur farther away from the cephalad-caudal mid-plane of the patient pre- and post-operatively. For enhanced accuracy, a plurality of points, e.g., three points, can be marked acquired and/or marked on the femur. The points can be spaced apart by an amount sufficient to provide increased accuracy. These three points can be used to confirm proper placement of the femur in abduction, rotation, and flexion.

One enhancement involves referencing the femoral neck to assure that after implanting the hip joint, the femur is positioned properly rotationally. For example, it may be desired to make sure that a feature of the femur like the greater trochanter resides in the same rotational orientation relative to an axis extending through the center of rotation of the femoral head and perpendicular to the plane of the acetabulum. To assure a substantially unchanged rotation orientation post-implantation, the system 100 can record one or more, e.g., three points on the femoral neck pre- and post-implantation. Three points that would be convenient from either the posterior approach or the anterior approach (discussed below in connection with FIGS. 18-24B) are the greater trochanter, lesser trochanter and the insertion of the obdurator externus.

The foregoing are some steps that can be used to determine and store a variety of parameters useful in a navigated hip procedures. After some or all of these steps have been performed, in one embodiment, the acetabulum can be prepared for receiving a cup. For example, the acetabulum can be reamed in a conventional manner. In some embodiments, the reamer can be coupled with an orientation device containing an inertial sensor to guide the reaming process. This is discussed in some detail in US2010/0076505, published march 25, 2010 which is incorporated by reference herein in its entirety for this purpose and for all disclosure therein generally.

Figure 10:
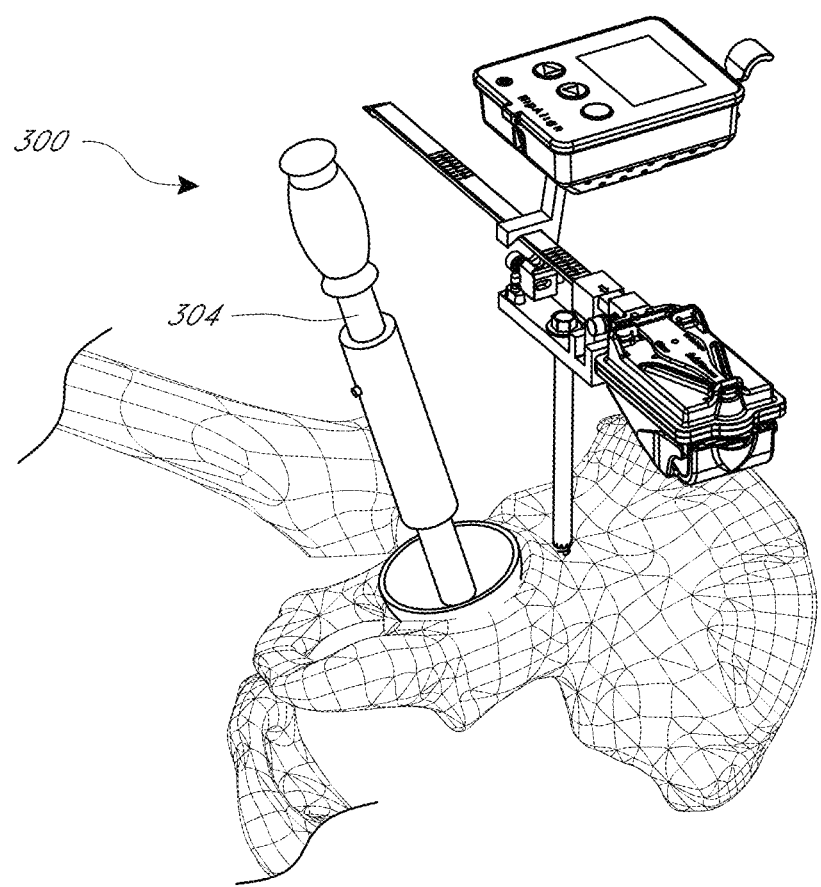
FIG. 10 illustrates initial placement of an impactor in the acetabulum.

FIG. 10 shows that after reaming, an impactor 300 may be used to place a cup of an artificial hip joint. The impactor handle 304 may be positioned in the approximate correct orientation, e.g., with a longitudinal axis of the impactor being disposed perpendicular to the plane navigated above or a plane determined based on the navigated plane. FIG. 10 shows that this initial placement can be done while the system 100 is in the park configuration 260. The impactor 300 can be substantially aligned at this time, based on visual inspection. As part of the step illustrated in FIG. 10 or shortly thereafter, the sensors can be initialized, e.g., zeroed as discussed above.

Figure 11:
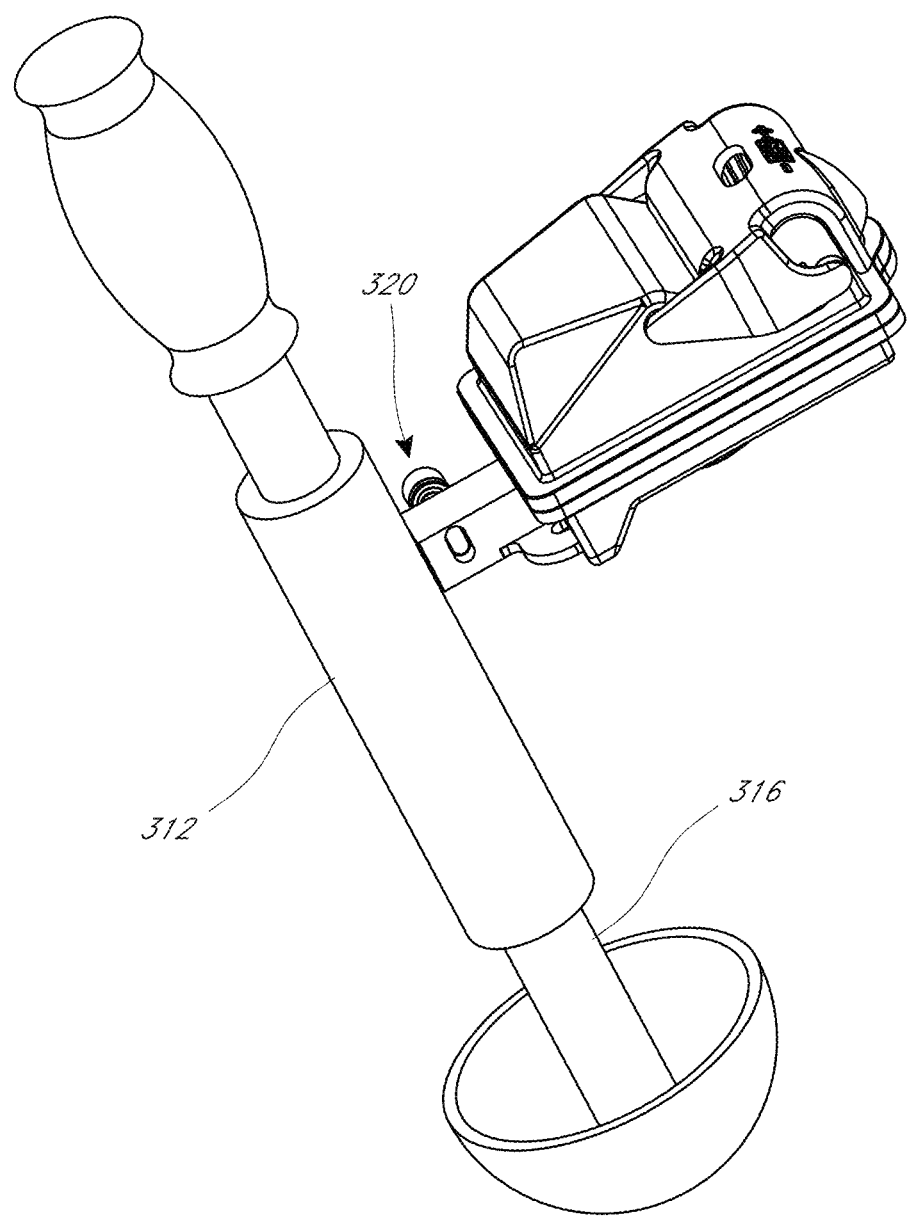
FIG. 11 illustrates a hip prosthesis placement system, including an inertial sensing device.

FIG. 11 shows that in a subsequent step the orientation sensing device 204 can be undocked from the proximal end 230 of the elongate member 224 and thereafter docked to the impactor 300. Preferably this step is performed while the impactor 300 is in place on the hip, close the proper alignment. In another embodiment, a third sensing device similar to the sensing device 204 be coupled with, e.g., pre-attached to, the impactor and the data collected above transferred to the third device. The impactor 300 and sensing device 204 comprise a cup orientation navigation assembly. Preferably the impactor 300 has a cylindrical shell 312 that is moveable relative to an inner shaft 316 of the handle 304. The shell has a docking device 320 that can receive the docking device of the sending device 204. The moveability of the shell 312 helps to isolate the sensing device 204 from the forces that are transmitted through the impactor 300. These forces are applied by a mallet or other device for forcibly moving the cup into position. By providing at least some force isolation between the shell 312 and the sensing device, impact on the sensors in the sensing device 204 can be reduced. Excessive force being applied to the sensing device 204 can put the device 204 out of service, for example until synched with the device 172.

Figure 11A:
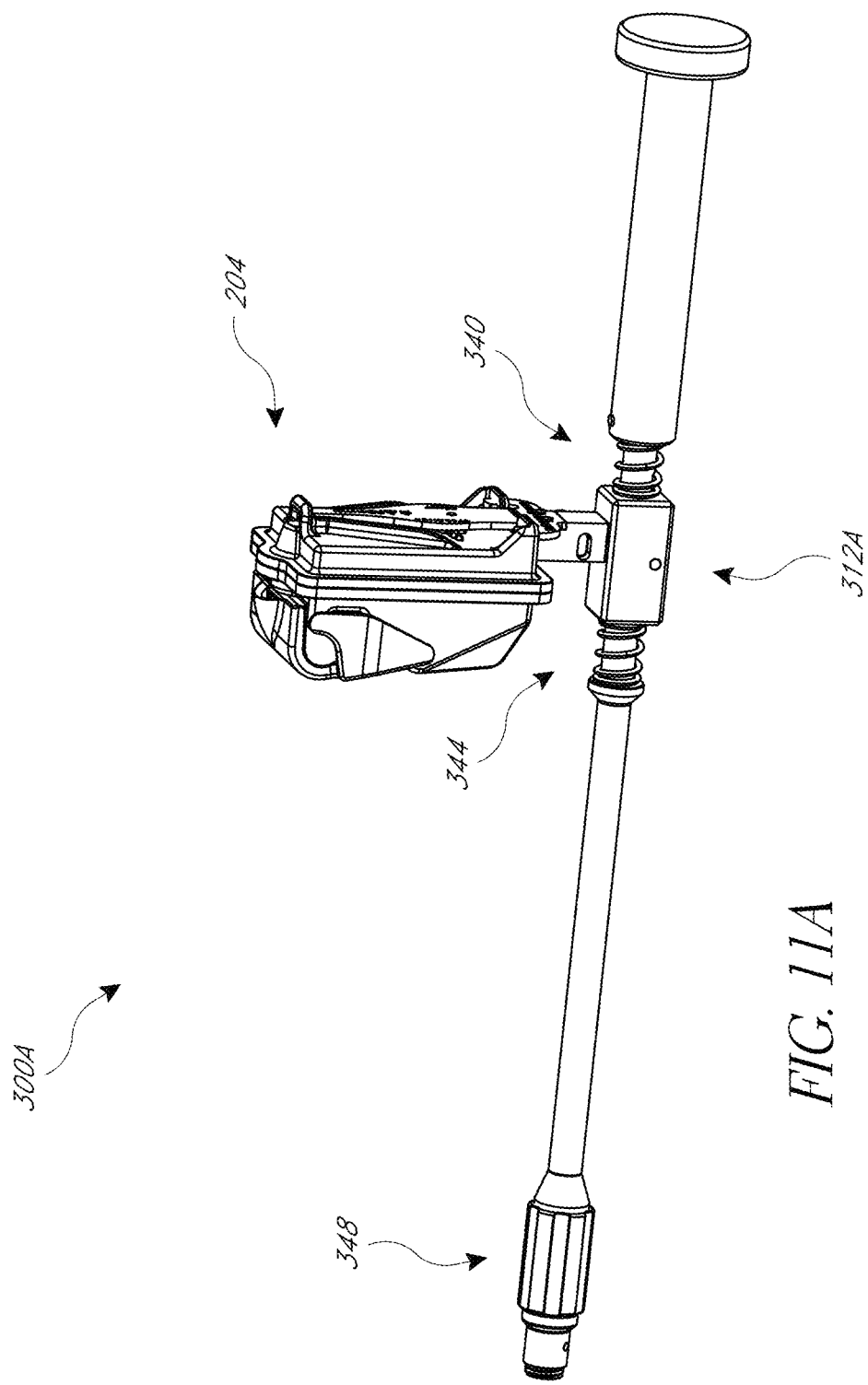
FIGS. 11A-11C illustrate an embodiment of an impactor assembly.

FIG. 11A illustrates a further embodiment of an impactor 300A in which the movement of a shell 312A is cushioned by a plurality of spring members 340, 344 which are configured to absorb at lease some of the shock of the impact on the impactor 300A. The impactor 300A also is configured to be modified to suit any of a plurality of hip prostheses. For example, a plurality of tip components 348 can be provided in a kit where each tip component is attachable to and detachable from a distal end of the shaft 316A of the impactor 300A.

Figure 11B:
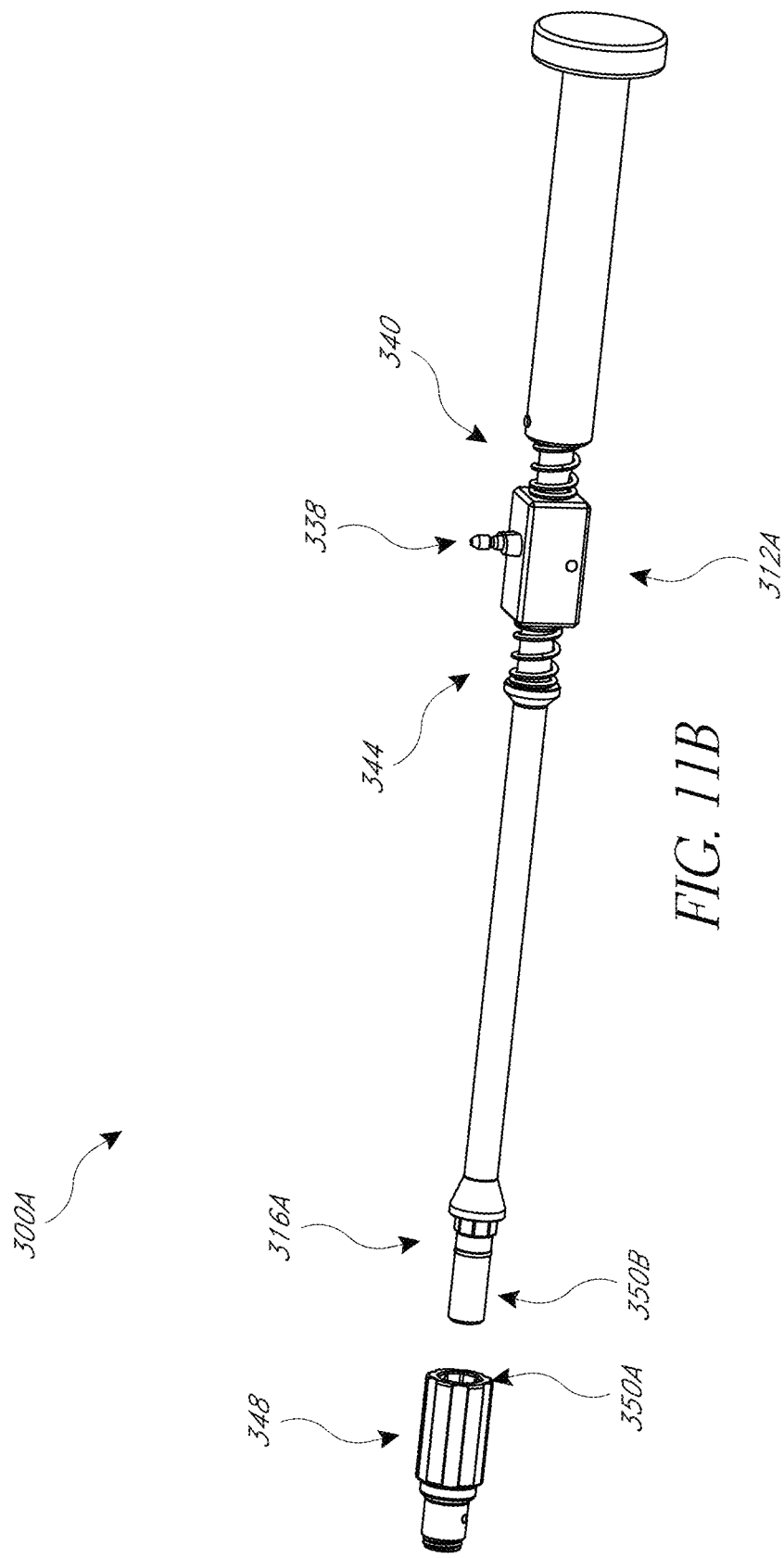
Figure 11C:
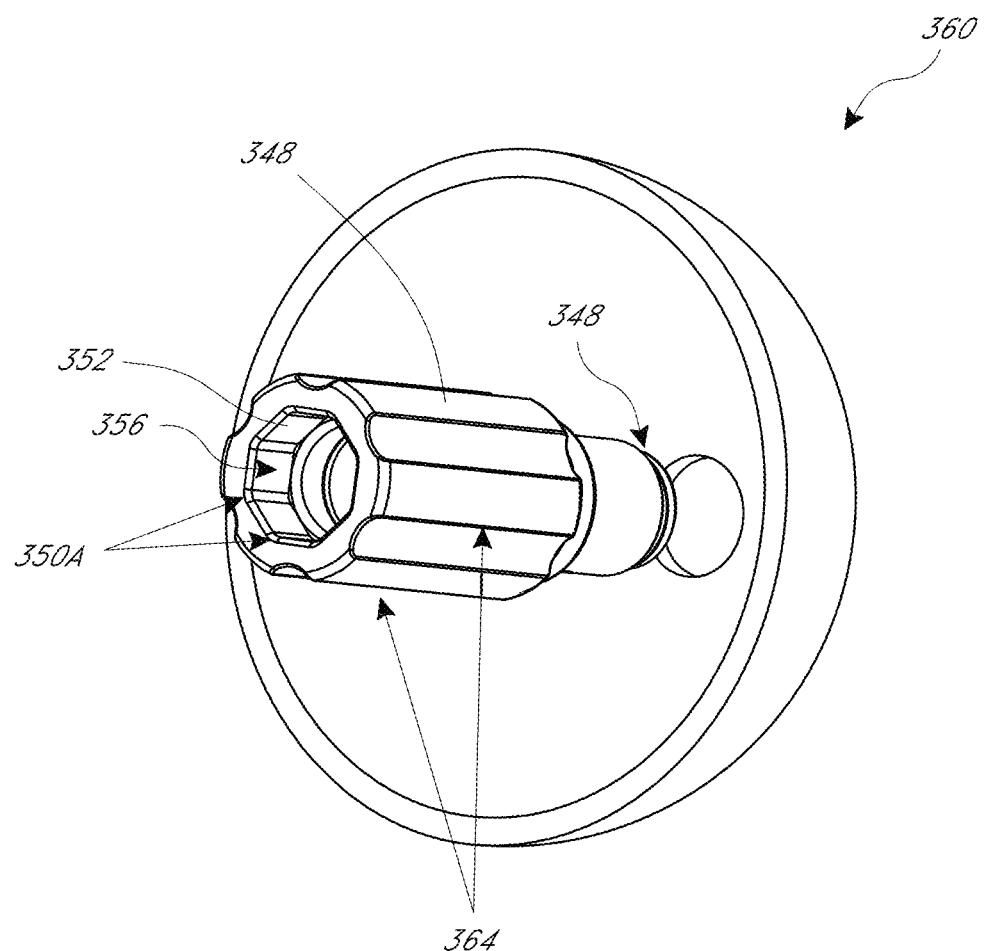

FIGS. 11B-C show more detail of distal features of the impactor 300A. In particular, the tip component 348 is removable from a shaft 316A of the impactor 300A. FIG. 11C shows that the tip component 348 can have a recess 352 formed on the proximal side thereof and an engagement device 356 formed on the distal side thereof. The recess 352 can comprises a plurality of flats 350A corresponding to a plurality of flats 350B on the distal end of the shaft 316A. The flats permit proximal-distal sliding of the recess 352 over the distal end of the shaft 316A. Preferably a detent device or other mechanism is provided between the tip component 348 and the shaft 316A so that the component does not fall off the shaft. The flats prevent the tip components 348 from rotating relative to the shaft 316A. The engagement device 356 comprises threads in one embodiment so that the cup 360 of the prosthetic hip can be screwed onto the distal end of the tip component 348. The sliding engagement of the tip component 348 on the shaft 316A is important because the impactor 300A is intended to be used with hip prostheses of a variety of manufacturers. Often the cup 360 will have a hole pattern for securing the cup to the prepared acetabulum that is unique to the manufacturer and that is dictated by the anatomy. The flats enable many discrete alternate relative angular positions of the tip component 348 (and hence the cup 360) to the shaft 316A. A plurality of flutes or elongate axial ridges 364 on the outer surface of the tip component 348 enable the user to securely grasp the tip component for mounting and dismounting the tip component on the shaft 316A.

Figure 12:
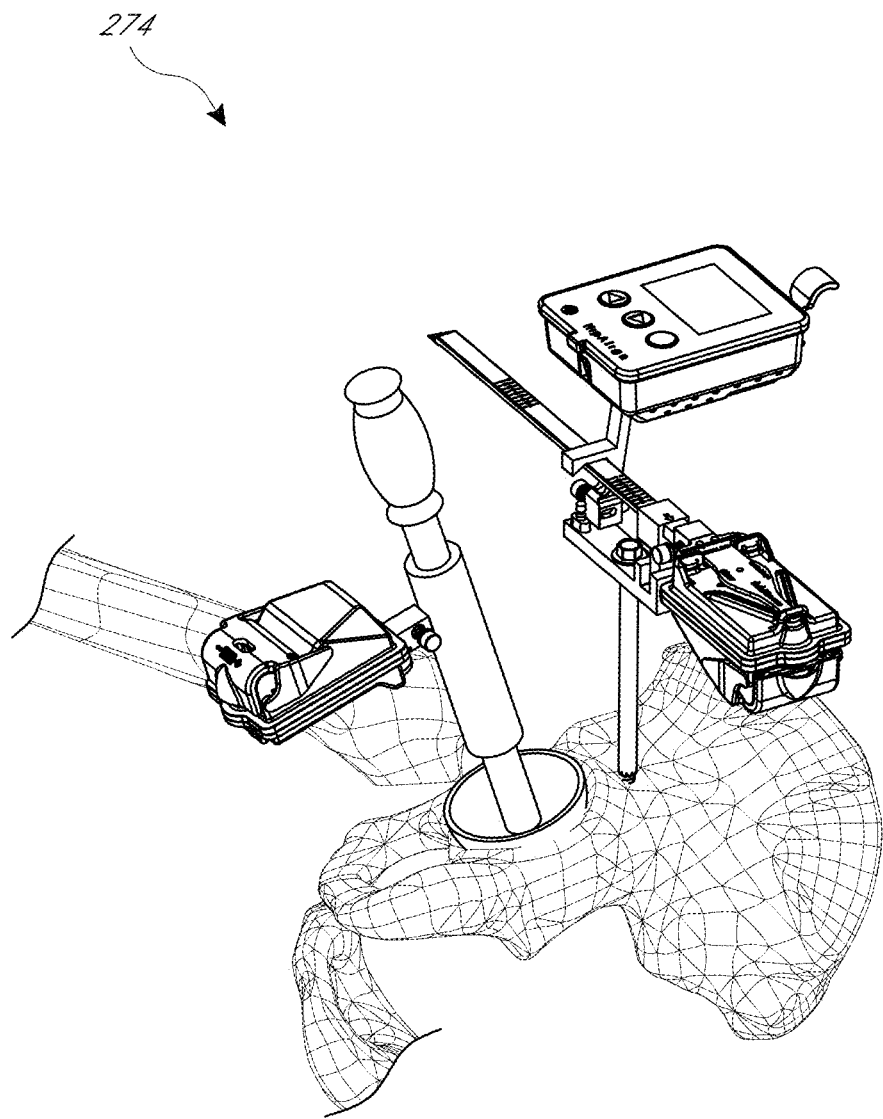
FIG. 12 illustrates a step of navigating placement of a cup portion of an artificial hip joint.

FIG. 12 shows the cup orientation placement navigation assembly of FIGS. 11A-C adjacent to the anatomy. This figure also illustrates a free-hand navigation configuration 274, in which at least the orientation devices 172, 204 are capable of six degrees of motion relative to each other. Any of the variations of FIG. 11A-11C could be substituted in the illustration. In particular, the handle 304 is oriented as desired. In one embodiment, the system 100 displays in real time the angle of the cup relative to the navigated plane, which was acquired as discussed above. Angles that can be displayed include any one or more of anteversion and abduction for example. Preferably the clinician can confirm the position of the cup within a short fixed time, such as within about 20 seconds. In one embodiment, the angles displayed can be adjusted by about 40 degrees abduction and 20 degrees anteversion. These angles are not critical, but they relate to the range of motion of the leg. It is preferred to be close to these angles because motion in abduction and anteversion extends on either side of these angles. It is believed that the systems discussed herein can increase the percentage of patients in a "safe zone" close to these angles, typically described as within 10 degrees of these angles. In contrast, studies show that conventional techniques yield close to 50% of patients outside the "safe zone."

Depending on the sensors and the timing of cup placement step of FIG. 12, the user may mount the sensing device 204 on the elongate member 224 again and may return the system 100 to the parked configuration 260 and also may initialize or zero the system 100.

The system 100 can be configured to provide a pre- and/or post-operative estimation of an angle relative to the angle of the table. In the posterior approach, the patient is placed on his/her side. In this approach, there is more chance for the patient's position to shift intra-operatively. In one embodiment, an alignment rod can be coupled with the sensing device 204 and aligned with the plane of the table. The orientation of the sensing device 204 when so aligned is recorded in the system. Later in the procedure, one or more angles is calculated and displayed to the user based on the assumption that the pelvis has not moved. At such later stages, the orientation of the sensing device 204 can be confirmed again relative to the table to provide information about whether the patient has moved. If significant movement has occurred, such that any assumptions of no movement are violated, some or all of the landmark acquisition steps can be repeated. Alternatively, the movement of the pelvis can be tracked by the sensing device and corrected for. The manner of incorporating the table orientation with landmark acquisition is discussed in greater detail below.

The user will have placed the artificial ball of the replacement hip join in the proximal femur and thereafter can place the ball in the cup, which was properly oriented using the techniques discussed above.

FIG. 1 shows that thereafter, the user can optionally confirm orientation and/or leg length using the system 100. The leg with the artificial hip joint assembled is placed in a neutral flexion and/or abduction and/or rotation position. The acquisition assembly 112 can be placed in the retracted configuration 266. The distal end 228 of the elongate member 224 can be brought into contact with a landmark, which may be the same landmark acquired in FIG. 6. Once contact is made with this landmark (e.g., the bovie mark), the orientation of the sensing device 204 is determined by the system 100. Also, the distance indicated on the scale 226 of the elongate member 224 is input into the system in any of the manners discussed above (e.g., manual or sensed). The system 100 can thereafter calculate components of vectors along the S-I axis (leg length) or M-L axis (offset).

Once leg length and offset are determined post-operatively, they can be compared the pre-operative measurements (FIG. 6) to let the surgeon know if any adjustments should be made before completing the hip replacement surgery.

Figure 13:
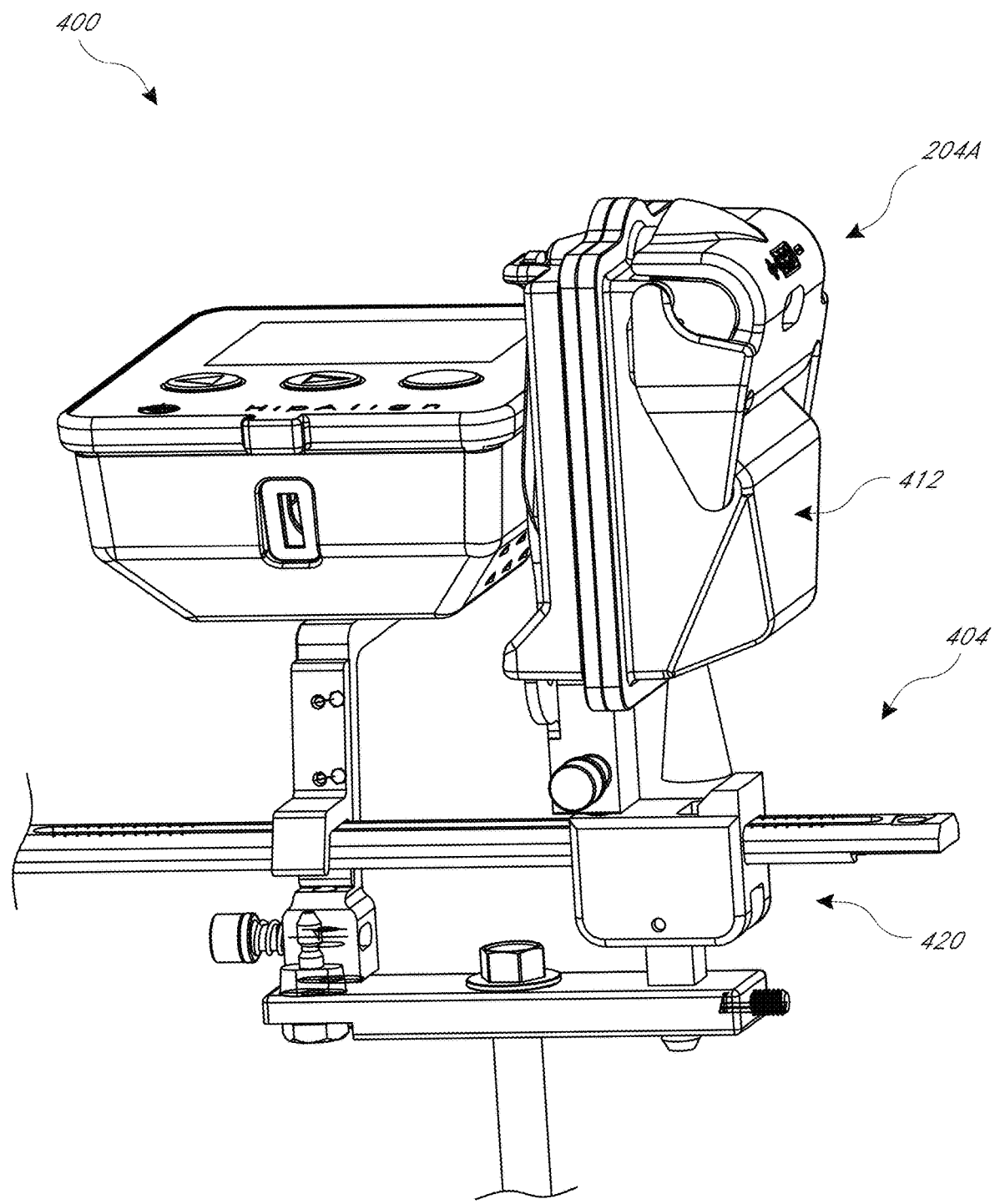
FIG. 13 is a perspective view of another embodiment of a hip navigation system.
Figure 14:
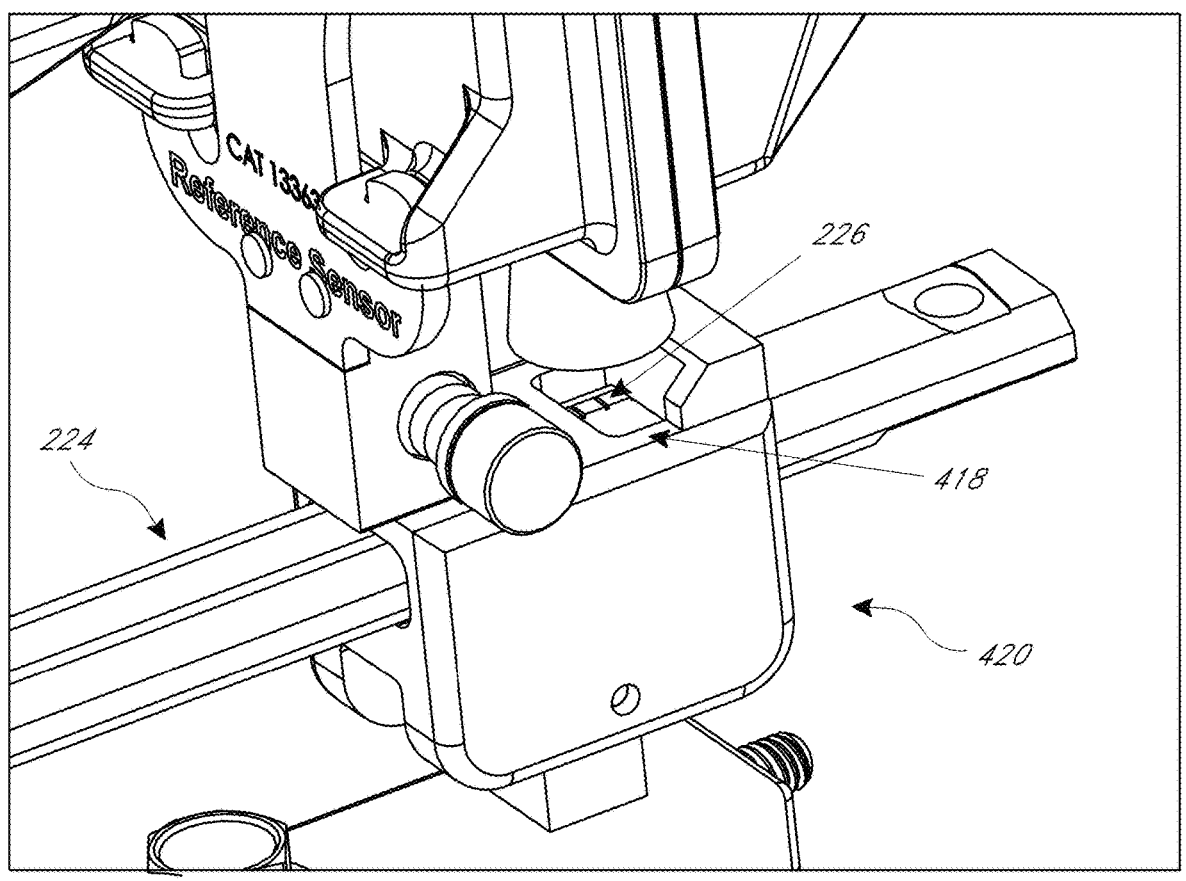
FIG. 14 is a detail view of portion of the system of FIG. 13, with a camera recording linear position of a registration arm.

FIGS. 13 and 14 show other embodiments of a hip navigation system 400 that can include any of the features discussed above. In addition, the system 400 includes a free-hand sensor mount 404 that can be used to mount a freehand orientation device 204A in one configuration. The freehand orientation device 204A preferably includes inertial sensors, similar to those hereinbefore described. The device 204A preferably also includes a camera 412. The field of view is illustrated by the cone projecting downwardly from the base of the freehand orientation device 204A. FIG. 14 shows that the field of view includes a window 418 in a sliding support 420. The window 418 enables the scale 226 to be viewed therethrough.

Because hip replacement procedures involve an open surgical field with a substantial amount of exposed tissue and blood the line of sight the camera 412 to the scales can become obstructed. In one embodiment, a hood is provided above the window 418. The hood keeps most of the blood and tissue out of the space where the camera views the scales. Additionally, a scrubber component, e.g., a thin rubber member, can be provided above the scales 226, 226A (discussed below) to prevent this tissue or fluids from entering into the field of view laterally.

One advantage of the system 400 is that the camera 412 can automatically process the image captured through the window 418 and thereby determine the position of the elongate member 224 relative to the sliding support 420. A further advantage of this is to eliminate one step from the navigation process, e.g., to eliminate the need to enter the linear dimension into the system 400. Eliminating the step can reduce time and/or personnel in the operating room. Also, the camera 412 can be configured to read a much higher resolution than can be read by a clinician. This can provide greater accuracy in the system overall. Not only that, but he camera can be configured to make fewer or no errors in reading the position, which can improve outcomes overall. For example, miniature cameras can produce data in JPEG or other image format that a processor in one or both the orientation devices 172, 204A can process to extract the linear position of the elongate member 224.

Figure 15:
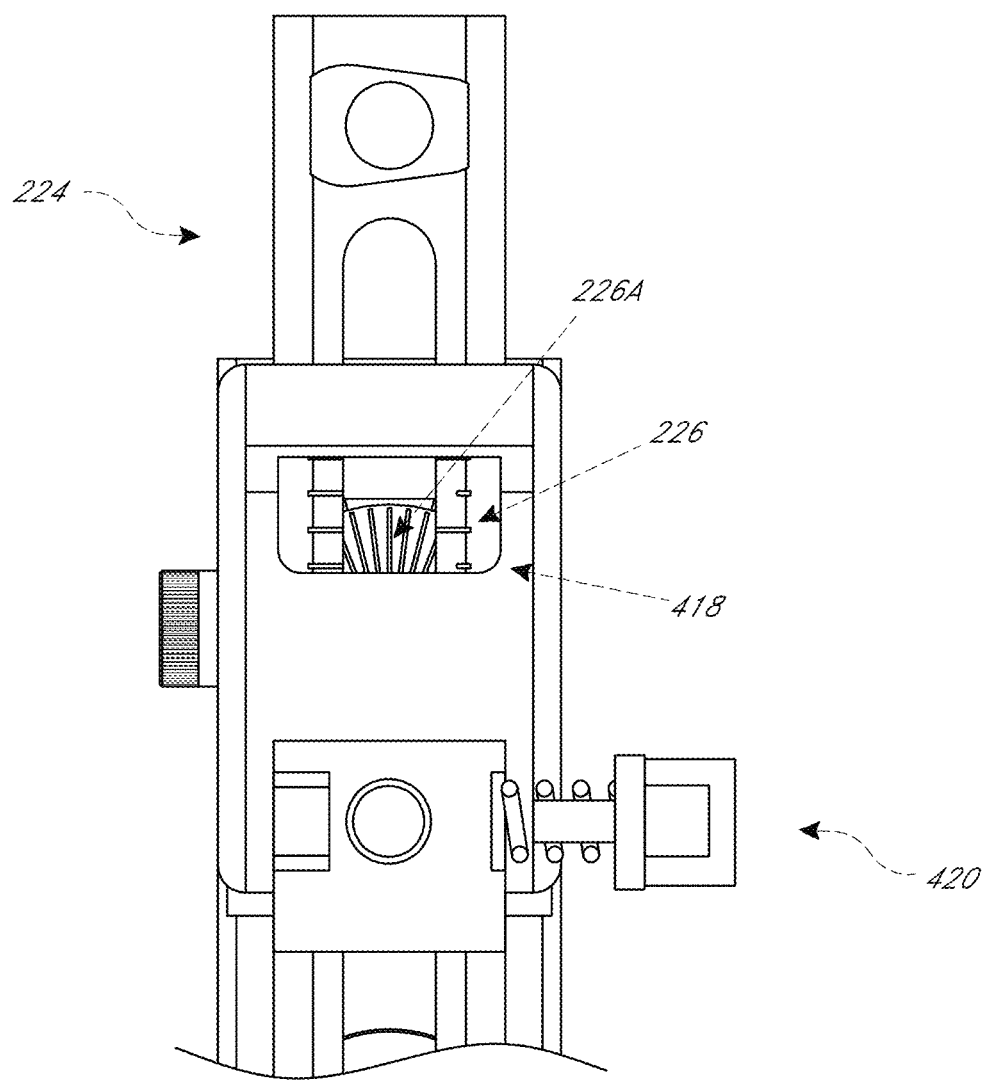
FIG. 15 shows a variation of the embodiment of FIGS. 13 and 14 in which rotational orientation and linear position can be acquired by a camera viewing a radial scale.
Figure 16:
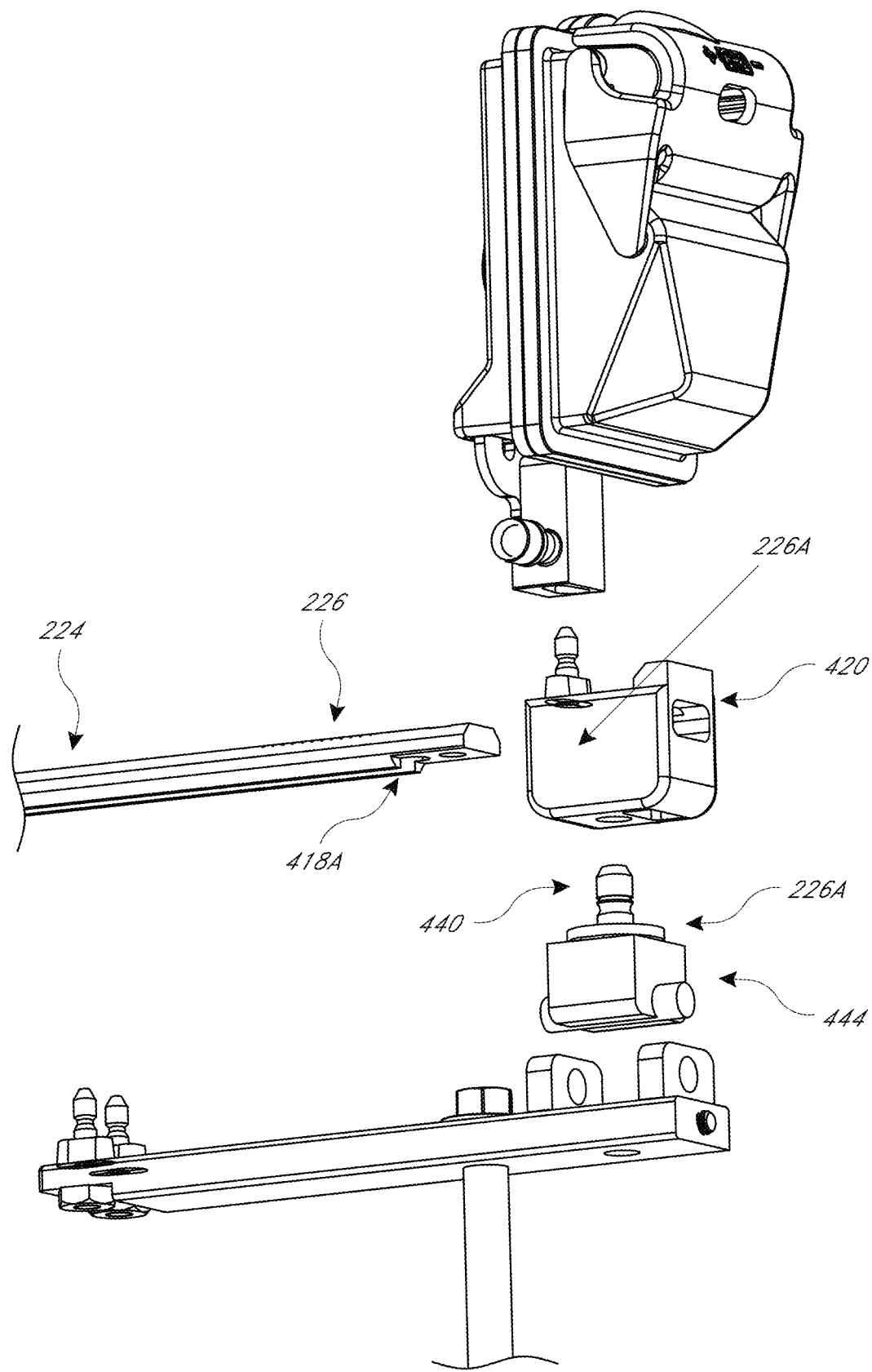
FIG. 16 is an exploded view of an assembly showing a tilt/rotation mechanism adapted to enable a camera to track at least one rotational position.

A further modified embodiment is described in FIG. 15, which shows an arcuate scale 226A that can be positioned on a structure beneath the elongate member 224, e.g., on a structure beneath the orientation device 204A that is rotationally fixed relative to an axis extending out of the page. FIG. 16 shows one configuration with this arrangement. A pivot 440 enables the sliding support 420 to rotate about an axis extending upward on the page. Although the pivot 440 is fixed about this upward extending axis, it can rotate about a pivot 444. A window 418A in the elongate member 224 enables the camera to see through the support to view the scale 226A disposed on an arcuate or disk shaped feature of the pivot 440. The scale 226A can be read by the camera 412 or a second camera to provide accurate determination of the rotational position of the elongate member 224. This can enable one of the sensors in the orientation device 204A to be eliminated or inactivated. In another embodiment, camera date derived from the scale 226A can be used to confirm the data from sensors in the orientation device 204A. Preferably the scale 226A has markings over a range of from about 15 to about 90 degrees, for example, between about 30 and about 60 degrees, e.g., at least between about 40 and about 50 degrees.

2. Posterior Approach: Systems Adapted for Accelerometer Sensitivity

Figure 17:
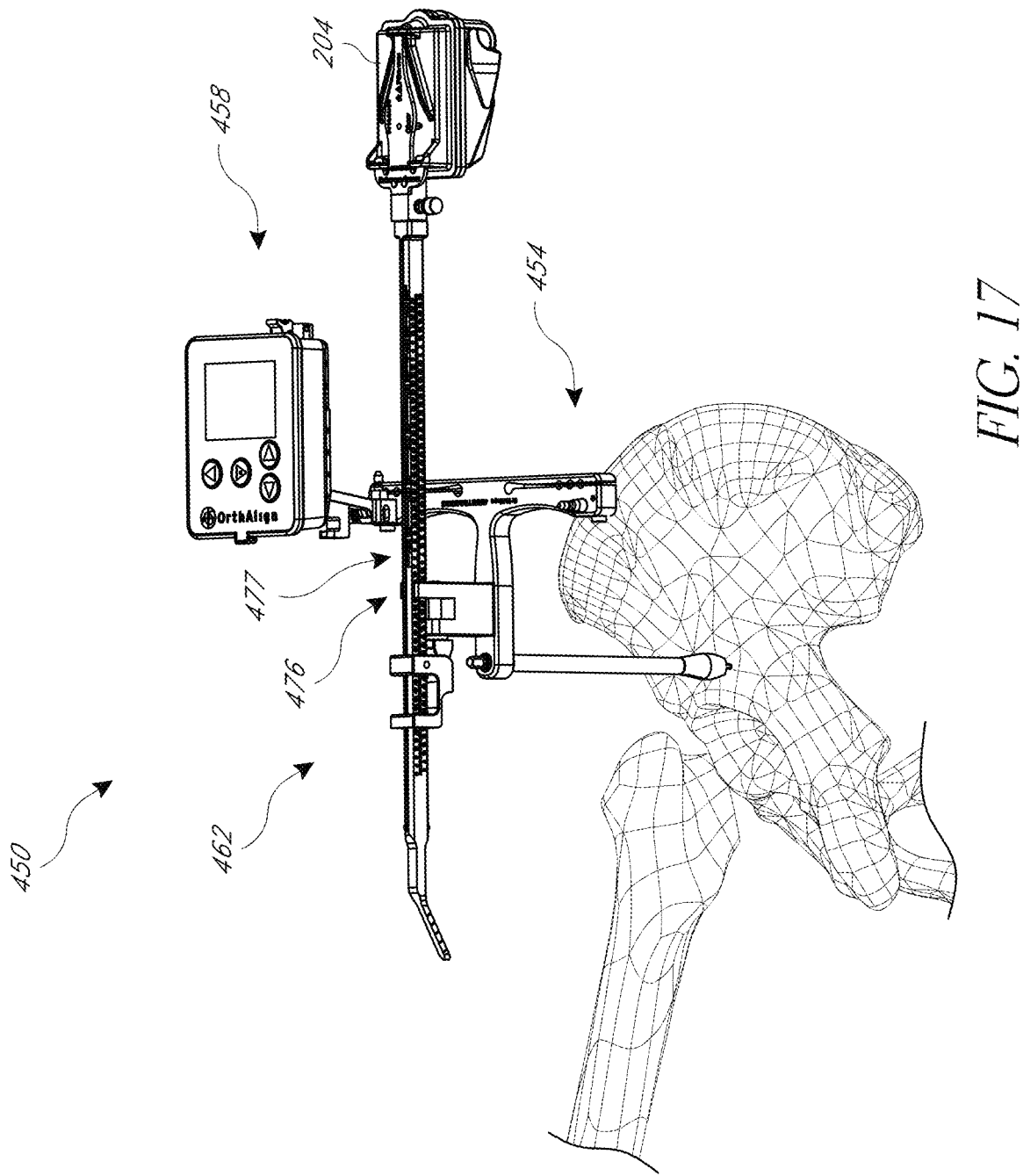
Figure 17A:
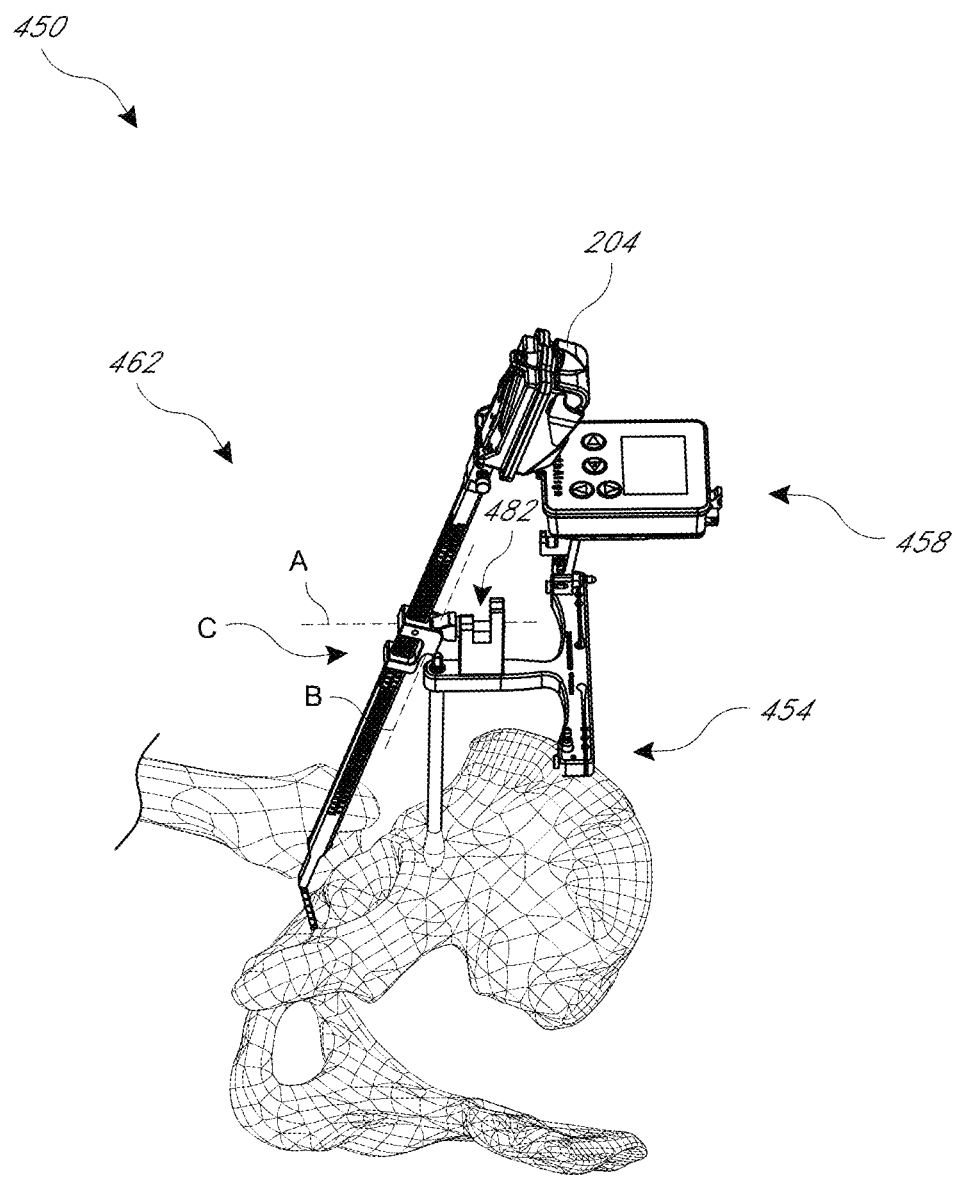
Figure 17B:
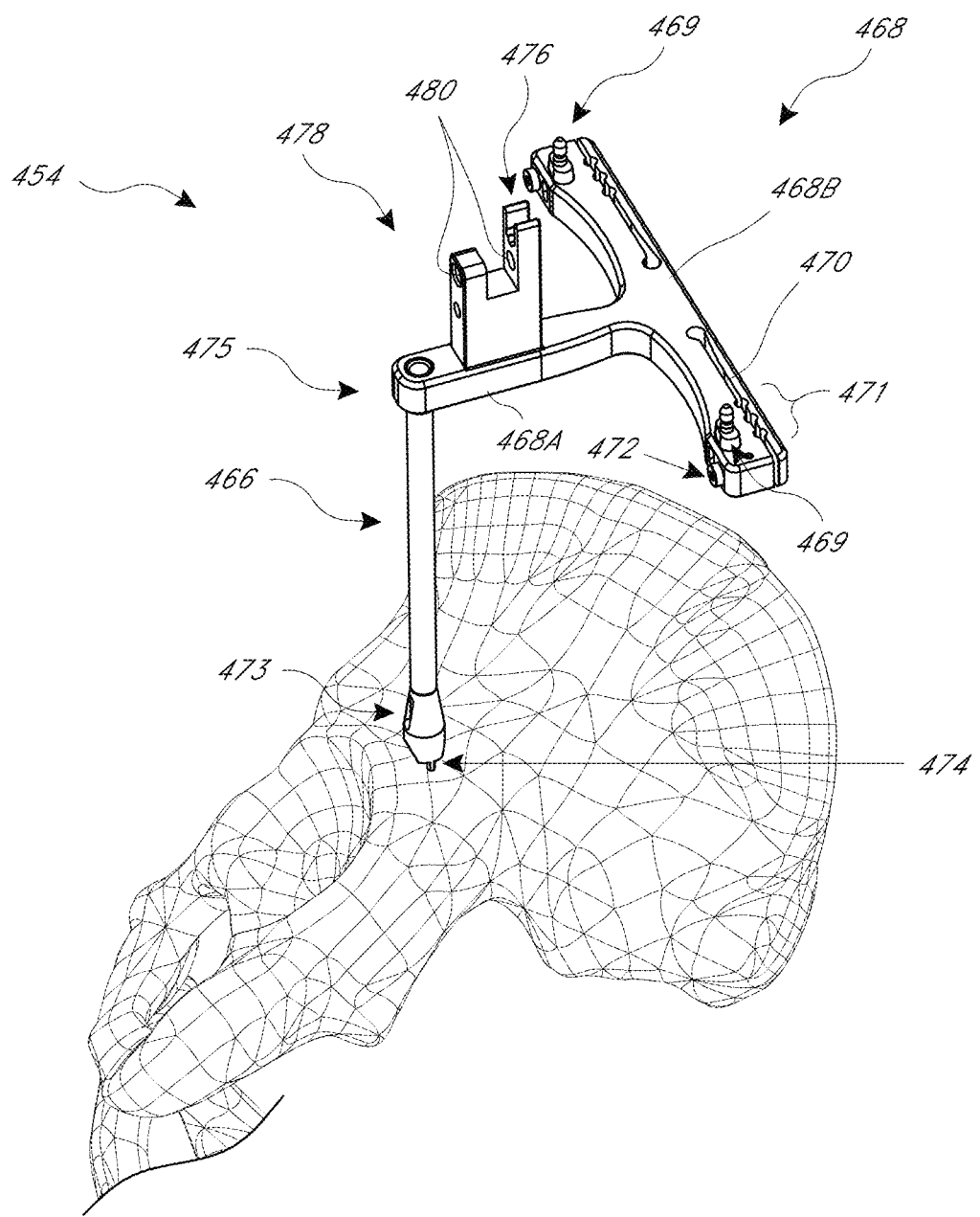
Figures 1, 17C:
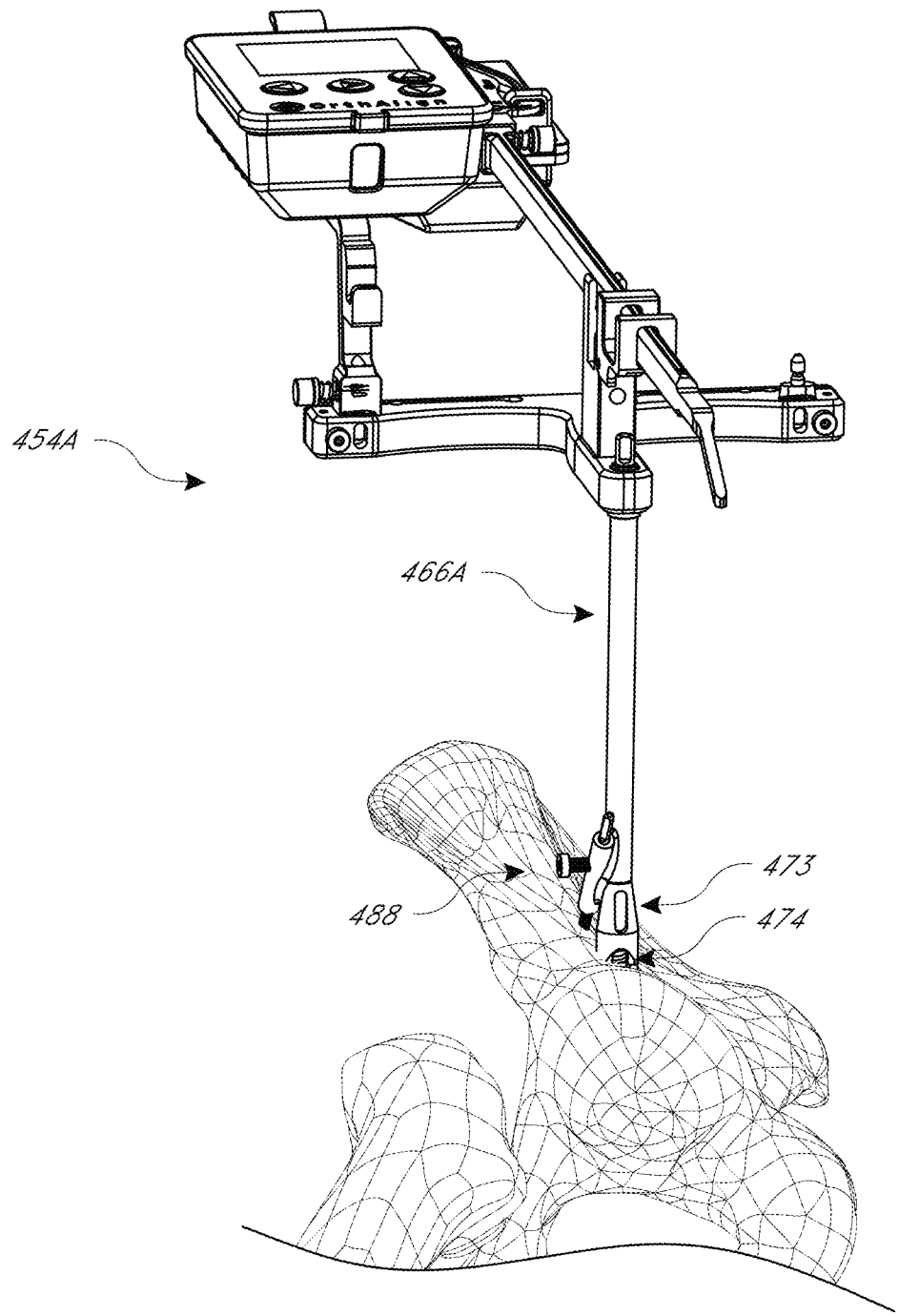
Figures 2, 17C:
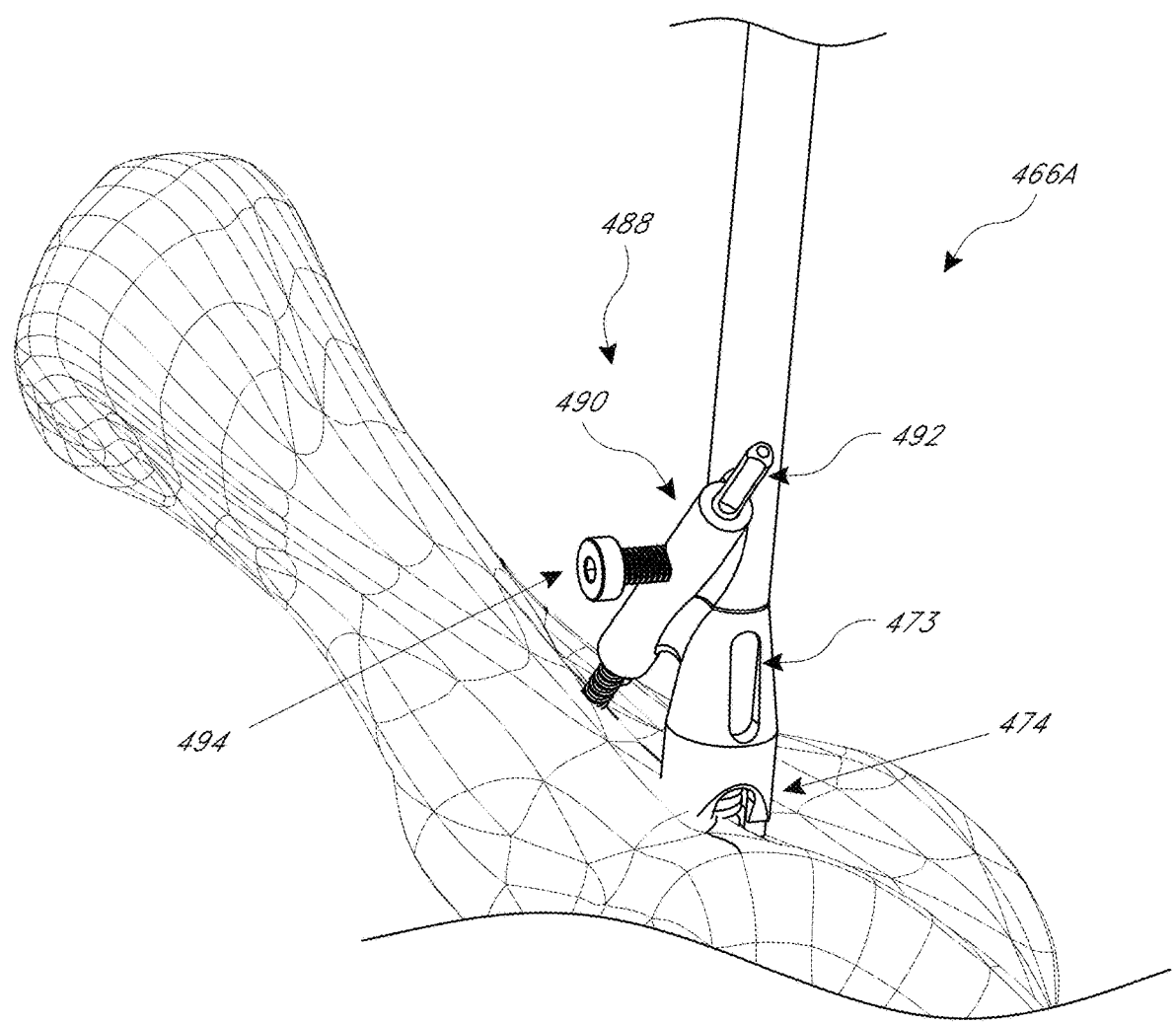

FIGS. 17-17C2 illustrate further embodiments. A system 450 is adapted for navigating a hip procedure from a posterior approach. The system 450 includes an anchor jig 454, an alignment system 458, and a landmark acquisition assembly 462. The components may be similar in some respects to those discussed above, and such descriptions are incorporated with this embodiment where consistent.

The jig 454 includes a hollow fixation member 466 and a platform 468 for coupling a plurality of devices to the pelvis. The platform has a generally T-shaped configuration including a first portion 468A coupled with the proximal end of the fixation member 466 and a second portion 468B disposed transversely to the first portion 468A. The first portion 468A provides a support for a cradle 476 discussed further below. The second portion 468B can include a plurality of docking devices 469 for coupling directly or indirectly with the orientation device 172. The T-shaped configuration provides the advantage that the docking devices 469 can be disposed father away from the surgical site than is the case with the system 100. This reduces any intrusion of the orientation device 172 into the working field.

In some cases, the fixation member 466 provides adequate stability in anchoring the system 450 to the pelvis. In other situations, the jig 454 can be coupled with the pelvis from the second portion 468B. For example, a slot 470 can be formed in the second portion 468B on one or both sides of location where the first portion 468A extends from the second portion 468B. The slots 470 can extend from a lateral edge of the second portion 468B toward location where the first portion 468A extends from the second portion 468B. The slots 470 can include a plurality of channels 471 configured to receive fixation pins (e.g., Steinmann pins) that can be advanced into the pelvis. The channels 471 extend generally parallel to the fixation member 466. The fixation pins can be securely connected to the second portion 468B in the channels 471 by a clamp device 472. The clamp device can include a screw configured to draw the portions of the second portion 468B on either sides of the slot 470 toward each other and thus to create large frictional forces on the pins in the slots 471.

The slots 470 preferably are aligned such that a plane extends along both of the slots 470 along their length. Because the slots 470 are long and slender this plane can be readily visualized in an X-ray image. It is preferred that the jig 454 be aligned to the pelvis such that the plane extending along the slots 470 is perpendicular to an axis of the patient (e.g., the intersection of the medial lateral plane and the transverse mid-plane of the patient). This feature provides a convenient way to visually confirm proper positioning of the jig 454 in one embodiment.

The fixation member 466 includes a registration feature 473 and a foot 474 adjacent to a distal end thereof and a coupling 475 adjacent to the proximal end thereof for connecting to the platform 468. The foot 474 includes a plurality of spaced apart spikes extending from a distal end thereof capable of preventing or limiting rotation of the jig 454 when the fixation member 466 is connected to the pelvis. FIG. 17 shows that securing the jig 462 to the pelvis can include positioning a pin or other bone engaging device through the fixation member 466. The pin and spikes extending from the foot 474 can provide three or more points of contact with the pelvis providing secure mounting of the jig 462.

The coupling 475 generally secures the platform 468 to the fixation member 466. In some embodiment, the coupling 475 has a rotational capability that enables the platform to be positioned at selective locations about the longitudinal axis of the pin 466, for example to enable the platform 468 to be initially positioned in the correct orientation or to be moved during or after the procedure to make space for other surgical devices. One arrangement provides matching splines that extend parallel to the longitudinal axis of the fixation member 466. This arrangement would permit splines on an upper portion of the coupling 475 to be disengaged from splines on a lower portion of the coupling 475. When disengaged, the platform 468 and the upper portion of the coupling 475 can be rotated relative to the lower portion of the coupling 475. The splines can thereafter be re-engaged.

The jig 454 also preferably includes a cradle 476 that can be used to hold a probe arm 477. The cradle 476 includes a U-shaped recess having a width between two upright members that is about equal to the width of an arm 477 of the landmark acquisition system 462. FIG. 17 shows the probe arm 477 in a parked configuration as discussed above. If the sensor 204 operates with components that are prone to accumulated error sources, the parked configuration can be used to eliminate such error. As discussed above, the system 450 can be configured such that the position and/or orientation of the sensor 204 relative to the orientation device 172 is known. Thus, when the arm 477 is in the cradle 476 any accumulated error of components of the sensor 204 can be eliminated.

The cradle 476 can provide other convenient functions even if the sensing devices in the sensor 204 are not subject to sources of accumulated error. As discussed elsewhere herein, for confirmation of accuracy of the system or to provide a simplified reference frame not requiring landmark acquisition, it may be desirable at some point of the procedure to use the probe arm 477 and the sensor 204 to estimate the plane of the surgical table upon which the patient is resting. If, as discussed above, the plane intersecting the slots 470 is oriented perpendicular to the axis of the patient when the jig 454 is mounted to the pelvis, the cradle will be parallel to the axis of the patient. If the fixation member 466 is oriented vertically, the arm 477 will be parallel to the plane of the table when in the cradle 476. The system 450 can thus use the plane of the table as a reference frame for guiding the placement of the cup without registering landmarks. Or, the plane of the table can be used in combination with registering the anatomy about the acetabular rim, as discussed above, to increase the accuracy of navigating the cup.

The cradle 476 also provides a convenient home position that keeps the arm 477 stationary and out of the way of other surgical instruments. FIG. 17A illustrates the probe arm 477 withdrawn from the cradle 476 and free to move into contact with landmarks.

The jig 454 also includes a pivot feature 478 that is disposed horizontally. FIG. 17B shows that the pivot feature 478 includes two horizontal apertures 480. One of the apertures 480 is formed in the same structure forming the cradle 476 but at an elevation below the cradle 476. The other aperture 480 formed between the cradle 476 and a projection of the fixation member 466. FIG. 17A shows that the probe arm 477 is connected to the pivot feature 478 by a shaft 482 that extends through the apertures. A movement device is provided between the shaft 482 and the arm 477 to enable a distal tip of the arm to be rotated about perpendicular axes and to be advanced linearly relative to the stationary jig 454. One axis of rotation A of the movement device is disposed parallel to and at an elevation above the platform 468. Another axis of rotation B is disposed generally perpendicular to the axis A. Sliding of the arm 477 is enabled by a snug but sliding fit of the arm in a housing C. By orienting the axis A in this manner, the sensitivity of accelerometers in the sensor 204 to small angular motions references points about the acetabulum is heighted or maximized. This can enable landmark acquisition with the system 450 based solely on accelerometers, which advantageously are not subject to accumulated error, which can simplify the landmark acquisition process.

The registration feature 473 is a convenient way to enhance the accuracy of the sensor 204. In particular, in one variation of the method discussed above, a distal tip of the probe arm 477 is brought into contact with the registration feature 473. In one embodiment, the registration feature 473 is a notch configured to receive and temporarily retain the tip. Thereafter, the user can interact with the orientation device 172 to initialize accelerometers within the sensor 204. Thereafter the points to be acquired can be sequentially contacted and the orientation and position of the sensor 204 can be sequentially recorded in the system 450. Because the accelerometers are initialized close to the points to be acquired, accuracy of the reading is enhanced as the angular error resulting from an error in the scale factor of the accelerometers is minimized due to the small arc from the registration feature. For example, the jig 454 is configured to enable the landmark acquisition assembly 458 to reach all points to be registered by moving less than about 45 degrees from an initial or home position in some embodiments. In other embodiments, the jig 454 is configured to enable the landmark acquisition assembly 458 to reach all points to be registered by moving less than about 25 degrees from the initial position. In other embodiments, the jig 454 is configured to enable the landmark acquisition assembly 458 to reach all points to be registered by moving less than about 15 degrees from the initial position.

The jig 454 also is configured to interact well with the soft tissue that is disposed around the surgical site in the posterior approach. In this approach, an incision is made in soft tissue that is kept as small as possible. In one approach, the fixation member 466 is positioned at the end of the incision. Where the incision is made as minimal as possible, the jig 454 can also function as a retractor. The T-shaped configuration is particularly well suited for this function because the first portion 468A of the platform 468 can be received between the middle and ring fingers of the user with the second portion 468B in the palm of the hand. With the foot 474 gripping the pelvis, the jig 454 can be tilted from the platform 468 away from the hip joint to retract the tissue away.

FIGS. 17C-1 and 17C-2 illustrate further embodiments of a posterior approach jig 454A having a mounting device 488 disposed adjacent to the distal end of a fixation member 466A, which is otherwise similar to the fixation member 466. The fixation member 466A includes a tubular body 490 coupled with the fixation member 466A, which in this embodiment acts as a primary fixation member. The tubular body 490 extends along a lumen that is angled relative to the lumen of the fixation member 466A. The lumen in the tubular body 490 is configured to accept a fixation pin 492 that can be driven into the bone, as illustrated in FIG. 17C-2 at an oblique angle. The fixation pin 492 supplements the fixation provided by the fixation member 466A. The fixation pin 492 can be used in conjunction with the optional long pin(s) extending through the channels 471, e.g., into the ilium or as a substitute for that option. The fixation pin 492 has the advantage of not requiring any additional holes in the skin because it is located within the primary incision made to access the joint in the procedure. The fixation pin 492 can be threaded to engage the bone in one embodiment. In some embodiments, a locking device 494 can be provided to secure the pin 492 in the lumen of the tubular body 490. A set screw is one example of a locking device 494 that can be used. The locking device 494 enables the fixation pin 492 to be headless, which avoids issues with screw threads stripping the hole in the bone into which the pin 492 is inserted.

3. Posterior Approach: Workflow Considerations

As noted above, a workflow problem arises in typical hip replacement procedures in that anatomical features that can be more easily references are unavailable in the traditional posterior approach for operating on the joint.

By performing a CT-based study of a large number of human pelvises, the assignee of this application has been able to calculate a population-based average relationship between multiple planes created by various points in, on or around the acetabulum that are accessible during posterior approach hip replacement (each plane, an "Acetabular Plane"), and the Anterior Pelvic Plane. One of the key features of posterior hip navigation for some embodiments disclosed herein is the ability of a module, e.g., software incorporated into a processor, which may be on a computer, or one or both of the orientation device 172 and sensor 204, to calculate a transformation from one reference frame to another. As described in more detail elsewhere herein, several points are referenced in, on or around the acetabulum and from these points a proxy Acetabular Plane is calculated.

Next, in certain embodiments described herein a module operable to process an algorithm, e.g., by executing software in one or both of the orientation device 172 and sensor 204 alone or with a separate computer, is able to calculate a transformation from the proxy Acetabular Plane to Anterior Pelvic Plane. The approach indirectly registers the Anterior Pelvic Plane without requiring a direct supine registration and subsequent patient movement and re-draping necessary in standard navigation. A module in certain embodiments described herein is then able to provide the user real time navigation data of the orientation of a hip instrument (e.g., the impactors 300, 300A) with respect to the Anterior Pelvic Plane.

In certain systems described herein, a further advantage is that the systems are able to implement the plane transformation algorithm to calculate an Anterior Pelvic Plane from one of any number of proxy Acetabular Planes that the surgeon chooses to register. This enables the surgeon to have greater flexibility in Acetabular Plane landmark selection to take into account the quality or accessibility of certain landmarks. For example, in cases of minimal deformity around the acetabular rim, the surgeon may choose to register landmarks around the rim, which are easily accessible. In cases where there is great deformity or high presence of osteophytes on the acetabular rim, the surgeon may instead choose to register an Acetabular Plane based on extra-acetabular landmarks (or described as "off-rim" elsewhere herein) outside of the rim that are unaffected by disease or prior hip replacement surgery.

Examples of anatomical landmarks that may be used to create a proxy Acetabular Plane and that are shown in FIG. 2 include but are not limited to:

Extra-Acetabular Landmarks (Ischium/Ilium/Pubis)
  (A) The lowest point of the acetabular sulcus of the ischium
  (B) The prominence of the superior pubic ramus
  (G) The confluence of the anterior inferior iliac spine (AIIS) and the outer border of the acetabular rim Acetabular Rim Landmarks
  (E) The center of the anterior insertion of the trans-acetabular ligament
  (F) The center of the posterior insertion of the trans-acetabular ligament
  (H) The most superior point of the acetabular rim.

Additional points can be combined with either of the groups of points listed above. For example, in one embodiment, point "D" is used. Point D is the midpoint of the inferior border of the acetabular notch. As discussed in connection with FIG. 36 below, point D corresponds to the bottom landmark 380B used to form the line 382. Point D is used in that approach to provide patient specific refinements to the positioning.

A further key benefit of certain embodiment discussed herein is that the foregoing plane transformation capabilities increase the accuracy of the transformation between the proxy Acetabular Plane registered and the Anterior Pelvic Plane above the general population average data by the user inputting certain patient-specific information, such as gender.

Additionally, certain embodiments of systems including one or more of the orientation device 172, sensor 204, or a separate computer may have modules that are operable, e.g., by processing software, to allow the user to input an angular or plane relationship between an proxy Acetabular Plane and Anterior Pelvic Plane that the surgeon measured based on pre-operative imaging, allowing for a partial or whole plane transformation based on patient-specific data rather than population data. By way of example, the surgeon may choose to pre-operatively measure an angle created by (a) landmarks that are both visible on an A/P pelvis x-ray and that can be referenced during posterior hip replacement, and (b) landmarks that are both visible on the pelvis x-ray and that are directly associated with inclination measurement in the Anterior Pelvic Plane. If this angular relationship is inputted into a module of a system including one or more of the orientation device 172, the sensor 204, or a separate computer, which module is capable of making calculations processing software and the surgeon registers the landmarks described in (a), inclination navigation will be based specifically on that patient rather than a population average. Landmarks (D) and (H) listed above are examples of landmarks that are both visible on an A/P pelvis x-ray and that can be referenced to create a proxy Acetabular Plane in posterior hip replacement.

These aspects of the systems adapted for posterior approach hip joint replacement can greatly enhance both workflow and accuracy in such procedures.

Figure 18:
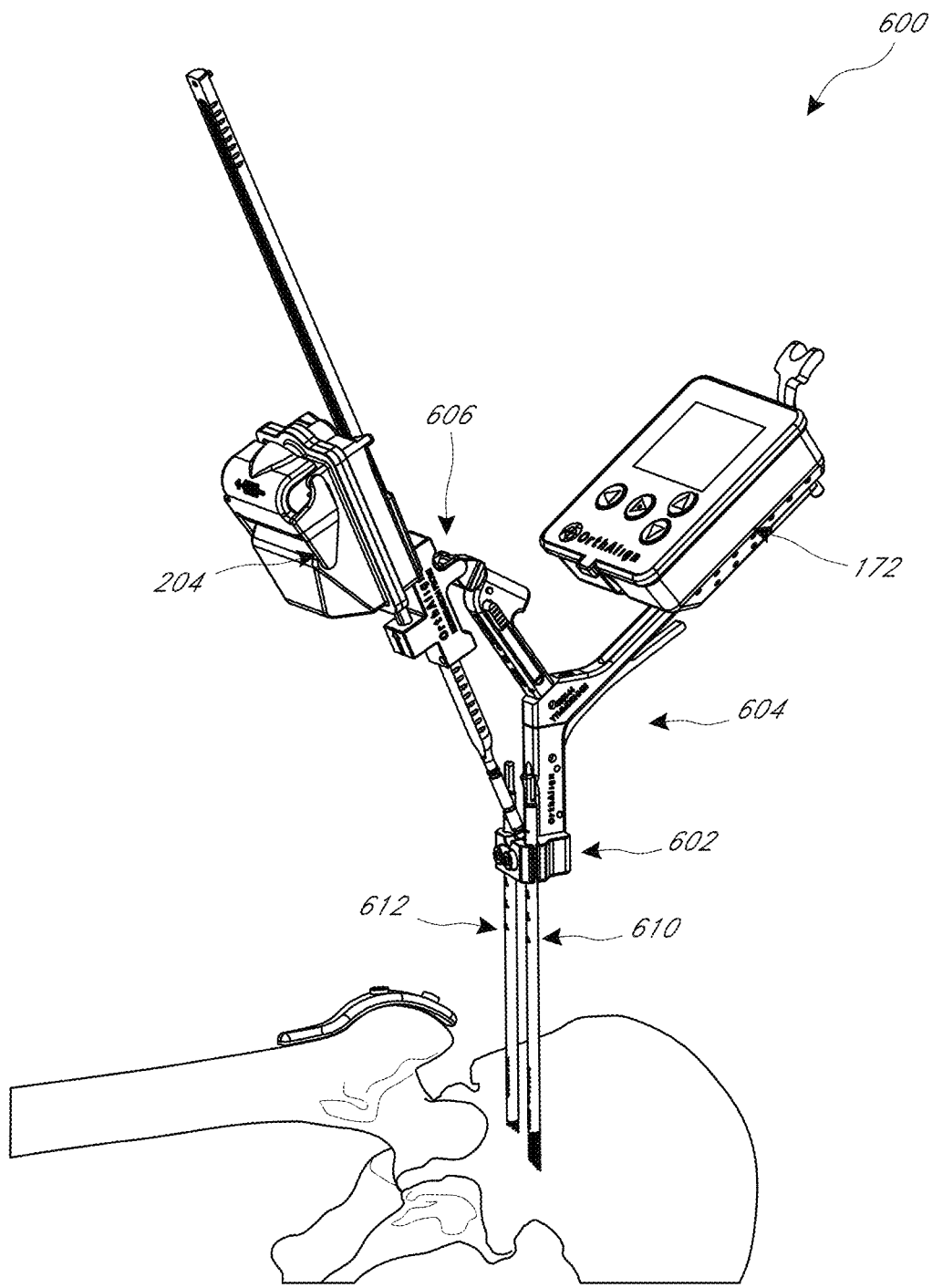
FIG. 18 is a perspective view of a hip navigation system applied to a patient.

4. Posterior Approach: Further Systems with an Orientation Sensing Device and Camera FIG. 18 shows a hip navigation system 600 adapted to navigate a hip joint procedure with reference to anatomical landmarks. The system 600 is shown mounted on a pelvis in a posterior approach in FIG. 18. FIG. 18 shows an early phase of a procedure prior to the joint being dislocated but after the system 600 is mounted to the pelvis. The system 600 can be adapted for various techniques. As discussed further below, such variations involve registering the femur prior to and after the joint is replaced to confirm an aspect of the relative position and/or orientation of the femur, e.g., leg length, joint offset, and rotational orientation of the femoral neck. The system 600 can include any component described herein. The system 600 can be used in any technique or method step described herein.

The system 600 can include a fixation base 602, a first assembly 604 and a second assembly 606. The first assembly 604 is rigidly connected to the hip in the illustrated configuration so that motion of the hip cause corresponding motion of sensor(s) in the first assembly 604 as discussed below. Sensing this motion enables the system 600 to eliminate movement of the patient as a source of error in the navigation. The second assembly 606 provides a full range of controlled motion and sensor(s) that are able to track the motion, in concert with sensor(s) in the first assembly 604. Additional details of systems, devices, sensors, and methods are set forth in U.S. Pat. No. 8,118,815; US US2010/0076505; and U.S. Pat. No. 8,057,479 which are all incorporated by reference herein in their entireties for all purposes. The sensors in assemblies 604, 606 preferably transfer data among themselves and in some cases with external devices and monitors wirelessly, using Bluetooth, Wifi® or other standard wireless telemetry protocol.

Figure 19:
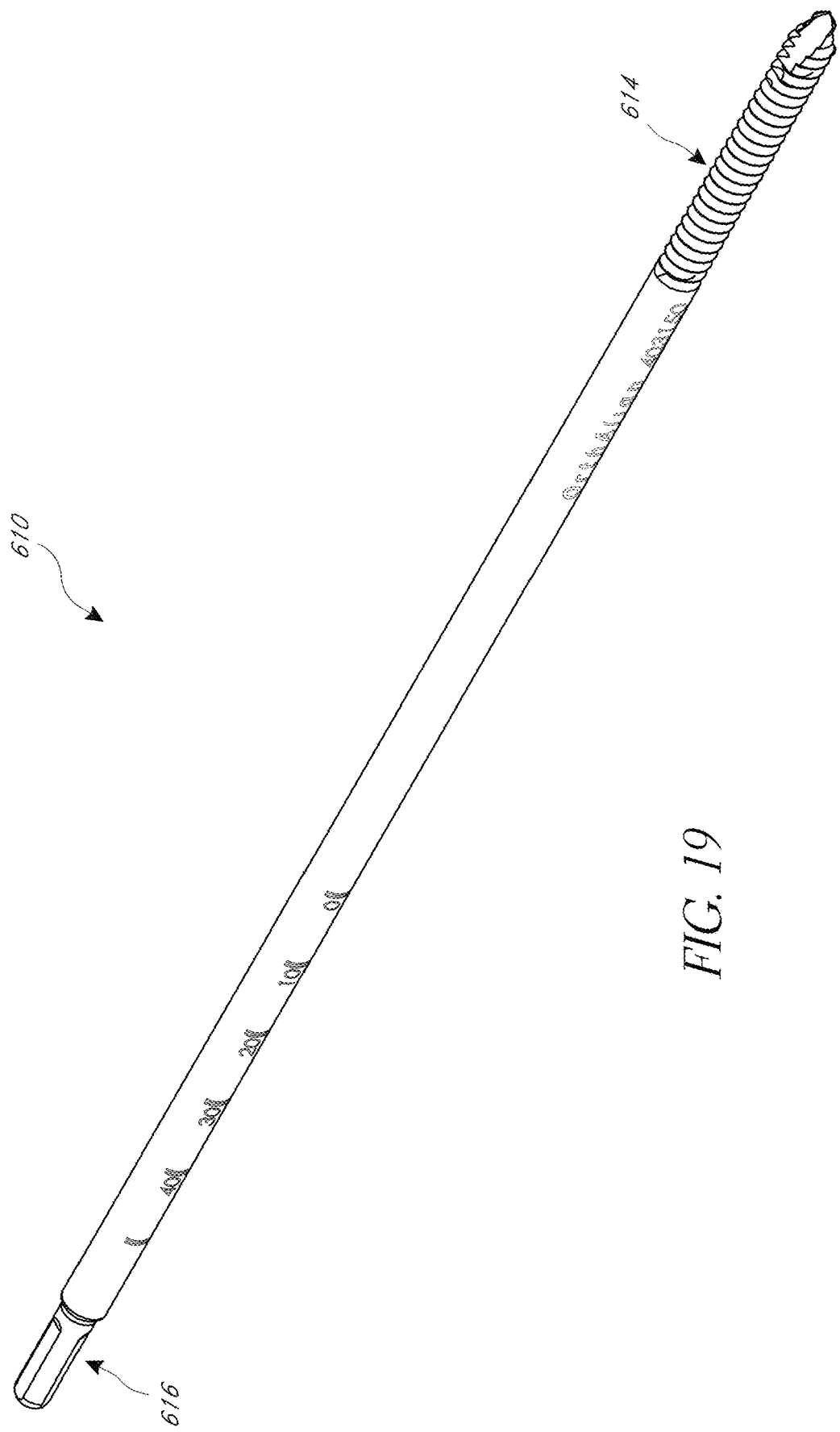
FIG. 19 is a perspective view of a fixation pin of the system of FIG. 18.

The system 600 can include one or more fixation pins. In the illustrated embodiment, a first fixation pin 610 and a second fixation pin 612 are shown. Other configurations are contemplated (e.g., one fixation pin, three fixation pins, four fixation pins, etc.). The fixation pins 610, 612 can be elongate structures. FIG. 19 shows the fixation pin 610. In some embodiments, the fixation pins 610, 612 are identical or substantially similar. In some embodiments, the fixation pins 610, 612 are different and can be adapted to be inserted into different anatomic locations.

The fixation pin 610 can be substantially cylindrical, as shown in FIG. 19. The fixation pin 610 can have a distal end 614 that can be advanced to a pelvic bone at an anatomical location or landmark or other selected location. In the illustrated embodiment, the distal end 614 is threaded. The distal end 614 can include a sharpened tip designed to penetrate bone. The fixation pin 610 can have a proximal end 616. The proximal end 616 can include attachments features to couple the fixation pin 610 with a driver. In the illustrated embodiment, the proximal end 616 includes a tri-flat shape designed to couple with a tri-flat socket. The fixation pin 610 can include one or more markings along the length of the fixation pin 610. The markings can indicate the orientation of the fixation base 602 relative to the fixation pin 610.

Referring back to FIG. 18, each fixation pin 610, 612 can be driven into the ilium on the pelvis. As discussed further below, each fixation pin 610, 612 can be coupled with other bones in other techniques. For example, one of the fixation pins 610, 612 can be coupled with the ischium or the pubis. In some techniques, one of the fixation pins 610, 612 is mounted to a pelvic bone but not at a landmark. One of the fixation pins 610, 612 can be coupled at a point superior to the superior-most point on the acetabular rim. In some techniques, one of the fixation pins 610, 612 is about 10 mm above the superior-most point on the acetabular rim. In some techniques, three or more anatomical landmarks disposed about the acetabulum can be acquired, as discussed below. When one of the fixation pins 610, 612 is coupled with a landmark, only two additional landmarks are acquired in some embodiments as discussed below. One reason for mounting the fixation pins 610, 612 away from the landmarks is that the landmarks may not be visible or accessible before dislocating the hip joint. If the clinician wishes to use the system 600 to reference the femur as discussed below, it may be required to mount the fixation pins 610, 612 away from the landmarks.

Figure 20A:
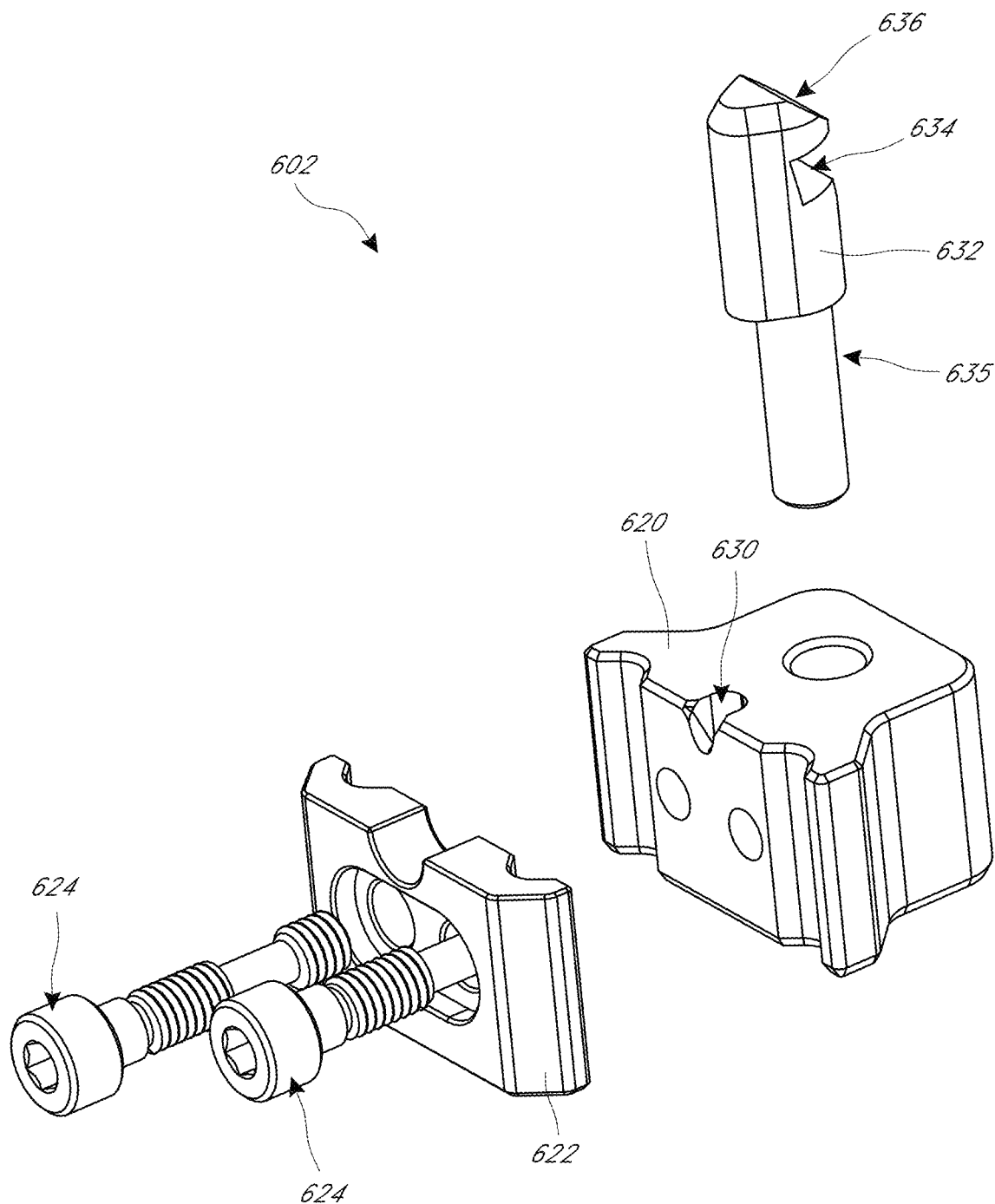

The system 600 can include the fixation base 602 shown in FIGS. 20A-20H. The fixation base 602 can function as a clamp with the one or more fixation pins 610, 612. FIG. 20A shows an exploded view of the fixation base 602. FIGS. 20B-20D show other views of the fixation base 602. The fixation base 602 can include a platform 620 and a support 622. The platform 620 can interact with the support 622 to function as a clamp. In the illustrated embodiment, the fixation base 602 can include one or more fixation devices 624. In the illustrated embodiment, two fixation devices are shown but other configurations are contemplated (e.g., one, three, four, etc.). The fixation devices 624 can include one or more threaded sections. In the illustrate embodiment, the fixation devices 624 are screws with a head and a threaded shank. The platform 620 can include one or more holes. The support 622 can include one or more holes. The fixation devices 624 can pass through or engage one or more holes in the support 622. In some embodiments, each hole in the support 622 is threaded. The fixation devices 624 can pass through or engage one or more holes in the platform 620. In some embodiments, each hole in the platform 620 is threaded. Rotation of the fixation devices 624 can cause the support 622 to move toward the platform 620 and/or the platform 620 to move toward the support 622.

The platform 620 and the support 622 form one or more channels therebetween, as shown in FIG. 20C. The number of channels can correspond to the number of fixation pins. In the illustrated embodiment, a first channel 626 and a second channel 628 are shown. The channels extend from a top surface of the platform 620 and/or the support 622 to a bottom surface of the platform 620 and/or the support 622. The channels 626, 628 extend in a direction transverse to the direction of the fixation devices 624 when the fixation devices 624 are engaged with the platform 620 and the support 622. The first channel 626 is sized to accept the first fixation pin 610 and the second channel 628 is sized to accept the second fixation pin 612. Rotation of the fixation devices 624 can cause the support 622 to move toward the platform 620. The channels 626, 628 can decrease in diameter with the rotation of the fixation devices 624. Upon rotation of the fixation devices 624, each fixation pin 610, 612 is retained between the platform 620 and the support 622. The fixation base 602 can include divot 630. The divot 630 can be associated with a parked configuration or home position, as described herein. The divot 630 is an example of a registration feature disposed on the system 600.

The fixation base 602 can include a first coupler 632. The first coupler 632 can couple to one or more components of the system 600. In some embodiments, the first coupler 632 is a universal coupler. The first coupler 632 can include an elongate post 635. In some embodiments, the first coupler 632 can have a regular shape (e.g., cylindrical). In some embodiments, the first coupler 632 can have an irregular shape (e.g., triangular, teardrop, elliptical, rectangular). The irregular shape may facilitate alignment of other components of the system 600 with the platform 620 of the fixation base 602. In the illustrated embodiment, the other components of the system 600 can mate with the first coupler 632 in a single orientation.

Figure 20E:
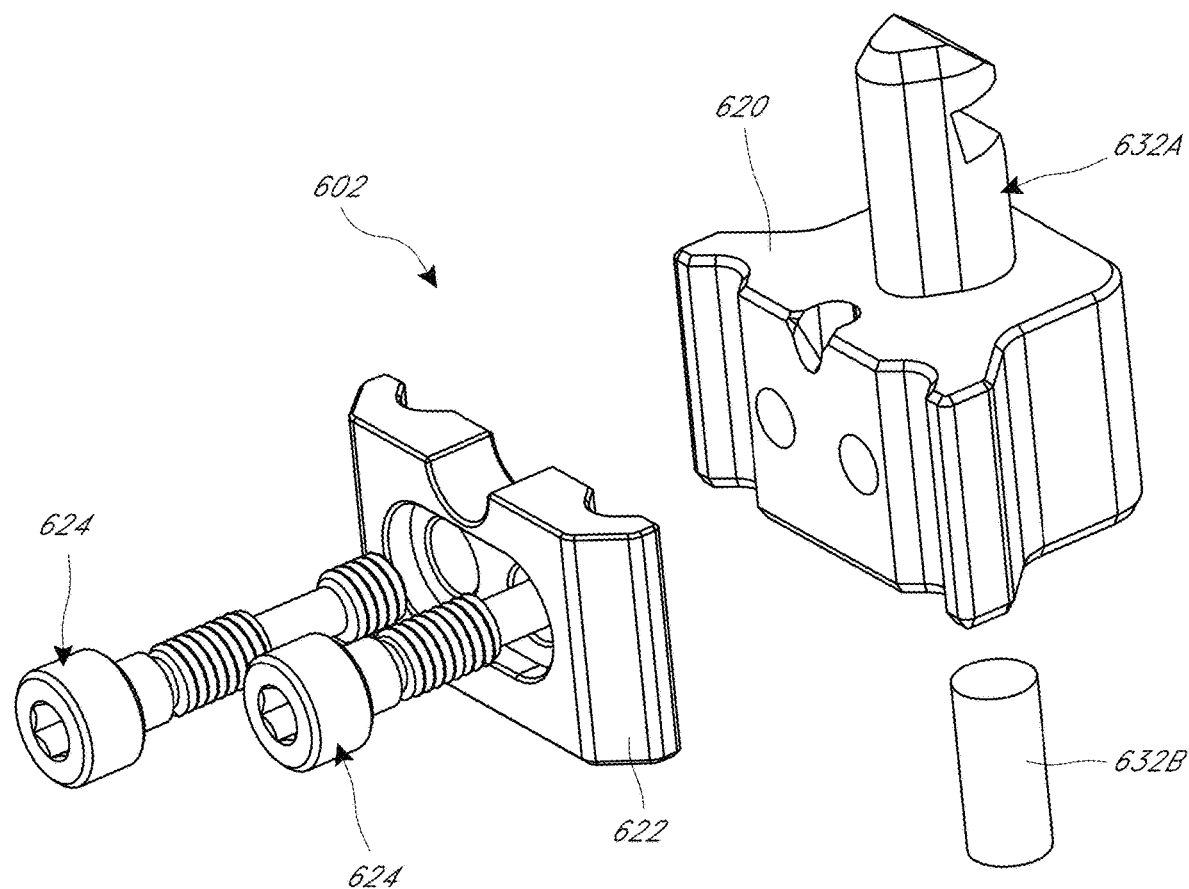
Figure 20F:
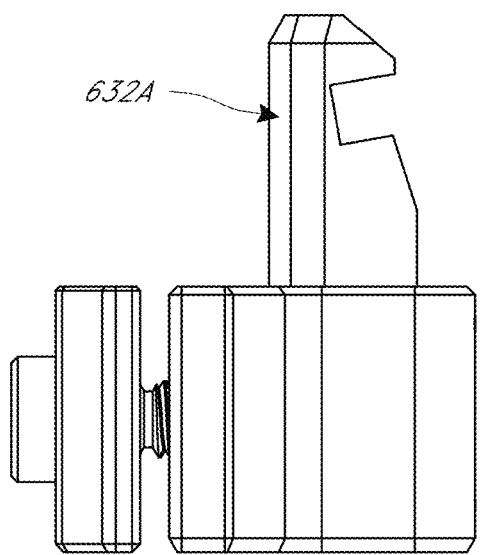
Figure 20H:
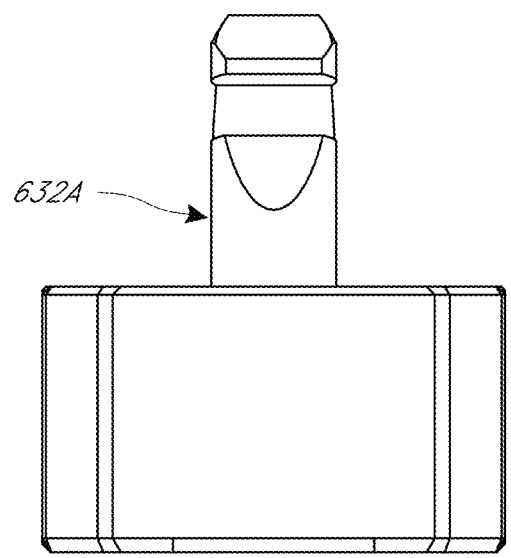
Figure 20G:
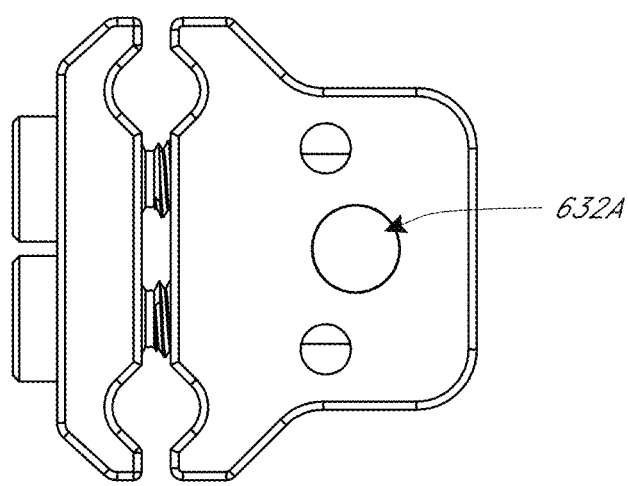
Figure 21A:
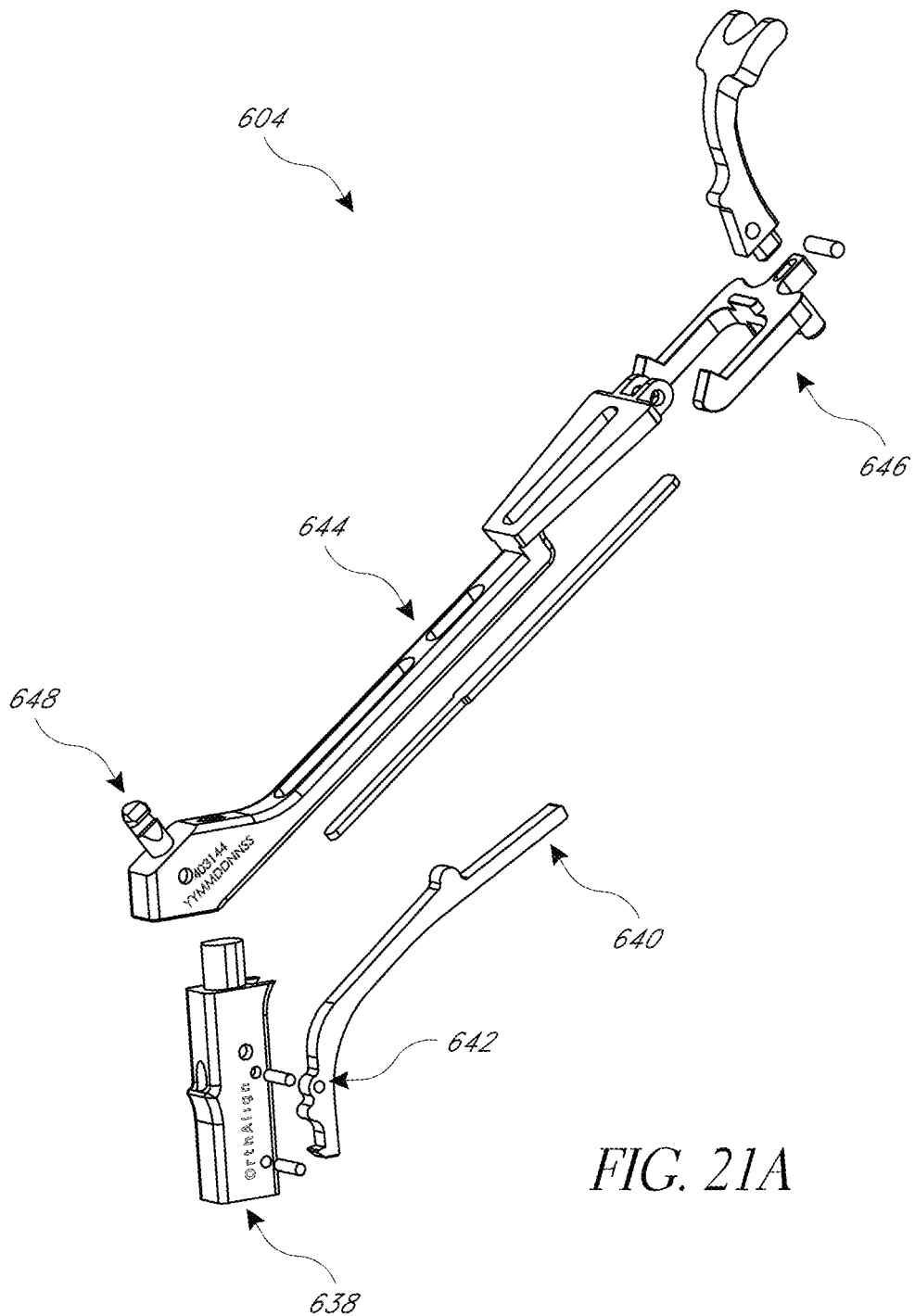
FIG. 21A-21G illustrate various view of embodiments of a first assembly of FIG. 18.
Figure 21B:
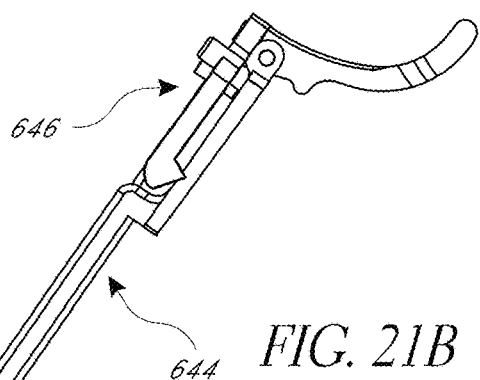
Figure 21C:
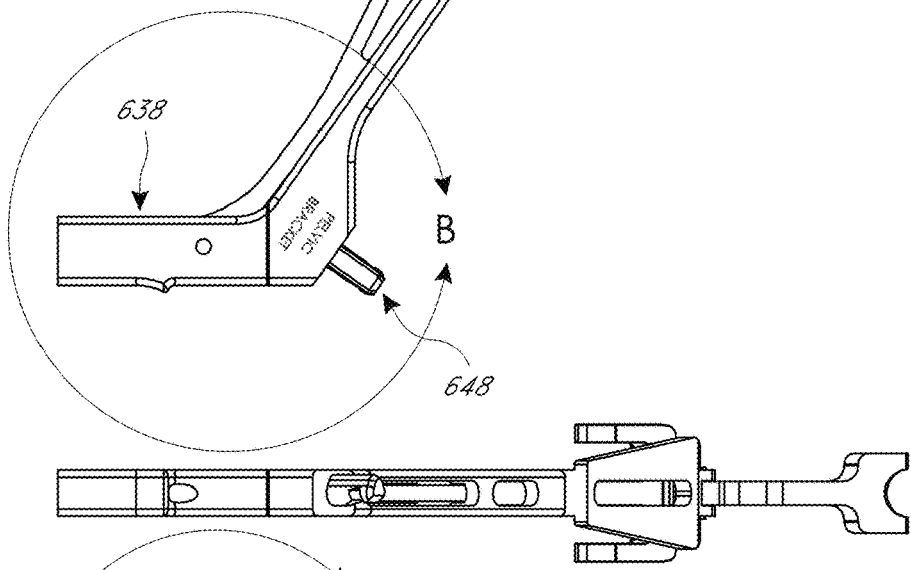
Figure 21D:
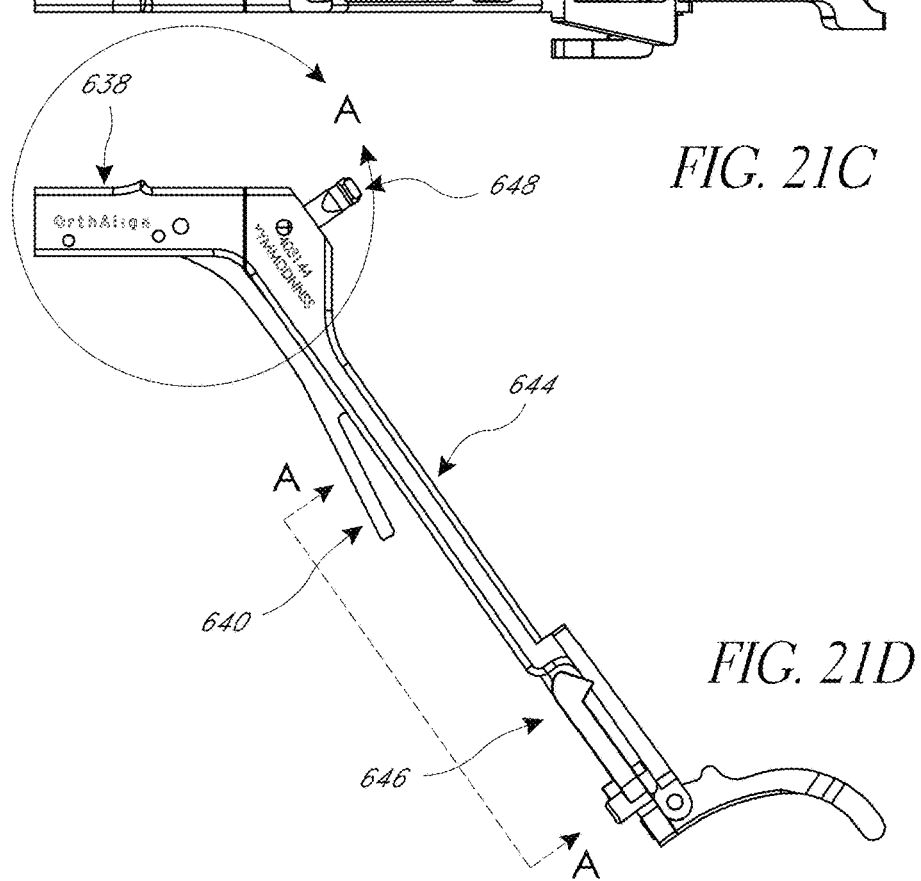
Figure 21E:
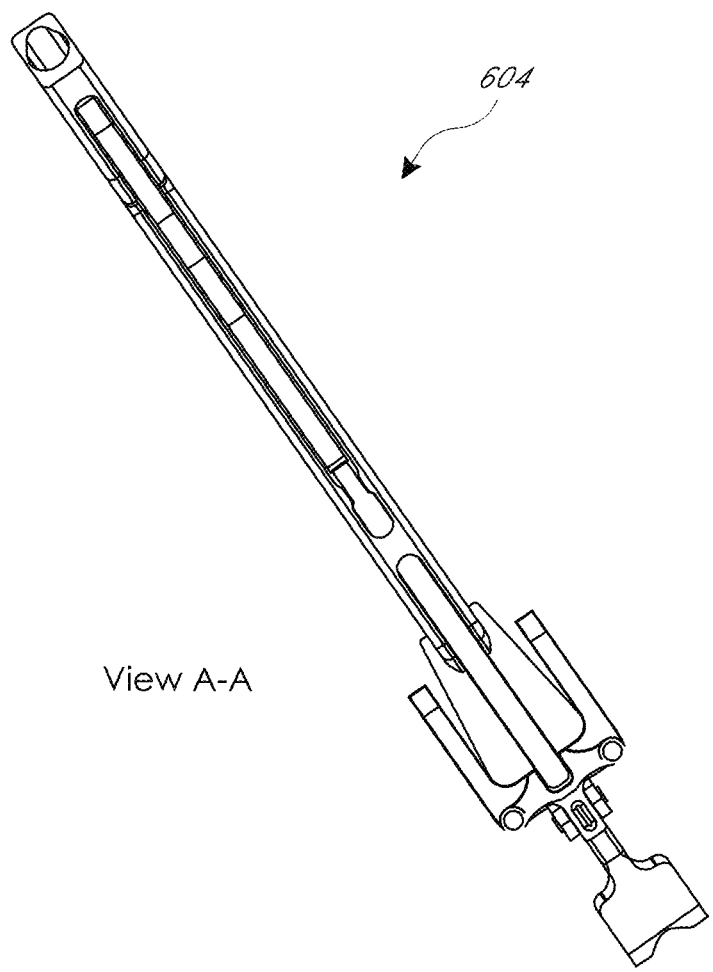
Figure 21F:
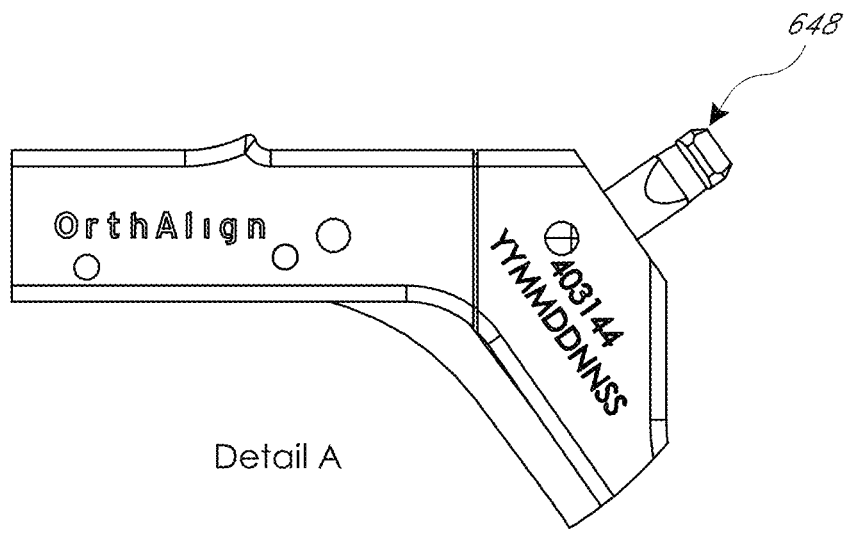
Figure 21G:
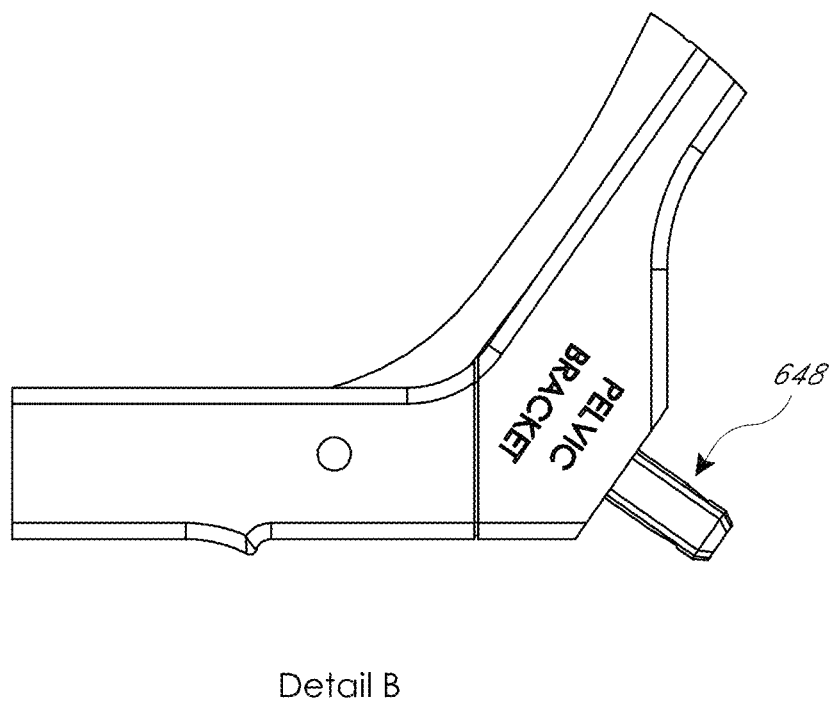

The first coupler 632 can include a slot 634. The slot 634 can be transverse to the longitudinal axis of the first coupler 632. The slot 634 can form an angle with an axis transverse to the longitudinal axis. This angle can be approximately 10°, between 5° and 15°, between 0° and 20°, etc. The slot 634 can be designed to interact with detents of other components of the system 600, as described herein. The first coupler 632 can include a tapered surface 636. The tapered surface 636 can facilitate entry of the first coupler 632 within other components of the system 600. The tapered surface 636 can move the detent of other components of the system 600 when the first coupler 632 is inserter within the other component. As shown in FIG. 20A, the first coupler 632 can include the elongate post 635 coupled to a hole on the top surface of the platform 620. As shown in FIG. 20E, in an alternative embodiment, the first coupler 632A is integrally formed with the platform 620. A post 632B can be inserted from a bottom surface of the platform 620 to support the first coupler 632A.

The system 600 can include the first assembly 604 shown in FIGS. 21A-21G. The first assembly 604 can include a pelvic bracket 638. In the illustrated embodiment, the pelvic bracket 638 can be substantially vertical in use, as shown in FIG. 18. The first assembly 604 can be designed to couple with the first coupler 632 of the fixation base 602. The first assembly 604 can include a lock lever 640. The lock lever 640 can be coupled to the pelvic bracket 638 with pivot pins. The lock lever 640 can be pivoted relative to the pelvic bracket 638. In some embodiments, the tapered surface 636 of the first coupler 632 causes the pivoting of the lock lever 640. In some embodiment, the surgeon causes the pivoting of the lock lever 640. The lock lever 640 can include a detent 642. The detent 642 is sized and shaped to be received within the slot 634. The engagement of the detent 642 and the slot 634 can rigidly couple the first assembly 604 with the fixation base 602.

The first assembly 604 can include an extension 644. The extension 644 can be coupled to the pelvic bracket 638. The extension 644 can include a mount 646 designed to couple with the surgical orientation device 172. In the illustrated embodiment, the mount 646 includes a lock and release lever that can pivot relative to the extension 644. The surgical orientation device 172 can include features to mate with the lock and release lever (not shown). Other configurations are contemplated. The surgical orientation device 172 is rigidly coupled to the extension 644 when engaged with the mount 646. The surgical orientation device 172 can be angled when coupled to the first assembly 604, as shown in FIG. 18. The surgical orientation device 172 can be angled approximately 35° from the horizontal axis. Other angles from the horizontal axis are contemplated, (e.g., 5°, 10°, 15°, 20°, 25°, 30°, 40°, 45°, 50°, 55°, 60°, 65°, 70°, 75°, 80°, or 85°, between 30°-40°, between 25°-45°). In some embodiments, the angle of the surgical orientation device 172 improves visibility. The angle is a compromise between tilting the surgical orientation device 172 up toward the surgeon and allowing another surgeon or surgical assistant on the other side of the patient to still see the display. One reason for angling the surgical orientation device 172 is that in an anterior approach, the surgeon stands toward the patient's feet while impacting the acetabular implant and a horizontal display would be difficult to see.

The surgical orientation device 172 detects orientation and rotation of the device 172 relative to a reference frame. The surgical orientation device 172 preferably comprises at least one sourceless sensor, such as an accelerometer, a gyroscope, or a combination of these sensors and other sensors. In some embodiments, the surgical orientation device 172 includes a three axis accelerometer to detect orientation relative to gravity and a plurality of gyroscopes to detect rotation. Other sensors could be used in various modifications. Examples of specific sensor combinations include Analog Devices ADIS 16445 and Invensense MPU-6050 or MPU-9150 among others. In some approaches, the surgical orientation device 172 can be disposable and so the sensors preferably are less expensive sensors. In some embodiments, the surgical orientation device 172 is disposable.

The extension 644 can include a second coupler 648. In some embodiments, the second coupler 648 is a universal coupler. The second coupler 648 can be substantially similar to the first coupler 632 described herein. The second coupler 648 can be designed to couple with the second assembly 606. The couplers 632, 648 are designed to secure to other components of the system 600 in a secure but releasable manner. The engagement between the coupler 632 and the first assembly 604 minimizes or prevents relative movement therebetween to avoid any mechanical relative movement during navigation procedures so that movement of the surgical orientation device 172 corresponds to movement of the hip. The second coupler 648 provides a stable manner to position the second assembly 606 relative to the first assembly 604.

The system 600 can include the second assembly 606 shown in FIG. 22A-22F. The second assembly 606 can include a probe bracket 652. In the illustrated embodiment, the probe bracket 652 can be substantially angled with respect to the pelvic bracket 638 when in use, as shown in FIG. 18. The second assembly 606 can be designed to couple with the second coupler 648 of the first assembly 604. The second assembly 606 can include a lock lever 654. The lock lever 654 can be coupled to the probe bracket 652 with pivot pins. The lock lever 654 can be pivoted relative to the probe bracket 652. In some embodiments, the tapered surface of the second coupler 648 causes the pivoting of the lock lever 654. In some embodiment, the surgeon causes the pivoting of the lock lever 654. The lock lever 654 can include a detent 656. The detent 656 is sized and shaped to be received within the slot of the second coupler 648. The engagement of the detent 656 and the slot can rigidly couple the second assembly 606 with the first assembly 604.

In the illustrated embodiment, the second assembly 606 includes a mount 658. The mount 658 can be coupled to the probe bracket 652 to allow relative movement therebetween. The mount 658 can be received within an opening in the probe bracket 652. The mount 658 can permit rotation about a longitudinal axis of the mount 658 relative to the probe bracket 652.

Figure 22A:
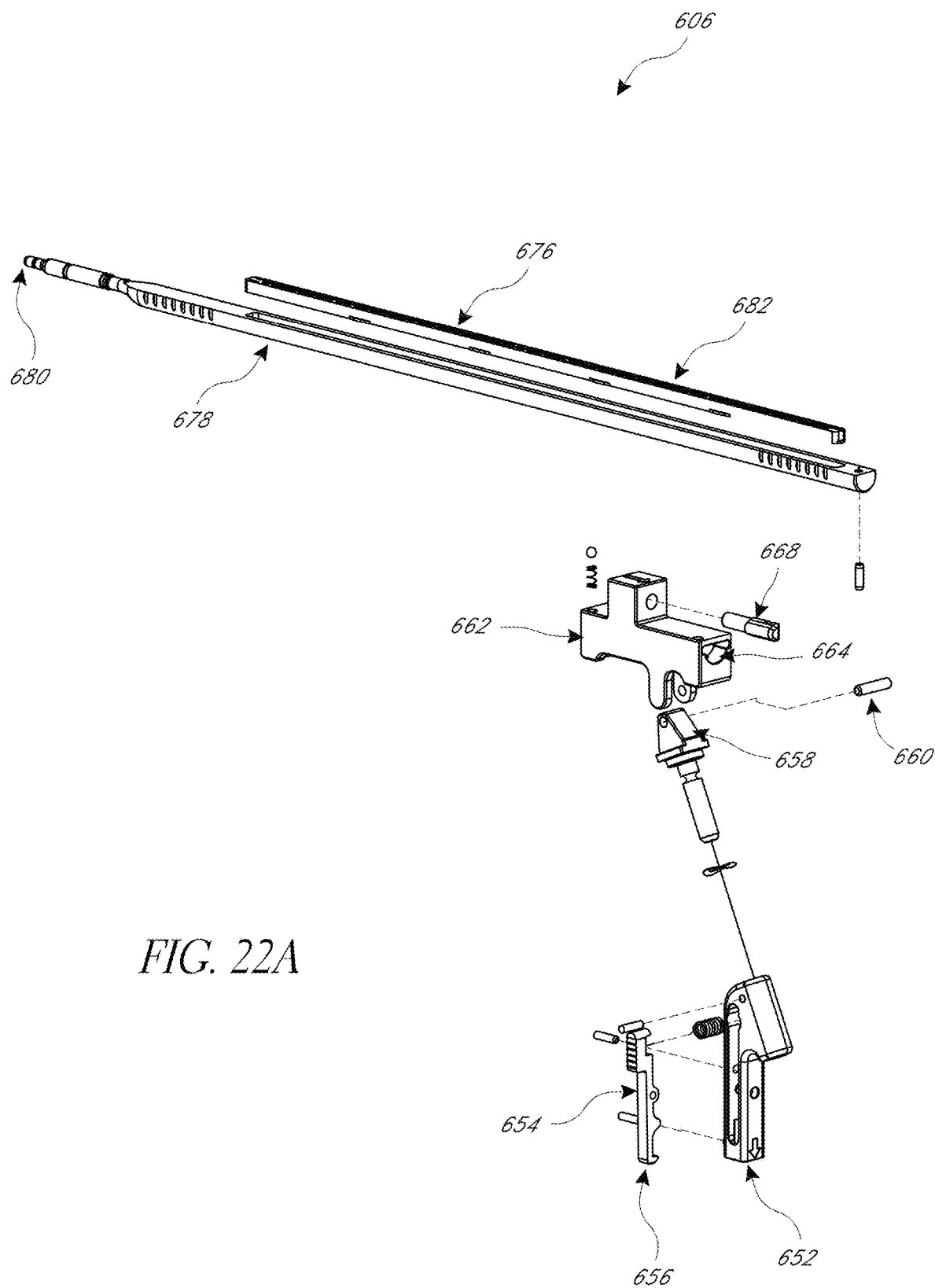
Figure 22D:
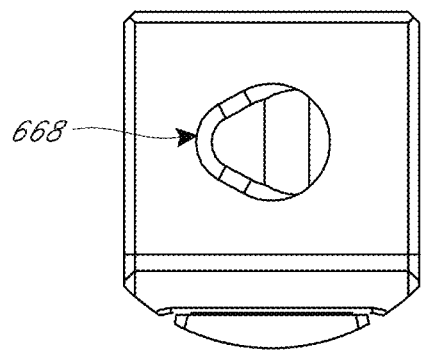
Figure 22E:
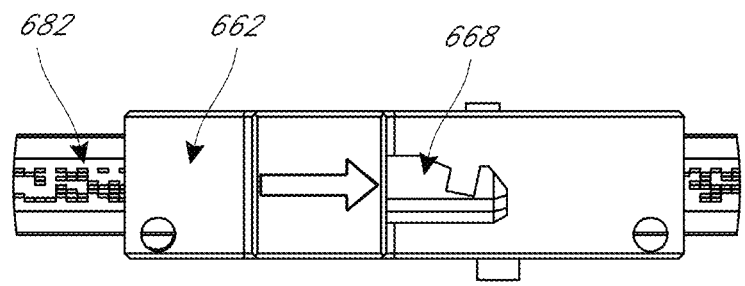
Figure 22F:
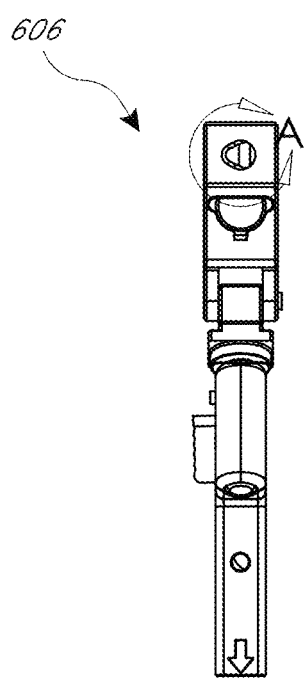

The second assembly 606 can include a dock 662. The dock 662 can be coupled to the mount 658 to allow relative movement therebetween. The dock 662 can be coupled to the mount 658 with one or more pivot pins 660. The dock 662 can have two degrees of freedom relative to the probe bracket 652 (e.g., rotational motion and pivoting motion). The dock 662 can include a sliding support with a through lumen 664. The through lumen 664 is sized to accept a probe 678. The probe 678 has a distal end 680 designed to touch locations, as described herein. The distal end 680 can be straight as shown in FIG. 22A. In other embodiments, the distal end 680 is slanted or curved, e.g., as shown in FIGS. 4 and 17.

The through lumen 664 of the dock 662 permits slideable extension of the probe 678. The dock 662 is movable relative to the probe bracket 652 (e.g., via rotation of the mount 658 and pivoting of the pivot pin 660). The dock 662 can be rotated about a longitudinal axis of the mount 658 to different rotational positions relative to the attachment location of the fixation pins 610, 612. This may require movement of the mount 658 in a rotational manner relative to the probe bracket 652. The dock 662 can be pivoted about the longitudinal axis of the pivot pins 660 to different positions relative to the attachment location of the fixation pins 610, 612. This may require movement of the dock 662 in a pivoting manner relative to the mount 658.

The probe 678 can be coupled to the dock 662 such that the probe 678 is movable relative to the probe bracket 652 (e.g., via rotation of the mount 658 and pivoting of the pivot pin 660). This maneuverability enables the distal end 680 of the probe 678 to pivot or rotate to contact anatomical landmarks, as discussed herein. The probe 678 can be slid relative to the dock 662 to different translational positions relative to the attachment location of the fixation pins 610, 612. The slideability of the probe 678 within the dock 662 enables the distal end 680 to move to reach anatomical landmarks in the same plane of the probe 678 but closer to or farther from the distal end 680.

The second assembly 606 permits a range of motion of a distal end 680 of the probe 678 to facilitate acquiring a plurality of landmarks that are different distances from the attachment location of the fixation pins 610, 612, as discussed further below. In other words, the distal end 680 of the probe 678 can be extended away from the axis of the sliding support of the dock 662 or can be retracted to a position closer to the axis of the sliding support of the dock 662.

Figure 23A:
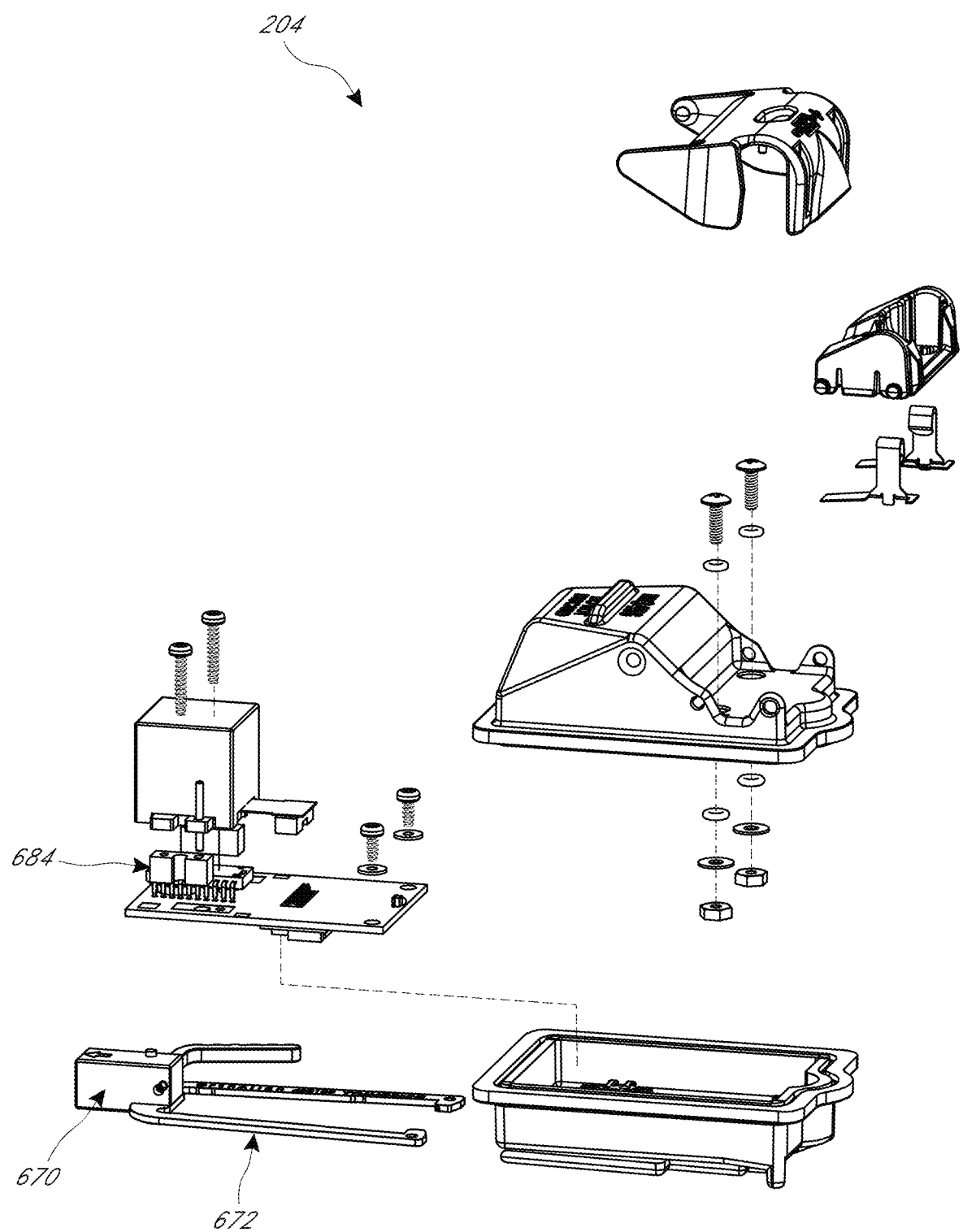
FIG. 23A-23C illustrate various view of embodiments of an orientation sensing device of FIG. 18.
Figure 23B:
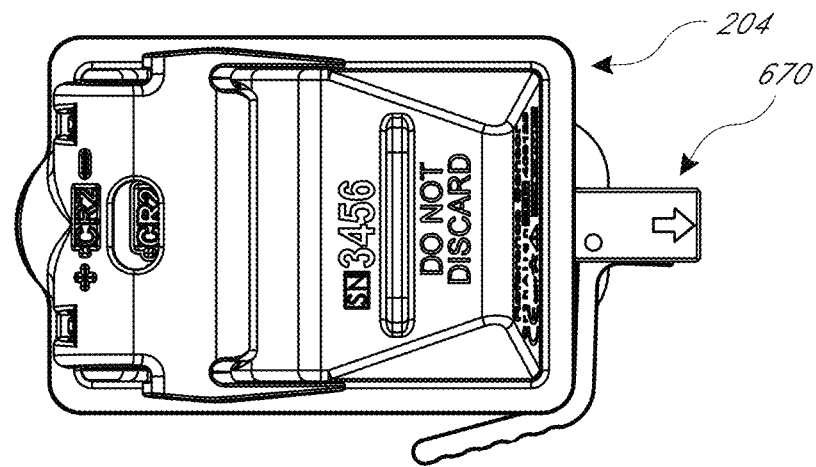
Figure 23C:
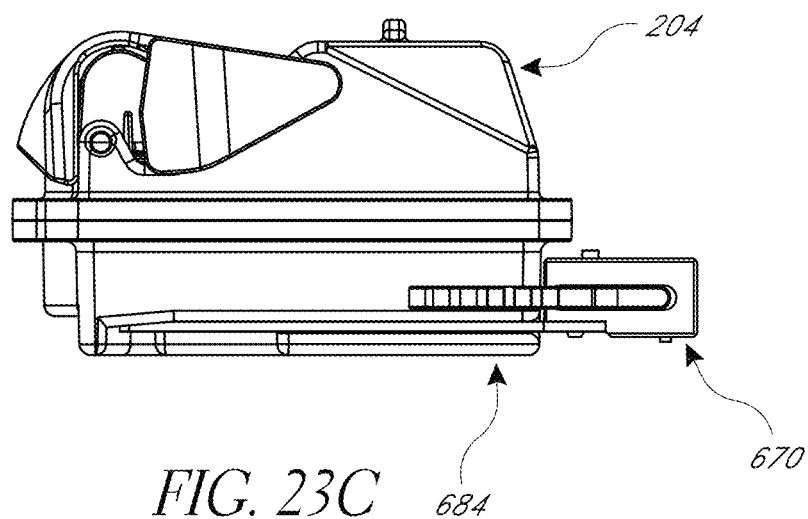

The dock 662 can include a third coupler 668. In some embodiments, the third coupler 668 is a universal coupler. In some embodiments, the third coupler 668 is identical or substantially similar to the second coupler 648. This permits the orientation sensing device 204 to couple to either the second coupler 648 or the third coupler 668, as described herein. In some embodiments, the third coupler 668 can be substantially similar to the first coupler 632 described herein. The third coupler 668 can be designed to couple with the orientation sensing device 204. FIG. 23A-23C illustrate an embodiment of the orientation sensing device 204. The second assembly 606 can include an extension 670. The extension 670 can couple to the third coupler 668 of the dock 662. The engagement between the third coupler 668 and the extension 670 minimizes or prevents relative movement therebetween to avoid any mechanical relative movement during navigation procedures. The extension 670 can include a mount 672 designed to couple with the orientation sensing device 204. In the illustrated embodiment, the mount 672 includes a lock and release lever that can pivot relative to the extension 670. The orientation sensing device 204 can include features to mate with the lock and release lever. Other configurations are contemplated. The orientation sensing device 204 is rigidly coupled to the extension 670 when engaged with the mount 672.

The orientation sensing device 204 can be angled when coupled to the second assembly 606, as shown in FIG. 18. The orientation sensing device 204 can be angled approximately 35° from the horizontal axis. Other angles from the horizontal axis are contemplated, (e.g., 5°, 10°, 15°, 20°, 25°, 30°, 40°, 45°, 50°, 55°, 60°, 65°, 70°, 75°, 80°, or 85°, between 30°-40°, between 25°-45°). In some embodiments, the angle of the orientation sensing device 204 improves visibility.

The orientation sensing device 204 detects orientation and rotation of the probe 678, as described herein. The orientation sensing device 204 preferably comprises at least one sourceless sensor, such as an accelerometer, a gyroscope, or a combination of these sensors and other sensors. In some embodiments, the orientation sensing device 204 includes a three axis accelerometer to detect orientation relative to gravity and a plurality of gyroscopes to detect rotation. Other sensors could be used in various modifications. In some embodiments, the orientation sensing device 204 is reusable.

Referring back to FIGS. 22A and 22C, the probe 678 can include a marking 682. The marking 682 can indicate length or extension of the probe 678 relative to the dock 662. The marking 682 can include a scale. In some embodiments, the marking 682 can be over a range of from about 8 inches, 10 inches, 12 inches, approximately 8-12 inches, etc. The marking 682 can be printed on the probe 678. In some embodiments, the marking 682 can be on a separate component such as a probe inlay 676. The probe inlay 676 can be received within a portion of the probe 678. In some embodiments, the probe inlay 676 is separated a distance from the distal end 680 of the probe 678.

Referring to FIG. 23C, the system 600 can include a camera 684. The camera 684 can capture images of the marking 682. In some embodiments, the camera 684 and/or the orientation sensing device 204 can include a light to illuminate the marking 682. In some embodiments, the light is a LED. In some embodiments, the dock 662 includes a window to permit the camera 684 to capture images. In other embodiments, the camera 684 captures images of the marking 682 extending beyond the dock 662. The camera 684 can read the marking 682 to provide accurate determination of the translational position of the probe 678 relative to the dock 662. This can enable one of the sensors in the orientation sensing device 204 to be eliminated or inactivated. In another embodiment, camera data derived from the marking 682 can be used to confirm the data from sensors in the orientation sensing device 204.

In some embodiments, the camera 684 is integrally formed with the orientation sensing device 204. In some embodiments, the camera 684 is a separate component from the orientation sensing device 204. The camera 684 can be held in a fixed position relative to the dock 662. The marking 682 can be positioned on the probe 678 beneath the camera 684 when the probe 678 is positioned within the through lumen 664. The camera 684 can be directly above the marking 682. The camera 684 can be fixed relative to the through lumen 664 of the dock 662. The dock 662, the camera 684 and the orientation sensing device 204 can move as a unit to allow positioning of the probe 678. One advantage of orienting the orientation sensing device 204 as illustrated in system 600 is improved visibility. The lower-profile construct is less likely to obstruct the user's view. One advantage of orienting the orientation sensing device 204 as illustrated in system 600 is ease of manufacturing. The camera 684 can be mounted flush on the circuit board. The corresponding transparent window (not shown), which can allow the camera 684 to capture images, in the housing of the orientation sensing device 204 is oriented in the direction of the mold pull. The shorter distance to the marking 682 also better accommodates the available camera, which has a short focal length. In some embodiments, the camera 684 captures an image though a lumen (not shown) in the dock 662. One advantage of having the camera 684 read the marking 682 through the lumen is this shields the camera 684 from outside light sources. Light, such as OR light, may interfere with the camera function such as the function of capturing an image of the marking 682. In other embodiments, the camera 684 may incorporate a shroud feature to block ambient light. In some embodiments, the camera 684 is pointed downward from a back side of the orientation sensing device 204. In some embodiments, the orientation sensing device 204 shields camera 684 from light.

Figure 24A:
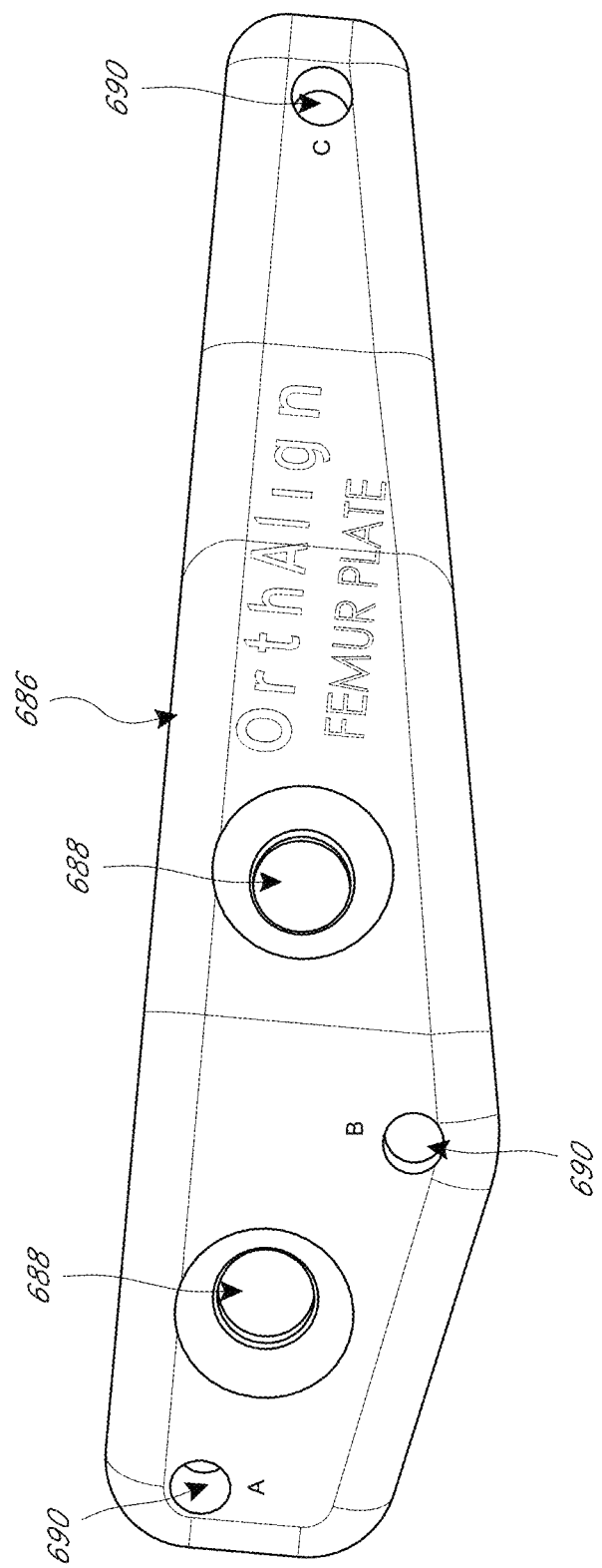
FIG. 24A-24B illustrate various view of embodiments of a femur tracker of FIG. 18.
Figure 24B:
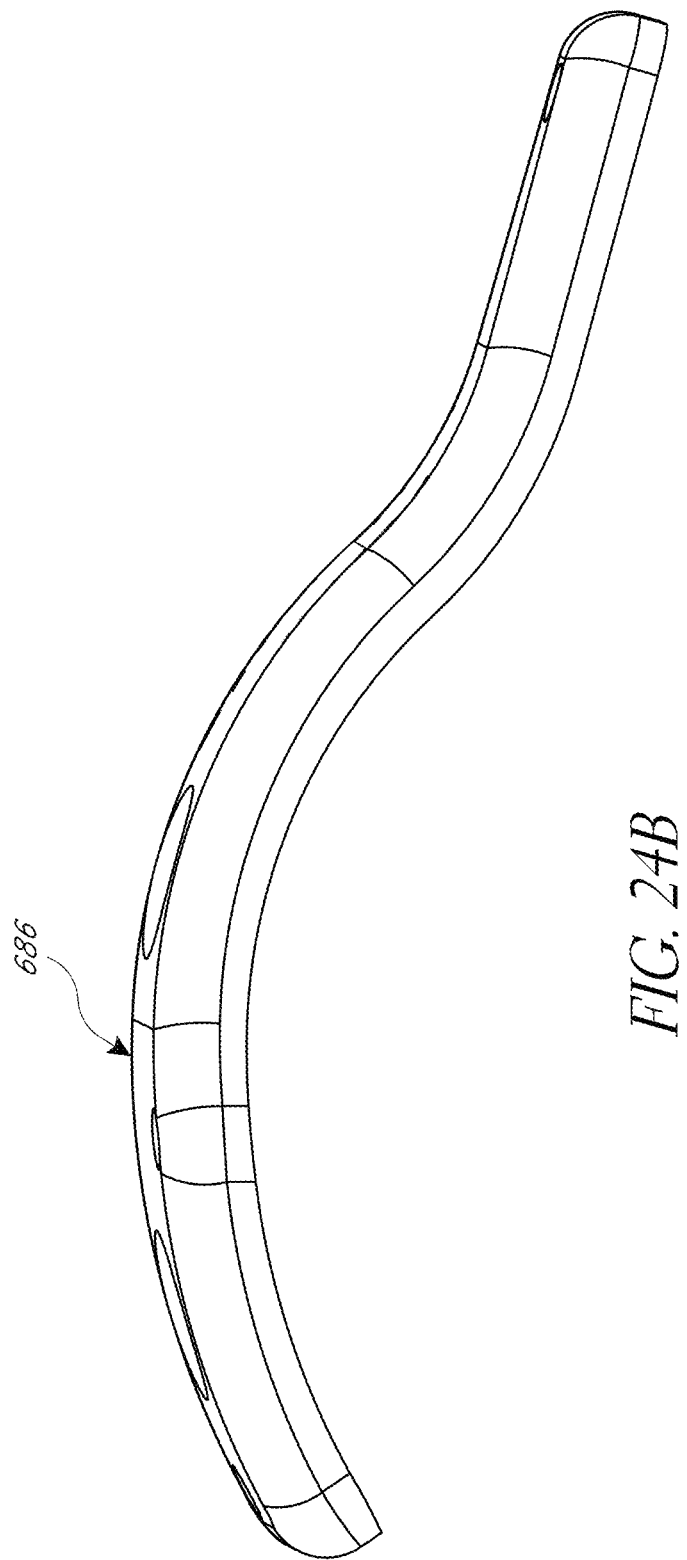

The system 600 can include a femur tracker 686 as shown in FIG. 24A-24B. The femur tracker 686 can be coupled to the femur as shown in FIG. 18. The femur tracker 686 can be used to track the position of the femur during the procedure. The femur tracker 686 can include one or more fixation structures. In the illustrated embodiment, the fixation structures are holes 688. The holes 688 are sized to permit a fastener therethrough (e.g., a screw, pin, k-wire, etc.). The femur tracker 686 can include one or more points 690. The points 690 can include Points A, B, C as described herein and shown in FIG. 24A. The femur tracker 686 can include three points 690. Other configurations are contemplated (e.g., one point, two points, four points, five points, etc.). The points 690 can include divots as shown in FIG. 24A. The points 690 can include markings. The femur tracker 686 can provide more consistent and repeatable results than a marking the femur. The femur tracker 686 can provide points 690 which are fixed relative to the femur. The femur tracker 686 can provide multiple points 690. One advantage to registering multiple points on the femur is that the software in the surgical orientation device 172 can then correct for changes in the femur angle with respect to the pelvis between the baseline measurement and the later measurement. The baseline measurement can be a preoperative measurement. The later measurement can be after the shell is positioned in the acetabulum. In some embodiments, the points 690 are located on the femur tracker 686. In some embodiments, one or more points are marks located directly on the femur Fm and one or more points are located on the femur tracker 686. In some embodiments, one or more points are marks located directly on the femur Fm. One advantage to using a femur tracker 686 is that the marks are easier to find for repeat registrations. One advantage to using a femur tracker 686 is that spacing the points 690 at known distances from each other allows software checks to verify that the correct points 690 are registered in the right sequence. One advantage to using a femur tracker 686 is that spacing the points 690 at known distances from each other allows software checks to verify that the femur and the pelvis have not moved in between point registrations. One advantage to using marks located directly on the femur Fm is that the components are not affixed to the femur. The marks do not require any drill holes or fasteners. This may prevent future fractures or damage to the proximal end of the femur. The femur tracker 686 can be a unitary structure. The femur tracker 686 can be a low profile component. The femur tracker 686 can be coupled to the femur throughout the procedure. The femur tracker 686 can form a smooth surface preventing the femur tracker 686 from hooking soft tissue. The femur tracker 686 can form a smooth surface preventing the femur tracker 686 from loosening in the bone.

FIG. 18 illustrates a parked configuration or home position of the probe 678. In some embodiments, a portion of the distal end 680 is moved into engagement with the platform 620. In some techniques, the distal end 680 of the probe 678 engages the divot 630 of the platform 620. The parked configuration enables the navigation system 600 to manage errors that can compound in some inertial sensors. For example, the parked configuration advantageously includes the ability to position and hold the devices 172, 204 stable for substantially no relative movement. Also the relative position of the sensors in the devices 172, 204 when coupled with the first and second assemblies 604, 606 can be known from the geometry of the first assembly 604 and the second assembly 606. For example, in one embodiment, gyroscopic sensors in the surgical orientation device 172 and in the orientation sensing device 204 can be synchronized when a stable and known orientation is detected and one or more of the gyroscopes, e.g., the gyroscope in the orientation sensing device 204, can be zeroed after that condition is met. Further techniques employing the parked configuration will be discussed further below.

At the surgeon's discretion the system 600 can be used to navigate a condition of the femur prior to hip replacement. The orientation sensing device 204 can be initialized or zeroed such as by placing it back in the parked configuration on the platform 620 as in FIG. 18. Thereafter, the distal end 680 of the probe 678 can be brought into contact with the points 690. The orientation sensing device 204 can be stationary relative to the dock 662. The surgical orientation device 172 can be stationary relative to the pelvis. The surgical orientation device 172 can be signaled to record the orientation of the orientation sensing device 204. The camera 684 can record the extension of the probe 678 relative to the dock 662. The distance from the camera 684 to the distal end 680 of the probe 678 or the distance from the system 600 to the anatomy being registered can then be recorded in the surgical orientation device 172. The position can be based on reading by the camera 684 of the marking 682. The distance can be captured automatically by the camera 684. In other embodiments, the user reads a measurement from the marking 682 and inputs the distance into the surgical orientation device 172.

The system 600 can include features that provide notable advantages for the surgeon. The system 600 can include modular instruments. In some embodiments, the fixation base 602 can include a low profile platform 620 and a low profile support 622. The low profile fixation base 602 can prevent the obstruction of the surgical field. The fixation base 602 can be easily removed when not in use. The clamping action between the platform 620 and the support 622 allow the fixation base 602 to be easily removed from the fixation pins 610, 612. In the illustrated embodiment, rotation of the fixation devices 624 can cause the support 622 to move away from the platform 620. The channels 626, 628 can increase in diameter. The platform 620 and the support 622 can be decoupled from the fixation pins 610, 612.

The one or more fixation pins 610, 612 can be spaced apart from one another. This can permit the fixation pins 610, 612 to be driven into different locations on the anatomy of the patient. In the illustrated embodiment, two fixation pins 610, 612 are provided. The utilization of two or more fixation pins may provide more stability for the fixation base 602. The fixation pins 610, 612 allow the surgeon much more flexibility when anchoring the system 600. The surgeon has flexibility in the location and/or depth of placement. The surgeon can optimize the penetration angle. In some techniques, the surgeon can enter the bone more perpendicularly. The fixation pins 610, 612 can be placed in locations to avoid sensitive anatomical structures.

The system 600 can include one or more couplers. The system 600 can include the first coupler 632 coupled to the platform 620 of the fixation base 602. The first coupler 632 can couple the fixation base 602 to the first assembly 604 as shown in FIG. 18. The first coupler 632 can couple the fixation base 602 to any other component of the system 600. The system 600 can include the second coupler 648 coupled to the first assembly 604. The second coupler 648 can couple the first assembly 604 to the second assembly 606 as shown in FIG. 18. The second coupler 648 can couple the first assembly 604 to the extension 670 as described herein. The second coupler 648 can couple the first assembly 604 to any other component of the system 600. The system 600 can include the third coupler 668 coupled to the dock 662 of the second assembly 606. The third coupler 668 can couple the dock 662 to the extension 670 as shown in FIG. 18. The third coupler 668 can couple the second assembly 606 to any other component of the system 600.

Other tools or assemblies, such as the tools and assemblies described herein can include one or more couplers. The couplers allow components to rigidly couple. In some embodiments wherein the couplers have an irregular shape, the couplers can couple components in a single orientation. The slot of the couplers, such as slot 634 of the first coupler 632, can be angled relative to the horizontal axis. This can prevent inadvertent detachment of the components from the couplers.

The system 600 can include the camera 684. The camera 684 can be a component of the orientation sensing device 204. The orientation sensing device 204 can be coupled to the dock 662 with the third coupler 668. The camera 684 can be in a fixed location relative to the probe 678. The camera 684 can remain fixed in position as the probe 678 is moved. The camera 684 can be oriented such that the camera 684 faces the marking 682. In addition, the orientation sensing device 204 can be in a fixed location relative to the probe 678. The orientation sensing device 204 can remain fixed in position as the probe 678 is moved. The orientation sensing device 204 can be oriented such that a flat back side of the orientation sensing device 204 faces the marking 682.

The camera 684 can capture an image of the marking 682. The image can correspond with a distance of the probe 678. The distance changes as the probe 678 slides through the through lumen 664 of the dock 662. In some embodiments, the camera 684 can read a binary code of the marking 682. In some embodiments, the camera 684 can read a scale or other markings. The camera 684 can be positioned directly over the marking 682.

The distance related to the extension of the probe 678 can be used in conjunction with the orientation and positional data from the orientation sensing device 204. The surgical orientation device 172 can use the length measurement from the camera 684 and the data from the orientation sensing device 204 to determine the location of the distal end 680 of the probe 678.

Figure 25A:
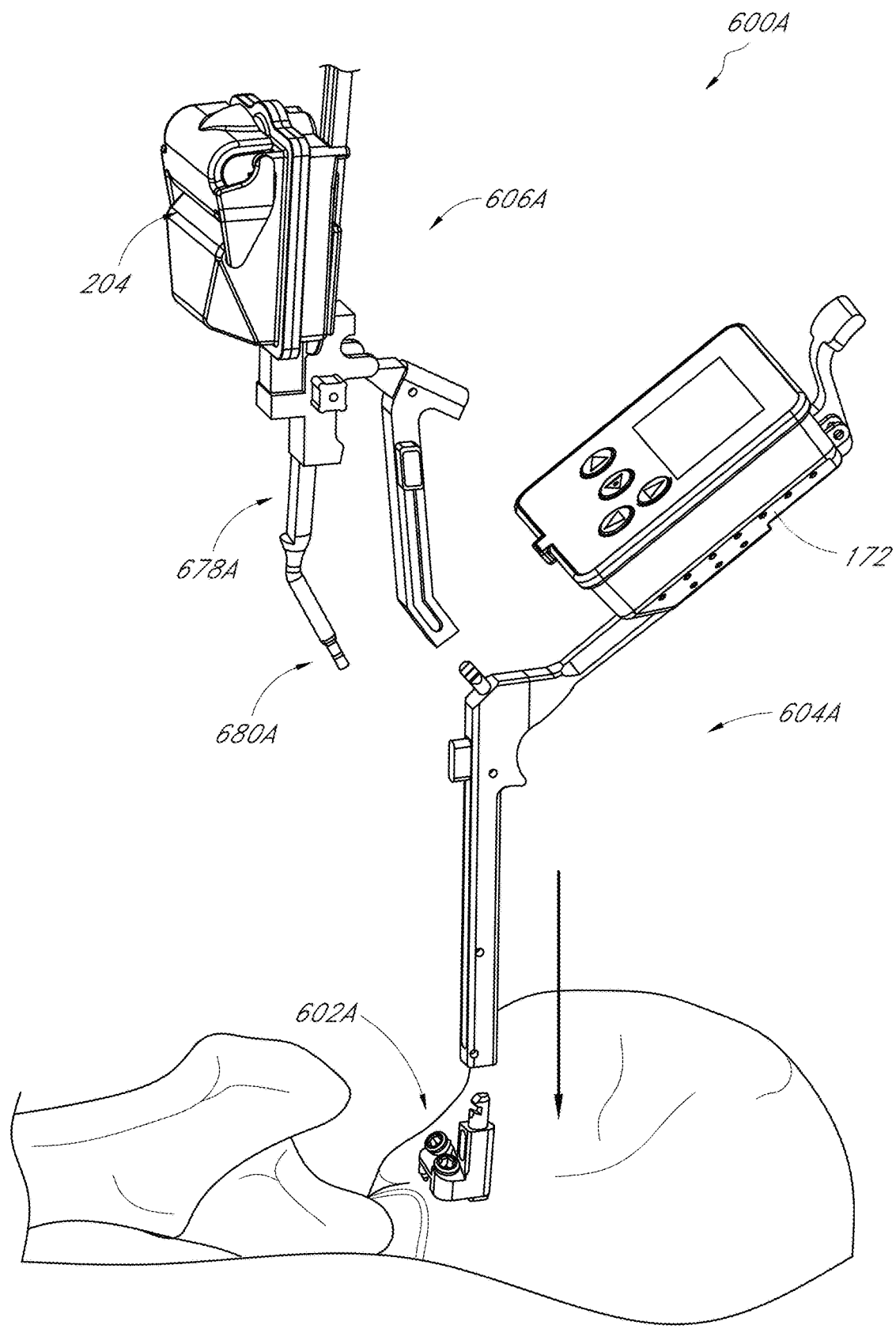
FIGS. 25A-25C are views of a hip navigation system applied to a patient.
Figure 25B:
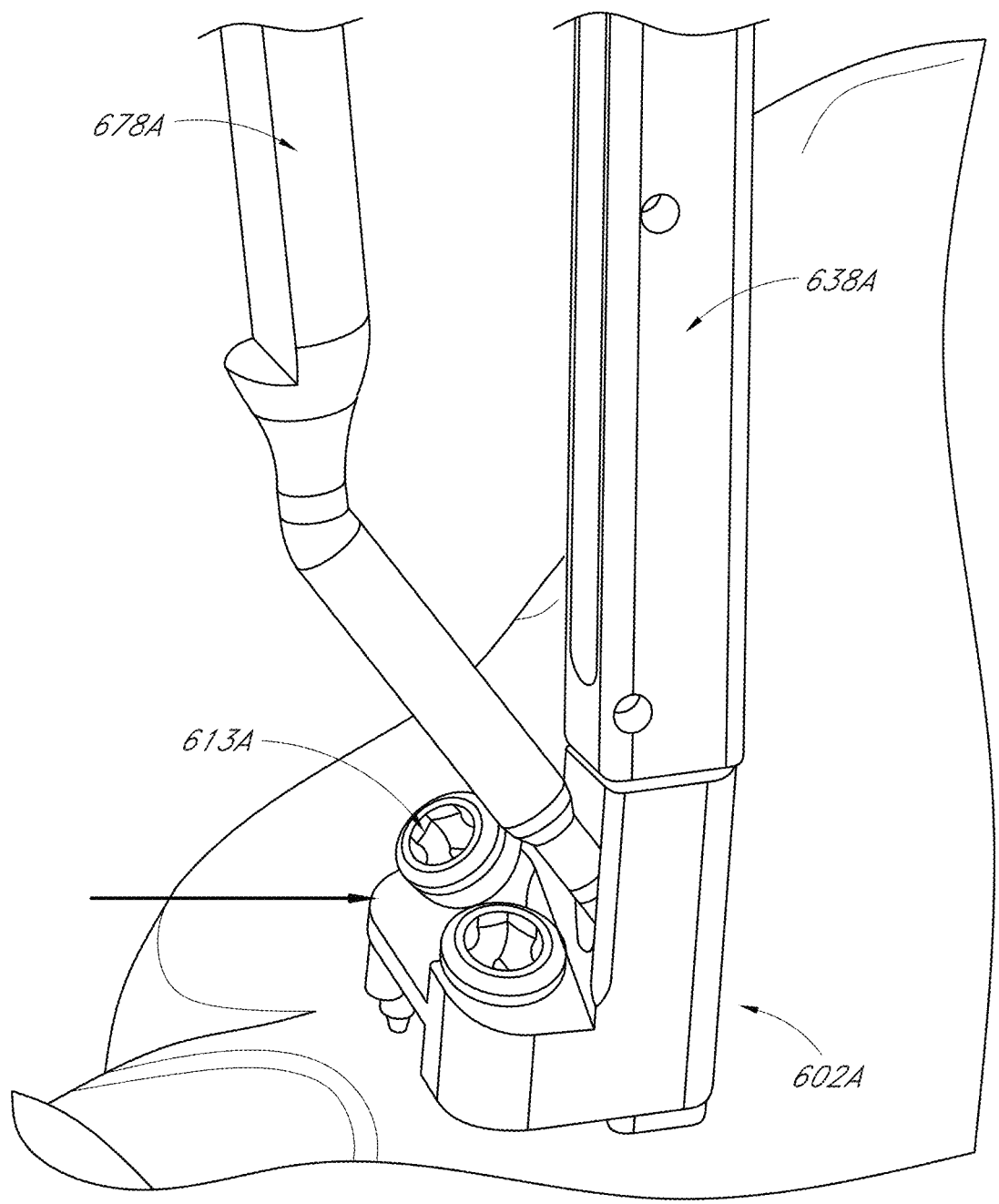
Figure 25C:
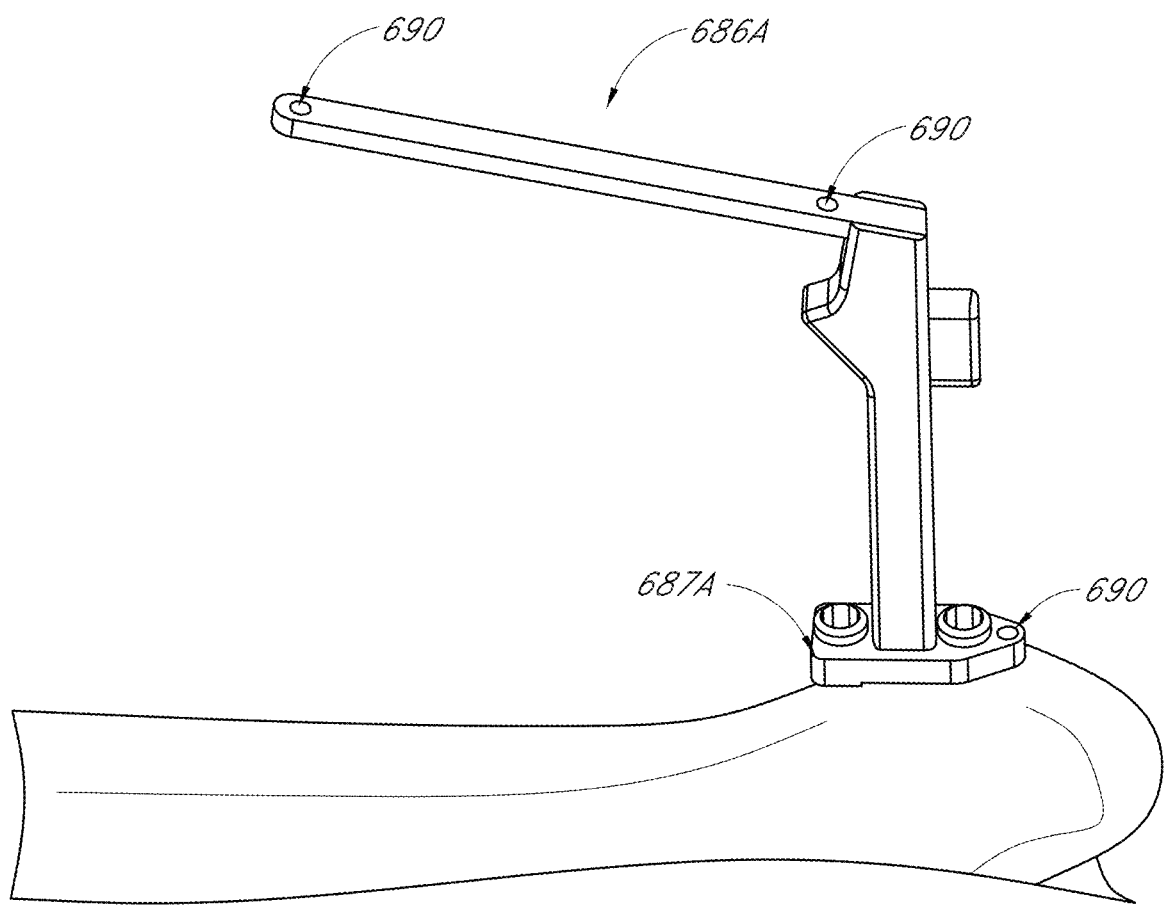

FIGS. 25A-25C show a hip navigation system 600A adapted to navigate a hip joint procedure with reference to anatomical landmarks. The system 600A is shown mounted on a pelvis in a posterior approach in FIGS. 25A-25C. The system 600A can include any of the features described above with reference to system 600 and any component described herein. The system 600A can be used in any technique or method step described herein. As one example, the system 600A can include the surgical orientation device 172 described herein. As another example, he system 600A can include the orientation sensing device 204 described herein. As an example, the system 600A includes a camera 684 described herein.

The system 600A can include a fixation base 602A, a first assembly 604A and a second assembly 606A. The first assembly 604A is rigidly connected to the hip in the illustrated configuration so that motion of the hip cause corresponding motion of sensor(s) in the first assembly 604A as discussed below. Sensing this motion enables the system 600A to eliminate movement of the patient as a source of error in the navigation. The second assembly 606A provides a full range of controlled motion and sensor(s) that are able to track the motion, in concert with sensor(s) in the first assembly 604A.

Figure 26B:
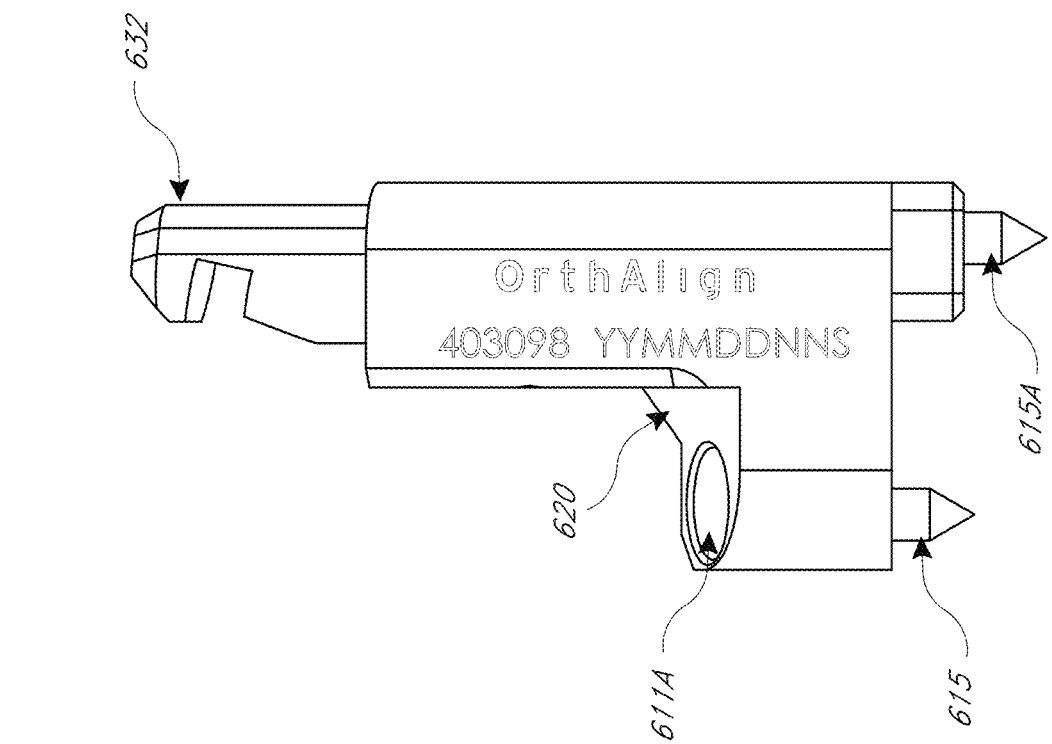
FIG. 26A-26C illustrate various view of embodiments of a fixation base of FIG. 25A.
Figure 26A:
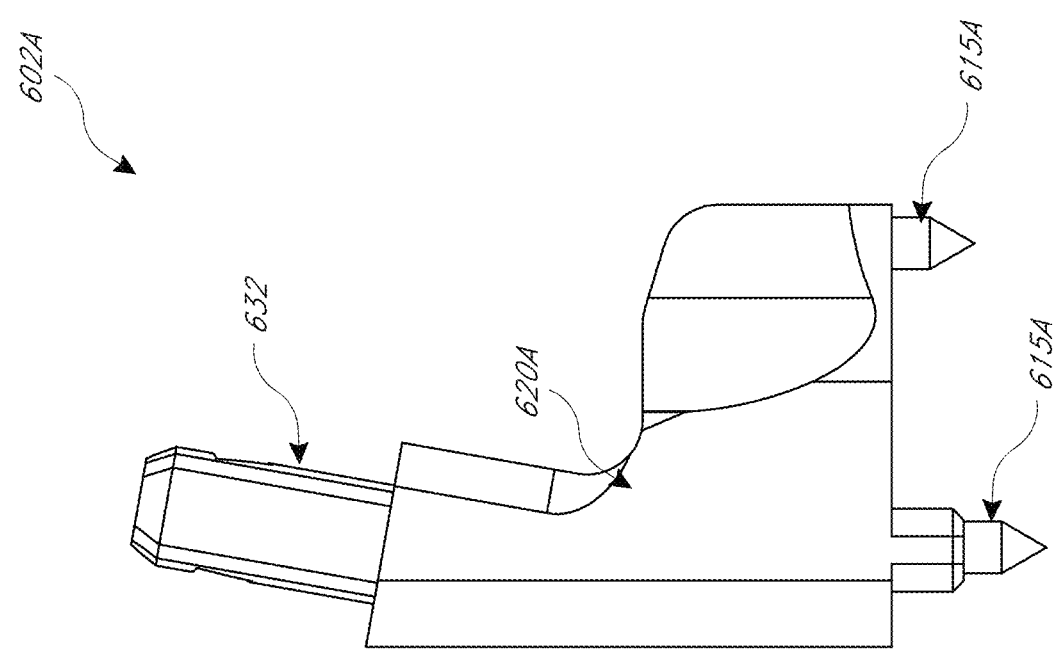
Figure 26C:
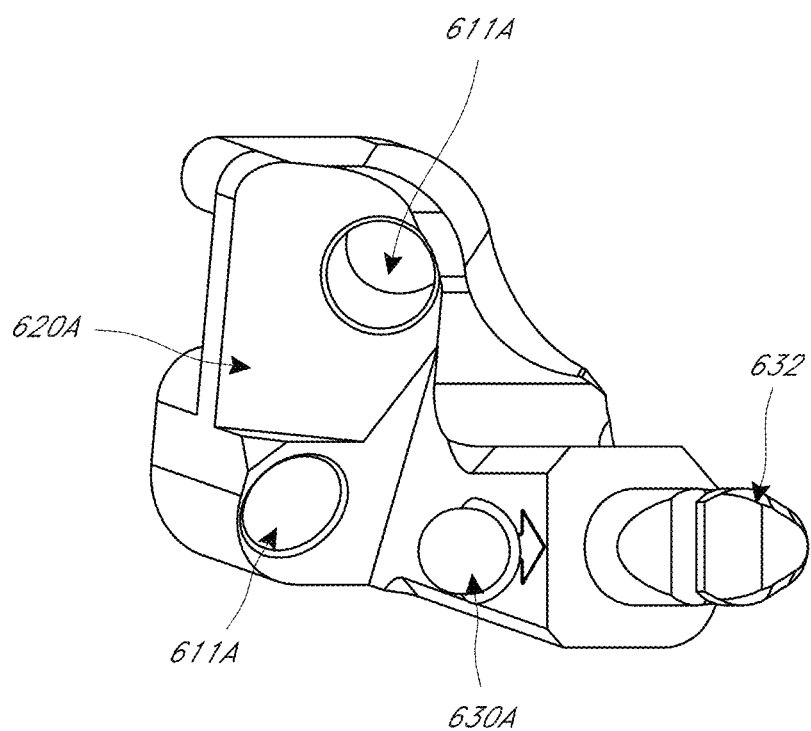

The system 600A can include the fixation base 602A as shown in FIGS. 26A-26C. The fixation base can include a platform 620A. The platform 620A can include one or more holes 611A. The holes 611A can be sized to accept a fastener 613A to secure the fixation base 602A to the bone, shown in FIG. 25B. The platform 620A can include one or more spikes 615A. The spikes 615A can secure the fixation base 602A to the bone. The fixation base 602A can include divot 630A. The divot 630A can be associated with a parked configuration or home position, as shown in FIG. 25B. The divot 630A can be a registration feature of the system 600.

Referring to FIG. 25B, each fastener 613A can be driven into the ilium on the pelvis. As discussed further below, each fastener 613A can be coupled with other bones in other techniques. For example, one of the fasteners 613A can be coupled with the ischium or the pubis. In some techniques, one of the fasteners 613A is mounted to a pelvic bone but not at a landmark. One of the fasteners 613A can be coupled at a point superior to the superior-most point on the acetabular rim. In some techniques, one of the fasteners 613A is about 10 mm above the superior-most point on the acetabular rim. In some techniques, three or more anatomical landmarks disposed about the acetabulum can be acquired, as discussed below. When one of the fasteners 613A is coupled with a landmark, only two additional landmarks are acquired in some embodiments as discussed below. One reason for mounting the fastener 613A away from the landmarks is that the landmarks may not be visible or accessible before dislocating the hip joint. If the clinician wishes to use the system 600A to reference the femur as discussed below, it may be required to mount the fasteners 613A away from the landmarks.

The fixation base 602A can include the first coupler 632. The first coupler 632 can couple to one or more components of the system 600A. The system 600A can include the first assembly 604A shown in FIGS. 25A-25B. The first assembly 604A can include a pelvic bracket 638A. In the illustrated embodiment, the pelvic bracket 638A can be substantially vertical in use, as shown in FIG. 25A. The first assembly 604A can be designed to couple with the first coupler 632 of the fixation base 602A. The pelvic bracket 638A of system 600A can be longer than the pelvic bracket 638 of system 600.

The system 600A can include the second assembly 606A shown in FIG. 25A. The distal end 680A of the probe 678A can pivot or rotate to contact anatomical landmarks, similar to probe 678A described herein. The distal end 680 can be angled, slanted or curved. The curvature of the distal end 680A of the probe 678A can facilitate the acquisition of landmarks or other points as described herein. The probe 678A can be slid to different translational positions relative to the attachment location of the fixation base 602A. The second assembly 606A permits a range of motion of a distal end 680A of the probe 678A to facilitate acquiring a plurality of landmarks that are different locations from the attachment location of the fixation base 602A.

Figure 28C:
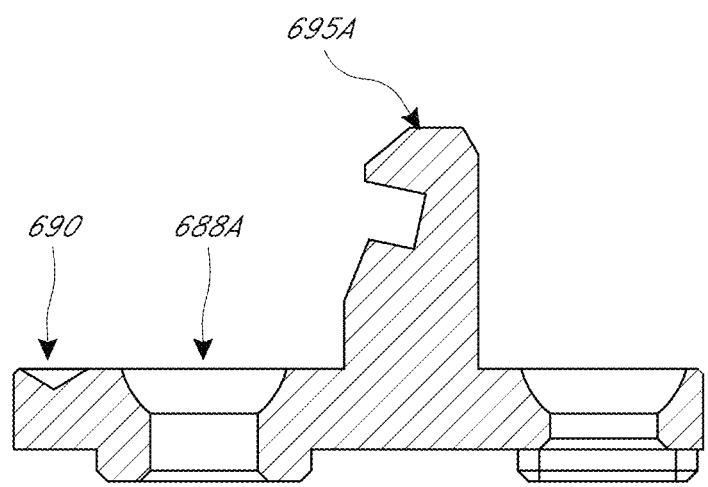

The system 600A can include a femur tracker 686A as shown in FIG. 25C. The femur tracker 686A can be coupled to a femur base 687A as shown in FIG. 25C. The femur tracker 686A can be used to track the position of the femur during the procedure. The femur base 687A can include one or more fixation structures. In the illustrated embodiment, the fixation structures are holes 688A shown in FIG. 28C. The holes 688A are sized to permit a fastener therethrough (e.g., a screw, pin, k-wire, etc.). The femur base 687A can include spikes 685A as shown in FIGS. 28A-28B. The spikes 685A can anchor the femur base 687A to the femur.

The femur tracker 686A and/or the femur base 687A can include one or more points 690. The points 690 can include Points A, B, C as described herein. The femur tracker 686A and/or the femur base 687A can include three points 690. In the illustrated embodiment, the femur base 687A includes one point 690 and the femur tracker 686A includes two points 690. Other configurations are contemplated (e.g., one point on the femur base 687A, two points on the femur base 687A, three points on the femur base 687A, four points on the femur base 687A, five points on the femur base 687A; one point on the femur tracker 686A, two points on the femur tracker 686A, three points on the femur tracker 686A, four points on the femur tracker 686A, five points on the femur tracker 686A, etc.). The points 690 can include divots. The points 690 can include markings. The femur tracker 686A and the femur base 687A can be separate components. In other embodiments, the femur tracker 686A and the femur base 687A can be a unitary structure.

Figure 27A:
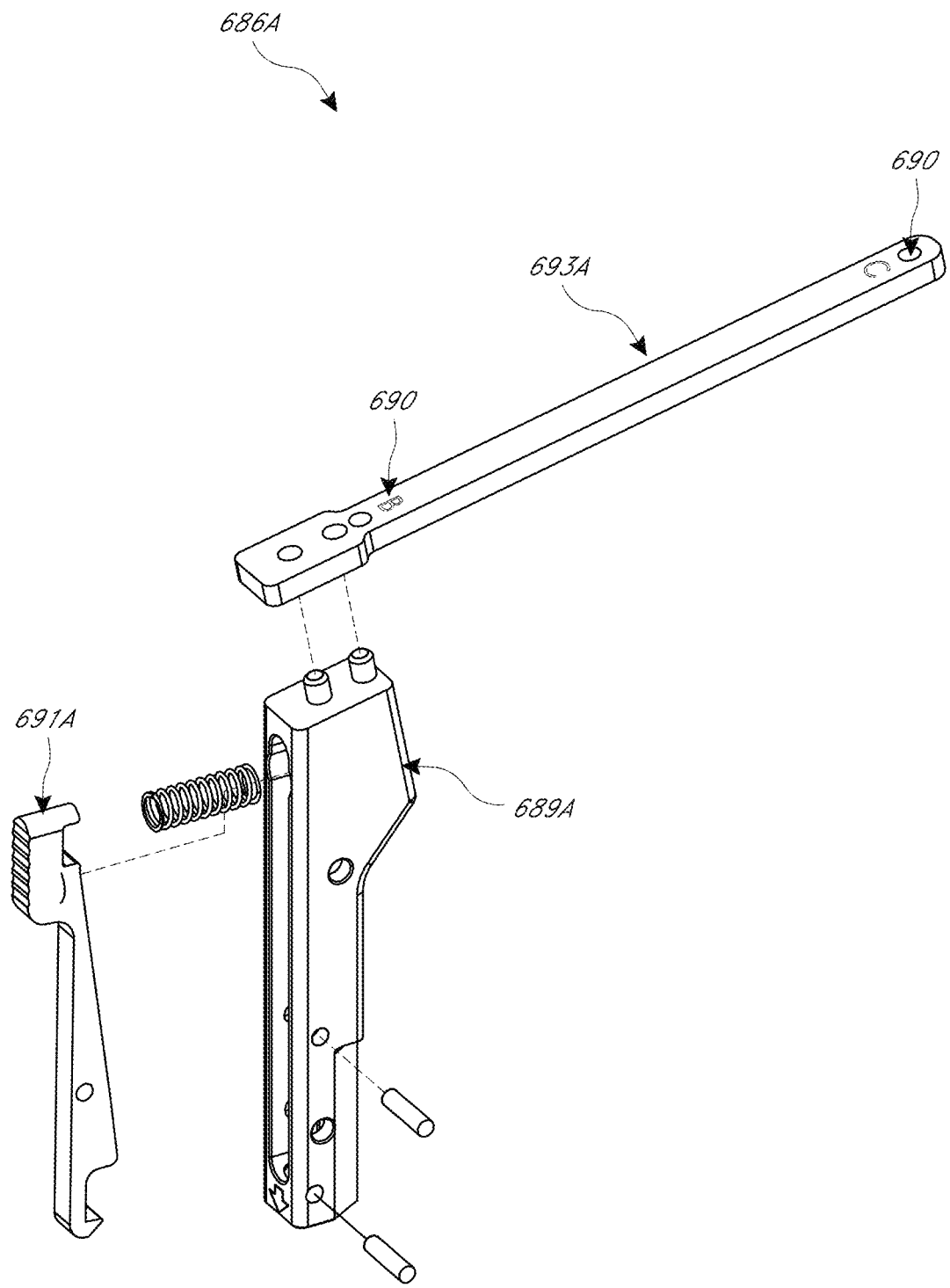

The femur tracker 686A can include a bracket 689A as shown in FIG. 27A-27C. In the illustrated embodiment, the bracket 689A can be substantially vertical in use, as shown in FIG. 25C. The femur tracker 686A can include a lock lever 691A. The lock lever 691A can be coupled to the bracket 689A with pivot pins. The lock lever 691A can be pivoted relative to the bracket 689A. The femur tracker 686A can include an extension 693A. The extension 693A can include the points 690.

The femur base 687A can include a fifth coupler 695A as shown in FIG. 28A-28C. The femur tracker 686A can be designed to couple with the fifth coupler 695A of the femur base 687A. In some embodiments, the tapered surface of the fifth coupler 695A causes the pivoting of the lock lever 691A. In some embodiment, the surgeon causes the pivoting of the lock lever 691A. The lock lever 691A can include a detent which is sized and shaped to be received within the slot 697A. The engagement of the detent and the slot 697A can rigidly couple the femur tracker 686A with the femur base 687A.

FIG. 25B illustrates a parked configuration or home position of the probe 678A. In some embodiments, a portion of the distal end 680A is moved into engagement with the platform 620A. In some techniques, the distal end 680A of the probe 678A engages the divot 630A of the platform 620A. At the surgeon's discretion the system 600A can be used to navigate a condition of the femur prior to hip replacement.

The system 600A can include features that provide notable advantages for the surgeon. The system 600A can include modular instruments. In some embodiments, the fixation base 602A can include a low profile platform 620A. The low profile fixation base 602A can prevent the obstruction of the surgical field. The first assembly 604A can be easily removed when not in use. The distal end 680A of the probe 678A can be angled, bent or curved to facilitate acquiring one or more landmarks or points. The distal end 680A of the probe 678A can be bent or curved to reach the home position. The femur tracker 686A can be releasably coupled to the femur base 687A. The femur tracker 686A can be easily removed when not in use. The femur tracker 686A and/or the femur base 687A can provide points on multiple planes.

5. Posterior Approach: Methods an Orientation Sensing Device and a Camera

FIGS. 18 and 25A illustrate a step of a navigated hip joint implant procedure discussed in detail below. Some of the preceding steps involve removing the to-be-replaced joint, navigating the hip joint, preparing the implant location for the artificial joint, and placing the joint, as elaborated below. As discussed further below, FIGS. 18 and 25B illustrate a technique for confirming that these steps were properly performed.

Figure 29:
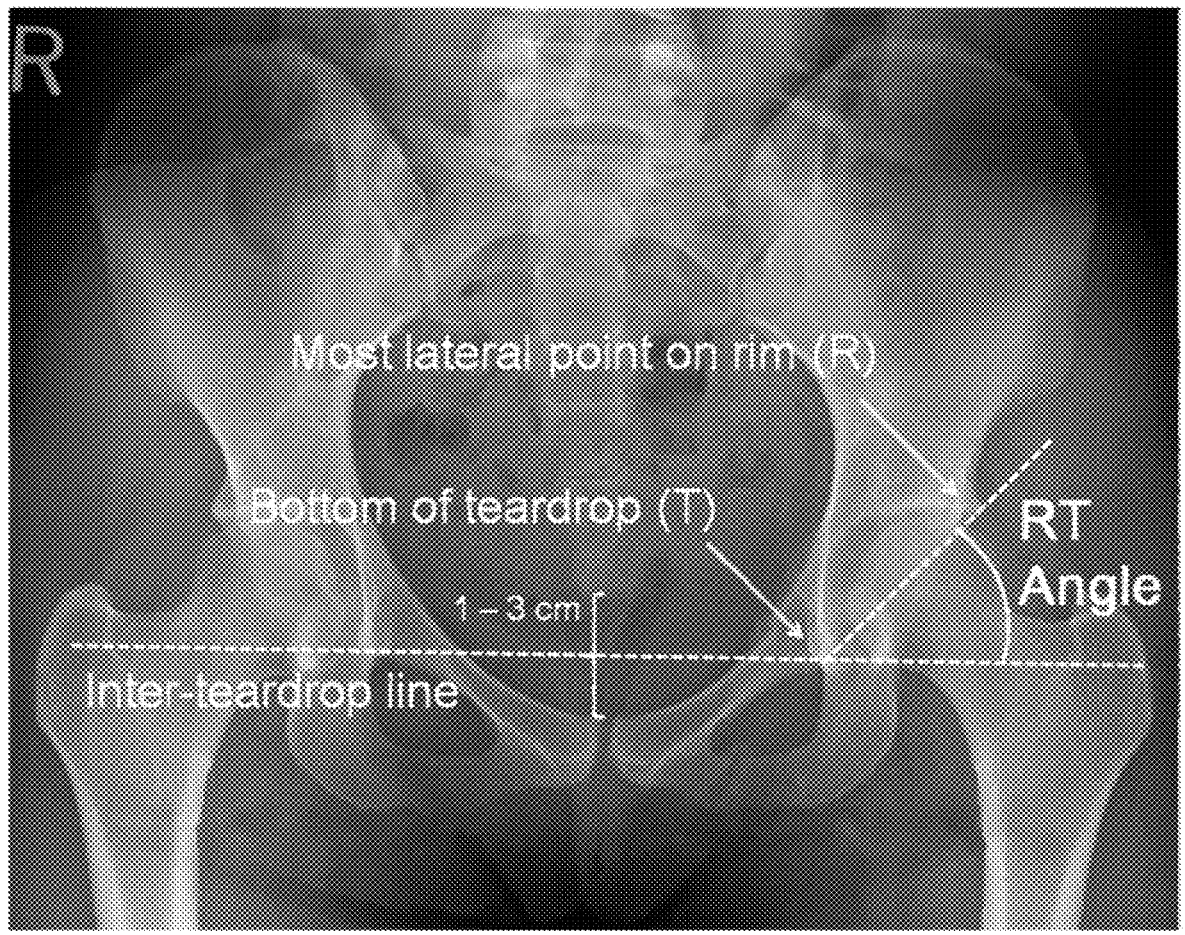
FIG. 29 is a pre-operative x-ray.

Referring back to FIG. 2, Points A-H are locations on the anatomy that may be relevant to various methods and systems herein. In some embodiments, the navigation system 600, 600A is configured to locate a relevant anatomical feature to aid in proper placement of a prosthetic hip joint. In some methods, pre-operative imaging techniques are used. In some methods of use, the surgeon can use a standing or supine anteroposterior (AP) pelvic x-ray. FIG. 29 shows standing AP radiograph taken with patient standing with feet in neutral rotation and shoulder width apart in stance. The x-ray tube-to-film distance should be 120 cm, with the crosshairs centered on the midpoint between the superior border of the pubic symphysis and a line drawn connecting the anterior superior iliac spines (ASIS). The coccyx should be centered in line with the pubic symphysis, and the iliac wings, obturator foramina and radiographic teardrops should be symmetrical in appearance. For appropriate pelvic inclination, a 1-3 cm gap should be seen between the tip of the coccyx and the superior border of the pubic symphysis. This positioning can be important for measuring the patient specific Rim Teardrop (RT) angle.

To obtain the patient specific Rim Teardrop (RT) angle from the AP pelvic x-ray the surgeon can complete one or more of the following steps. The surgeon can draw a line on the x-ray connecting the bottom of the teardrops. The surgeon can draw a line from the most lateral point on the rim of the acetabulum (R) on the operative side through the bottom of the teardrop (T) to the horizontal inter-teardrop line. If osteophytes are present on the rim (R), the surgeon can draw a line through the most lateral osteophyte. The surgeon can measure the angle between the inter-teardrop line and the RT line just drawn. This patient specific RT inclination angle can be an input for the system 600, 600A.

Figure 30:
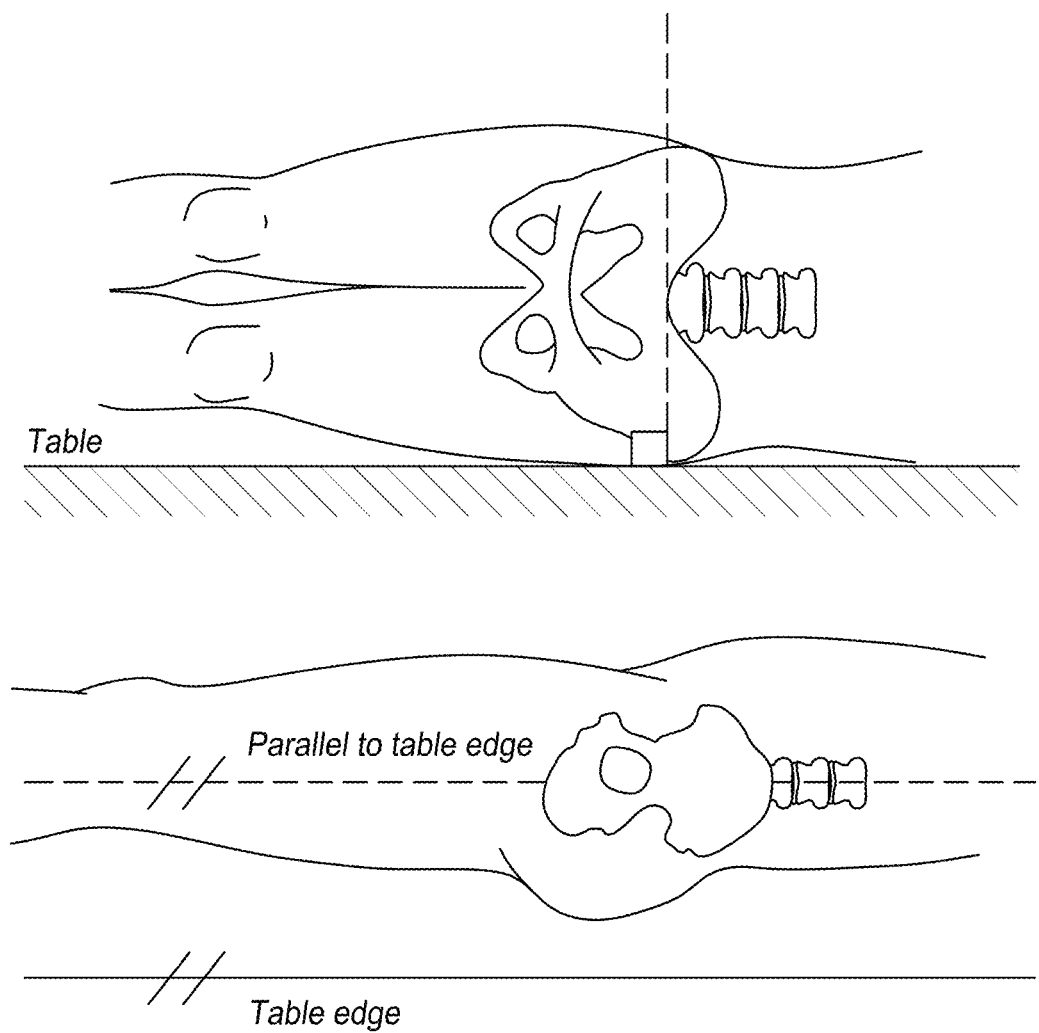
FIG. 30 illustrates pre-operative positioning of a patient for a posterior approach technique.

FIG. 30 shows the patient positioning for the posterior hip approach. In the posterior hip approach, the patient should be placed in the lateral decubitus position. When positioning the patient prior to surgery, the surgeon should take care to align the anterior pelvic landmarks (both ASIS and pubic tubercle) in a vertical plane parallel to the long edge of the operating table. The surgeon should ensure that the pelvis is securely held by an appropriate positioning device such as a peg board or vise-type patient positioner.

The surgical orientation device 172 and the orientation sensing device 204 should be turned on. If different programs are present, the surgeon should select the hip procedure program. If different programs are present, the surgeon should select the posterior hip approach. The surgeon can verify that patient is positioned in the standard lateral decubitus position. The surgical orientation device 172 can include a display screen. The display screen can confirm the communication between the surgical orientation device 172 and the orientation sensing device 204.

Figure 31:
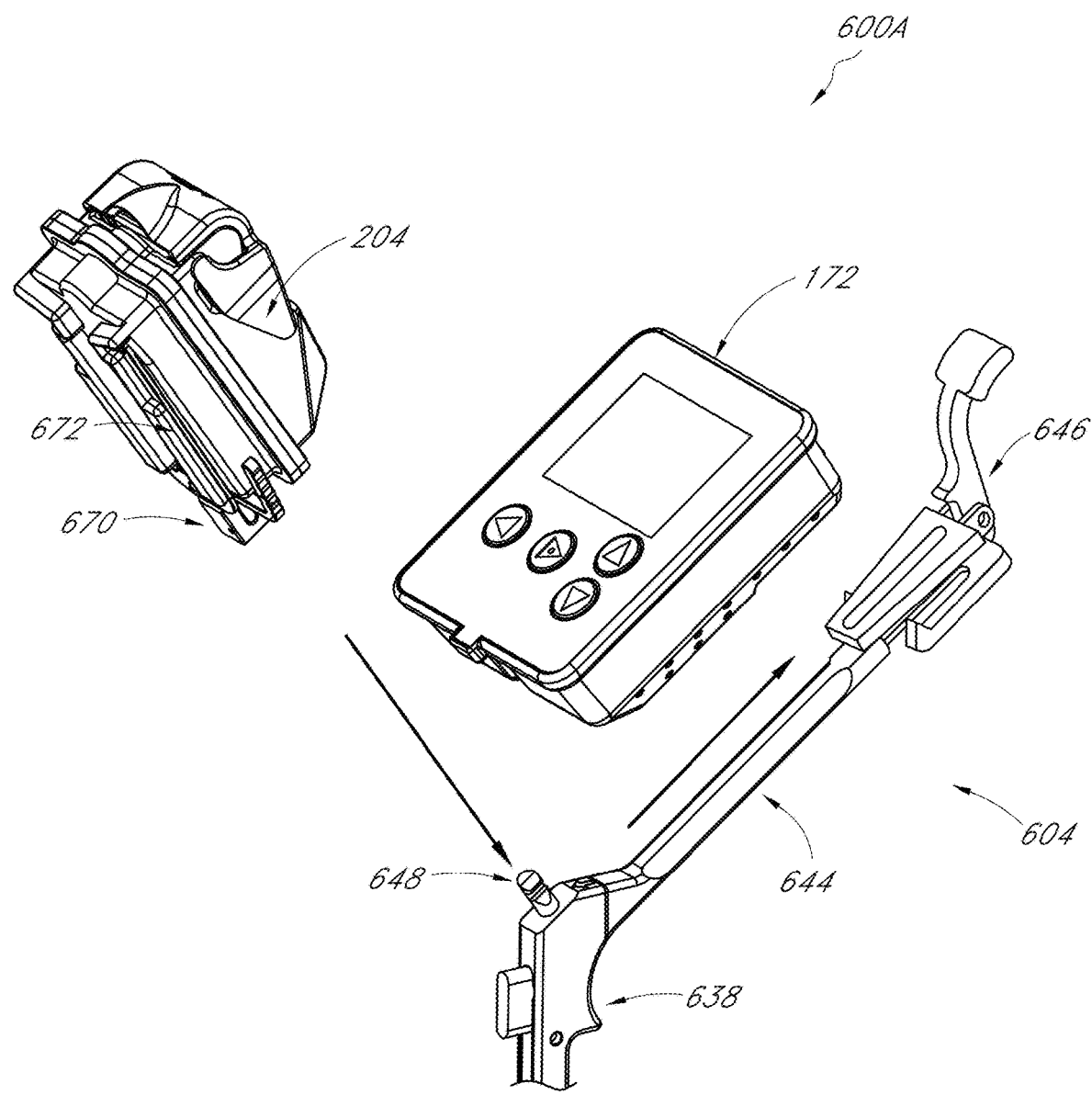
FIG. 31 illustrates a configuration of the system of FIG. 18.

The system 600, 600A can be partially assembled for calibration as shown in FIG. 31. The pelvic bracket 638 can be coupled to the extension 644, if separate components. The surgical orientation device 172 can be coupled to the mount 646. In some techniques, the extension 670 can be coupled to the second coupler 648. The orientation sensing device 204 can be coupled to the mount 672. The surgical orientation device 172 and the orientation sensing device 204 form a general V-shaped configuration. The orientation sensing device 204 can be fixed in position relative to the surgical orientation device 172.

The surgical orientation device 172 and the orientation sensing device 204 can be calibrated. The assemblies 604, 606 or 604A, 606A can be angled forward so that the backside of the surgical orientation device 172 rests on a level surface. The surgeon can hold the assemblies 604, 606 or 604A, 606A steady until the surgical orientation device 172 indicates completion. The assemblies 604, 606 or 604A, 606A can be angled backward so that the backside of the orientation sensing device 204 rests on a level surface. The surgeon can hold the assemblies 604, 606 or 604A, 606A steady until the surgical orientation device 172 indicates completion. The assemblies 604, 606 or 604A, 606A can be placed on the left side so that the left side of the surgical orientation device 172 rests on a level surface. The surgeon can hold the assemblies 604, 606 or 604A, 606A steady until the surgical orientation device 172 indicates completion. The assemblies 604, 606 or 604A, 606A can be angled forward again so that the backside of the surgical orientation device 172 rests on a level surface to verify calibration. The surgeon can hold the assemblies 604, 606 or 604A, 606A steady until the surgical orientation device 172 indicates completion. In some embodiments, the displayed angles should be less than 2°, less than 1°, approximately 0° etc. to verify calibration.

The extension 670 can be decoupled to the second coupler 648. The second assembly 606, 606A can be assembled as shown in FIGS. 22B and 25A. The mount 658 can be coupled to the probe bracket 652. The mount 658 can rotate relative to the probe bracket 652. The mount 658 can be coupled to the dock 662. The dock 662 can pivot relative to the mount 658 about one or more pivot pins 660. The extension 670 can be coupled to the third coupler 668 of the dock 662. The orientation sensing device 204 can be coupled to the mount 672. The probe bracket 652 can be coupled to the second coupler 648. The first assembly 604, 604A can be coupled to the second assembly 606, 606A as shown in FIGS. 18 and 25A.

The probe 678 can be inserted within the through lumen 664 of the dock 662. The marking 682 can be beneath the camera 684. The surgeon can verify the camera 684 is capturing the measurements of the marking 682 by sliding the probe 678 to different positions. The surgical orientation device 172 can display different positions of the probe 678 as the probe 678 is moved. The probe 678A can be similarly positioned within the second assembly 606A as shown in FIG. 25A.

The system 600, 600A can be attached to the pelvis. The fixation pins 610, 612 can be inserted into the bone. In some techniques, one or more of the fixation pins 610, 612 are positioned approximately 10 mm above the most superior point on the acetabular rim. The fixation pins 610, 612 can be perpendicular to the long axis of the patient. The fixation pins 610, 612 can be inserted by use of a driver. In other embodiments, the fixation pins 610, 612 are driven into bone with a mallet until the distal ends are fully seated within the bone.

The fixation pins 610, 612 can be inserted into the channels 626, 628 prior to or after the fixation pins 610, 612 are driven into the bone. The support 622 can be brought toward the platform 620, thereby decreasing the diameter of the channels 626, 628. The fixation pins 610, 612 can be secured to the fixation base 602. The first assembly 604 can be coupled to the first coupler 632. The surgical orientation device 172 can be coupled to the first assembly 604. The second assembly 606 can be coupled to the second coupler 648. The orientation sensing device 204 can be coupled to the second assembly 606. The system 600 can be positioned as shown in FIG. 18. The fixation base 202A can be affixed with fasteners 613A, as shown in FIG. 25B. The system 600A can be positioned as shown in FIG. 25B.

The femur tracker 686, 686A can be coupled to the femur. The femur tracker 686 can be positioned on the greater trochanter. The curved end of the femur tracker 686 can be pointing toward the head of the patient. One or more fixation devices can be placed through the each hole 688 of the femur tracker 686 to secure the femur tracker 686 to the femur. The femur tracker 686 can be positioned as shown in FIG. 18. The femur base 687A can be positioned on the greater trochanter. The femur tracker 686A can be assembled as shown in FIG. 25C. The femur tracker 686A can be coupled to the femur base 687A as described herein.

If different programs are present, the surgeon should select which hip is being operated on (e.g., right or left hip). The surgeon can verify that patient is positioned in the standard lateral decubitus position. If different programs are present, the surgeon should select the gender of the patient being operated on (e.g., male or female). If different programs are present, the surgeon should select the target cup inclination angle. This angle can be selected based upon the radiographic inclination angle. If different programs are present, the surgeon should select the target cup anteversion angle. This angle can be selected based upon the radiographic anteversion angle. If different programs are present, the surgeon should select the RT inclination angle. This angle can be selected based upon the radiographic RT inclination angle, such as from the A/P pelvic x-ray.

The surgeon can register a parked configuration or home position. In some techniques, the distal end 680, 680A of the probe 678, 678A can be engaged with a point on the platform 620, 620A. The platform 620, 620A can include the divot 630, 630A. The divot 630, 630A can be sized to accept the distal end 680, 680A of the probe 678, 678A. This position is shown in FIGS. 18 and 25B. The probe 678, 678A can be angled relative to vertical in the home position. The dock 662 can be angled relative to vertical in the home position. The orientation sensing device 204 coupled to the dock 662 can be angled relative to vertical in the home position. The surgical orientation device 172 can be also angled relative to vertical in the home position.

The orientation sensing device 204 can register the operating table, in other words perform table registration. The patient can be positioned so that the sagittal plane of the pelvis is level. The surgeon can align the probe 678, 678A with the horizontal. The probe 678, 678A can be parallel with the coronal plane. The system 600, 600A can calculate cup angles based on the assumption that the pelvis of the patient is correctly positioned during table registration.

The femur can be positioned in a neutral reference position with respect to flexion, abduction and rotation. This neutral position can be representative of a standing position of the patient. The femur should be maintained in this position during the initial registration of points 690, such as Points A, B, and C, shown in FIGS. 24A and 25C. The surgeon can confirm that the orientation sensing device 204 is coupled to the dock 662. The surgeon can position the distal end 680, 680A of the probe at Point A of points 690. In some methods, the distal end 680, 680A is place within a divot at Point A on the femur tracker 686, femur base 687A.

The surgeon can enter an input to register Point A (e.g., depress a button on surgical orientation device 172). The surgical orientation device 172 can indicate that Point A was recorded. The surgeon can position the distal end 680, 680A of the probe at Point B of points 690. In some methods, the distal end 680, 680A is place within a divot at Point B on the femur tracker 686, 686A. The surgeon can enter an input to register Point B (e.g., depress a button on surgical orientation device 172). The surgical orientation device 172 can indicate that Point B was recorded. The surgeon can position the distal end 680, 680A of the probe at Point C of points 690. In some methods, the distal end 680, 680A is place within a divot at Point C on the femur tracker 686, 686A. The surgeon can enter an input to register Point C (e.g., depress a button on surgical orientation device 172). The surgical orientation device 172 can indicate that Point C was recorded.

Figure 32:
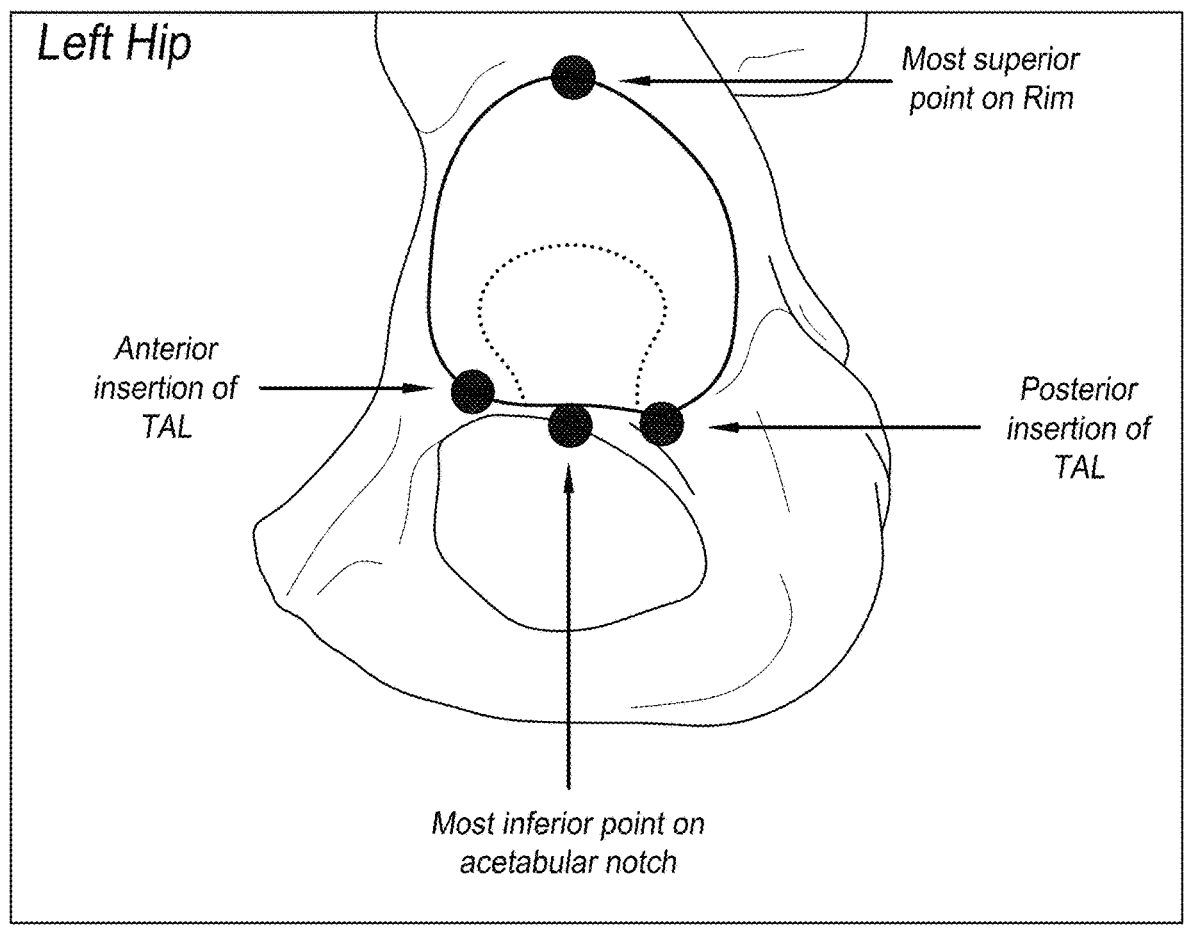
FIG. 32 illustrates anatomical landmarks registered during some embodiments.

The surgeon can position the distal end 680, 680A of the probe 678, 678A at various anatomical landmarks. FIG. 32 illustrates four landmarks which can be utilized in some techniques. In one technique, Point 1 is the most superior point of rim. The surgeon should not remove any osteophytes from this landmark prior to registration of Point 1. Point 1 registered landmark should match the anatomy identified on the pre-operative x-ray. In some methods, the distal end 680, 680A of the probe 678, 678A is placed at Point 1. The surgeon can enter an input to register Point 1 (e.g., depress a button on surgical orientation device 172). The surgical orientation device 172 can indicate that Point 1 was recorded.

Point 2 can be the most inferior point of the acetabular notch. The surgeon should not remove any osteophytes from this landmark prior to registration of Point 2. Point 2 registered landmark should match the anatomy identified on the pre-operative x-ray. The transverse acetabular ligament (TAL) straddles the inferior limit of the bony acetabulum. It is a strong load-bearing structure and, in the normal hip, in association with the labrum, provides part of the load-bearing surface for the femoral head. In some methods, the distal end 680, 680A of the probe 678, 678A is placed at Point 2. The surgeon can enter an input to register Point 2 (e.g., depress a button on surgical orientation device 172). The surgical orientation device 172 can indicate that Point 2 was recorded.

Point 3 can be the posterior insertion of the transverse acetabular ligament (TAL). The surgeon should remove any osteophytes from this landmark prior to registration of Point 3. This will uncover or replicate native anatomy of the landmark. In some methods, the distal end 680, 680A of the probe 678, 678A is placed at Point 3. The surgeon can enter an input to register Point 3 (e.g., depress a button on surgical orientation device 172). The surgical orientation device 172 can indicate that Point 3 was recorded.

Point 4 is the anterior insertion of the transverse acetabular ligament (TAL) in one embodiment. The surgeon should remove any osteophytes from this landmark prior to registration of Point 4. This will uncover or replicate native anatomy of the landmark. In some methods, the distal end 680, 680A of the probe 678, 678A is placed at Point 4. The surgeon can enter an input to register Point 4 (e.g., depress a button on surgical orientation device 172). The surgical orientation device 172 can indicate that Point 4 was recorded.

When registering the anatomical points or points 690 on the femur tracker 686, the camera 684 captures an image of the marking 682. The camera 684 can read the marking 682 to provide accurate determination of the translational position of the probe 678 relative to the dock 662. The camera 684 can be directly above the marking 682. In some methods, the camera 684 can read a binary code of the marking 682.

In some methods, the orientation sensing device 204 converts the image of the camera 684 into an extension measurement of the probe 678. In some embodiments, the surgical orientation device 172 converts the image of the camera 684 into an extension measurement of the probe 678. The distance related to the extension of the probe 678 can be used in conjunction with the orientation and positional data from the orientation sensing device 204. The surgical orientation device 172 can use the length measurement from the camera 684 and the data from the orientation sensing device 204 to determine the location of the distal end 680 of the probe 678. In some embodiments, the surgeon will enter an input (e.g., depress a button) to collect data from the orientation sensing device 204. In some methods, the surgeon will enter an input (e.g., depress a button) to collect data from the camera 684. In some embodiments, the surgeon will enter an input (e.g., depress a button) to collect data from the orientation sensing device 204 and the camera 684 simultaneously. In some methods, the orientation sensing device 204 and/or the camera 684 will only send data to the surgical orientation device 172 if the orientation sensing device 204 is stable or non-moving. The points 690 can include divots to stabilize the distal end 680, 680A of the probe 678, 678A when the points 690 are registered.

The surgeon can set the angle of the cup. Later in the procedure, the surgeon can check cup angle after the angle has been set. The surgeon can remove the second assembly 606, 606A from the first assembly 604, 604A. The surgeon can remove the extension 670 from the third coupler 668. The surgeon can couple the extension 670 to an impactor 300B, shown in FIGS. 56A-56F. The impactor 300B can have a fourth coupler 338B. In some embodiments, the fourth coupler 338B is a universal coupler. In some embodiments, the fourth coupler 338B is identical or substantially similar to the second coupler 648 and the third coupler 668. This permits the orientation sensing device 204 to couple to either the second coupler 648, the third coupler 668 or the fourth coupler 338B, as described herein The fourth coupler 338B can be similar to the first coupler 632 described herein. The fourth coupler 338B can extend from a side surface of the impactor 300B. The fourth coupler 338B can extend perpendicularly to the longitudinal axis of the impactor 300B. The extension 670 can couple to the fourth coupler 338B. The mount 672 can be coupled to the orientation sensing device 204. The acetabular shell can be threaded onto the shell adaptor, similar to FIG. 11C. The shell adaptor can be snapped onto the end of the impactor 300B, similar to FIG. 11B.

The acetabular shell can be inserted into the acetabulum and positioned at the desired angle. The surgical orientation device 172 can guide the surgeon in setting the appropriate cup angle. The surgical orientation device 172 can graphically display when the orientation sensing device 204 is located at the inclination and anteversion angles entered previously. The surgical orientation device 172 can graphically display the inclination and anteversion angles as the orientation sensing device 204 is moved. The surgeon can enter an input to set the desired angle (e.g., depress a button on surgical orientation device 172). The surgical orientation device 172 can output all inclination and anteversion angles according to radiographic definitions. Anteversion (Radiographic Anteversion) is the angle between the acetabular axis and the coronal plane. Inclination (Radiographic Inclination) is the coronal plane projection of the angle between the acetabular axis and the longitudinal axis of the body. Once the orientation sensing device 204 is coupled to the impactor 300B, the surgical orientation device 172 can display the radiographic inclination and anteversion angles of the impactor 300B relative to the frontal pelvic plane.

The inclination and anteversion cup angles can be displayed statically. The inclination and anteversion cup angles can be displayed statically. The anatomic angles are those calculated by the system 600 based on the pelvic landmark registration. The table angles are those calculated by the system 600 based on the initial positioning of the pelvis during table registration. In some embodiments, the orientation sensing device 204 can register the operating table by aligning the probe 678, 678A with the horizontal. In some embodiments, only the direction of the projection of the probe 678, 678A onto a horizontal plane is used. The probe 678, 678A can be in an infinite number of angles from horizontal, which would result in the same software result. This is convenient due to the mechanical constraints imposed by the pivot configuration of the system 600. The angles displayed can be an average between the anatomic reference and table reference. The inclination angle is calculated based as an average between the anatomic reference and table reference. The anteversion angle is calculated based on the table reference. The surgeon can check cup angle after the angles are set.

Figure 33:
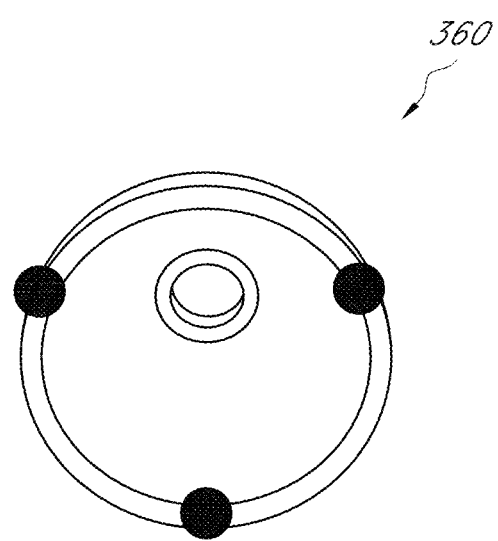
FIG. 33 illustrates a first set of points on the rim of the shell.

The surgeon can register the hip center. The surgeon can couple the second assembly 606, 606A to the first assembly 604, 604A as shown in FIGS. 18 and 25A. The mount 672 can be coupled to the orientation sensing device 204. The mount 646 can be coupled to the surgical orientation device 172. The surgeon can confirm that the components of system 600, 600A are rigidly coupled. The surgeon can select the first set of points on the rim of the shell 360 to be registered, as shown in FIG. 33. In the illustrated method, the first set of points is selected on the rim of the shell. The surgeon can place the distal end 680, 680A of the probe 678, 678A on each of the first set of points shown in FIG. 33. In some methods, the surgeon can select the second set of points on the rim of the shell to be registered. In the illustrated method, the second set of points is selected on the rim of the shell. The surgeon can place the distal end 680, 680A of the probe 678, 678A on each of the second set of points. In some methods, the surgeon should select the third set of points on the rim of the shell to be registered. In the illustrated method, the third set of points is selected on the rim of the shell. The surgeon should place the distal end 680, 680A of the probe 678, 678A on each of the third set of points. In some methods, the minimum separation distance allowed between points is 25 mm. In some methods, the maximum separation distance allowed between points is 65 mm.

The inclination and anteversion angles of the shell are displayed on the surgical orientation device 172. These angles are based on the plane determined by the three points registered on the rim. The surgeon can enter the offset of the liner to be used. The offset is the distance from the center of the shell face to the center of the femoral head. If the shell is hemispherical and the head and shell are concentric, the surgeon can enter zero. In some methods, the offset is between 0 mm and 10 mm. The surgeon can repeat this step if the linear offset is changed later in the procedure. The surgical orientation device 172 can calculate the center of rotation (COR) of the hip using the set of points on the rim of the shell.

The surgeon can register the leg length and offset after implantation of the acetabular shell. The surgeon can couple the second assembly 606, 606A to the first assembly 604, 604A as shown in FIGS. 18 and 25A. The mount 672 can be coupled to the orientation sensing device 204. The mount 646 can be coupled to the surgical orientation device 172. The surgeon can confirm that the components of system 600, 600A are rigidly coupled. The femur can be repositioned within +/−20° flexion from the pre-operative position. The femur can be repositioned within +/−15° abduction from the pre-operative position. The femur can be repositioned within +/−20° rotation from the pre-operative position.

In some methods, the distal end 680, 680A of the probe 678, 678A is place within a divot at Point A of points 690. The surgeon can enter an input to register Point A (e.g., depress a button on surgical orientation device 172). The surgeon can position the distal end 680, 680A of the probe at Point B of points 690. The surgeon can enter an input to register Point B (e.g., depress a button on surgical orientation device 172). The surgeon can position the distal end 680, 680A of the probe at Point C of points 690. The surgeon can enter an input to register Point C (e.g., depress a button on surgical orientation device 172). The surgical orientation device 172 can indicate that Points A, B, and C were recorded. Using Points A, B, and C, the surgical orientation device 172 can calculate the change in angle between the pelvis and the femur since the initial registration prior to dislocation. The surgical orientation device 172 can mathematically rotate the femoral points, Points A, B, and C, around the center of rotation (COR) of the hip to align the femur with its initial position. The new position of the centroid of the femoral points, Points A, B, and C, is compared to the initial position. The femoral points, Points A, B, and C, can be located on the femur tracker 686, 686A or femur base 687.

The leg length and offset are displayed on the surgical orientation device 172. The change in leg length is in the proximal distal direction. The joint offset is in the medial lateral direction. If the angle between the femur and the pelvis has changed by more than a hard coded limit in any axis, then the surgical orientation device 172 can display an error message. The hard coded limit can be 15°, between 10-20°, between 5-25°, etc. The surgical orientation device 172 can display guidance on repositioning the femur (e.g., abduct femur, flex femur, etc.). The surgeon can exchange or reposition the shell to adjust leg length and offset. The surgeon can exchange or reposition the shell based upon goals from pre-operative templates or images. If desired and possible, the leg length and offset may be adjusted according to the surgeon's standard surgical procedure.

The surgeon can register the home position. The surgeon can couple the second assembly 606, 606A to the first assembly 604, 604A as shown in FIGS. 18 and 25A. The mount 672 can be coupled to the orientation sensing device 204. The mount 646 can be coupled to the surgical orientation device 172. The surgeon can confirm that the components of system 600, 600A are rigidly coupled. The surgeon can verify the parked configuration or home position. The distal end 680, 680A of the probe 678, 678A can be engaged with a point on the platform 620, 620A. The platform 620, 620A can include the divot 630, 630A. The divot 630, 630A can be sized to accept the distal end 680, 680A of the probe 678, 678A. This position is shown in FIGS. 18 and 25B. The change in the home position is displayed on the surgical orientation device 172. The number may not be zero due to mechanical play and/or sensor noise. If the displayed number is greater than 3 mm, the surgeon may wish to verify the rigid connection between the components of the system 600, 600A.

B. Navigation Using Inertial Sensors and Jigs for Referencing Anatomical Landmarks with Anterior Approach 1. Anterior Approach: Systems with an Orientation Sensing Device Coupled to a Probe FIGS. 34-38 illustrate a hip navigation system 500 adapted to navigate a hip joint procedure from an anterior approach. Anterior approach to hip replacement advantageously can be less invasive than posterior approach. In particular, the anterior approach can enable smaller incisions, less soft tissue dissection, and shorten recovery time for patients. The system 500 includes an anchor system 504, an alignment assembly 508 and a landmark acquisition assembly 512.

Figure 34:
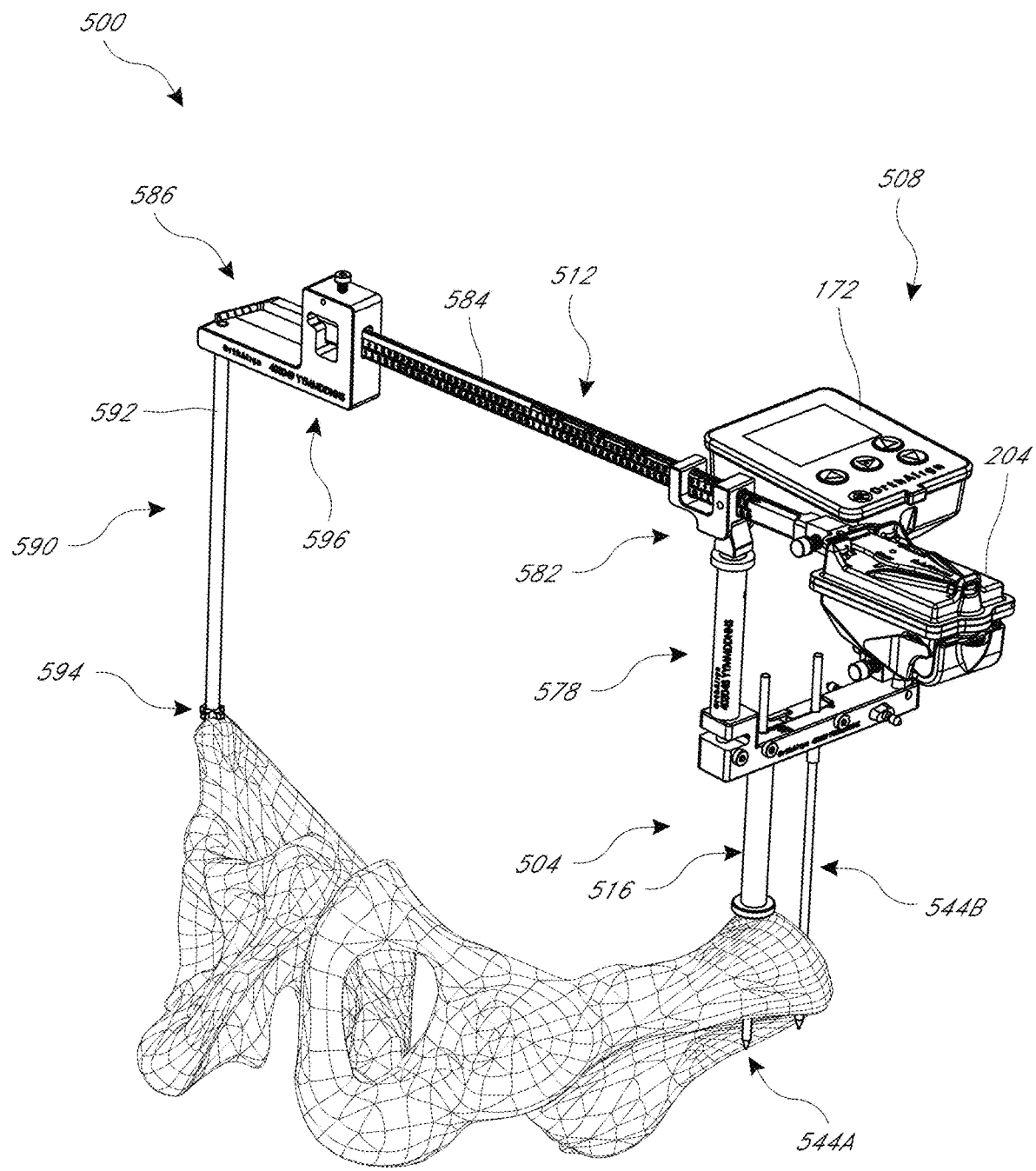
FIGS. 34-38 illustrate a hip navigation system configured for anterior approach hip replacement procedures, and various aspects of such procedures.

FIG. 34 shows the anchor system 504 in more detail. The system 504 is configured to securely couple the navigation system 500 to the hip, such that movement between the system and the hip are minimized or eliminated. The anchor system 504 includes a cannula 516 having a distal end 520 and a proximal end 524 with a lumen 532 extending between the distal and proximal ends. The proximal end 524 of the cannula 516 is coupled with a platform 536, for example adjacent to one lateral end of the platform. The platform 536 is similar to those hereinbefore described having a plurality of docking device 538, 538A disposed away from the location where the proximal end 524 and the platform 536 are connected.

The docking devices 538 are configured to couple with detachable mounting devices that securely but temporarily couple sensor to the anchor system 504. The two docking device 538 on the top surface of the platform 536 enable the anchor system 504 to be used for either left or right hip procedures. As shown in FIG. 34, the docking device 538 on the side of the platform 536 closest to the medial plane of the patient is preferably used for docking. The top side docking feature not in use in FIG. 34 would in fact be used in performing a procedure from the other side of the patient. The docking device 538A on the side surface of the platform 536 is provided for a temporary intra-procedure mounting of a sensor to the platform 536. As discussed further below, this temporary mounting provides a known orientation and/or location of two sensors relative to each other during a procedure, which enables the system 500 to control sources of error with certain types of sensors.

The platform 536 also can have a channel 540 disposed away from the cannula 516. The channel 540 can have a lumen disposed along an axis substantially parallel to the lumen 532 of the cannula 516. In one embodiment, the anchor system 504 is configured to securely couple the platform 536 to the hip by placement of two spaced apart pins 544A, 544B. FIG. 34 shows that the pin 544A can be advanced through the cannula 516 such that a distal end of the pin 544A contacts and penetrates a bony prominence of the pelvis. In one technique the pin 544A is positioned at or as close as possible to the anterior superior iliac spine (ASIS) of the pelvis. The pin 544B is advanced through the channel 540 and into the pelvis at a location offset form the ASIS. The distance between the pins 544A, 544B and the precise positioning of the pin 544B are not critical, but are determined by the locations of the connection of the cannula 520 to the platform 536 and of the channel 540.

The pins 544A, 544B can take any suitable form but preferably have the same cross-sectional profile as the lumens in the cannula 520 and in the channel 540, e.g., they can be circular in cross-section. The pins 544A, 544B can be modified Stienmann pins, e.g., configured to extend at least about 5 cm above the platform 536 and having a diameter of about 4 mm.

The anchor system 504 also has a locking device 556 for securing the platform 536 to the pins 544A, 544B. In one embodiment, the portion of the platform disposed around the pins comprises medial and lateral portions 560M, 560L that can move away from each other to release the pins 544A, 544B or toward each other to frictionally engage the pins. For example, a pair of hex-driven screws can engage the medial and lateral portion 560M, 560L to translate them toward and away from each other respectively. The locking device 556 preferably is quickly and easily removed from the pins such that other instrument, such as X-Ray or other diagnostic devices can be brought into the vicinity of the surgical field during the procedure. Preferably the pins 544A, 544B have markings along their length such that if the platform 536 is removed for imaging or other reasons it can be quickly re-positioned at the same elevation.

The cannula 520 also has a foot 568 adjacent to or at the distal end 528 to minimize or eliminate error that could arise due to uneven penetration depth of the anchor system 504 when compared to the position of a distal probe of the landmark acquisition system 512 when landmarks are being acquired. The foot 568 can include an annular projection disposed outward of the cannula 520. Preferably the foot 568 extends laterally from the outer surface of the cannula 520 by a distance equal to or greater than the wall thickness of the cannula 520. In some embodiment, the surface area beneath the foot is equal to or grater than the surface area of the cannula when viewed in cross-section at a location where the foot 568 is not located, e.g., at an elevation about the foot 568.

The alignment assembly 508 is similar to those hereinbefore described. It can have a rigid extension 570 configured to detachably secure a orientation device 172 to the docking device 538.

Figure 35:
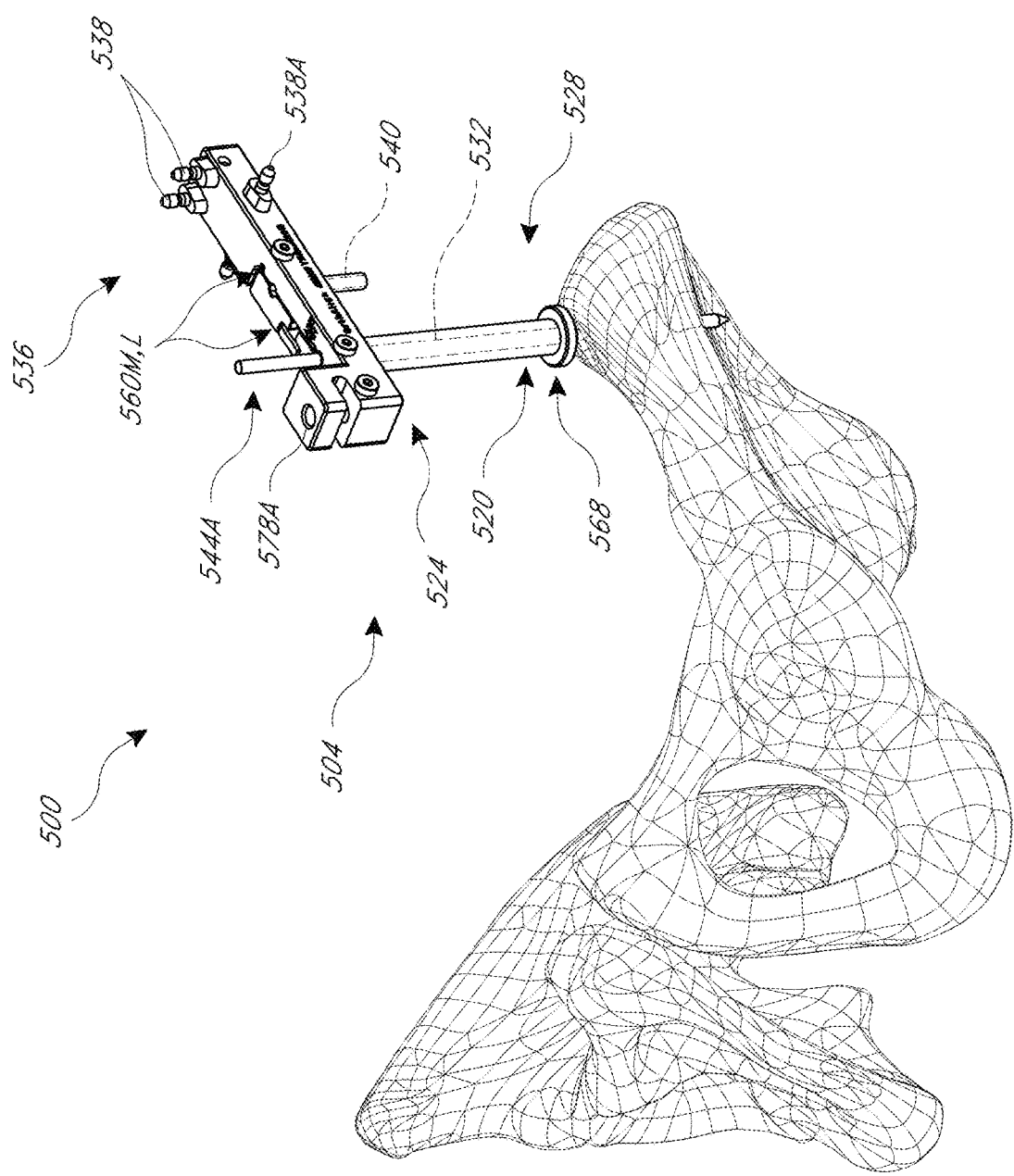

The landmark acquisition assembly 512 is similar to those hereinbefore described, but is configured to be unobstructed in use by soft tissue anterior to the pelvis of the patient. In one embodiment, an extension 578 is provided to elevate a pivoting and sliding mechanism 582. The pivoting and sliding mechanism enables a probe arm 584 to slide away from the extension 578 toward the location of landmarks to be acquired. The pivoting and sliding mechanism 582 can be similar to any of those discussed above. The distal (lower) end of the extension 578 can be coupled to the platform 536 in any suitable way. For example, the distal end can include a pin-like projection that is received in, e.g., friction fit in, an aperture 578A having the same shape. Detents or other locking features can be provided to securely connect the extension to the platform 536 in the aperture 578A. FIG. 35 shows that the aperture 578A can be formed in a portion of the platform 536 that is elevated compared to the portions of the platform through which the pin 544A extends. This portion is elevated to provide sufficient bearing engagement to minimize play. It also has a slot generally parallel to the top surface of the platform 536 which serve the function of engaging a ball detent on the lower end of the extension 578.

The probe arm 584 can be configured as an elongate member with a plurality of markings, discussed below. A distal end of the probe arm 584 can include an angled tip 586 that assists in probing anatomy in some techniques, e.g., portions of the femur for leg length and femoral head positioning confirmation. In the posterior approach, the angled tip 586 is used to directly contact anatomy.

In the anterior approach, the angled tip 586 is coupled with a probe extension 590 configured to contact selected anatomy. The probe extension 590 has an upright member 592 that is configured to extend, in the anterior approach, between the elevation of the probe 584 down toward the elevation of the tissue to be probed. A foot 594 on the distal (lower) end of the upright member 592 is configured to engage the tissue in a way that minimizes error due to uneven tissue compression between the point of mounting of the pin 544A and the foot 594. For example, the foot 594 can have a cross configuration that spreads out the force or pressure applied by the landmark acquisition system 512 in use. The proximal end of the extension 590 includes a coupler 596 that connects a distal end of the probe arm 584 with the upright member 592. Preferably the coupler 596 is easily manipulable by the user to modify connect to the probe arm 584. The coupler can include an L-shaped member with an aperture configured to receive the tip 586 of the probe arm 584. A set screw can be advanced through the L-shaped portion to lock the arm 584 in place. The L-shaped portion is configured to couple to the arm 584 such that the tip of the angled tip 586 rests on a projection of the longitudinal axis of the upright member 592.

2. Anterior Approach: Methods with an Orientation Sensing Device Coupled to a Probe The system 500 can be used to navigate from an anterior approach in the following ways. The orientation device 172 and the sensor 204 can be paired such that they are in wireless communication with each other. This permits one or other of the device 172 and sensor 204 to control the other, store data from the other, and/or display information based on signals from the other. In one method, the orientation device 172 has a display that confirms to the surgeons certain angles based on the data sensed by the sensor 204. The pairing the device and sensor 172, 204 can involve coupling them together and comparing sensor output between the two devices at a plurality of orientations, e.g., horizontal, vertical, and angled at 30 degrees. Some of these positions may be repeated with a plurality of attitudes, e.g., vertical with left side up, vertical with right side up, and vertical with top side up.

As noted above, the components discussed herein can be provided as a kit that enables the surgeon to select among different surgical approaches, e.g., posterior and anterior approaches. The orientation device 172 and sensor 204 may operate differently in these different approaches. Thus, in one method the user will enter into one or both of the orientation device and sensor 172, 204 which approach is being used. This will implement a software module in the orientation device 172 (or in the sensor 204 is the processor running the software is located there) corresponding to the selected approach.

In various embodiments suitable for the anterior approach, the orientation device 172 and the sensor 204 can both have a plurality of sourceless sensors. These components can have both accelerometers and gyroscopes in some embodiments. Some gyroscopes are subject to accumulated error that can be significant in the time frames relevant to these methods. Accordingly, various methods are provided to prevent such errors from affecting the accuracy and reliability of the angles displayed to the surgeon by the system 500. Some approaches can be performed with accelerometers only. For example, variations of the anterior approach can be performed with accelerometers with somewhat less but still acceptable accuracy using accelerometers only. The reduction in accuracy of the accelerometers is balanced against the benefit of eliminating the accumulated error that arises with some gyroscopes. The resolution of accelerometers is sufficient because the points navigated are relatively far apart.

The calculations performed by the system 500 are unique to the hip being treated in some embodiment, so the system receives input of the hip being treated.

The foot 568 is placed on a selected anatomical location, e.g., on the ASIS as discussed above. With the cannula 520 in an approximately vertical orientation the platform 536 is secured to the hip. Securing the platform 536 to the hip can be done in any suitable way, such as with two spaced apart Stienmann pins. Thereafter, the orientation device 172 and the sensor 204 are attached to the platform 536 in the manner shown in FIG. 36A. Depending on the nature of the sensing devices deployed in the sensor 204 it may be advantageous to initialize the sensor at this point of the procedure. As discussed above, certain inertial sensors (e.g., some gyroscopes) are subject to accumulated error. One technique for managing this error source is to periodically initialize or zero out this error. Some techniques involve initialing at this point.

In some embodiment, a frame of reference based on the plane of the table can be input into the system 500. The table reference frame can be a secondary reference frame. In one technique, the sensor 204 is moved from the platform dock position of FIG. 36A to the navigating position on the probe arm 584 as shown in FIG. 34. The probe arm 584 is then pivoted by the mechanism 582 such that the arm points in a direction that is parallel to the patient's medial-lateral midplane and the angled tip 586 superiorly (generally toward the patient's head). The probe arm 584 is also held substantially parallel to the plane of the table. With this heading and orientation the user interacts with a user interface on the orientation device 172 to signal to the orientation system 508 to capture the orientation of the sensor 204. This orientation provides an estimation of the orientation of the anterior pelvic plane. This estimation may be tracked in the system 500 and may alone provide an improvement over the state of the art in un-navigated hip replacement, which involves discrete maneuvers guided by the unaided eye.

At the surgeon's discretion the system 500 can be used to navigate a condition of the femur prior to hip replacement. A mark Fm may be made on the proximal femur. Thereafter the sensor 204 can be initialized or zeroed such as by placing it back in the dock position on the platform (as in FIG. 36A). Thereafter, the probe tip 586 can be brought into contact with the femur mark Fm and locked in place in such contact. See FIG. 37. The sensor 204 can be transferred to the proximal end of the probe 584 and the orientation device 172 can be signaled to record the orientation of the sensor 204. A distance from the point of attachment of the cannula 520 to the ASIS to the marked position on the femur can then be recorded in the orientation device 172. The position can be based on reading graduated marks on the probe 584 or can be captured automatically by a camera system or a sensor built into the system 500. In one embodiment, graduated marks are read at an upright edge 598 within a bight of a sliding portion of the pivoting and sliding mechanism 582.

Figure 36A:
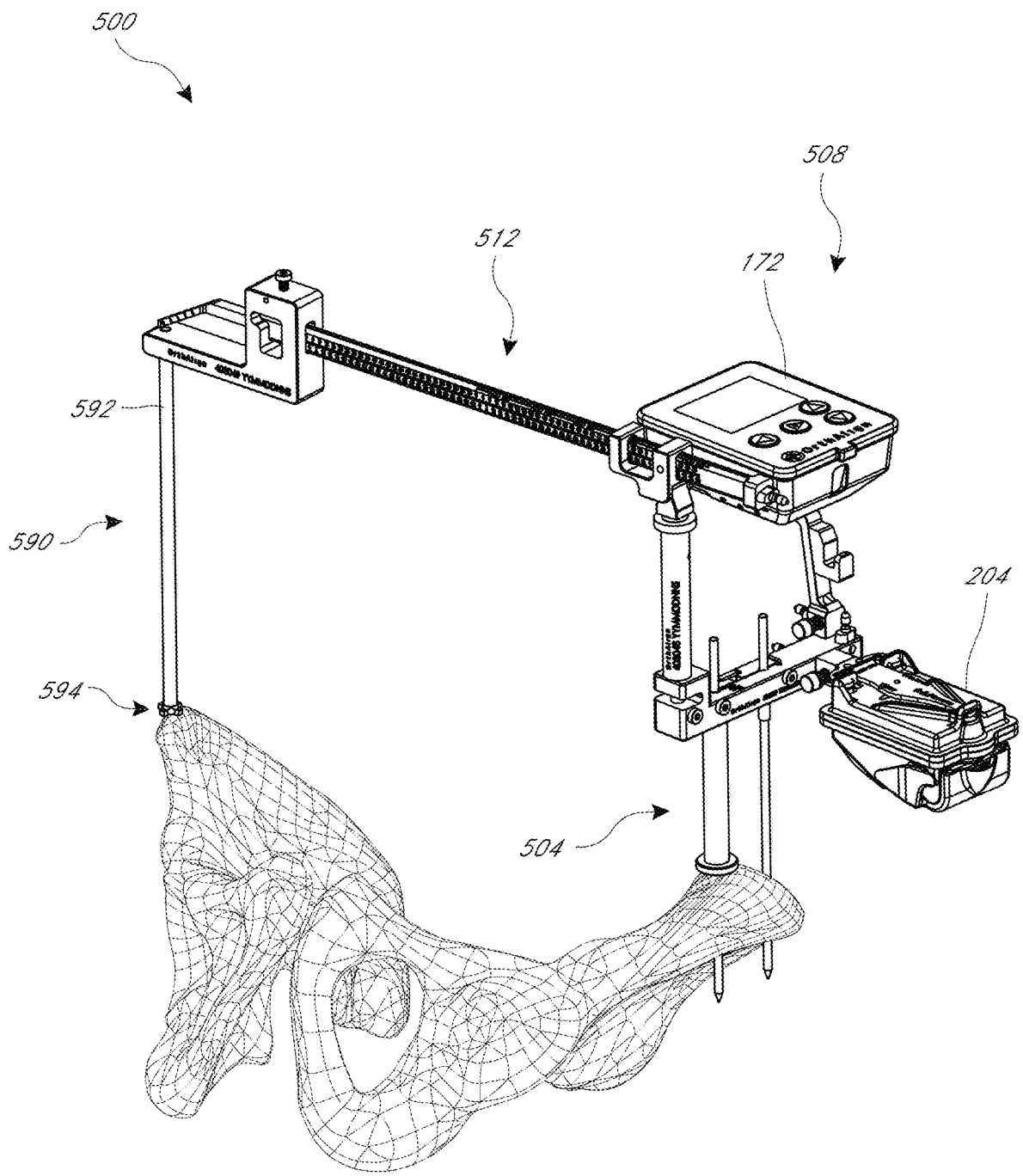

FIG. 36A illustrates a further step of navigating the anterior pelvic plane. As shown, the sensor 204 is docked on the platform 536, in which position any accumulated error associated with some sensors can be eliminated. In a preceding step, the extension 590 is coupled with the distal portion of the probe 584. The foot 594 is brought into contact with the contralateral ASIS. Thereafter, the sensor 204 can be attached to the proximal end of the probe 284 as shown in FIG. 34. The landmark acquisition system 512 can be immobilized and the orientation of the sensor 204 can be recorded in memory in the orientation device 172. Additionally, the distance that the probe 584 is extended to contact the contralateral ASIS can be recorded in the orientation device 172. As noted above, that distance can be read from the scale on the probe 584 at the upright edge 598.

Figure 36B:
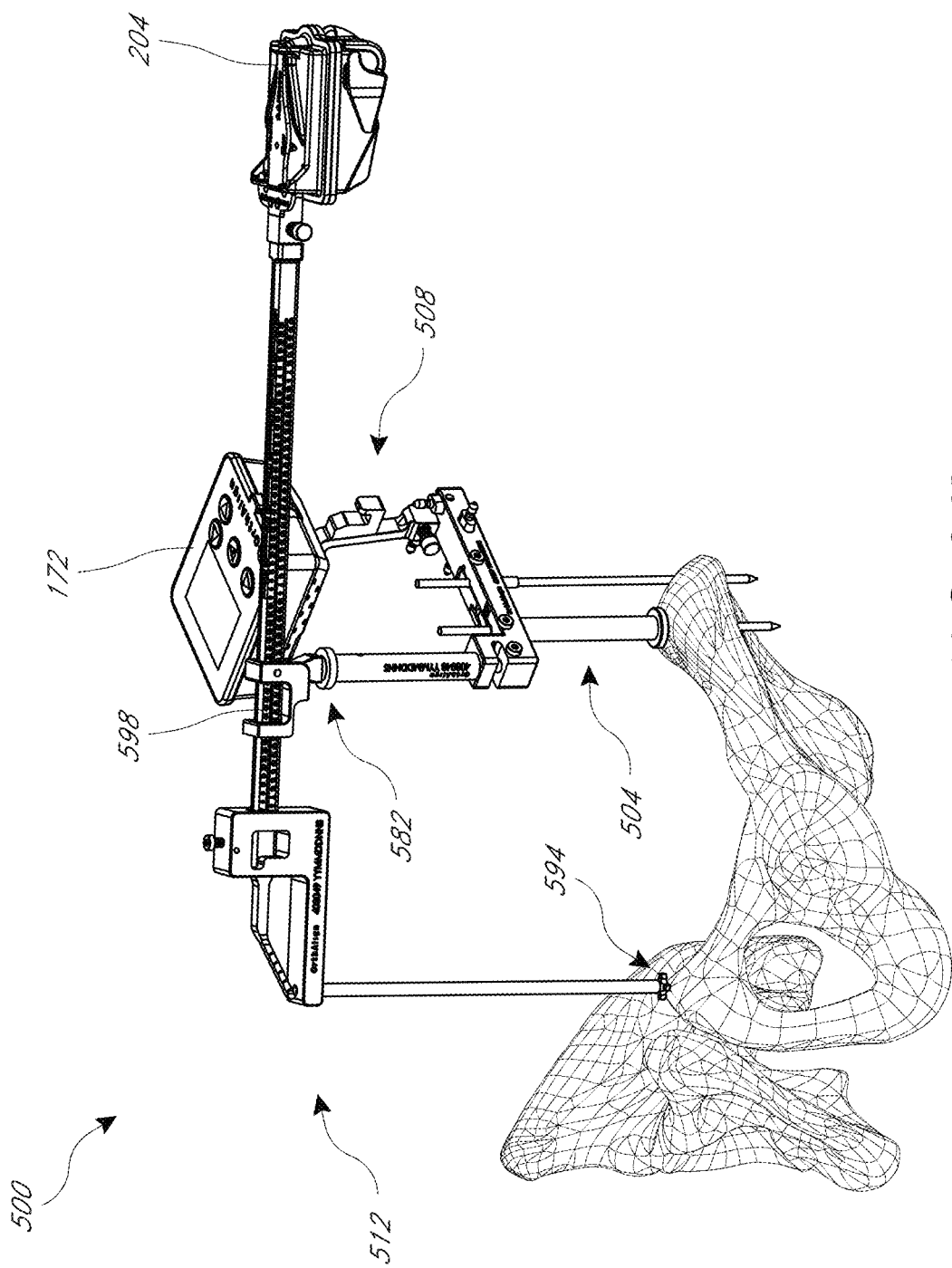
Figure 37:
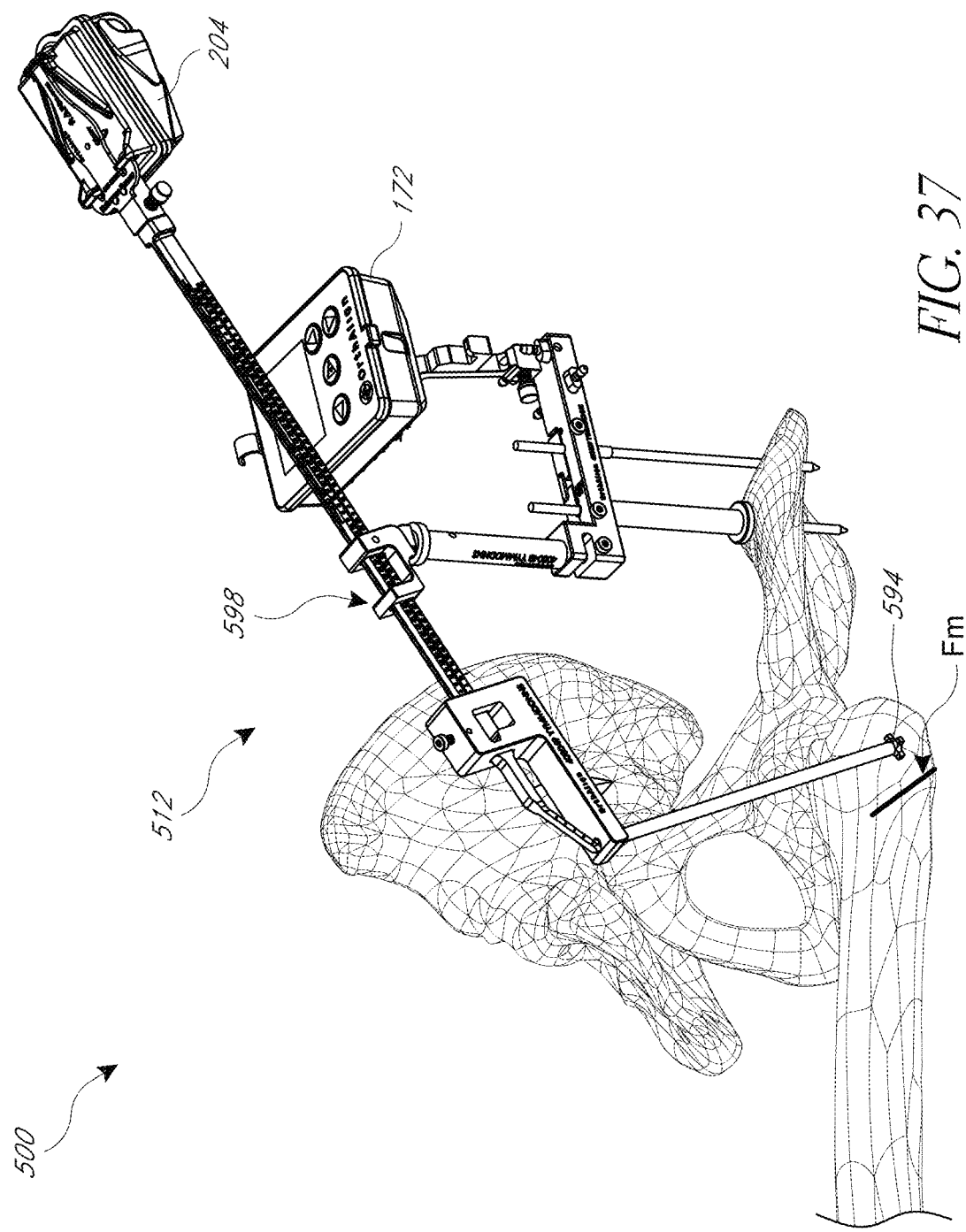
Figure 38:
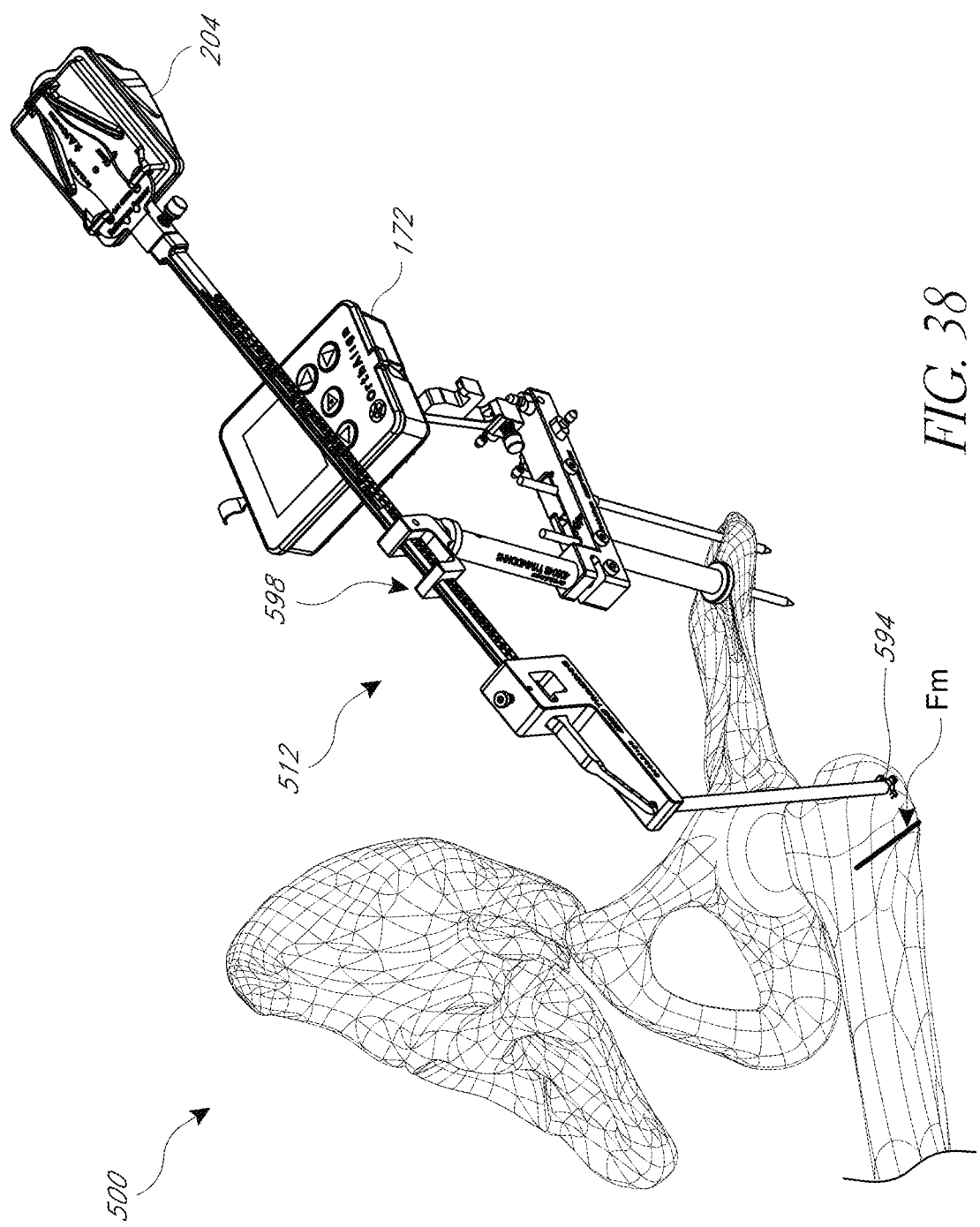

The process to record the contralateral ASIS can be repeated for one or more additional points. The sensor 204 can be docked to the platform as in FIG. 36A to eliminate sources of accumulated error. The probe 584 can then be moved to cause the foot 594 to be in contact with a pubic tubercle. The probe 584 can be immobilized and the sensor coupled with the proximal end as shown in FIG. 36B. Thereafter data indicative of the orientation of the sensor 204 and the distance to the pubic tubercle are recorded in the orientation device 172 in any of the manners discussed above.

Once the foregoing points of the pelvis have been navigated and the data recorded into the orientation device 172 the anterior pelvic plane can be calculated from data indicating the navigated points. The orientation of the anterior pelvic plane is a baseline for placement of the cup portion of a hip prosthesis.

The sensor 204 and the orientation device 172 can at this point be used to guide placement of the cup 360 in the prescribed orientation. Prior to placement the impactor 300, 300A is provided. For example, the impactor 300A can be provided by selecting the appropriate tip component 348 onto the distal end of the shaft 316A. The tip component 348 is coupled with the cup 360, e.g., by threads. The rotational orientation of the cup 360 to the shaft 316A that is most convenient given hole patterns and position of the sensor 204 is selected by matching up the flats 350A, 350B as appropriate. During the process of providing the impactor 300 the sensor 204 can be docked to the platform 536 and source of accumulated error can be eliminated just prior to navigating the cup 360 into place in the acetabulum.

In one technique, the cup 360 is inserted into the acetabulum and placed to approximately the correct orientation. Thereafter the sensor 204 is connected to a docking device 338 on the impactor as shown in FIG. 11A. The orientation device 172 is the activated to display angles indicative of the orientation of the cup, e.g., degrees of inclination and anteversion with respect to the anterior pelvic plane. The angle displayed can directly reflect the table reference frame discussed above. The angle displayed can directly reflect the frame of reference from the acquisition of landmarks. In some cases, angles can be displayed that directly reflect both table reference frame and landmark reference frame. In other embodiments, the table reference frame is not displayed but rather causes a user instruction to be displayed on the orientation device 172, such as a direction to re-acquire landmarks due to disagreement between the angles generated by the two reference frames.

Any of the foregoing combinations of table and landmark reference frames provides redundancy that ensures that the angle information provided to the user is accurate and reliable such that the procedures performed will be better contained within the "safe zone".

When the correct angles are achieved, a tool is used to strike the proximal end of the impactor 300 to lodge the cup 360 in place at the desired angle. In some techniques, the sensor 204 is removed prior to striking the proximal end of the impactor 300. The system 500 includes a module that monitors signals from the sensor 204 and if a large deviation in the readings occurs, the module prevents the angles on the display of the orientation device from changing. This "freezing" of the display is both a safety and an accuracy precaution because a large force due to impact can affect the accuracy of the sensor 204.

If femoral landmarks are acquired in the procedure prior to separating the natural joint, the same landmarks can be acquired after the prosthetic joint is placed to confirm that the replacement of the joint has not changed either the length of the leg, the off-set of the leg from the trunk of the patient or both. For example, the sensor 204 can be docked to the docking device 538A as shown in FIG. 36A. Sources of accumulated error can be eliminated by initializing the sensor 204. Thereafter, the probe arm 538 can be brought into contact with the same landmark (e.g., Fm) acquired early in the procedure. See FIG. 38. The probe arm 538 can be locked into place and thereafter the sensor 204 can be coupled with the proximal end of the probe arm 538. The orientation of the sensor and the distance to the probe arm 538 can be input into the orientation device 172. These data enable the orientation device 172 to output amounts of change in leg length and leg offset.

In one variation a plurality of points, e.g., three points, on the femur are acquired before and after the joint is replaced. This approach enables a further confirmation that the rotation orientation of the neck of the femur relative to an axis extending through the center of the cup 360 perpendicular to the plane of the acetabulum is unchanged after the procedure.

Of course, the femur registration procedures enable correction of diagnosed deformities including excessive leg length offset and joint offset, as well as mal-orientation of the femoral neck in the natural joint. In other words, the surgeon can begin the procedure with the intent of adding some offset or changing rotational orientation to improve the patient's bone positions and/or orientations post-operatively.

3. Anterior Approach: Systems with an Orientation Sensing Device and Camera

Figure 39:
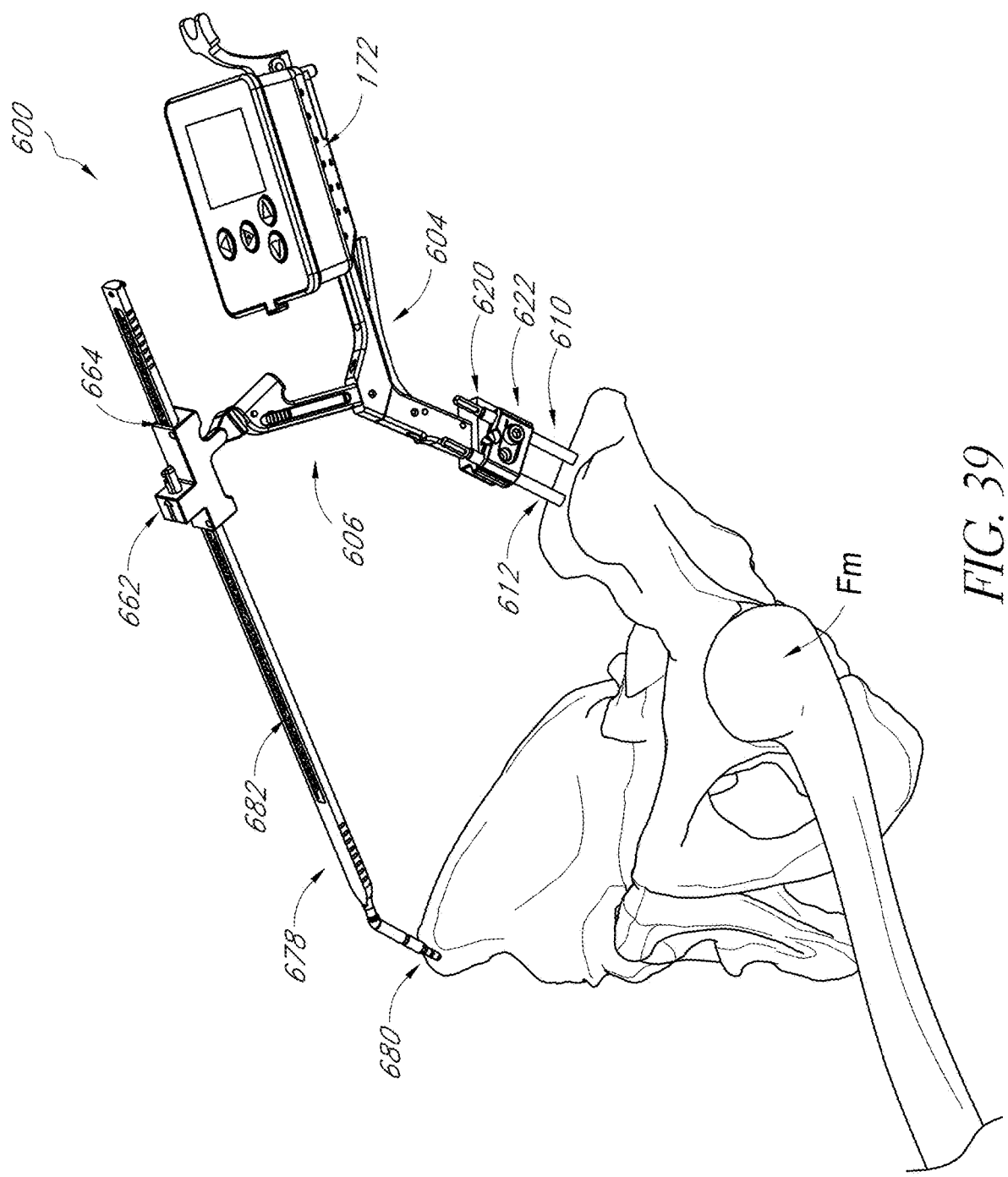
FIG. 39 illustrates the positioning of the system of FIG. 18 in an anterior approach.

FIG. 39 shows the system 600 adapted to navigate a hip joint procedure with reference to anatomical landmarks from an anterior approach. The system 600 can include the orientation sensing device 204, not shown in FIG. 39, as described above The system 600 can be adapted for either a posterior approach as described above, or an anterior approach.

Figure 40:
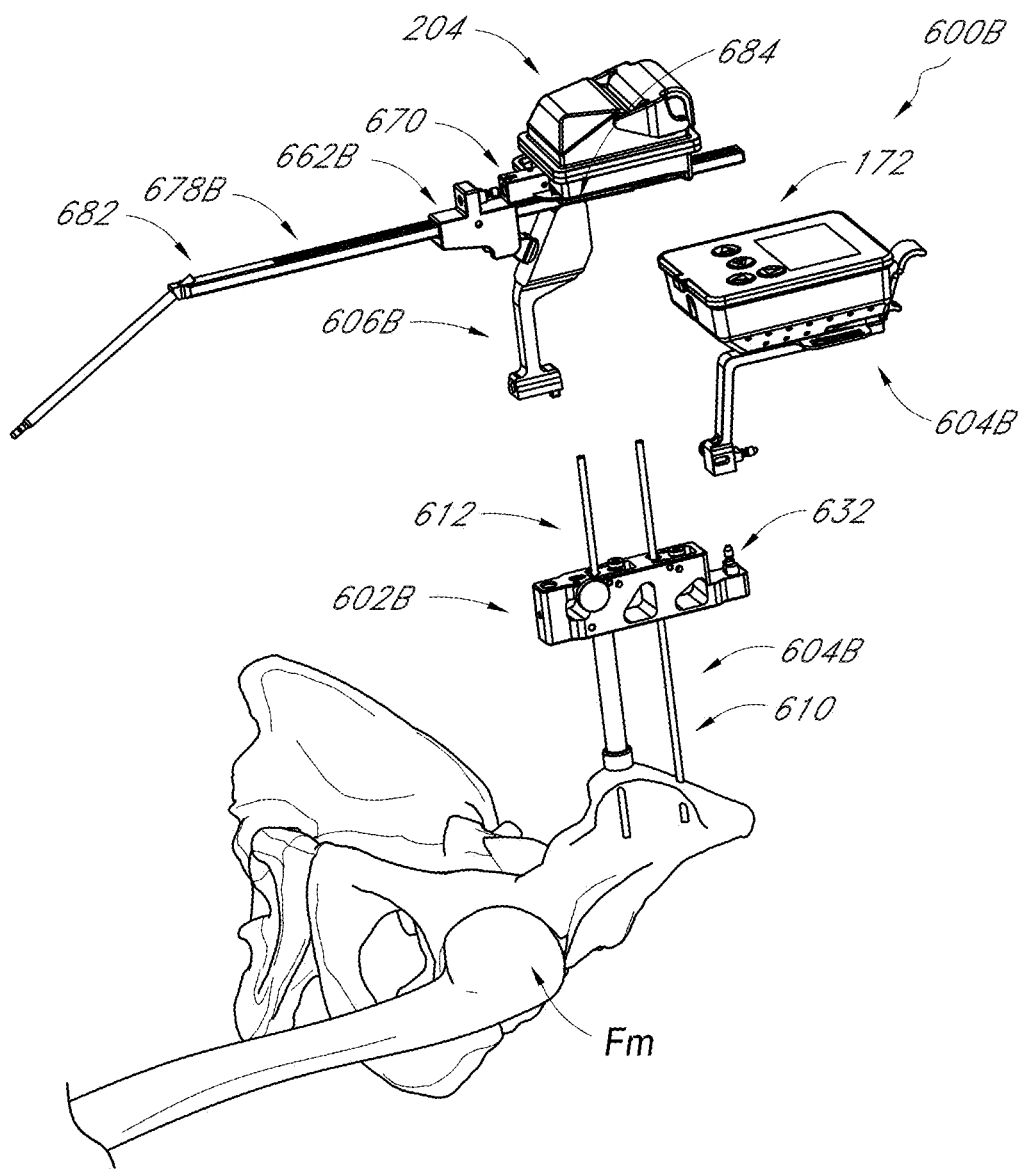
FIGS. 40-42 illustrate the positioning of another hip navigation system in an anterior approach.
Figure 41:
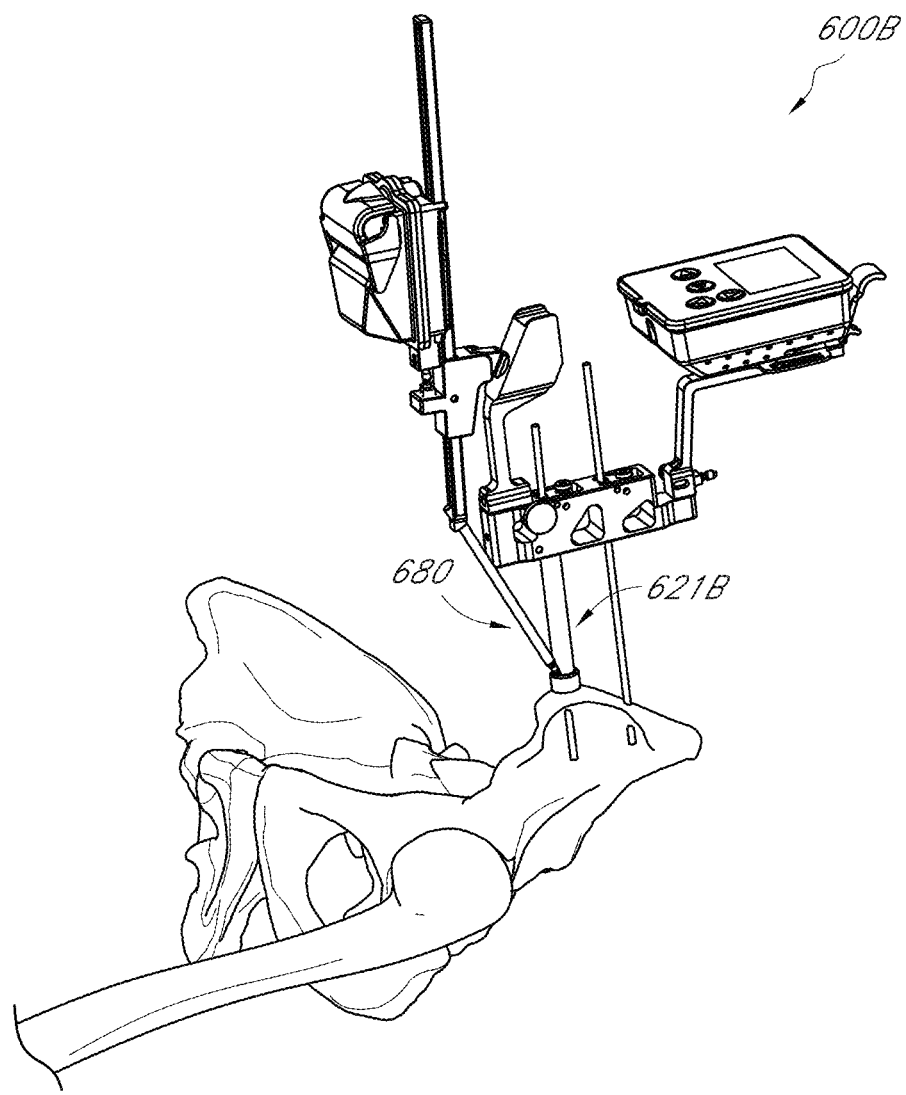
Figure 42:
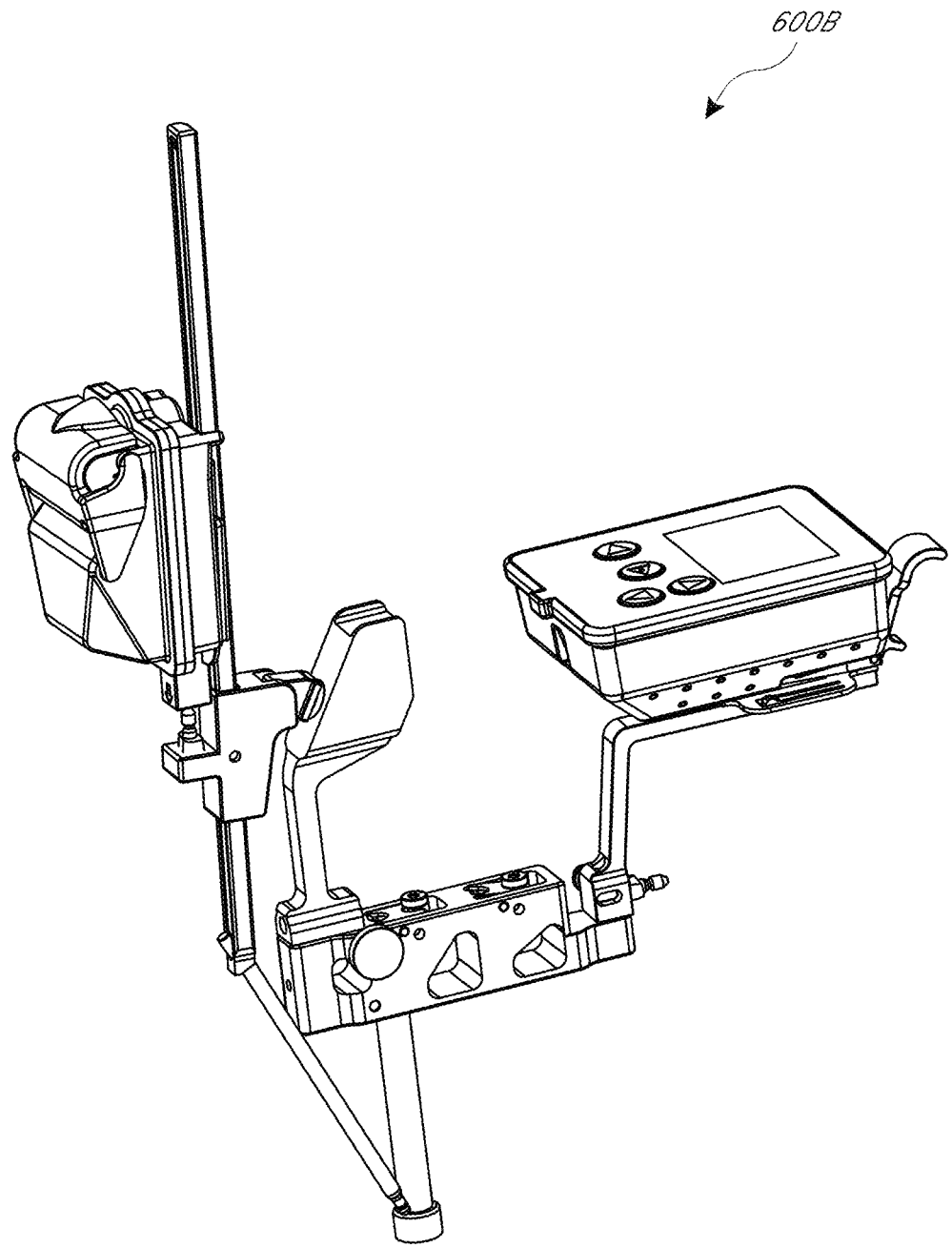

FIG. 40-42 shows a hip navigation system 600B adapted to navigate a hip joint procedure with reference to anatomical landmarks from an anterior approach. As noted above, in the anterior approach, the patient is in the supine position. The system 600B can include any of the features described above, including with reference to system 600. The system 600B can be used in any technique or method step described herein. The system 600B can include the surgical orientation device 172 described herein. The system 600B can include the orientation sensing device 204 described herein. The system 600B can include a camera 684 described herein.

The surgical orientation device 172 and the orientation sensing device 204 can be turned on before the procedure begins. If the system can be used in a posterior or anterior approach, one method can involve a surgeon selecting a module corresponding to the approach. For example, the surgeon can select an anterior hip approach module or a posterior hip approach module in the surgical orientation device 172. In some embodiments, the method can involve the step of inputting the surgical technique into the surgical orientation device 172. The surgeon can verify that patient is positioned in an appropriate position, e.g., in a supine position. The surgical orientation device 172 can include a display screen. The display screen can confirm the communication between the surgical orientation device 172 and the orientation sensing device 204.

The system 600, 600B can be partially assembled for calibration. In some embodiments, the first assembly 604 can be assembled. The pelvic bracket 638 can be coupled to the extension 644, if separate components. The surgical orientation device 172 can be coupled to the mount 646. In some techniques, the extension 670 can be coupled to the second coupler 648. The orientation sensing device 204 can be coupled to the mount 672. The surgical orientation device 172 and the orientation sensing device 204 form a general V-shaped configuration, similar to the orientation shown in FIG. 31. The orientation sensing device 204 can be fixed in position relative to the surgical orientation device 172.

The surgical orientation device 172 and the orientation sensing device 204 can be calibrated. The surgical orientation device 172 can be rested on a level horizontal surface with the display pointed upward. The surgeon can hold the assemblies 604, 606 or 604B, 606B steady until the surgical orientation device 172 indicates completion. The surgical orientation device 172 can be rested on a level vertical surface with the display pointed sideways. The surgeon can hold the assemblies 604, 606 or 604B, 606B steady until the surgical orientation device 172 indicates completion. The assemblies 604, 606 or 604B, 606B can be placed on the left side so that the left side of the surgical orientation device 172 rests on a level surface. The surgeon can hold the assemblies 604, 606 or 604B, 606B steady until the surgical orientation device 172 indicates completion. The assemblies 604, 606 or 604B, 606B can be angled forward to verify calibration. The surgeon can hold the assemblies 604, 606 or 604B, 606B steady until the surgical orientation device 172 indicates completion.

The extension 670 can be decoupled from the second coupler 648, as described herein. The second assembly 606 can be assembled as shown in FIGS. 39 and 40. The first assembly 604, 604B can be coupled to the second assembly 606, 606B as shown in FIGS. 39 and 40. The probe 678, 678B can be inserted within the through lumen of the dock 662, 662B. The marking 682 can be beneath the camera 684. The surgeon can verify the camera 684 is capturing the measurements of the marking 682 by sliding the probe 678, 678B to different positions. An error message can be displayed if the camera 684 is not reading the markings 682.

The system 600, 600B can be attached to the pelvis. The fixation pins 610, 612 can be inserted into the bone. In some techniques, one or more of the fixation pins 610, 612 are positioned over the ASIS on the operative side. In some techniques, one or more of the fixation pins 610, 612 are positioned on the iliac crest. The fixation pins 610, 612 can be approximately vertical. The fixation pins 610, 612 can be inserted by use of a driver. The fixation base 602, 602B can be rotated as needed to place the fixation pins 610, 612 within the channels 626, 628 as shown in FIG. 20C. The support 622 can be brought toward the platform 620, thereby decreasing the diameter of the channels 626, 628. The fixation pins 610, 612 can be secured to the fixation base 602, 612B.

The first assembly 604, 604B can be coupled to the first coupler 632 as described herein. The surgical orientation device 172 can be coupled to the first assembly 604, 604B. The second assembly 606, 606B can be coupled to the second coupler 648 as described herein. The orientation sensing device 204 can be coupled to the second assembly 606. The system 600 can be positioned as shown in FIGS. 39 and 41.

The surgeon can register a parked configuration or home position as shown in FIG. 41. In some techniques, the distal end 680, 680B of the probe 678, 678B can be engaged with a point on the platform 620 or cannula 621B. The platform 620 or cannula 621B can include the divot 630 as described herein. The divot 630 can be sized to accept the distal end 680, 680B of the probe 678, 678B. The distal end 680, 680B of the probe 678, 678B can be curved or bent to facilitate locating anatomical landmarks or points, as shown in FIGS. 39 and 40. The probe 678, 678B can be vertical in the home position. The orientation sensing device 204 can be vertical in the home position.

The orientation sensing device 204 can register the operating table or perform table registration for the anterior approach. The patient can be positioned so that the coronal plane of the pelvis is level. In some embodiments, the surgeon can align the probe 678, 678B with the horizontal. In some embodiments, only the direction of the probe's 678, 678A projection onto a horizontal plane is used. The probe 678, 678A can be in an infinite number of angles from horizontal, which would result in the same software result. This is convenient due to the mechanical constraints imposed by the pivot configuration of the system 600. The probe 678, 678B can be parallel with the sagittal plane. The system 600, 600B can calculate cup angles based on the assumption that the pelvis of the patient is correctly positioned during table registration.

At the surgeon's discretion the system 600, 600B can be used to navigate a condition of the femur prior to hip replacement. A mark Fm may be made on the proximal femur. Thereafter the orientation sensing device 204 can be initialized or zeroed such as by placing it back in the home position, as described herein. Thereafter, the distal end 680, 680B of the probe 678, 678B can be brought into contact with the femur mark Fm. The surgical orientation device 172 can be signaled to record the orientation of the orientation sensing device 204. A distance from the point of attachment of the fixation pins 610, 612 to the marked position on the femur can then be recorded in the surgical orientation device 172. The position can be based on capturing the markings 682 the probe 678, 678B or probe inlay 676 by the camera 684, in combination with inertial data from the orientation sensing device 204.

The femur can be positioned in a neutral reference position with respect to flexion, abduction and rotation. This neutral position can be representative of a standing position of the patient.

The surgeon can position the distal end 680, 680B of the probe 678, 678B at various anatomical landmarks. The surgeon can hold the hip stable. In some methods, Point 1 of the system is the mounting point of one or more fixation pins 610, 612. Referring back to FIG. 39, each fixation pin 610, 612 can be driven into the pelvis. In some techniques, one of the fixation pins 610, 612 is mounted to a pelvic bone at a landmark. When one of the fixation pins 610, 612 is coupled with a landmark, only two additional landmarks are acquired in some embodiments as discussed below. In some methods, the distal end 680, 680B of the probe 678, 678B is placed at the contralateral ASIS landmark. The surgeon can enter an input to register Point 2 (e.g., depress a button on surgical orientation device 172). The surgical orientation device 172 can indicate that Point 2 was recorded. The probe 678, 678B can be immobilized and the orientation of the orientation sensing device 204 can be recorded by the surgical orientation device 172. Additionally, the distance that the probe 678, 678B is extended, as captured by the camera 684, to contact the contralateral ASIS can be recorded by the orientation device 172.

The process to record the contralateral ASIS can be repeated for one or more additional points. In some methods, the distal end 680, 680B of the probe 678, 678B is placed at the pubic tubercle. The surgeon can enter an input to register Point 3 (e.g., depress a button on surgical orientation device 172). The surgical orientation device 172 can indicate that Point 3 was recorded. In some methods, either pubic tubercle may be used as a reference. The probe 678, 678B can be immobilized and the orientation of the orientation sensing device 204 can be recorded by the surgical orientation device 172. Additionally, the distance that the probe 678, 678B is extended, as captured by the camera 684, to contact the pubic tubercle can be recorded by the orientation device 172.

When registering the anatomical points, the camera 684 captures an image of the marking 682. The camera 684 can read the marking 682 to provide accurate determination of the translational position of the probe 678, 678B relative to the dock 662. The camera 684 can be directly above the marking 682. In some methods, the camera 684 can read a binary code of the marking 682.

In some methods, the orientation sensing device 204 converts the image of the camera 684 into an extension measurement of the probe 678, 678B. In some embodiments, the surgical orientation device 172 converts the image of the camera 684 into an extension measurement of the probe 678, 678B. The distance related to the extension of the probe 678, 678B can be used in conjunction with the orientation and positional data from the orientation sensing device 204. The surgical orientation device 172 can use the length measurement from the camera 684 and the data from the orientation sensing device 204 to determine the location of the distal end 680, 680B of the probe 678, 678B. In some embodiments, the surgeon will enter an input (e.g., depress a button) to collect data from the orientation sensing device 204. In some methods, the surgeon will enter an input (e.g., depress a button) to collect data from the camera 684. In some embodiments, the surgeon will enter an input (e.g., depress a button) to collect data from the orientation sensing device 204 and the camera 684 simultaneously. In some methods, the orientation sensing device 204 and/or the camera 684 will only send data if the orientation sensing device 204 is stable or non-moving.

Once the foregoing points of the pelvis have been navigated and the data recorded into the surgical orientation device 172, the anterior pelvic plane can be calculated from data indicating the navigated points. The orientation of the anterior pelvic plane is a baseline for placement of the cup portion of a hip prosthesis.

The orientation sensing device 204 and the surgical orientation device 172 can at this point be used to guide placement of the cup in the prescribed orientation. The surgeon can set the angle of the cup. Later in the procedure, the surgeon can check cup angle after the angle has been set. The surgeon can remove the second assembly 606 from the first assembly 604. The surgeon can remove the extension 670 from the third coupler 668. The surgeon can couple the extension 670 to an impactor 300B, shown in FIGS. 56A-56F. The impactor 300B can have the fourth coupler 338B. This permits the orientation sensing device 204 to couple to the fourth coupler 338B. The acetabular shell can be threaded onto the shell adaptor, similar to FIG. 11C. The shell adaptor can be snapped onto the end of the impactor 300B, similar to FIG. 11B.

The acetabular shell can be inserted into the acetabulum and positioned at the desired angle. The surgical orientation device 172 can guide the surgeon in setting the appropriate cup angle. The surgical orientation device 172 can graphically display when the orientation sensing device 204 is located at the inclination and anterversion angles entered by the surgeon. The surgical orientation device 172 can graphically display the inclination and anterversion angles as the orientation sensing device 204 is moved. The surgeon can enter an input to set the desired angle (e.g., depress a button on surgical orientation device 172).

The inclination and anteversion cup angles can be displayed statically. The anatomic angles are those calculated by the system 600 based on the pelvic landmark registration. The table angles are those calculated by the system 600 based on the initial positioning of the pelvis during table registration. The surgeon can check cup angle after the angles are set.

If femoral landmark Fm is acquired in the procedure prior to separating the natural joint, the same landmark can be acquired after the prosthetic joint is placed to confirm that the replacement of the joint has not changed either the length of the leg, the off-set of the leg from the trunk of the patient or both. Thereafter, the distal end 680, 680B of the probe 678, 678B can be brought into contact with the same landmark (e.g., Fm) acquired early in the procedure. The orientation of the orientation sensing device 204 and the extension of the probe 678, 678B can be input into the surgical orientation device 172. These data enable the surgical orientation device 172 to output amounts of change in leg length and leg offset.

In one variation described above in connection with the system 600, 600B and FIG. 24A, a plurality of points, e.g., three points, on the femur are acquired before and after the joint is replaced, for instance with the use of the femur tracker 686. This approach enables a further confirmation that the rotation orientation of the neck of the femur relative to an axis extending through the center of the cup perpendicular to the plane of the acetabulum is unchanged after the procedure.

The surgeon can register the home position. The surgeon can couple the second assembly 606, 606B to the first assembly 604, 604B as shown in FIGS. 39 and 40. The mount 672 can be coupled to the orientation sensing device 204 as described herein. The mount 646 can be coupled to the surgical orientation device 172 as described herein. The surgeon can confirm that the components of system 600, 600B are rigidly coupled. The surgeon can verify the parked configuration or home position. The distal end 680, 680B of the probe 678, 678B can be engaged with a point on the platform 620 or cannula 621B. The platform 620 or cannula 621B can include the divot 630 as described herein. The divot 630 can be sized to accept the distal end 680, 680B of the probe 678, 678B. The change in the home position is displayed on the surgical orientation device 172.

C. Navigation Using Pre-Operative Imaging and Patient Specific Jigs

Although the foregoing approaches can improve the standard of care currently in place, further increases in accuracy and even better outcomes and streamlining of the procedure can be provided if the system is configured to account for patient specific anatomical variability.

1. Patient Specific Jigs: Navigation Using Fixation Pins Mounted Therethrough

Figure 43:
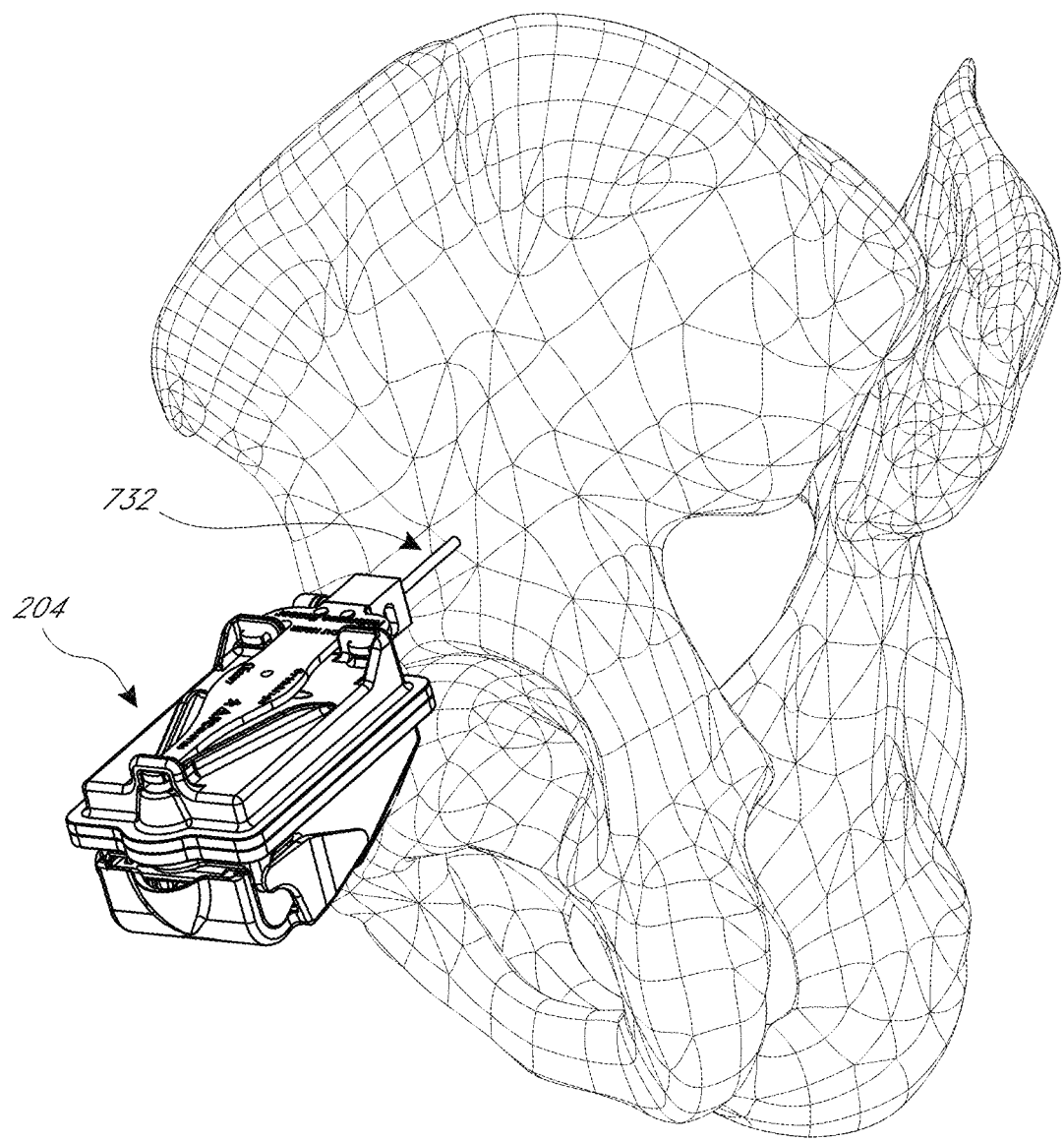

FIG. 43 shows the placement of a hip movement tracking sensor 204 on a pin 732 adjacent to the acetabulum. This position is not limiting, in that the hip movement tracking sensor 204 can be mounted anywhere on the pelvis, but adjacent to the acetabulum is convenient. The pin 732 has been placed with the aid of a pre-operative characterization of the hip of the specific patient. In these methods the pin 732 is placed without the need for intra-operative landmark acquisition.

In one approach, a pre-operative three-dimensional characterization of the acetabulum is performed using any suitable technology, such as CT scan or MM. This pre-operative procedure can be performed to fully characterize the pelvis and, in some cases, the proximal femur. Thereafter, the shape, location and orientation of the acetabulum are known. Also, the bony features around the acetabulum are known. From this data, a custom jig 700 can be fabricated specific to the patient. The custom jig 700 not only has features that are specific to the individual patient's anatomy but also a registration feature 702 that will be at a known orientation to the plane of the acetabulum and to the anterior pelvic plane.

FIG. 44 shows an example of the custom jig 700. The jig 700 has an anterior side 704 and a posterior side 708. The posterior side 708 is formed with an acetabular portion 712 configured to mate with at least one feature of the acetabulum in a secure manner. For example, the acetabular portion 712 can fit snugly over the acetabular rim with a central portion of the posterior side 708 positioned in the acetabulum. The jig 700 preferably has only one pre-defined orientation. A surface on a posterior portion of the jig can define a plane that corresponds to a preferred orientation angle of the cup post-implantation. One or more channels 716 can be formed on the posterior side 708 that receive the local bony prominences of the acetabular rim only when the jig 700 is in the proper position and orientation. In another approach, the registration feature 702 of the jig 700 has a face or a hole that is oriented in the desired orientation for the shell or cup of the implant. Thus, once the jig 700 is placed, the sensing device 204 can be positioned against the face or surface or, if coupled with a pin 732, the pin can be inserted into the hole. From the orientation of the device when so placed, the orientation of the acetabular rim or a proxy thereof can be recorded in one or both of the devices 172, 204. The hole 702 preferably extends from the anterior side 704 to the posterior side 708 of the jig 700. The distance between the anterior and posterior surfaces 704, 708 provides the depth of the hole 702 being sufficient to guide a pin to specific anatomy along a specific direction.

Figure 45:
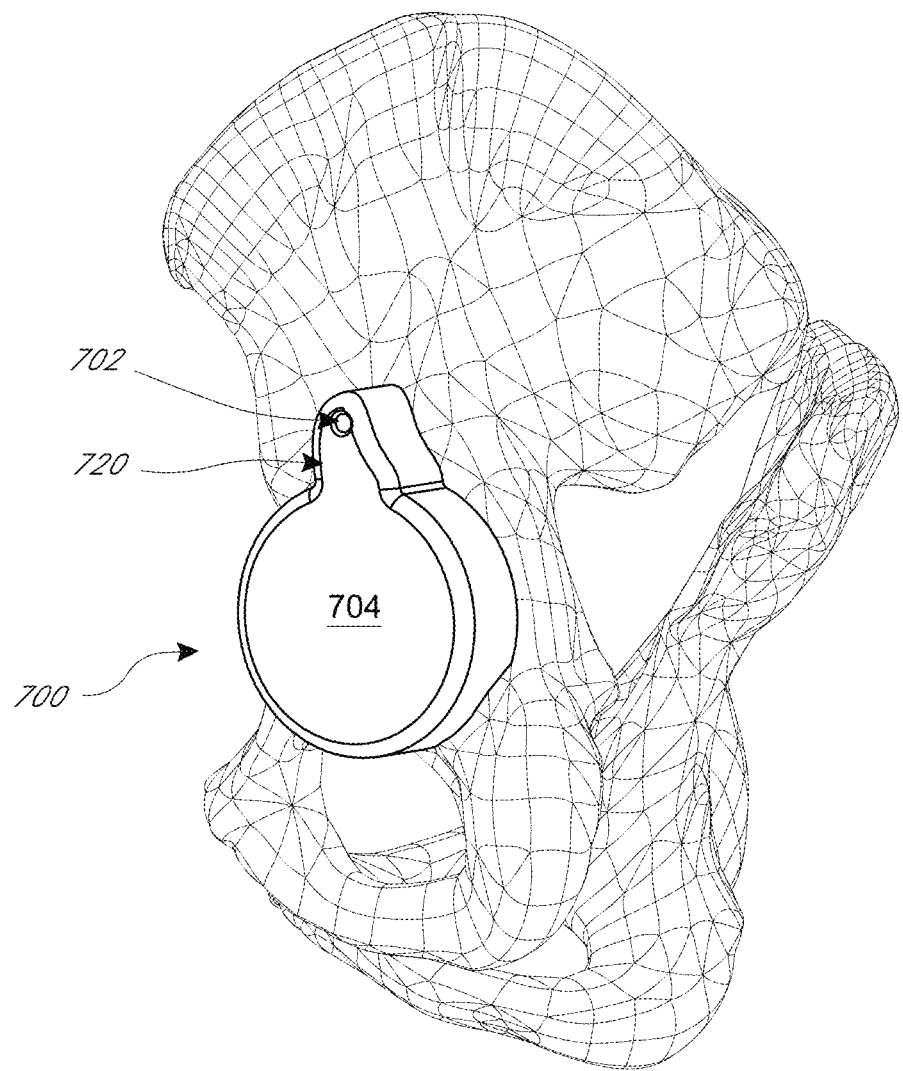

FIG. 45 shows initial placement of the jig 700 in the acetabulum in an orientation dictated by the fit of the jig 700 over the anatomy. The profile of the posterior side 708 including the channel(s) 716 receives the specific patient's acetabular rim including local prominences and recesses of the bone at and around the acetabulum. The hole 702 is located on a peripheral projection 720 of the jig 700. The configuration of the projection 720 is such that the hole 702 is disposed over a specific bone or bone region of the hip. In this example, the projection 720 is configured to be disposed over the bone superior to the acetabulum. Other regions of bone around the acetabulum can be used if sufficiently thick or strong and in a convenient position to not block actions of the surgeon during the procedure. The precise location of the projection 720 chosen can be determined by the pre-operative imaging and factored into the forming the custom jig 700.

Figure 46:
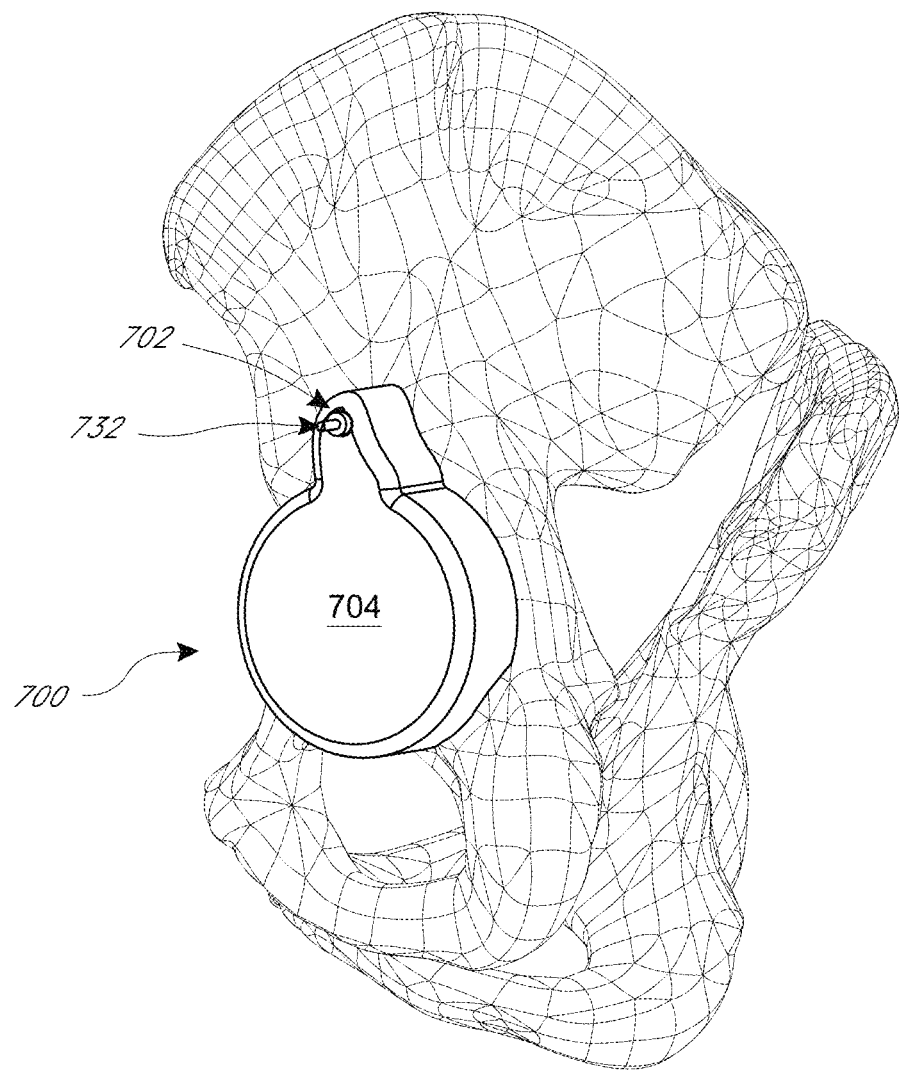

FIG. 46 shows that after the jig is placed the pin 732 can be placed through the hole 702. The pin 732 has a length that extends above the anterior surface 704 of the jig 700 such that the sensor 204 can be mounted thereto. Once the sensor 204 is mounted to the pin, the sensor can track any movement of the pelvis during the procedure. There is no need for registration of landmarks in this technique because the position and orientation of the pin relative to the acetabulum and/or to the anterior pelvic plane are known from the pre-operative imaging.

Figure 47:
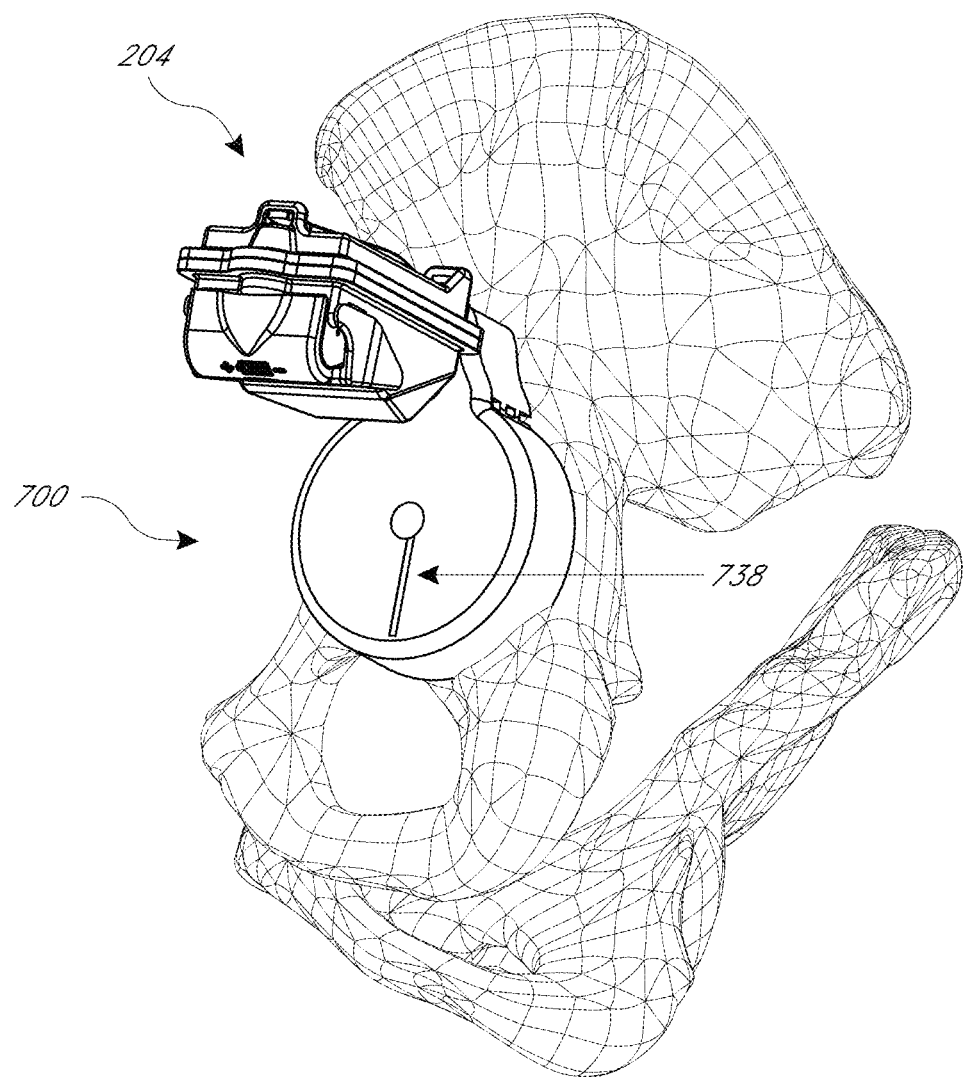
Figure 48:
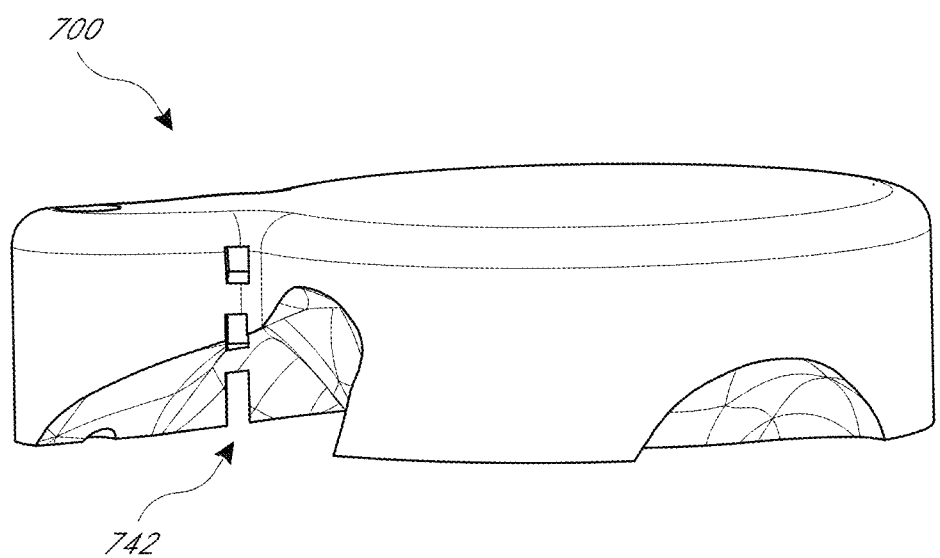

FIG. 47 shows that the plug 700 advantageously can include an alignment guide 736 to control rotational orientation of the sensor 204 on the pin 732. The alignment guide 736 can be a line extending along a specific direction relative to the registration feature 702. As noted above, the sensing devices inside the sensor 204 can be sensitive to the direction of gravity. Tilting of the sensor about the pin 732 can change the readings of these sensing devices. To eliminate sources of error associated with this sensitivity, the navigation system incorporating the sensor 204 can be programmed to assume that the sensor will be at a specific rotation position about the longitudinal axis of the pin 732. The sensor 204 may be mechanically or visually aligned with the guiding mark 738 to assure that this assumption is met in use. In one variation, the sensor 204 has a laser that projects onto the jig 700 and can be aligned with the mark 736 to facilitate alignment. Alternatively, the pin 732 may be configured to only enter the hole in a unique orientation (for example, with an asymmetric non-circular cross-section), and to allow the sensor to mount to the pin in a unique orientation (by including asymmetric coupling features).

Figure 49:
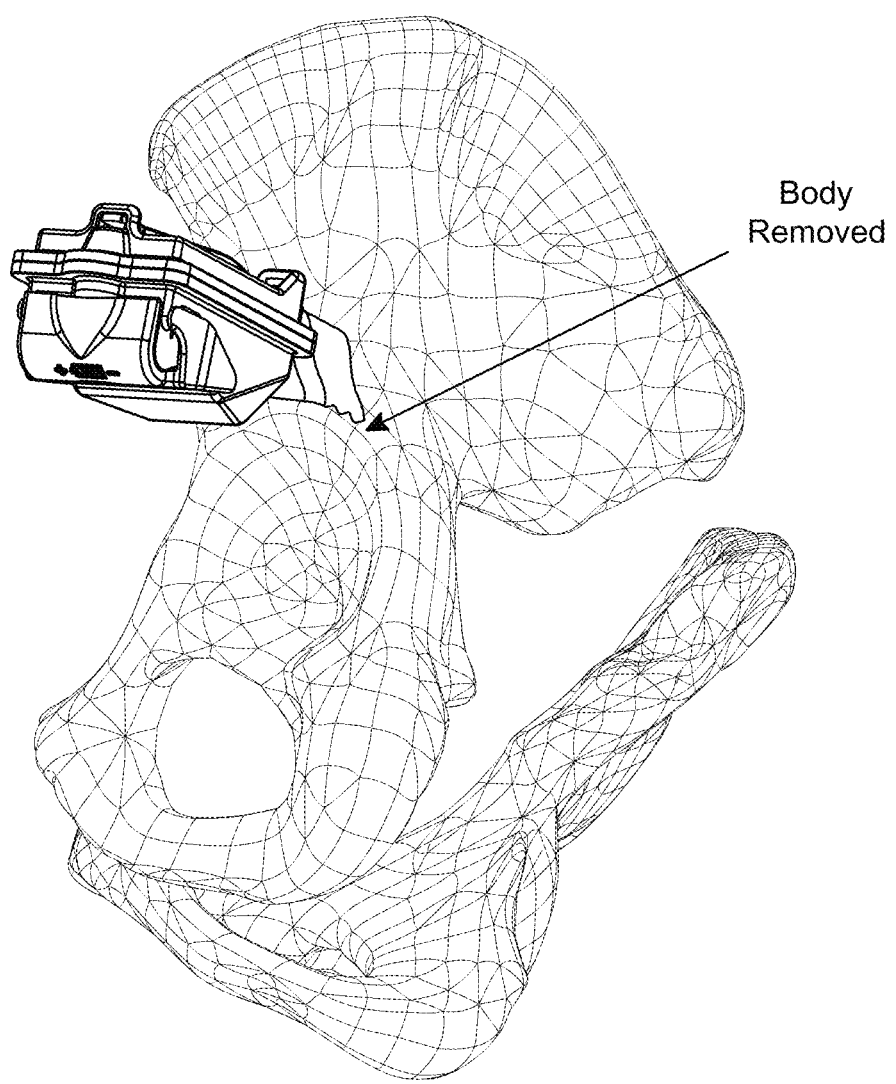

Once the sensor 204 is mounted to the pin 732, the jig 700 can be removed from the surgical area. For example, the jig 700 can be made of material can be cut along a line 742 in a lateral edge of the jig. A saw or rongeur can be used to cut through the jig 700. Thereafter, the majority of the body of the jig 700 can be removed from the surgical area. FIG. 49 shows that in some methods, the projection 720 is left in place so that the position and orientation of the sensor 204 is not disrupted.

A second sensor 204 is attached to a cup impactor, which may be the same as in FIGS. 11A-11C. The impactor guides the placement of the cup with reference to the signals from the sensor 204 mounted on the pin 732 on the pelvis. Signals from the sensor on the impactor can be corrected if movement of the hip is detected by the sensor on the pin 732.

Figure 50:
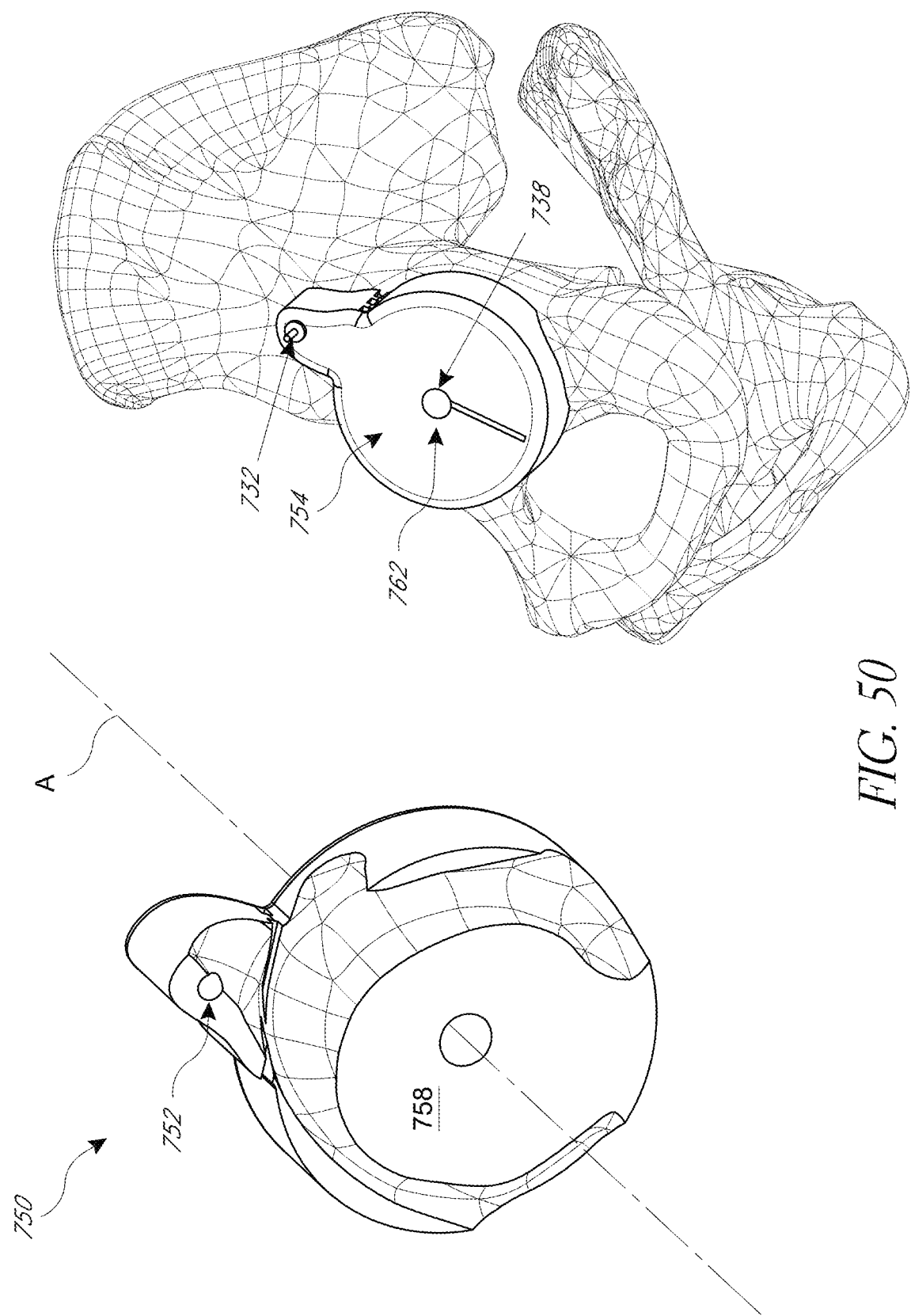
Figure 51:
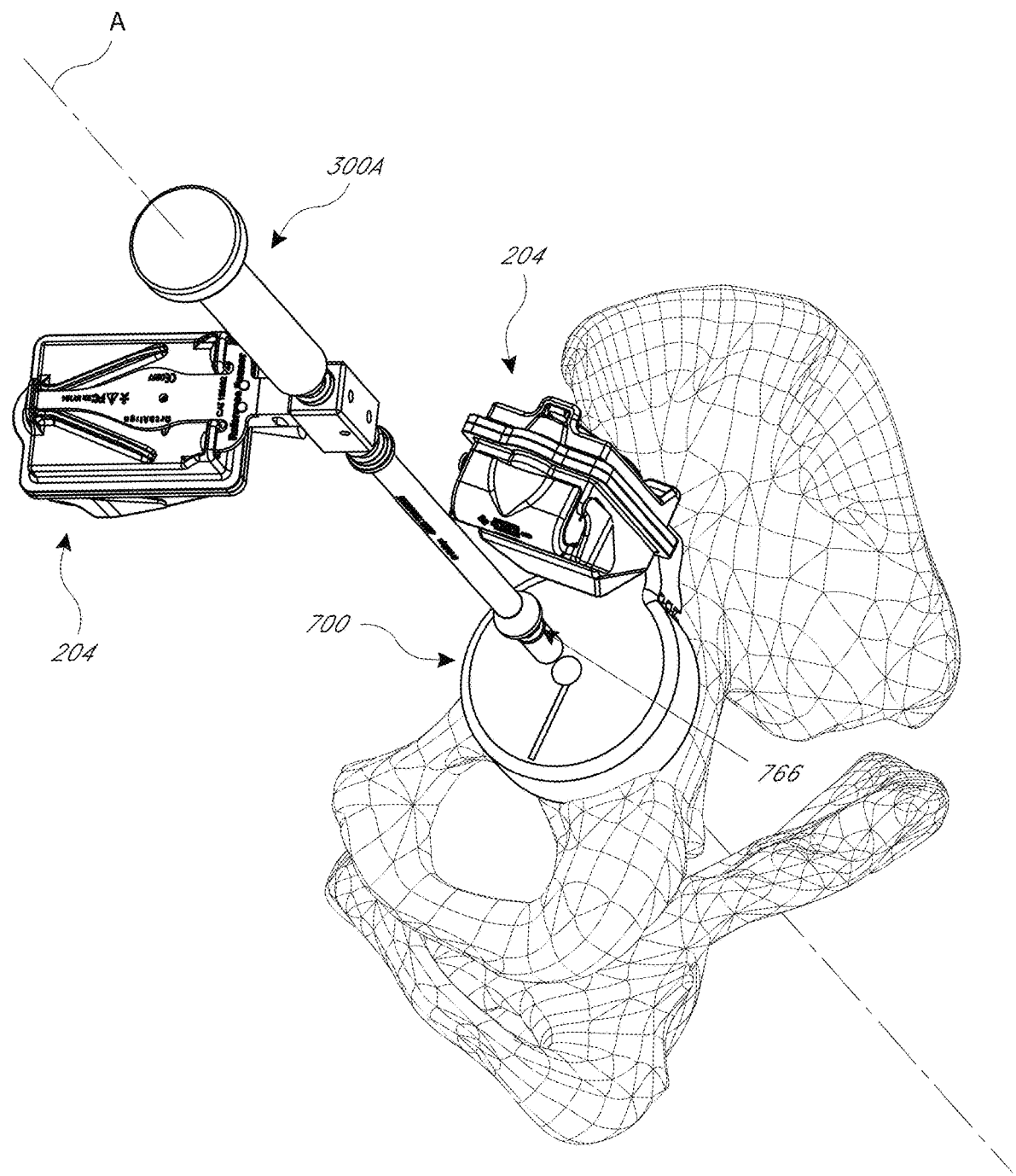
Figure 52:
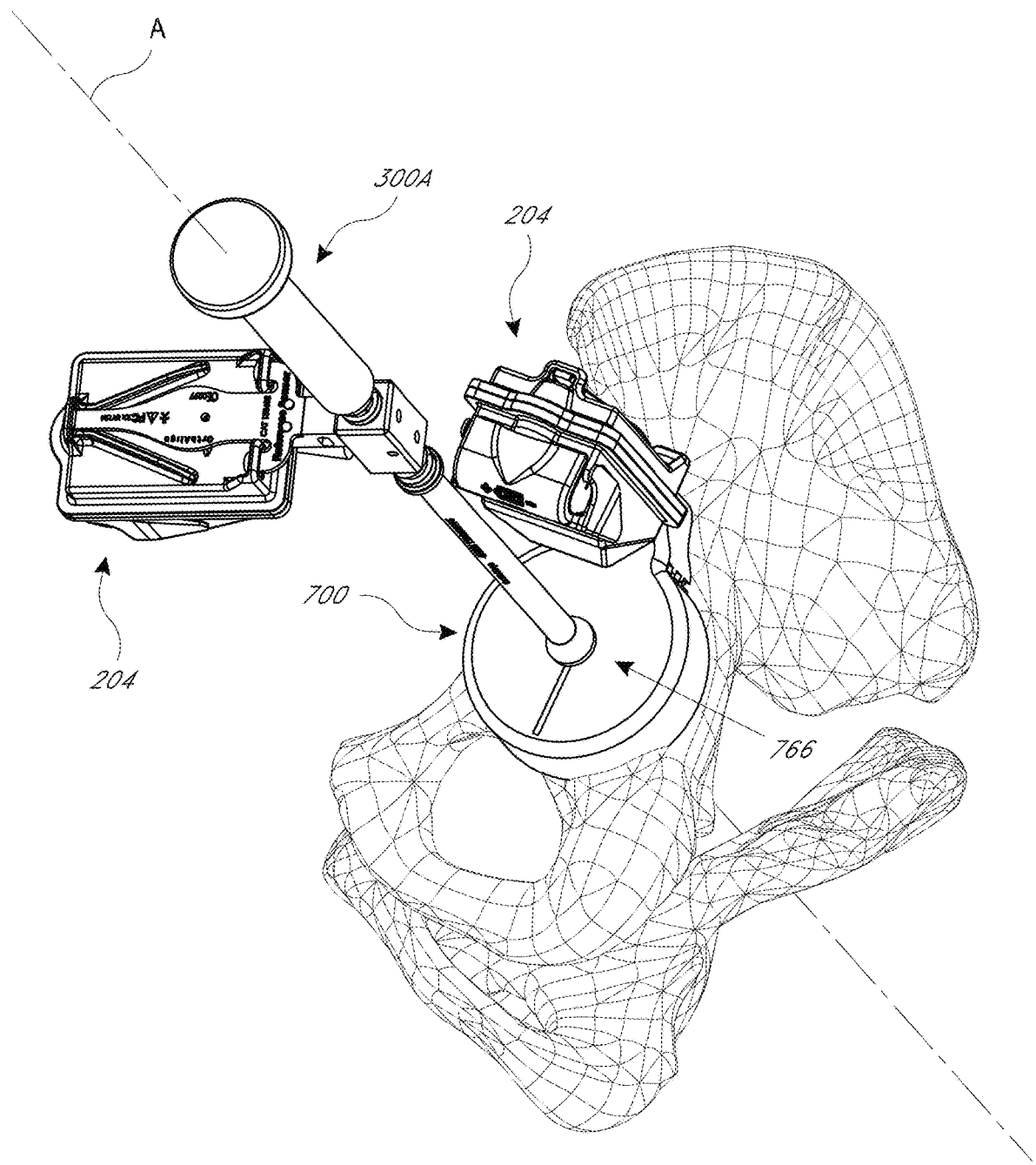

FIGS. 50-52 illustrate one way of implementing cannulated guide delivery methods. Cannulated methods are advantageous in that once a guide member is mounted, the tracking of orientation is simplified and may no longer be necessary in some cases, which can eliminate accumulated errors, sensor drift, or erroneous readings of other sorts as a concern.

A custom jig 750 is formed by the process discussed above in connection with the jig 700. The jig 750 has many of the same components as those of the jig 700, including a registration feature 752 extending between the anterior and posterior surfaces 754, 758. A guiding mark 738 can be provided on the anterior surface 754 to align the sensor 204 rotationally about the pin 732. The jig 750 also has a guide channel 762 located generally centrally in the jig 750. The guide channel 762 has an anterior opening on the anterior surface 754, a posterior opening on the posterior surface 758, and a wall extending between these openings. The wall is disposed about a central axis A. The position and orientation of the axis A can be determined based on the pre-operative characterization of the acetabulum. In one embodiment, an MM or CT scan reveals an optimal axis for delivering a prosthetic cup along. The wall forming the guide channel 762 is formed about the axis A which coincides with this optimal axis when the jig 750 is placed on the specific patient's acetabulum.

FIG. 51 shows that the impactor 300A can then be advanced along the axis A into the guide channel 762. A distally facing shoulder 766 on the impactor 300A can mate in a pre-defined way with the anterior surface 754 and the entrance to the channel 762 and when so mated the orientation of the sensor 204 on the impactor 300A can be recorded. In this technique, the jig 750 is a cannula with the channel 762 configured to receive the impactor 300A. If patient movement is possible, the sensor 204 on the pin 732 can be retained in place to track such movement. If not, the sensor 204 on the pin 732 can be removed. The sensor 204 on the impactor 300A will have stored the orientation of the axis A in memory and will be able to inform the user of any variance of the impactor from this axis. It is preferred to retain the sensor 204 on the pin 732, as the orientation can only be accurate stored by the sensor 204 on the impactor 300A for a short time due to accumulated error (e.g., drift) of some sensors, e.g., some lower cost gyroscopes.

In one variation, the impactor 300A has a central channel that coincides with the axis A when the impactor is placed into the guide channel 762 and the shoulder 766 abutted with the surface 754. A guide pin can be advanced through this channel and into the acetabulum. The guide pin can be lodged in the base of the acetabulum. The sensor 204 coupled with the pelvis by the pin 732 can be removed because the guide pin placed through the channel of the impactor 300A provides a mechanical way of tracking movement of the hip. Thereafter the impactor 300A with the cup mounted thereon can be slide over the guide pin and into place in the acetabulum.

In a further variation, the sensor 204 coupled with the impactor 300A can also be removed. In this further variation, the guide pin is configured along with the cup to prevent tilting of the prosthetic cup relative to the axis A. In particular, an interface between the guide member and the cup of the hip prosthesis could be made to have sufficient length along the axis A that tilting is prevented by this interface. In some cases, the cup 360 is coupled to the impactor 300, 300A. A variation of the impactor 300, 300A can be tubular or have another feature for interfacing with, e.g., tracking along the guide pin in the pelvis.

2. Patient Specific Jigs: Navigation Using Inertial Sensors Mounted on Impactor

FIGS. 53-60 shows another embodiment of a custom jig. The systems described herein can be used with a patient specific jig 1000, shown in FIG. 55. In some embodiments, the system 600, 600A, 600B or components thereof, can be used with the patient specific jig 1000.

Figure 53:
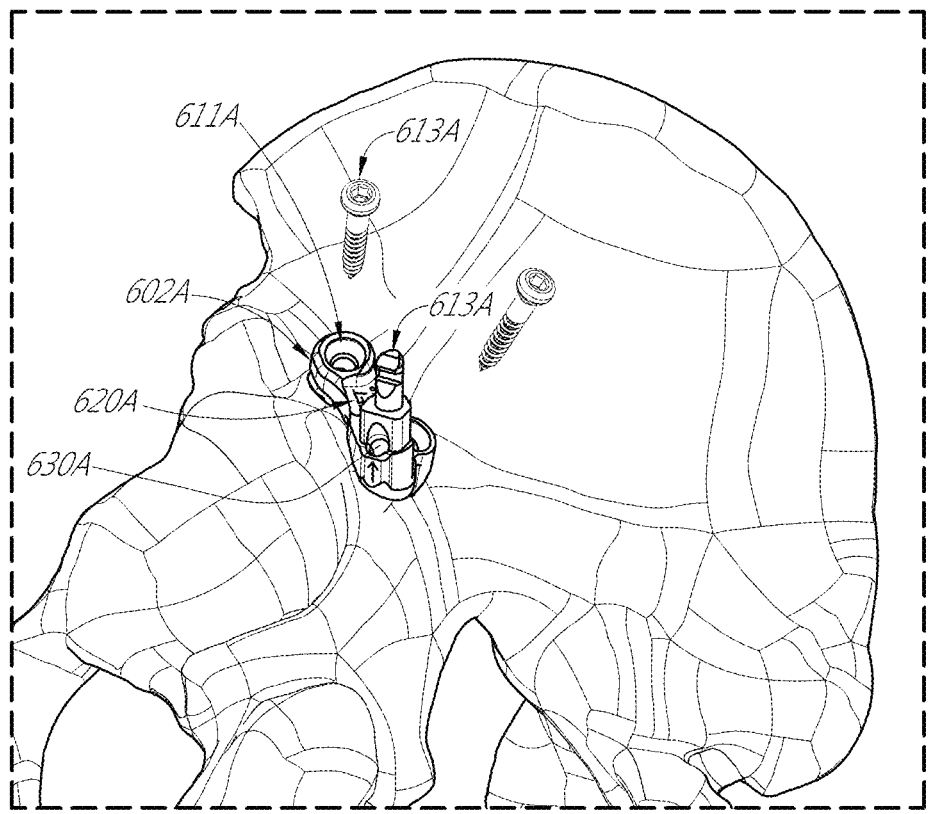
FIGS. 53-60 illustrate various aspects of methods involving patient-specific positioning jigs.

Referring to FIG. 53, the system 600A can include a fixation base 602A. The fixation base 602A can include a platform 620A. The platform 620A can include one or more holes 611A. The holes 611A can be sized to accept a fastener 613A to secure the fixation base 602A to the pelvis. The fixation base 602A can include divot 630A. The divot 630A can be a registration feature associated with a parked configuration or home position. Each fastener 613A can be driven into the ilium on the pelvis. As discussed further below, each fastener 613A can be coupled with other bones in other techniques. For example, one of the fasteners 613A can be coupled with the ischium or the pubis. One of the fasteners 613A can be coupled at a point superior to the superior-most point on the acetabular rim. In some techniques, one of the fasteners 613A is about 10 mm above the superior-most point on the acetabular rim.

Figure 54:
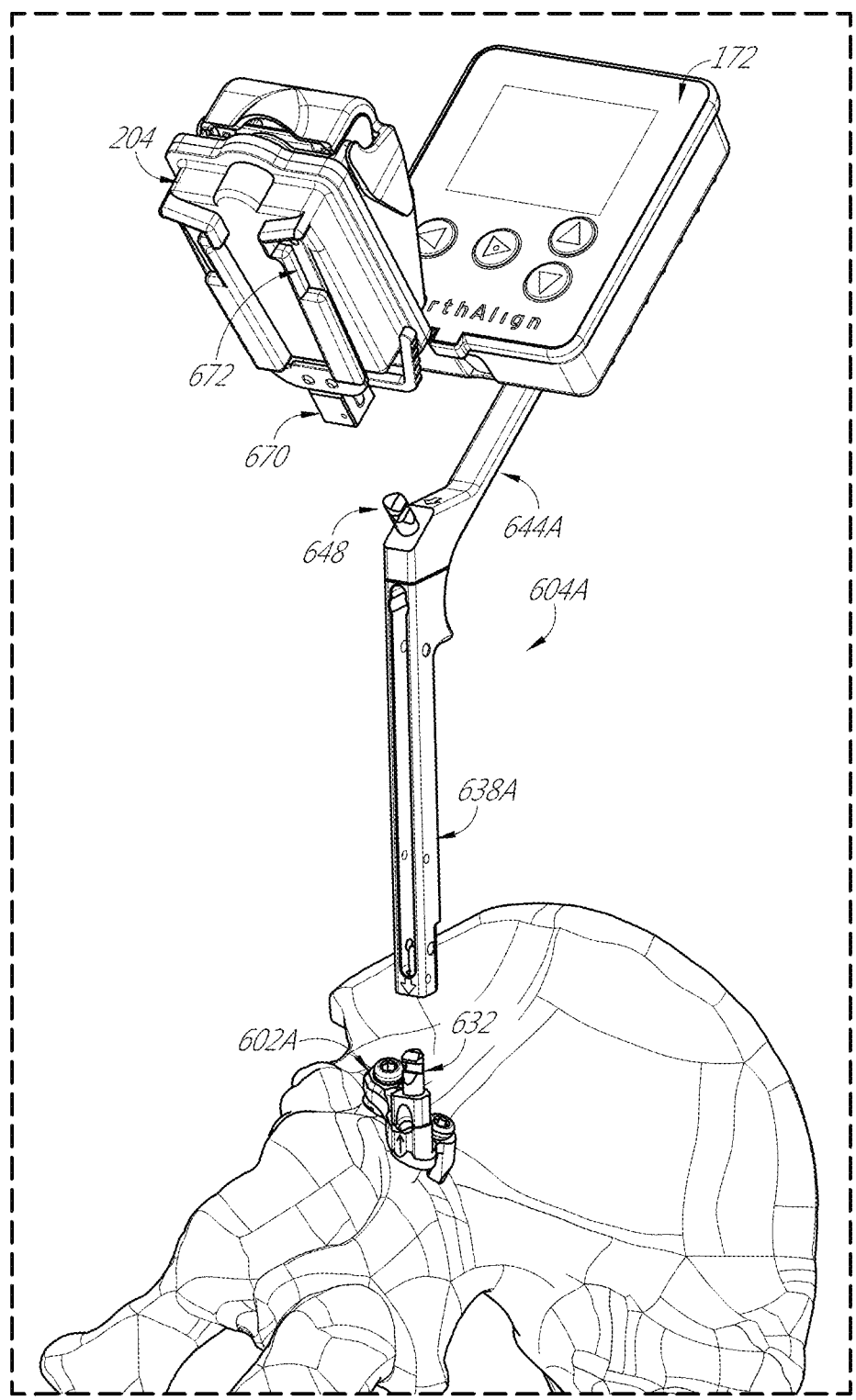

The fixation base 602A can include the first coupler 632. The first coupler 632 can couple to one or more components of the system 600A. The system 600A can include the first assembly 604A shown in FIG. 54. The first assembly 604A is rigidly connected to the hip in the illustrated configuration so that motion of the hip cause corresponding motion of sensor(s) in the first assembly 604A as discussed below. The first assembly 604A can include a pelvic bracket 638A. In the illustrated embodiment, the pelvic bracket 638A can be substantially vertical in use, as shown in FIG. 54. The first assembly 604A can be designed to couple with the first coupler 632 of the fixation base 602A.

The first assembly 604A can include an extension 644A. The extension 644 can be coupled to the pelvic bracket 638A. The extension 644A can include a mount (not shown) designed to couple with the surgical orientation device 172. The surgical orientation device 172 can include features to mate with the mount (not shown). The surgical orientation device 172 is rigidly coupled to the extension 644A when engaged with the mount.

The system 600A can include the second assembly 606A or a portion thereof. The second assembly 606A can include an extension 670. The extension 670 can couple to the second coupler 648. The engagement between the second coupler 648 and the extension 670 minimizes or prevents relative movement therebetween to avoid any mechanical relative movement during navigation procedures. The extension 670 can include a mount 672 designed to couple with the orientation sensing device 204. In the illustrated embodiment, the mount 672 includes a lock and release lever that can pivot relative to the extension 670. The orientation sensing device 204 can include features to mate with the lock and release lever. Other configurations are contemplated. The orientation sensing device 204 is rigidly coupled to the extension 670 when engaged with the mount 672. In some methods of use, the system 600, or a portion thereof, is coupled to the pelvis instead of the system 600A.

The surgeon can select the hip (e.g., right or left) using the surgical orientating device 172. The surgeon can input the target cup inclination angle into the surgical orientation device 172. The inclination angle can be radiographic inclination as described herein. The surgeon can input the target cup anteversion angle into the surgical orientation device 172. The anteversion angle can be radiographic anteversion as described herein.

The second assembly 606 includes the extension 670 and the mount 672, as shown in FIG. 23A. The orientation sensing device 204 can be coupled to the mount 672. The extension 670 can be coupled to the second coupler 648. The orientation sensing device 204 and the surgical orientation device 172 can be calibrated as described herein. The system 600 can be mounted similar to system 600A shown in FIG. 54. The method step of coupling the orientation sensing device 204 with the second coupler 648 can relate the orientation data of the orientation sensing device 204 to a reference frame of the surgical orientation device 172.

In some embodiments, a pre-operative three-dimensional characterization of the acetabulum is performed using any suitable technology, such as CT scan or MM. This pre-operative procedure can be performed to fully characterize the pelvis and, in some cases, the proximal femur. Thereafter, the shape, location and orientation of the acetabulum are known. Also, the bony features around the acetabulum are known. From this data, the patient specific jig 1000 can be fabricated specific to the patient. The patient specific jig 1000 not only has features that are specific to the individual patient's anatomy but also a registration feature 1002 shown in FIG. 55 that will be at a known orientation to the plane of the acetabulum and to the anterior pelvic plane.

Figure 55:
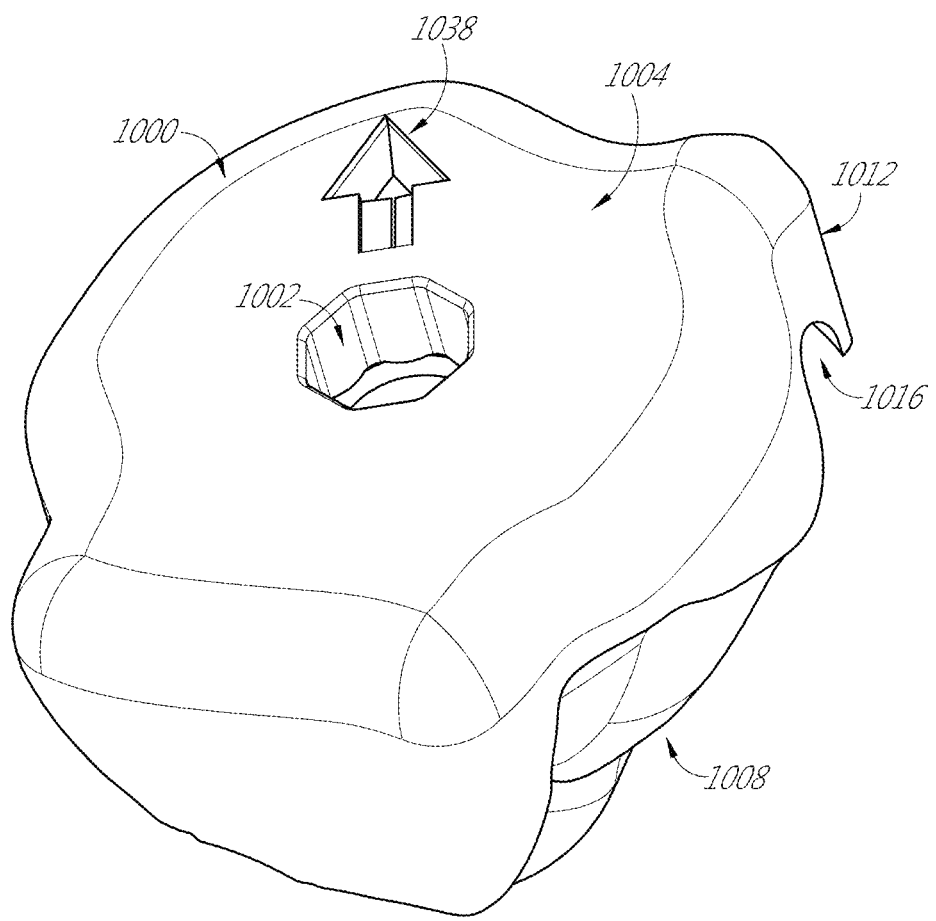

FIG. 55 shows an example of the patient specific jig 1000. The patient specific jig 1000 has an anterior side 1004 and a posterior side 1008. The posterior side 1008 is formed with a three dimensional shape configured to mate with at least one feature of the acetabulum in a secure manner. For example, an acetabular projection 1012 can be provided that fits snugly over the acetabular rim with a central portion of the posterior side 1008 positioned in the acetabulum. The patient specific jig 1000 preferably has only one pre-defined orientation. A surface on a posterior side 1008 of the patient specific jig 1000 can define a plane that corresponds to a preferred orientation angle of the cup post-implantation. One or more channels 1016 can be formed on the posterior side 1008 that receive the local bony prominences of the acetabular rim only when the patient specific jig 1000 is in the proper position and orientation.

In some embodiments, the registration feature 1002 of the patient specific jig 1000 can include a recess, a hole, or a projection. In one method of using the illustrated embodiment, the orientation sensing device 204, not shown but described herein, is coupled to an impactor 300B. The impactor 300B can be inserted into the registration feature 1002. Thus, once the patient specific jig 1000 is placed, the orientation sensing device 204 can be positioned in a known orientation relative to the registration feature 1002. From the orientation of the orientation sensing device 204 when so placed, the orientation of the acetabular rim or a proxy thereof can be recorded in one or both of the devices 172, 204. The registration feature 1002 preferably extends from the anterior side 1004 toward the posterior side 1008 of the patient specific jig 1000. The distance between the anterior and posterior surfaces 1004, 1008 provides the depth of the registration feature 1002 being sufficient to securely couple to the impactor 300B. In other embodiments, the registration feature 1002 extends anteriorly of the anterior side 1004 of the jig 1000, e.g., as a projection or post.

Figure 56A:
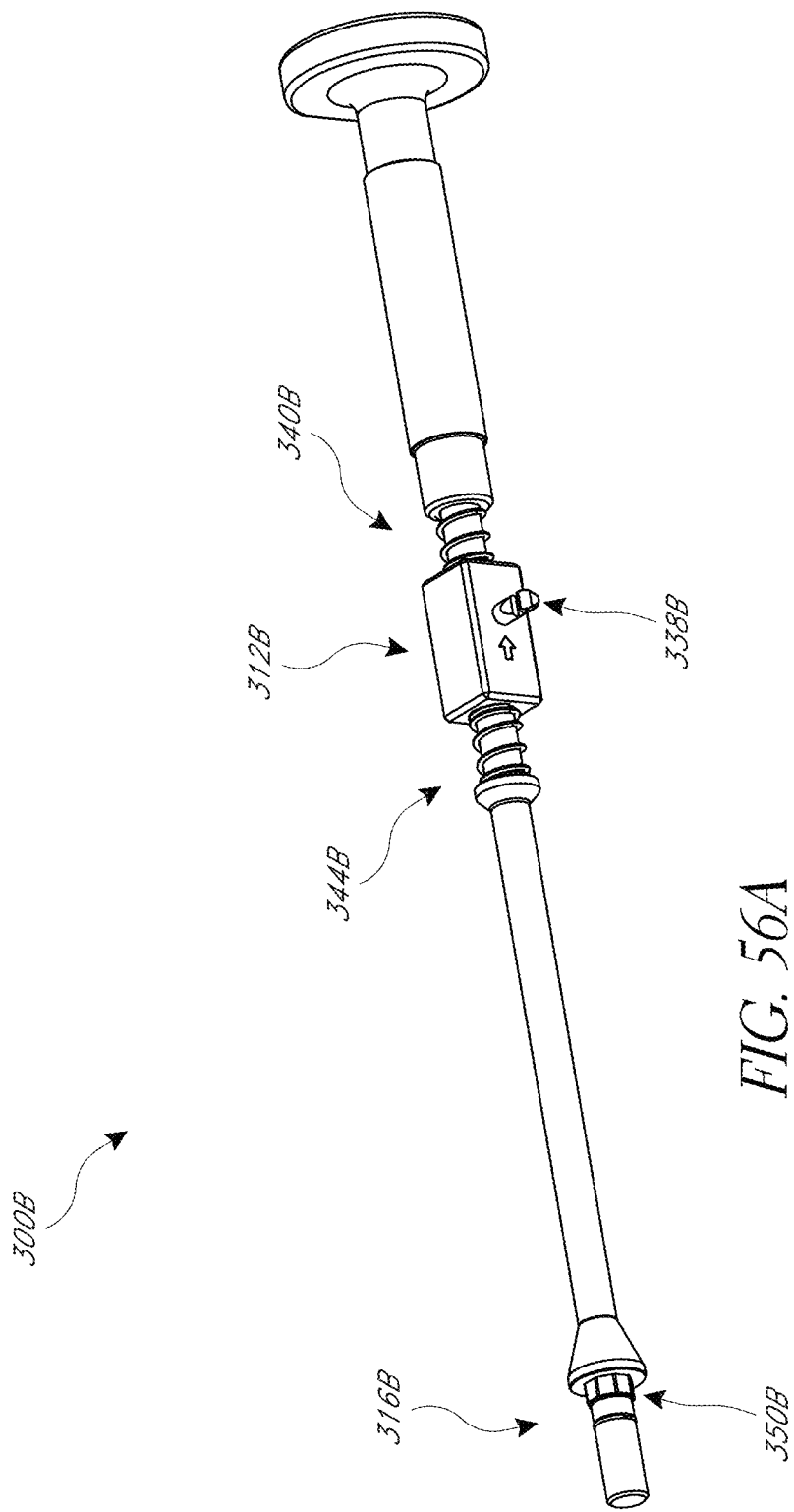
Figure 56F:
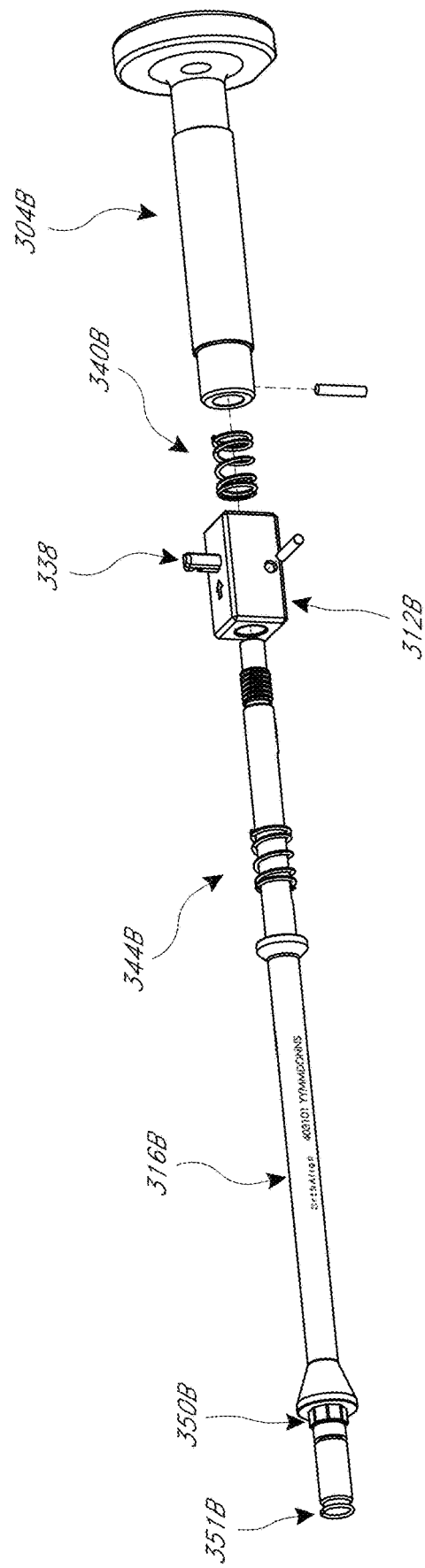
Figure 57:
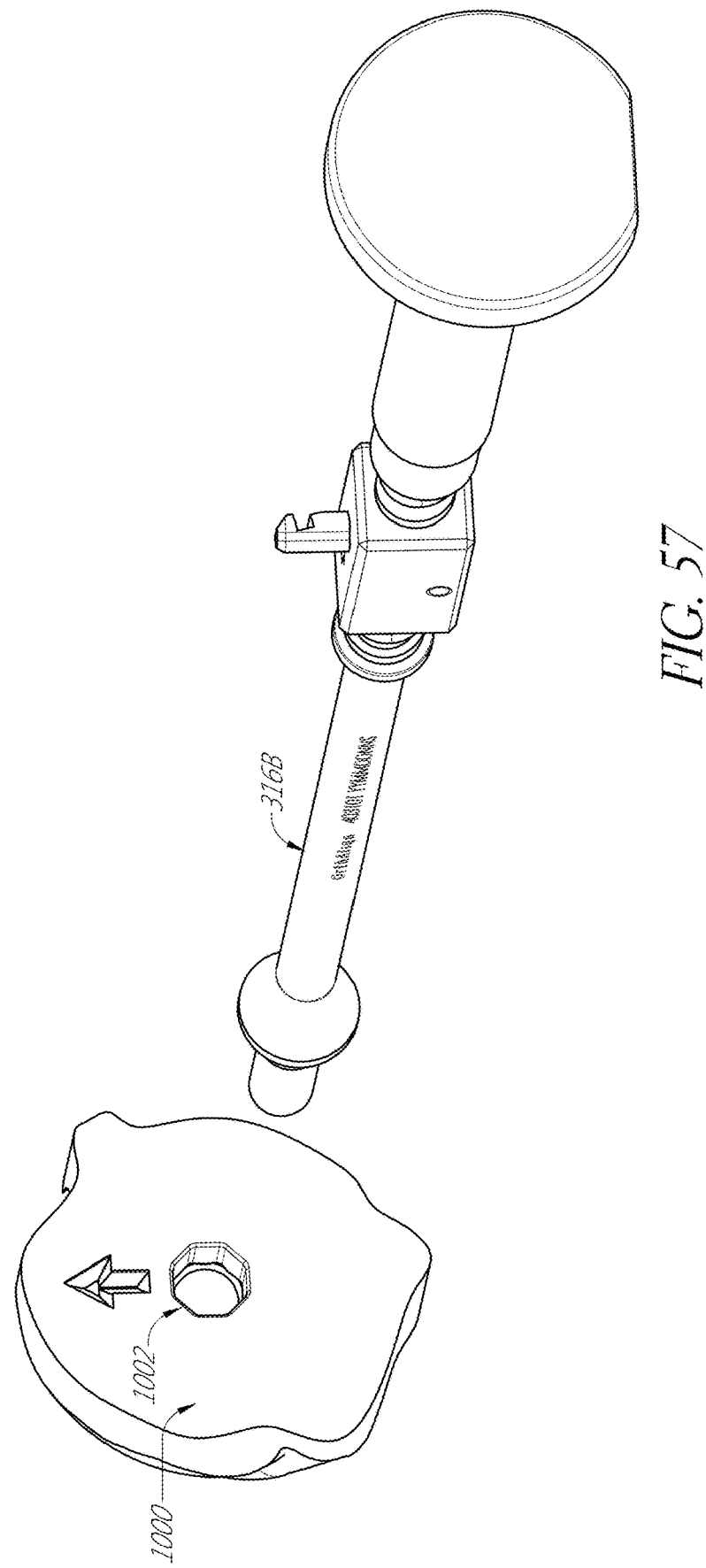

FIGS. 56A-56F show the impactor 300B. The impactor 300B can be substantially similar to impactors described herein, and can include any features of impactors described herein. The shaft 316B can include plurality of flats 350B on the distal end of the shaft 316B as shown in FIG. 56F. The flats 350B permit proximal-distal sliding of the registration feature 1002 of the patient specific jig 1000 over the distal end of the shaft 316B into or out of the feature 1002 shown in FIG. 57. In some embodiments, a detent device 351B or other locking mechanism is provided between the shaft 316B and the registration feature 1002. This mechanism may prevent inadvertent release of the patient specific jig 1000 from the impactor 300B. The flats prevent the shaft 316B from rotating relative to the patient specific jig 1000. The flats 350B can enable many discrete alternate relative angular positions of the patient specific jig 1000 to the shaft 316B. The number of orientations of the impactor 300B relative to the patient specific jig 1000 can depend on the number of flats.

Figure 58A:
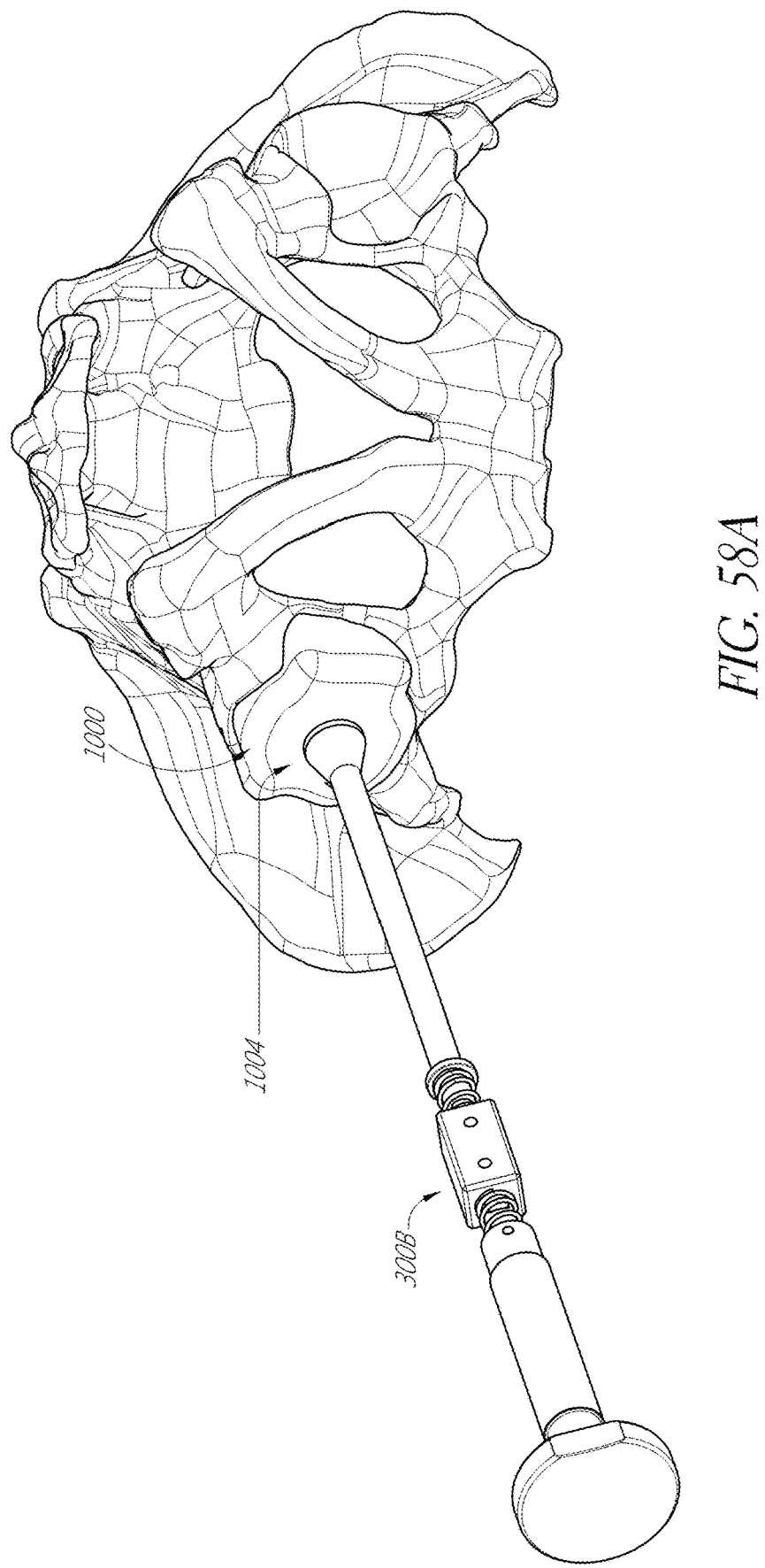
Figure 58B:
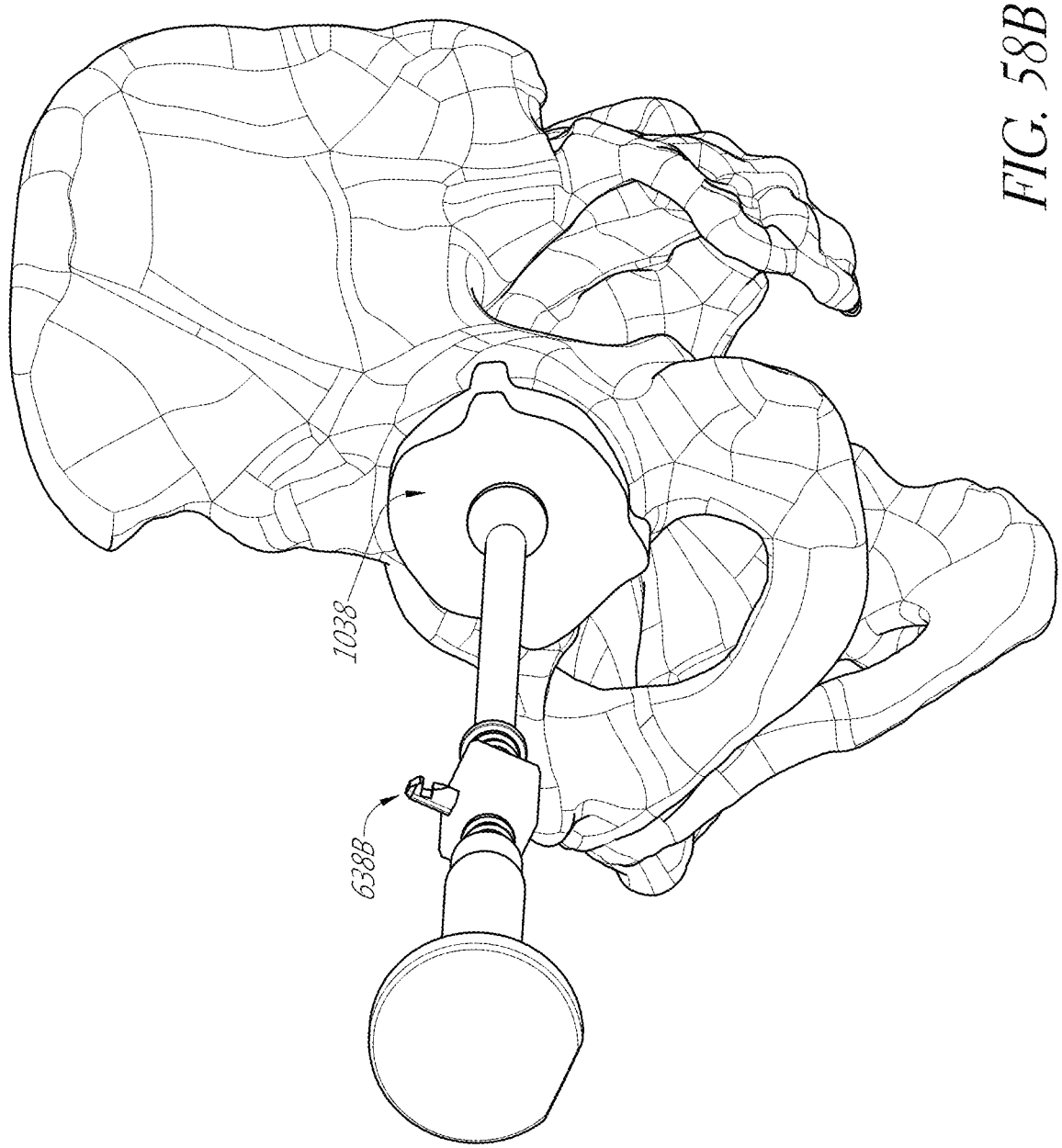

FIG. 58A-58B shows initial placement of the patient specific jig 1000 in the acetabulum in an orientation dictated by the fit of the patient specific jig 1000 over the anatomy. The method can include the step of coupling the patient specific jig 1000 to a rim of the acetabulum. The profile of the posterior side 1008 including the channel(s) 1016, shown in FIG. 55, receives the specific patient's acetabular rim including local prominences and recesses of the bone at and around the acetabulum. The acetabular projection 1012 can be peripheral projection of the patient specific jig 1000. The configuration of the acetabular projection 1012 is such that the acetabular projection 1012 is disposed over a specific bone or bone region of the hip. In this example, the acetabular projection 1012 is configured to be disposed over the bone superior to the acetabulum. Other regions of bone around the acetabulum can be used if sufficiently thick or strong and in a convenient position to not block actions of the surgeon during the procedure. The precise location of the acetabular projection 1012 chosen can be determined by the pre-operative imaging and factored into the forming the patient specific jig 1000.

The impactor 300B can be placed in the registration feature 1002 before or after the patient specific jig 1000 is placed in the acetabulum. The impactor 300B has a length that extends above the anterior surface 1004 of the patient specific jig 1000 such that the sensor 204 can be mounted thereto. Referring back to FIG. 54, the orientation sensing device 204 can be undocked from the second coupler 648. The orientation sensing device 204 can thereafter docked to the fourth coupler 638B of the impactor 300B. The fourth coupler is shown in FIG. 58B.

The patient specific jig 1000 can include an alignment guide 1038 to control rotational orientation of the orientation sensing device 204 on the impactor 300B. The alignment guide 1038 can be a line extending along a specific direction relative to the registration feature 1002. As noted above, the orientation sensing device 204 can be sensitive to the direction of gravity. The rotation of the orientation sensing device 204 about the impactor 300B can change the readings of these sensing devices. To eliminate sources of error associated with this sensitivity, the navigation system incorporating the orientation sensing device 204 can be programmed to assume that the orientation sensing device 204 will be at a specific rotation position around the longitudinal axis of the impactor 300B. The alignment guide 1038 can correspond to the desired rotation position orientation sensing device 204.

In the illustrated embodiment, the fourth coupler 338B may be mechanically or visually aligned with the alignment guide 1038 to assure that this assumption is met in use. In the illustrated embodiment, the alignment guide 1038 is an elongate arrow. The elongate arrow can align with the longitudinal axis of the fourth coupler 338B. The surgeon can look down the impactor 300B from the proximal end to the distal end. The surgeon can verify the alignment of the alignment guide 1038 and the fourth coupler 338B. The alignment between the alignment guide 1038 and the fourth coupler 338B constrains the orientation sensing device 204 in the third degree of freedom. The surgical orientation device 172 can be programed with this known angle of the orientation sensing device 204 when the impactor 300B is coupled to the patient specific jig 1000. In some embodiments, the surgeon will enter an input (e.g., depress a button) when the patient specific jig 1000 is seated with the impactor 300B and the orientation sensing device 204 coupled thereto. The surgical orientation device 172 can calculate the orientation of the surgical orientation device 172 relative to the pelvis when the input is pressed. This step may replace registering the pelvic landmarks with the probe, as discussed herein.

In some embodiments, the orientation sensing device 204 has a laser that projects onto the patient specific jig 1000 and can be aligned with the alignment guide 1038 to facilitate alignment. Alternatively, the impactor 300B may be configured to only enter the registration feature 1002 in a unique orientation (for example, with an asymmetric non-circular cross-section), and to allow the orientation sensing device 204 to mount to the patient specific jig 1000 in a unique orientation (by including asymmetric coupling features).

Once the orientation sensing device 204 is mounted to the impactor 300B, the surgeon can hold the orientation sensing device 204 steady. In some embodiments, the surgeon will enter an input (e.g., depress a button) to collect data from orientation sensing device 204. The data can include the impactor angle. The impactor angle can be fixed during the method such that the angle can be known to the system or in the method in directing placement of the hip implant components. In some embodiments, the impactor angle can be 10° inclination, 20° inclination, 30° inclination, 40° inclination, 50° inclination, 60° inclination, 70° inclination, 80° inclination, 90° inclination, between 30°-70° inclination, between 40°-60° inclination, etc. In some embodiments, the impactor angle can be 10° anteversion, 20° anteversion, 30° anteversion, 40° anteversion 50° anteversion, 60° anteversion, 70° anteversion, 80° anteversion, 90° anteversion, between 0°-40° anteversion, between 10°-30° anteversion, etc. In the illustrated embodiment, the impactor angle is 50° inclination, 20° anteversion. The impactor angle can be based upon the orientation of the registration feature 1002 relative to the patient specific jig 1000. The impactor angle can be set during fabrication of the patient specific jig 1000. In some embodiments, the impactor angle must be known by the software of the surgical orientation device 172. In some embodiments, the impactor angle is constant for all jigs and hard-coded into the surgical orientation device 172. In some embodiments, the impactor angle can be input by the user at the time of surgery. The surgeon can input the impactor angle into the surgical orientation device 172 using the user interface as described herein.

The orientation sensing device 204 can transmit orientation and positional data to the surgical orientation device 172. The surgical orientation device 172 can register the guide angle when the orientation sensing device 204 is coupled to the patient specific jig 1000. In some methods, the surgical orientation device 172 can perform a bias elimination step. The surgical orientation device 172 can track motion of the pelvis and to generate an output that eliminates error due to the movement of the pelvis. The surgical orientation device 172 can include a display providing a user interface. The method can include the step of registering the orientation of a proxy for the plane of the acetabular rim using the orientation sensing device 204 coupled with the patient specific jig 1000.

The orientation sensing device 204 can track any movement of the pelvis during the procedure. There is no need for registration of landmarks in this technique because the position and orientation of the impactor 300B and/or orientation sensing device 204 relative to the acetabulum and/or to the anterior pelvic plane are known from the pre-operative imaging. From the known orientation of the orientation sensing device 204 with respect to the pelvis, the system can calculate the orientation of the surgical orientation device 172 with respect to the pelvis.

Figure 59:
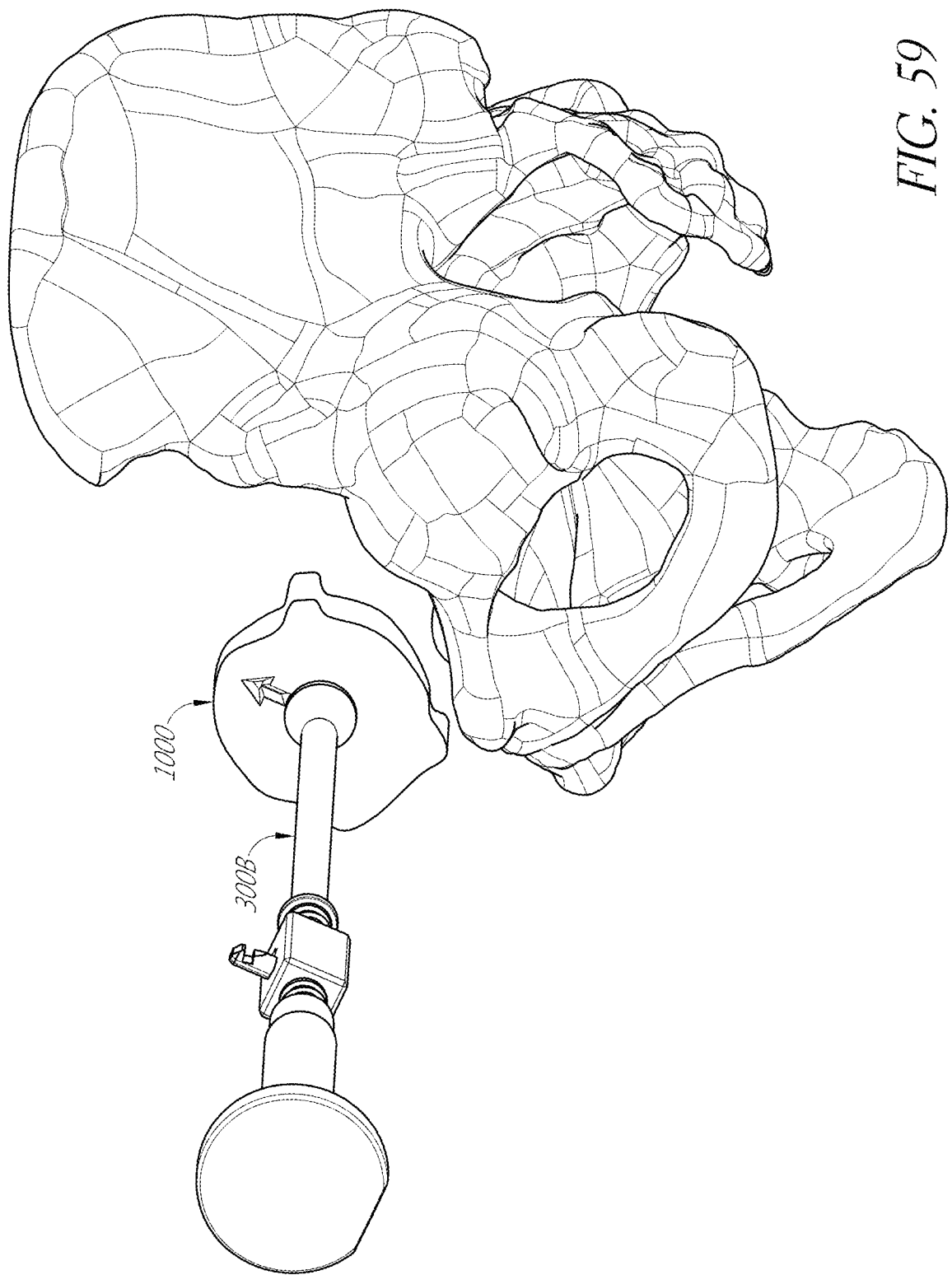
Figure 60:
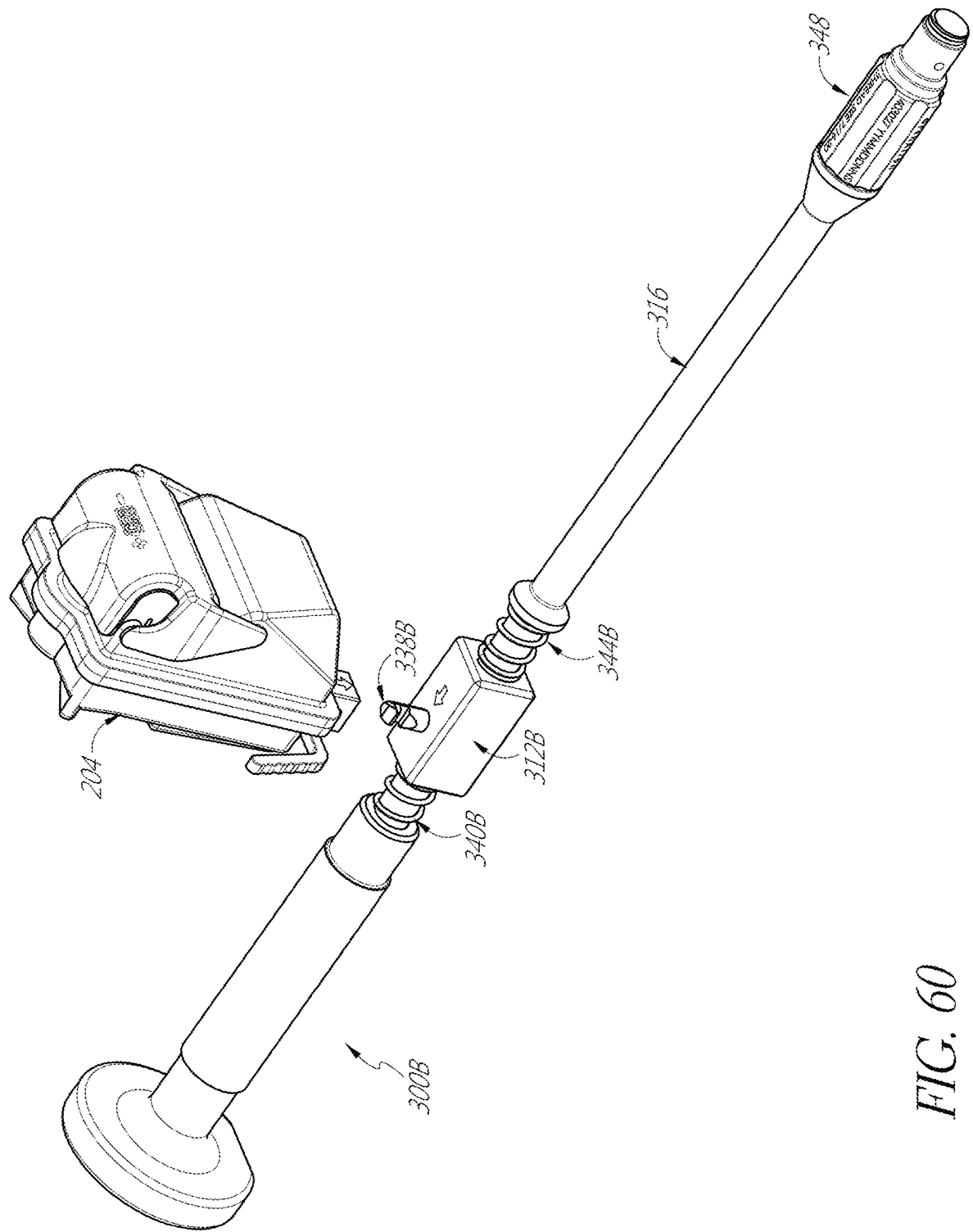

The surgeon can remove the patient specific guide 1000 from the patient as shown in FIG. 59. The surgeon can remove the impactor 300B from the patient specific guide 1000. The surgeon can prepare the acetabulum. In some embodiments, the surgeon can ream the acetabulum. The impactor 300B can be used to position a shell in the acetabulum. The shaft 316B can include plurality of flats 350B on the distal end of the shaft 316A as shown in FIG. 56F. Referring to FIGS. 11B-C and 60, the impactors described herein can be coupled with the tip component 348. FIG. 11C shows that the tip component 348 can have a recess 352 formed on the proximal side thereof. The recess 352 can comprises a plurality of flats 350B corresponding to a plurality of flats 350B on the distal end of the shaft 316B. The flats 350B permit proximal-distal sliding of the recess 352 over the distal end of the shaft 316B. Preferably a detent device or other mechanism is provided between the tip component 348 and the shaft 316B so that the tip component 348 does not disengage. The flats 350B prevent the tip components 348 from rotating relative to the shaft 316B The engagement device 356 comprises threads in one embodiment so that the cup of the prosthetic hip can be screwed onto the distal end of the tip component 348. The flats enable many discrete alternate relative angular positions of the tip component 348 (and hence the cup) to the shaft 316B. A plurality of flutes or elongate axial ridges 364 on the outer surface of the tip component 348 enable the user to securely grasp the tip component for mounting and dismounting the tip component on the shaft 316B. The surgeon can position the cup in the acetabulum. The surgeon can hold the impactor 300B steady.

During orienting, inertial data from the orientation sensing device 204 can be used to confirm a proper orientation of the acetabular cup. The surgical orientation device 172 can register the guide angle when the cup is positioned within the acetabulum. In some embodiments, the surgeon will enter an input (e.g., depress a button) to collect data from orientation sensing device 204. The surgical orientation device 172 can display the cup angle. The surgeon can move the cup to change the inclination angle. The surgeon can move the cup to change the anteversion angle. The surgeon can move the shell until the inclination angle and anterversion angle matches the preoperative angles. The method can include the step of changing the orientation of the impactor 300B in response to an output reflecting the inertial data generated by the orientation sensing device 204. In the illustrated embodiment, the preoperative impactor angle can be 50° inclination, 20° anteversion. In some methods, the surgical orientation device 172 can perform a bias elimination step. In some methods, the surgical orientation device 172 can perform a gyro propagation step. Examples of bias elimination steps and gyro propagation steps are discussed in U.S. Ser. No. 13/011,815, filed Jan. 21, 2011, which is hereby incorporated by reference for this and all other purposes. The surgical orientation device 172 and/or the orientation sensing device 204 can include any of the software algorithms described therein.

The surgeon can seat the cup in the acetabulum using the impactor 300B. The surgical orientation device 172 can remain coupled to the first assembly 604. The orientation sensing device 204 can be coupled to the fourth coupler 338B on the impactor 300B, as shown in FIG. 60.

In some embodiments, the surgeon will enter an input (e.g., depress a button) to collect data from orientation sensing device. The data can include the impactor angle. The impactor angle can be known. At this step, the impactor angle can be 50° inclination, 20° anteversion. The impactor angle can be based upon the orientation of the registration feature 1002 relative to the patient specific jig 1000. The impactor angle can be set during fabrication of the patient specific jig 1000. In some embodiments, the impactor 300B can be rotated to a set number of positions within the registration feature 1002. The impactor 300B can be rotated by the surgeon to align a feature of the impactor 300B with the alignment guide 1038. The fourth coupler 338B can be aligned with the alignment guide 1038. The impactor 300B can be positioned such that the fourth coupler 338B can be pointed superiorly. In other embodiments, the impactor 300B has a single orientation within the registration feature 1002. The position of the orientation sensing device 204 can be therefore known relative to the patient specific jig 1000, when the orientation sensing device 204 is coupled to the impactor 300B. The surgical orientation device 172 can calculate and record the orientation of the surgical orientation device 172 with respect to the pelvis.

The impactor 300B may be struck to seat the implant. In some embodiments, the orientation sensing device 204 remains on the impactor 300B as the impactor 300B is struck. Referring to FIG. 60, the impactor 300B has a shell 312B that is moveable relative to the shaft 316B. The shell 312B can include the fourth coupler 338B that can couple to the orientation sensing device 204. The moveability of the shell 312B helps to isolate the orientation sensing device 204 from the forces that are transmitted through the impactor 300B. These forces are applied by a mallet or other device for forcibly moving the cup into position. By providing at least some force isolation between the shell 312 and the orientation sensing device 204, impact on the sensors in the orientation sensing device 204 can be reduced. Excessive force being applied to the orientation sensing device 204 can put the orientation sensing device 204 out of service, for example until synched with the surgical orientation device 172. The movement of a shell 312B is cushioned by a plurality of spring members 340B, 344B which are configured to absorb at least some of the shock of the impact on the impactor 300B.

3. Custom Jigs: Navigation Using Fixation Pins Mounted Therethrough

Figure 61:
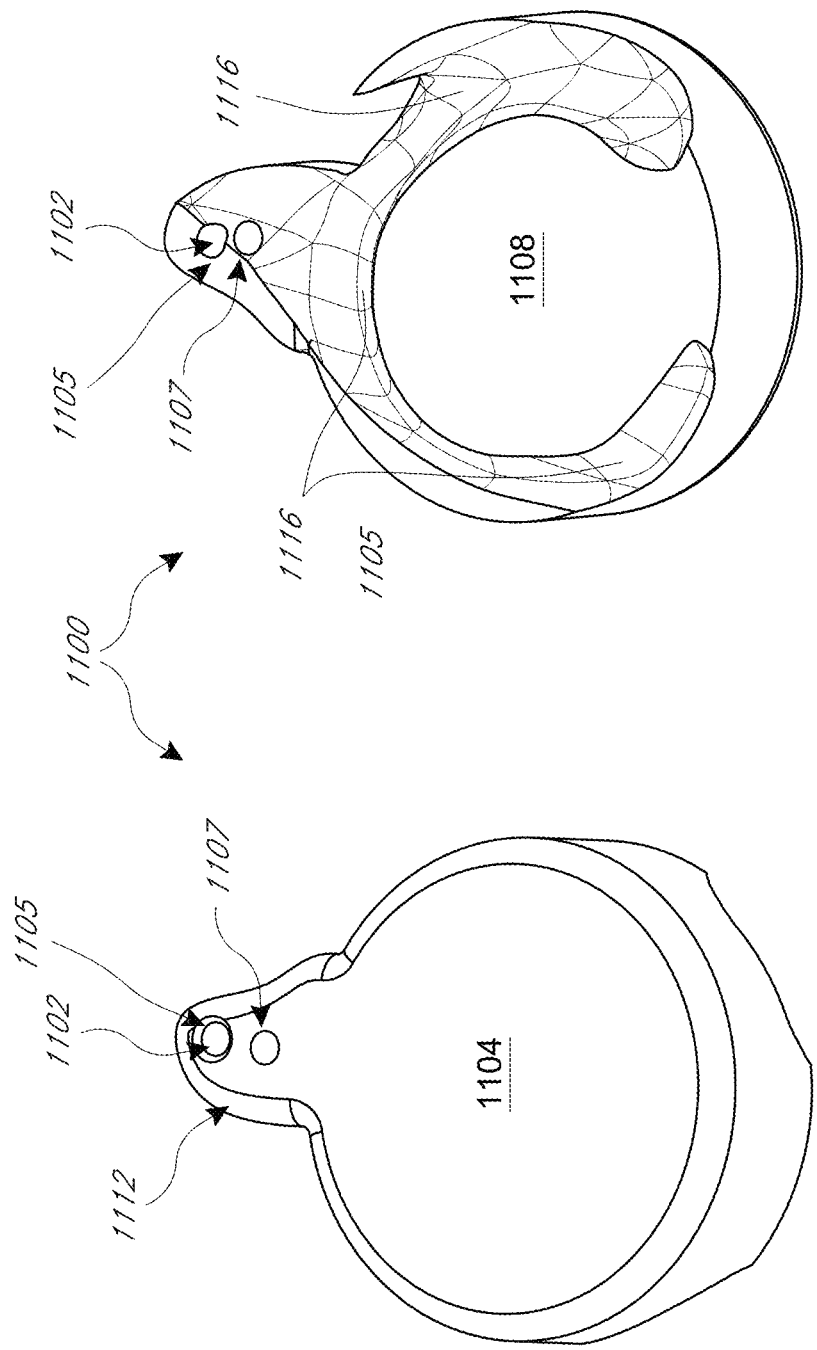
Figure 62:
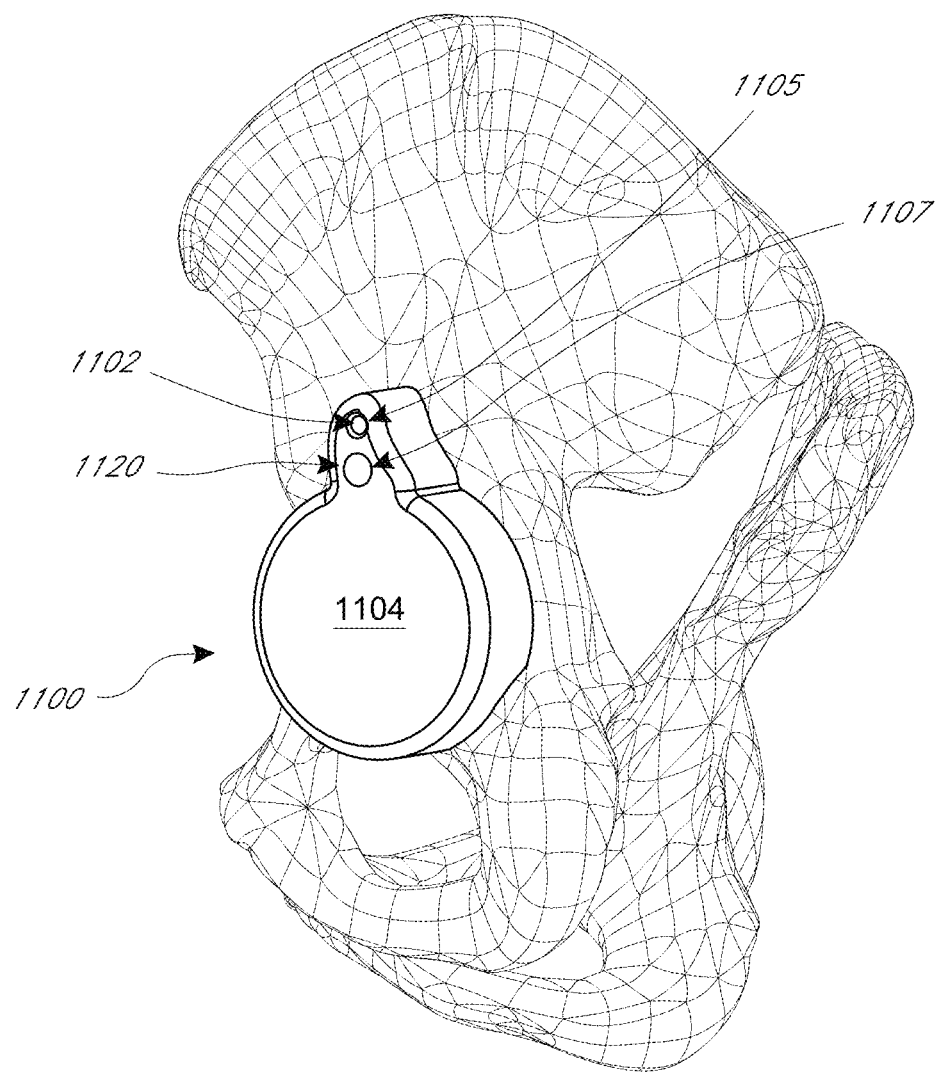
Figure 63:
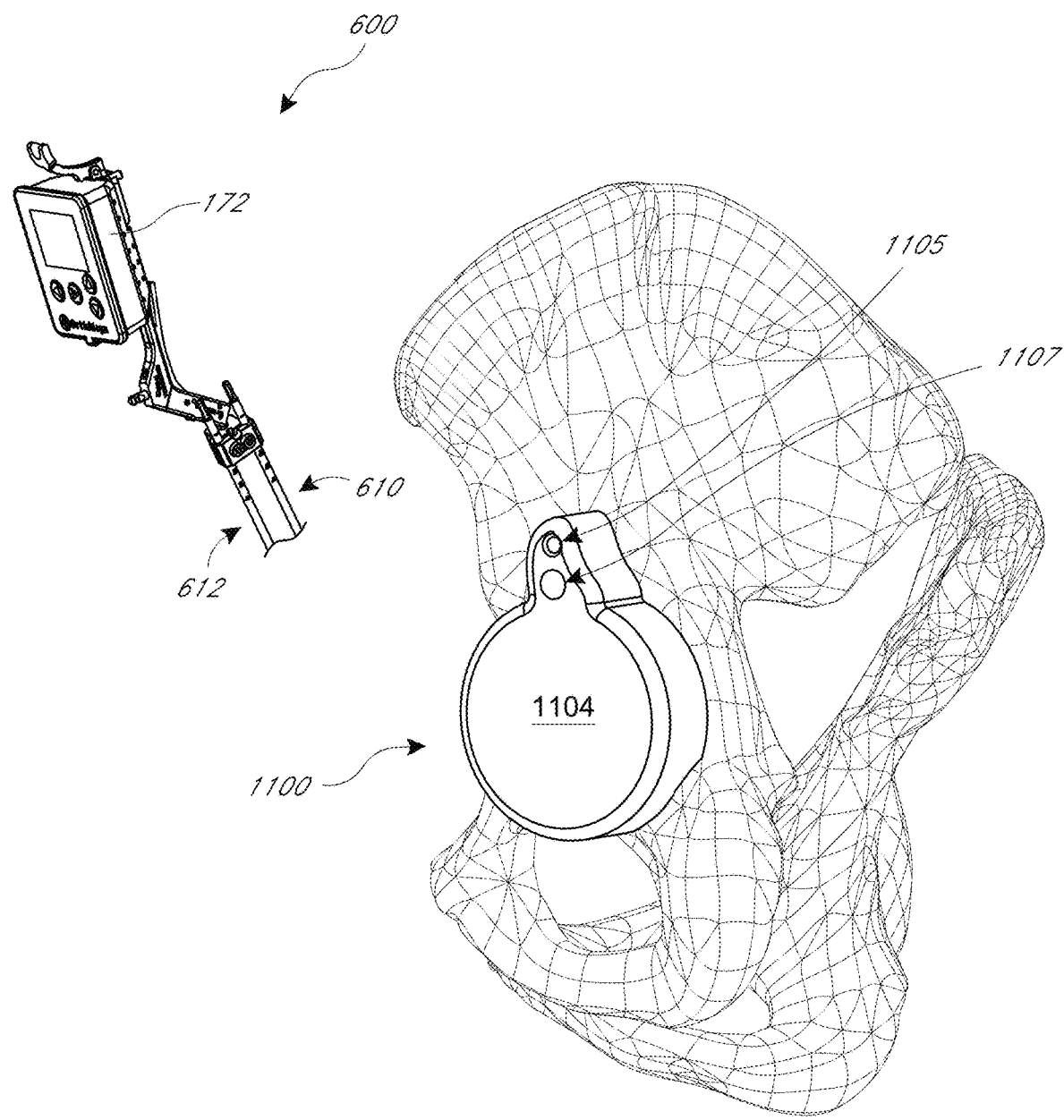

FIGS. 61-63 show an example of the custom jig 1100. The jig 1100 has an anterior side 1104 and a posterior side 1108. The posterior side 1108 is formed with an acetabular portion 1112 configured to mate with at least one feature of the acetabulum in a secure manner. The jig 1100 preferably has only one pre-defined orientation. In some embodiments, a registration feature 1102 of the jig 1100 has a plurality of, e.g., two, holes. The registration feature 1102 can be located on the acetabular portion 1112 or any other portion of the custom jig 1100. The holes are sized to accept fixation pins 610, 612 of the system 600. In a variation of FIGS. 44-52, a patient specific guide can be provided with a registration feature including a single hole. The hole or holes can accept fixation pin(s) 610 in a single orientation relative to the patient or relative to the custom jig 1100. The method can include the step of inserting at least a fixation pin 610 through the patient specific jig 700 or jig 1100 along an axis disposed at a pre-defined angle corresponding to the reference frame of the surgical orientation device 172.

The first hole 1105 of the registration feature 1102 can accept a fixation pin 610 and a second hole 1107 can accept fixation pin 612. The system 600 can be placed in a single orientation relative to the custom jig 1100. Thus, once the jig 1100 is placed, the surgical orientation device 172 and/or the orientation sensing device 204 can be positioned in a known orientation. In some embodiments, from the orientation of the system 600 when so placed, the orientation of the acetabular rim or a proxy thereof can be recorded in one or both of the devices 172, 204. In some embodiments, the reference frame can be based directly on more general pelvic landmarks such as the anterior pelvic plane. The acetabular rim or a proxy can be used as an intermediate step to get to the reference frame based directly on more general pelvic landmarks. The registration feature 1102 preferably extends from the anterior side 1104 to the posterior side 1108 of the jig 1100. The distance between the anterior and posterior surfaces 1104, 1108 provides the depth of the holes 1105, 1107 being sufficient to guide the fixation pins 610, 612 to specific anatomy along a specific direction. The method can include the step of inserting at least two fixation pins 610, 612 through the patient specific jig 1100 along axes disposed at a pre-defined angle corresponding to the reference frame of the surgical orientation device 172.

Once the devices 172, 204 are mounted to the system 600, the sensors can track any movement of the pelvis during the procedure. There is no need for registration of landmarks in this technique because the position and orientation of the fixation pins 610, 612 relative to the acetabulum and/or to the anterior pelvic plane are known from the pre-operative imaging.

4. Navigation Using Inertial Sensors and Pre-Operative Imaging

In another technique using less comprehensive imaging, a correspondence between one or more linear dimensions and an angle can be exploited to enhance accuracy. For example, a clinician can use an X-ray or other standard radiographic imaging device to provide an anterior pelvic bone image. This image can be read to derive the location of the anterior pelvic plane and a dimension on the anatomy. For example, an angle between top and bottom landmarks around the acetabulum (as further describe below) and a trans-ischial line or other anatomic medial-lateral reference line can be a useful patient specific variable to minimize patient-to-patient variation in at least one relevant angle, e.g., the abduction angle.

Patient specific data can be provided for use by the surgeon based on best medical judgment. For example, any of the systems herein can be used in a mode that is based on broad population studies. Such studies can define a distribution of patients with sufficient clarity and detail to enable significant improvement over the current standard of care. In one mode, the dimensions taken from radiograph or CT can be used to inform the surgeon whether some patient specific adjustments should be considered. Alternatively, patient specific adjustments can be coded into the system described herein so that they are transparent to the doctor. Such adjustments can be downloaded to either or both of the devices 172, 204 or into a separate monitor or control device that communicates wirelessly with the devices 172, 204. Thus, the system described herein can either fully implement patient specific adjustment, e.g., for anteversion, abduction, leg length, joint offset, or other parameter or can enable the surgeon to make a judgment as to whether to do so.

Figure 68:
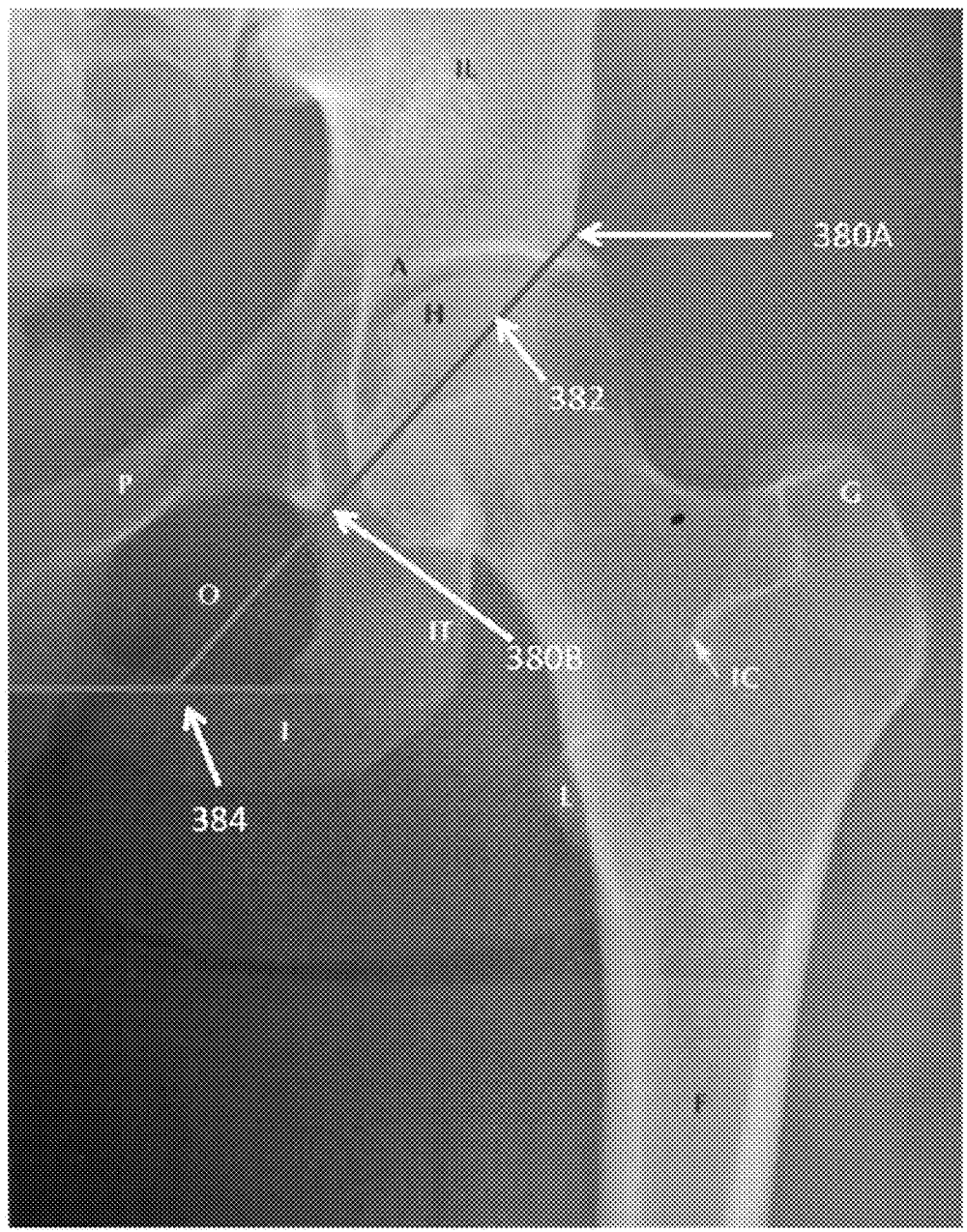
FIG. 68 is a pre-operative image that can be used to enhance alignment in a hip procedure by providing patient specific data.

FIG. 68 illustrates an example of a pre-operative image that can be used in one technique. The lines 380 point to landmarks which are used intraoperatively and are also visible in an anterior pelvic radiograph. The top landmark 380A is about 1 cm superior to most superior point of acetabulum. In another approach, the top landmark 380A can be the most superior point on the acetabular rim. The bottom landmark 380B is adjacent to or at the acetabular notch (tear drop). An angle between line 382 and the line 384 is a patient-specific abduction of line formed by landmarks, which can be entered into an interface of the system 100 (or the other systems herein) at time of surgery to provide patient specific reference frame. Line 384 may be any anatomic medial-lateral reference line. Examples include trans-ischial line and line across the inferior borders of the obturator foramina (shown in FIG. 68).

5. Navigation Using Drift Insensitive Inertial Sensors

In one variation, one or both of the devices 172, 204 can comprise only accelerometers and can be configured as tilt meters, or the devices could be put into a mode that relies mostly on the accelerometer data or otherwise be configured to be insensitive to accumulated errors that arise from integration of data. If the patient is set in a reproducible and stable position, patient movement and mis-orientation can be eliminated. This enables some methods to be performed without using rate sensor data. In one variation of this tilt-meter approach, one or both of the sensors 172, 204 can be configured to inform the surgeon if a condition is sensed that suggests a landmark acquisition approach would yield a superior alignment outcome. This method can advantageously be used for procedures that do not require complex movements, like freehand motions. Where freehand motion is involved, incorporating some indication of heading (gyroscopes, magnetometer, or other indication of heading) would be useful.

6. Navigation Using Inertial Sensors to Track Motion to Define a Patient-Specific Safe Zone In another technique illustrated by FIG. 64, a patient-specific "safe zone" is defined by recording the patient's natural range of motion of one more of the patient's joints. For example, if a hip procedure is to be performed, the patient's range of motion can be recorded pre-operatively. If the hip to be replaced is not overly arthritic, the range of motion can be determined on the hip to be replaced. If the range of motion of the hip to be replaced is unnatural due to disease state, the contralateral hip can be characterized.

In one hip replacement technique a sensor S is coupled with the femur. The sensor can be coupled above the knee to prevent movements at the knee from affecting the measurements made. The sensor S can be connected below knee if the knee is immobilized. The sensor S can be initialized and otherwise prepared to record accurate readings. Thereafter one or more movements of the hip joint can be performed with the output of the sensor recorded and processed. The movements can include, for example, movement in anterior and posterior (A-P) directions to the full extent of the range of motion and movement in medial and lateral (M-L) directions to the full extent of the range of motion. These motions define the patient's natural range of motions in these planes.

Figure 64:
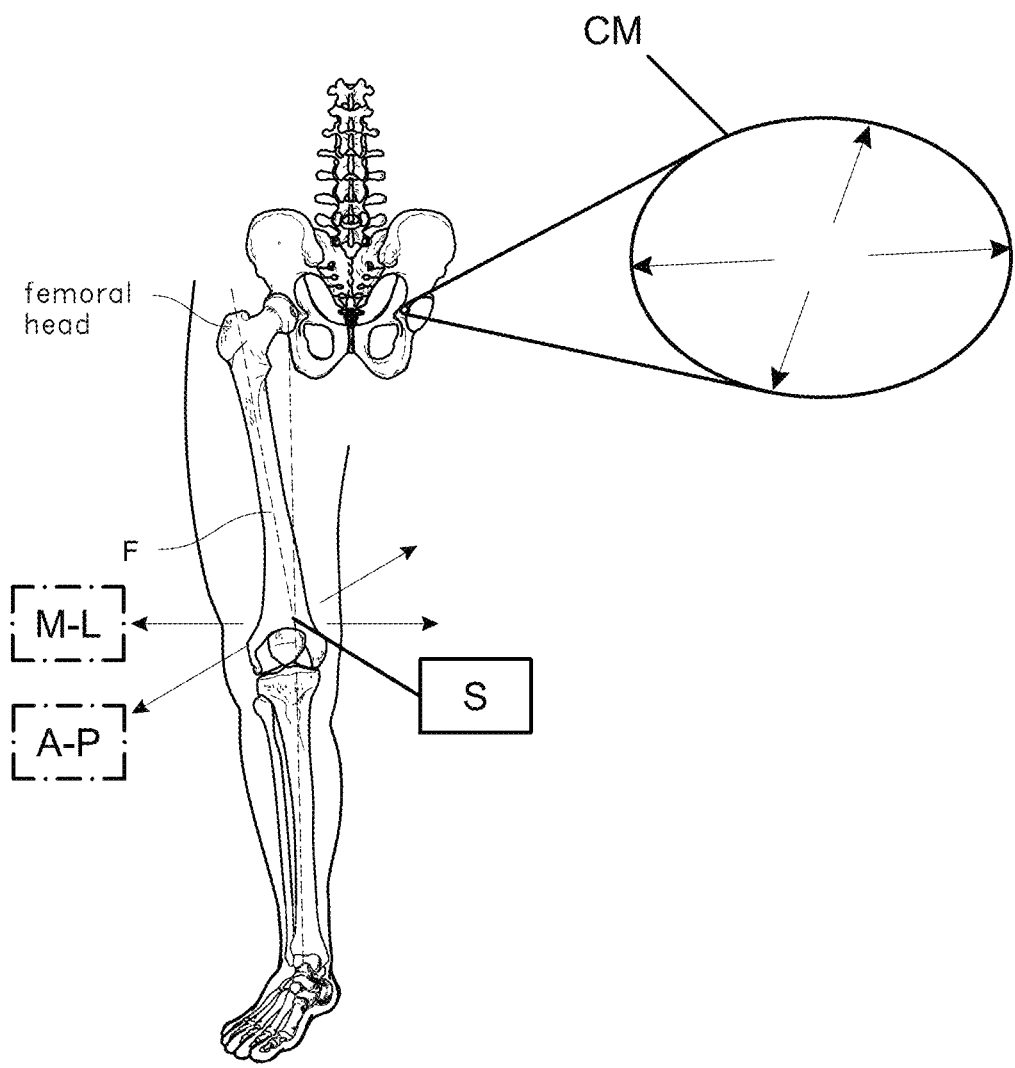
FIG. 64 illustrates methods for defining a patient-specific safe zone in a hip placement procedure.

Based on the extents of motion in the A-P and M-L directions, a cone of motion CM can be defined. The cone of motion CM can be defined as originating at a point defined as the center of rotation of the femoral head and extending out from the acetabulum to a circular base located a distance from the center of rotation equal to the distance to the mount point of the sensor. The circular base can be defined as having a radius equal to the average extent of motion in the A-P and M-L directions. In FIG. 64, the cone of motion is shown on the contralateral side for clarity. As noted above, the data collected to estimate the cone of motion can be based on the leg to be treated or the contralateral leg.

Placement of the cup of the hip prosthesis is dictated by some metric of centering within the cone of motion. For example, the cup can be centered such that an axis extending perpendicular to the plane of the entrance to the cup crosses the circular base of the cone of motion precise in the center of the cone. In some systems, the orientation of the cup is controlled such that the crossing point of the axis so projecting is closer to the center of the circular base than it is to the periphery of the circular base. In other systems, the orientation of the cup is controlled such that the crossing point of the axis so projecting is within a distance from the center point that is less than 25% of the radius of the circular base.

In a class of patients, the movement of the hip is not symmetrical in each of the A-P and M-L directions. As such, the cone of motion can have a more complex geometry. For example, the cone of motion can originate at the center of rotation of the femoral head and extend to a base having an oblong shape, for example shortened in the medial direction, but longer in the lateral, anterior, and/or posterior directions. Various metrics of "within the safe zone" can be defined based on these irregular shaped cones. For example the geometric center of a complex base shape can be calculated and the cup of the prosthetic joint can be centered such that an axis extending perpendicular to the plane of the entrance to the cup crosses the irregular shaped base of the cone of motion at or within some maximum distance of the centroid of the cone.

Any suitable set of motions can be used to obtain the center of rotation of the femoral head and/or the boundaries of the base of the cone of motion. Examples of methods for determining the center of rotation of a femoral head using inertial sensors are discussed in U.S. Pat. No. 8,118,815, which is hereby incorporated by reference for this and all other purposes. A more complete perimeter of the base of the cone of motion can be directly recorded using sensors that are capable of tracking both position and orientation. For example, several other points between the A-P and M-L direction can be taken so that six, eight, ten, twelve or more extents are recorded. In other embodiments, arcuate motions of along all or portions of the perimeter of the base of the cone of motion can be traced and recorded. Because several degrees of freedom of the sensor S are constrained, the sensor can operate based on accelerometers only in some approaches, which simplifies sensor S and enables it to be disposable and/or less expensive to make. Such approaches may be most accurate if rotations about a vertical axis are minimized or eliminated.

In one embodiment, the procedure illustrated in FIG. 64 generates an origin and a direction that can be input to a cup placement system. The origin can be the center of rotation of the femoral head and the corresponding center of rotation of a prosthetic socket. The direction can be a line connecting the origin and the point of intersection with the base of the cone of motion. This data is transferred to a cup placement system, such as any of those discussed above. For example, the impactor 300A can include the sensor 204 to which this data has been saved. Thereafter movements of the impactor 300A can be tracked with reference to this origin and direction to assure proper placement of the cup. Such placement can be with the aid of a patient movement tracking sensor pinned to the pelvis for example.

In other embodiments, cannulated systems can be used to minimize the number of steps during which inertial sensors are used. For example, once the origin and direction of the axis connecting the center of rotation and the intersection with the base of the cone of motion are determined, a guide member can be placed via a cannulated impactor (or other cannula). The guide member can dock with an impactor-mounted cup. The cup can be slid over the guide member into place in the acetabulum. The direction and origin information collected in the steps illustrated by FIG. 64 are preserved by the guide member and by the tilt preventing features on the guide member and/or prosthetic cup.

If the patient's joint is subject to extensive disease, a cone of motion can be established by a combination of data collected in motions similar to those discussed above in connection with FIG. 64 and pre-operative imaging. For example, X-rays can be taken when the femoral neck is moved close to the acetabular rim to supplement some of the data points defining the cone of motion. Thus, the cone of motion can be in part established by inertial sensing and in part by imaging to characterize the native anatomy.

D. Adaptable Systems for Anterior or Posterior Approach

The systems described herein can be adapted for use in the anterior approach, the posterior approach or both the anterior and posterior approach. As one example, system 600 is shown herein mounted for a posterior approach in FIG. 18, the anterior approach in FIG. 39, and in combination with a patient specific jig in FIG. 63.

FIGS. 69-72 illustrate a system 900 for navigating a hip procedure. The system 900 can be adapted for use in both the anterior approach and the posterior approach. The system 900 can be similar to some of those discussed above. But, while some of the foregoing systems are specialized for a particular approach, the system 900 includes a first sub-system 900A adapted for a posterior approach and a second sub-system 900B adapted for an anterior approach. As discussed more below, both systems 900A, 900B are configured to enable navigation to be conducted without requiring gyroscopic or other sensors that are subject to accumulated error (drift). This refinement makes the system simpler to implement and to use in a wider variety of settings and with more patients.

The system 900A includes a jig 904A that is adapted for hip joint navigation from a posterior approach. The jig 904A is similar in some respects to the jig 454, and any consistent description thereof is incorporated herein. The jig 904A includes a platform 908, a cannula coupling device 912, and a registration jig mounting feature 914. The platform 908 can have any shape, but in some implementations can be elongate, e.g., having a first end 916 and a second end 920. The elongate shape enables at least a portion of the jig 904A to be low profile in one direction and to provide a plurality of positions along a length for coupling devices to the jig. The first end 916 is configured to be oriented inferiorly and the second end 920 to be oriented superiorly when the navigation jig is applied to the patient. The medial-lateral dimensions or extent can be minimized to not obstruct the surgical field or the surgeon.

The cannula coupling device 912 is disposed adjacent to the first end 916 and is configured to enable a cannula 924 to be held adjacent to a bottom surface of the platform 908. The cannula 924 can have a top surface connected to a bottom surface of the platform 908. A connection between these components can be secured by a device disposed above within or below the platform 908. In one form, a proximal structure of the cannula 924 can be received within a bottom recess of the platform 908 and can be held within the recess by a compression device, such as a set screw S. Details of several variants of cannula coupling devices 912 are discussed below in connection with FIGS. 73-75B. A connection to a bone adjacent to a hip joint is made through the cannula 924. For example, a pin 928 can be placed through the platform 908 and the cannula 924 into the bone.

Figure 71:
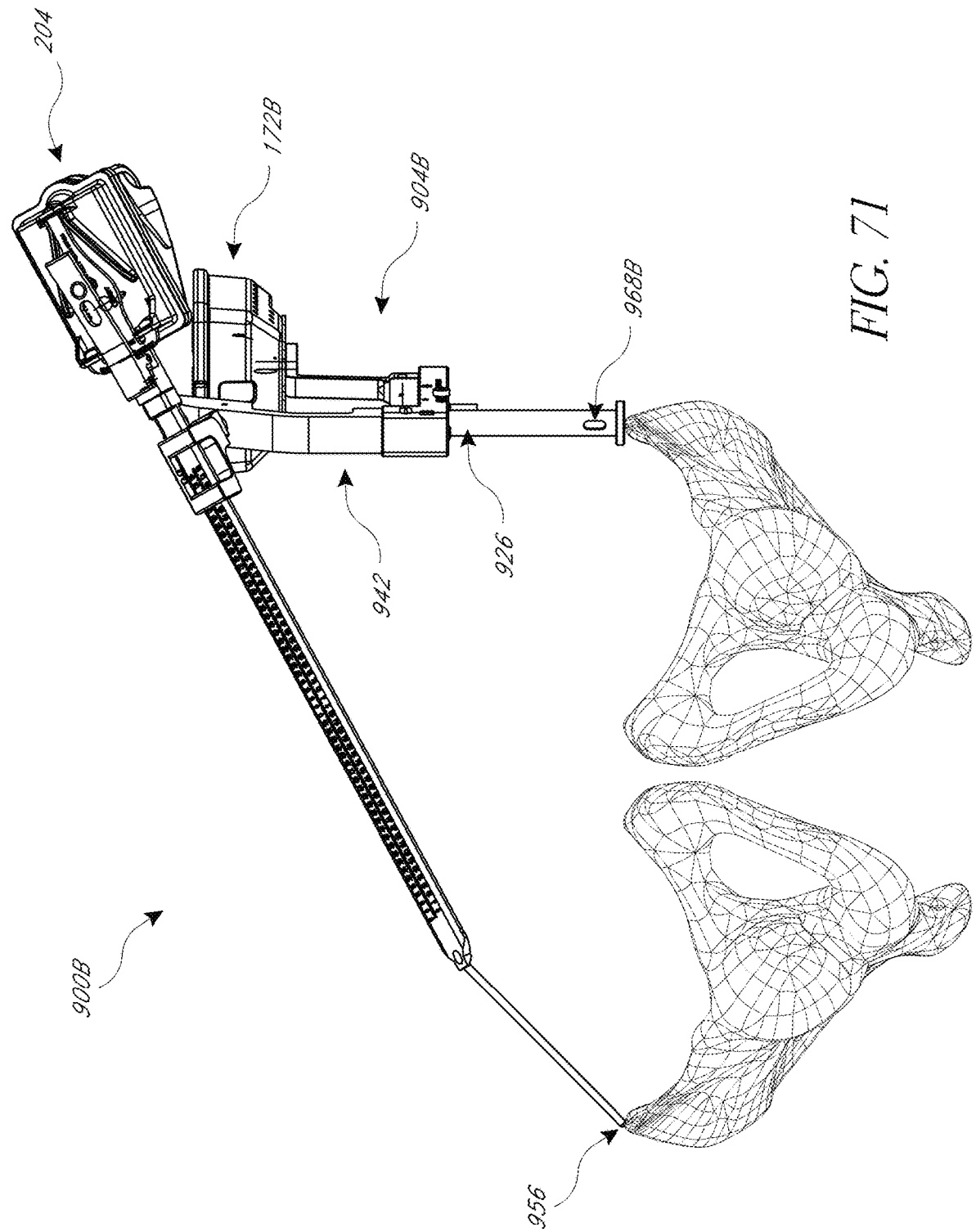
FIGS. 71 and 72 are view of the hip procedure navigation system of FIG. 69-70 modified and applied to a pelvis in an anterior approach.
Figure 72:
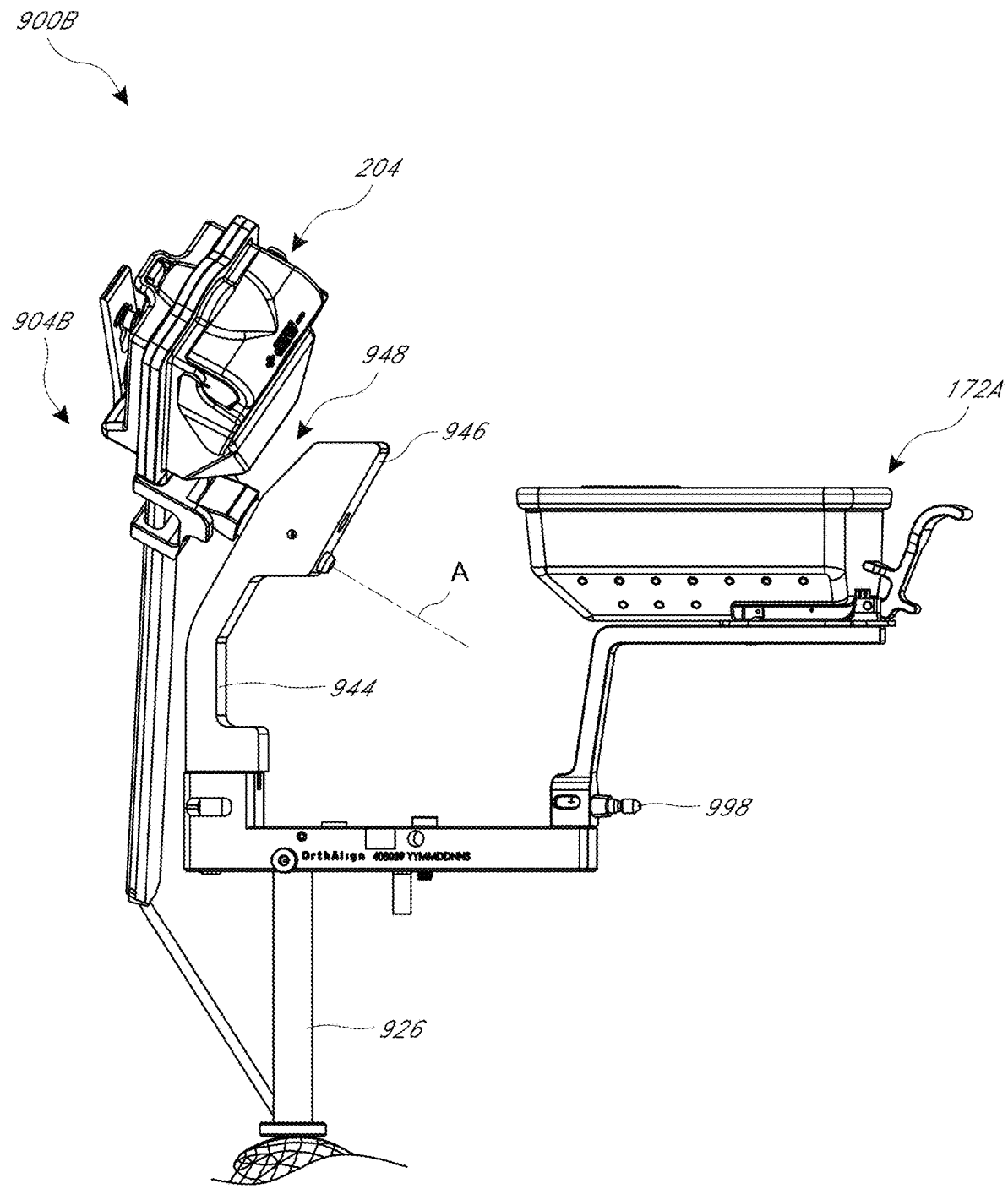

An anterior approach cannula 926 is shown in FIGS. 71 and 72 and is similar to the cannula 516, the description of which is incorporated herein. The description of the cannula coupling device 912 applies equally to the cannula 924 for posterior approach and to the cannula 926 for anterior approach.

Figure 73:
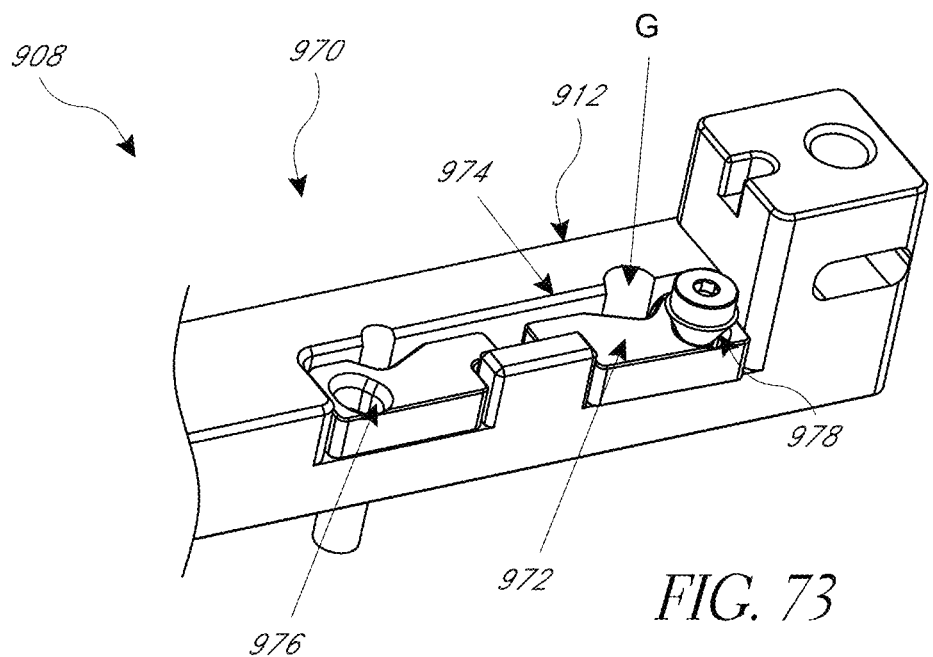
FIGS. 73-73A illustrate a first embodiment of pin securement devices.

The registration jig mounting feature 914 is disposed on a top surface 932 of the platform 908 adjacent to the first end 916. In one form, the mounting feature 914 includes an elevated portion of the platform. The mounting feature can include one or more, e.g., two recesses into which pins can be received. In one embodiment, the elevated portion includes a window, e.g., a through hole, for viewing such a pin to confirm correct placement. As illustrated in FIG. 73, in one variant, a circular recess can be provided for a first pin and an U-shaped slot can be provided for another pin or member.

The hip navigation jig 904A also includes registration jig 940. The registration jig 940 can have some features similar to those discussed above. The registration jig 940 includes an upright member 942, a rotatable member 948, and a probe 952. The upright member 942 is configured to be detachably coupled to the platform 908 at the registration jig mounting feature 914. For example, a plurality of (e.g., two) pins can project from a lower surface of the upright member 942, the pins being configured to be received in corresponding recesses in the registration jig mounting feature 914. One of such pins is visible through the window in the registration jig mounting feature 914 seen in FIG. 70. The upright member 942 includes a first portion 944 and a second portion 946 disposed above the first portion 944. The first portion 944 is substantially vertical and increases the elevation of the second portion 946 when the registration jig 940 is mounted to the registration jig mounting feature 914. The second portion 946 is inclined away from a vertical longitudinal axis of the first portion 944. The incline of the second portion 946 provides several advantages. It enables the upright member 942 to be out of the way of the range of motion of the probe 952, as discussed below. This is important because the probe 952 has to be able to easily and quickly reach a plurality of anatomical features.

The incline of the second portion 946 also provides a simple way to incline an angle of rotation of the rotatable member 948 relative to a vertical axis. The rotatable member 948 is coupled with the upright member 942 for rotation about an axis A that is not vertical when the jig is mounted to the bone adjacent to a hip joint and the upright member is disposed generally vertically. This arrangement is one way to enable a navigation system employing inertial sensors to eliminate the need to manage sensor drift. As discussed above, certain sensors, such as gyroscopes, are more subject to accumulated errors (drift). The orientation of the axis A enables the jig 904 to be used in a system that includes accelerometers and other sensors that are sufficiently sensitive if activated and moved about axes that are not vertical.

As in the registration devices discussed above, other degrees of freedom of rotation and position can be provided in the registration jig 940 and such description is incorporated here.

The probe 952 had a tip 956 for engaging anatomy. The anatomy engaging tip 956 is disposed at a distal end of an elongate body 960 coupled with the rotatable member for rotation about the axis. The orientation and position of the elongate body 960 of the probe can be adjusted to bring the anatomy engaging tip into contact with a plurality of anatomical landmarks during a landmark acquisition maneuver. Such adjustments can be by sliding through a sliding support, similar to those hereinbefore described.

The upright member 942 can include a cradle 954 that allows the elongate body 960 of the probe 952 to be held in place when not in use during a procedure. The cradle 954 can be used to latch the sensor 204, as discussed above. In various implementations, the system 900 does not require any steps of zeroing, however, since the sensors are configured to be generally drift insensitive. Eliminating sensitivity to drift can be achieved by configuring the sensor 204 as a tilt meter, and/or by using any sort of inertial sensor that will not introduce excessive error due to drift during the procedure time. As such, even sensors that have some drift can be used, so long as their accumulation of error does not reach a significant level until during the procedure. The cradle 954 could be used to zero error if a procedure was unexpectedly long and the sensor were subject to some drift. In one advantageous embodiment, the sensor 204 can operate solely with signals from accelerometers, which are insensitive to drift.

FIGS. 69-72 show that the systems 900A, 900B can include one or more sensors for detecting orientation of the probe 952. The sensors can take any form, e.g., can include the surgical orientation device 172 and the sensor 204 discussed above. Accordingly, the jig 904 can include a sensor mounting feature 962 disposed on the platform 908. Where the platform is elongate, the sensor mounting feature 962 can be disposed at the second end 920. Another advantage of the jig 904A, 904B is that it is symmetrical and can be used on both hips. The jig 904A, 904B thus can have a single sensor mounting feature disposed on a plane of symmetry. If the platform 908 is elongate, the sensor mounting feature 962 can be located on a vertical mid-plane of the platform. Vertical here refers to the orientation of the jig 904A, 904B when applied to the hip in a posterior or anterior approach.

The registration jig 940 can include a sensor mounting feature 964 disposed thereon for movement with the probe 952. For example, the sensor mounting feature 964 can be located at a proximal end of the elongate body 960. This location is one of convenience, placing the sensor 204 at the proximal end. However, the sensor mounting feature 964 and the sensor 204 could be located on a side surface of the elongate body 960.

As discussed herein, the orientation of the axis of rotation A of the rotatable member 948 enables the change of orientation of the sensor 204 to be other than in the horizontal plane. This is accomplished by orienting the axis A other than in the vertical direction. With this arrangement, it is possible to configure at least the sensor 204 as a tilt meter, e.g., using primarily or only accelerometers to output a signal indicative of orientation of a component, such as of the prove 952. Example of angles or ranges of angles of the axis A that can be provided include about 20 degrees from horizontal, about 30 degrees from horizontal, about 45 degrees from horizontal, at less than about 60 degrees from horizontal.

Figure 70:
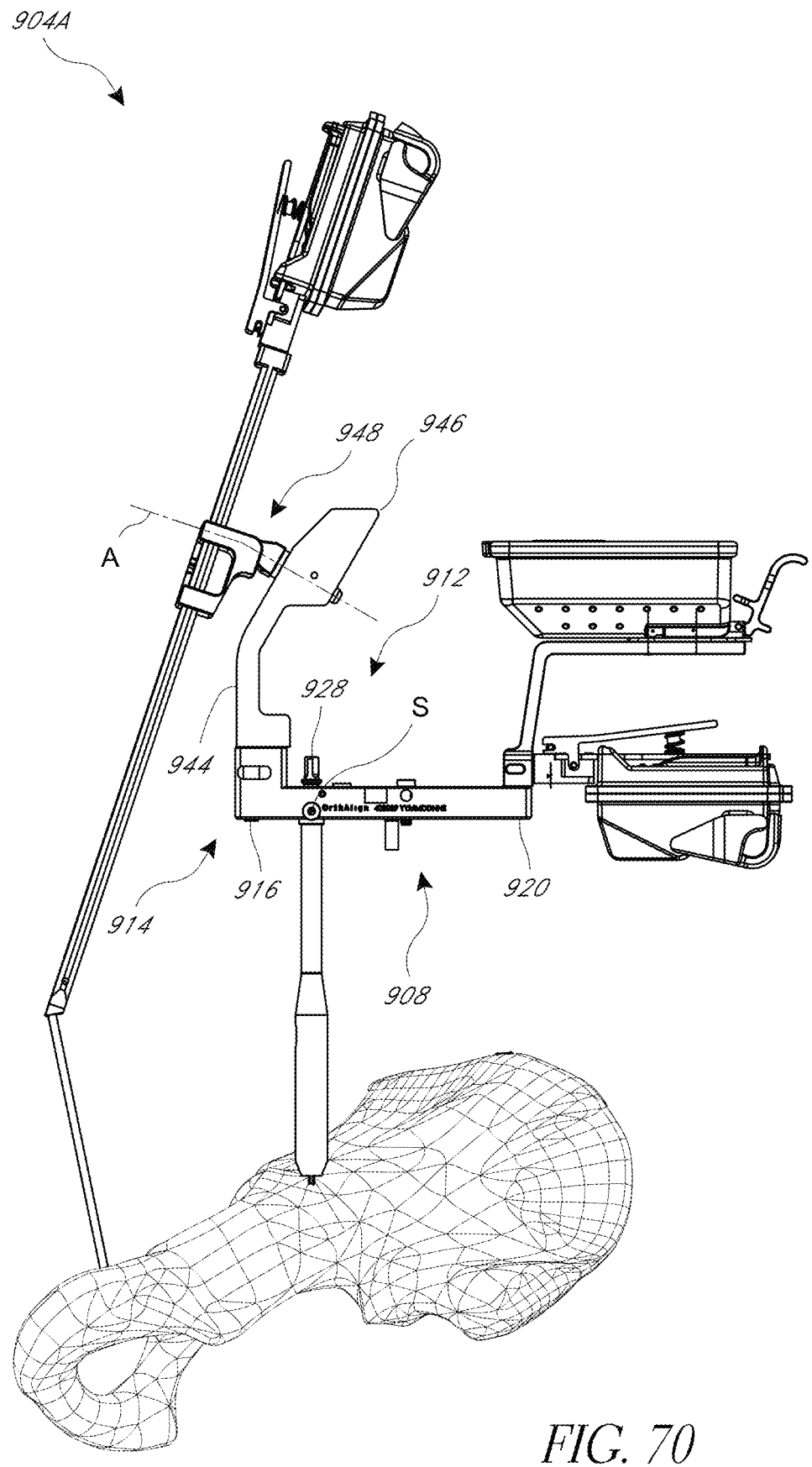

FIG. 70 shows a further feature of the system 900A, which includes the jig 904A and the cannula 924. The cannula 924 is adapted for posterior approach is similar to or the same as the hollow fixation member 466. An upper or first end of the cannula 924 is configured to couple with the cannula coupling device 912, such as by a set screw as discussed above. A second end of the cannula 924 is configured to couple with a bone adjacent to the hip joint. The bone can be any of those discussed above for coupling the fixation member 466 or other analogous structures discussed in any embodiments above. A home point feature 968 is disposed adjacent to the second (lower) end of the cannula 924. The home point feature 968 is in a predefined, known position and can receive the anatomy engaging tip 956 of the probe 952. When these structures contact, they are in a predefined position and orientation. The home point feature 968 can be similar to the registration feature 473 discussed above.

Because the system 900 can be adapted for posterior approach or for anterior approach (discussed below), the cannula 924 should be made removable from the platform 908 in the operating room or at a back table in preparation for surgery. As such, the connection between the cannula 924 and the platform 908 can be made orientation specific. This reduces a potential source of operator error, i.e., the home point feature 968 always faces toward the surgical field from the hip bone attachment location, e.g., faces inferiorly if the jig 904 is mounted to a superior location of the surgical field. For example, a projection on a proximal portion of the cannula 924 and a corresponding projection in a recess on the lower side of the platform 908 can define only one rotational orientation of the cannula relative to the platform in which these components can be coupled.

As discussed above, the cannula 926 is provided in the system 900 to enable a surgeon to switch to an anterior approach. Anterior approach is discussed in great detail above, e.g., in connection with FIGS. 34-42, which description are incorporated here as well. The system 900B differs from the system 500 in that the orientation of the axis A of rotation in the system 900B is not vertical, as discussed above. As such, the sensors can be greatly simplified compared to the system 500. The cannula 926 has a home point feature 968B. The home point feature 968B is in a predefined, known position and can receive the anatomy engaging tip 956 of the probe 952. When these structures contact, they are in a predefined position and orientation. The home point feature 968B can be similar to the registration feature 473 discussed above. The cannula 926 and the platform 908 can be configured for limited, e.g., only one, rotational position of attachment. This assures that when the jig 904B is assembled in the operating room or back table that the jig 904B will be properly set up.

In one method to maximize the accuracy of the landmark acquisition, jig 904B is coupled with the patient in an anterior approach. The tip 956 is put into contact with the home point feature 968B. Thereafter, user input can be applied to the surgical orientation device 172A to indicate that the tip 956 is in the home point feature 968B. Thereafter, the system registers movements and landmark acquisition in the manner discussed above. These data provide a basis to guide the placement of the acetabular cup, as discussed above.

Figure 69:
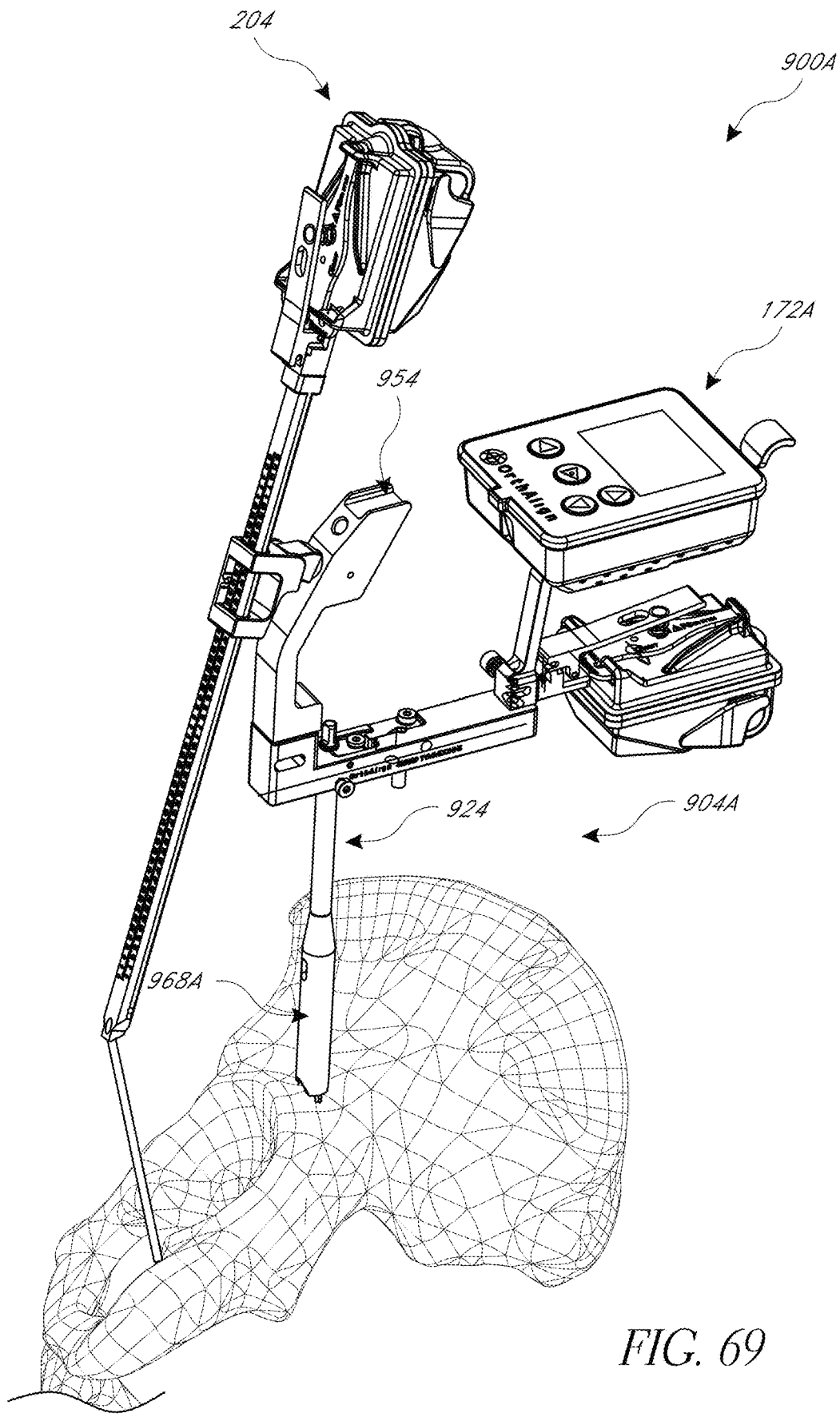
FIGS. 69 and 70 are views of a hip procedure navigation system applied to a pelvis in a posterior approach.

The placement of the acetabular cup using a device such as the impactor 300A can be an operation that benefits from inertial sensors that may include one or more drift-sensitive sensors, e.g., gyroscopes. The system 900 provides a calibration mount 998 for coupling a sensor 204 in a known, fixed position and orientation relative to the surgical orientation device 172A. The calibration mount 998 is a docking device that positions the sensor 204 just prior to a step of eliminating any potential source of accumulated error, e.g., zeroing a drift-sensitive sensor. FIG. 69-70 show that they system 900A can include two sensors 204, one mounted to the registration jig 940 and one to the calibration mount 998. These two sensors 204 can be identical or can be dedicated for their specific function. FIGS. 71 and 72 shows only one sensor 204. In this system, a single sensor 204 is used to gather landmark data and to work in combination with the impactor 300A to place an acetabular implant.

Figure 73A:
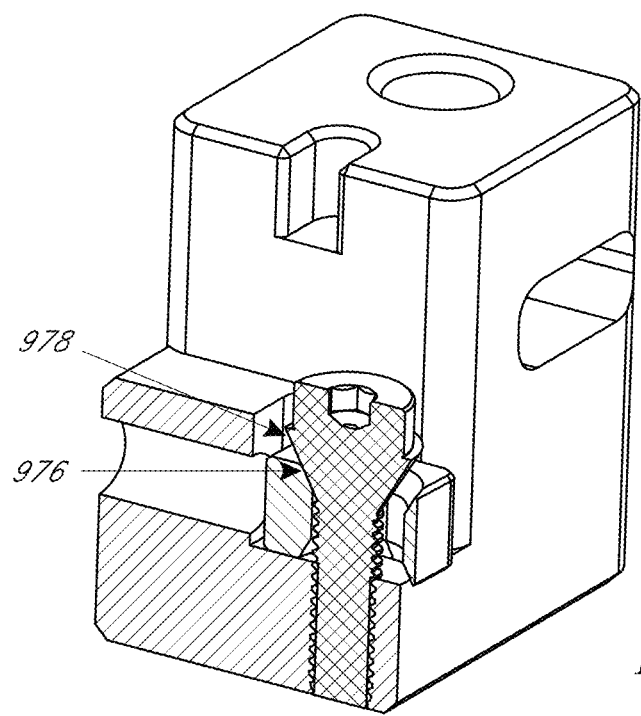

FIGS. 73-75B illustrate various features for clamping structures to the platform 908. In particular, these figures show fixation pin securement devices 970 that are incorporated into the platform 908. The fixation pin securement devices 970 can have low profile to be out of the way of other tools in the surgical field. FIG. 73-73A show one embodiment of a pin securement device 970 that includes a compression member 972. The cannula coupling device 912 can include a similar mechanism to clamp a pin disposed through the cannula 924. The platform 908 includes a slot or plurality of slots formed on a surface thereof, e.g., on the top surface. The slots 974 are larger in at least one direction than the compression member 972 such that the compression member can fit in the slot and move to some extent therein. The compression member 972 has a tapered channel 976. Movement of a tapered member 978 vertically in the tapered channel 976 shifts the compression member 972 to narrow a gap G between the compression member 972 and a rigid feature of the platform. The gap G can be between a curved lateral surface of the compression member 972 and a curved surface of the platform 908.

In one method, a pin or other fixation member is advanced through the gap G and into the bone. The platform 908 is positioned on the fixation member at an appropriate height and the pin securement device 970 is affixed to the fixation member. The fixation member can be a Steinmann pin or other similar device. In one technique, the tapered member 978 is a threaded elongate body that is advanced along internal threads formed in the platform 908 until the tapered surface thereof acts on the tapered surface 976 to shift the compression member 972 laterally to narrow the gap G. Further advancement of the tapered member 978 further shifts the compression member 972 to enhanced securement of the fixation member. The method can be repeated for a second pin, where one pin extends through the cannula 924 and one extends parallel to the cannula 924, but off-set superiorly therefrom on the patient.

FIGS. 74-74B illustrate another approach to a fixation pin securement devices 970A in which the fixation pin securement device comprises a compression member 972A pivotally mounted to the platform 908. FIG. 74A shows two compression members 972A, each of which is mounted to pivot about a pin or shaft 980. The securement device 970A on the left in FIG. 74A corresponds to a configuration in which a fixation member can freely pass through a gap G in the mechanism. The securement device 970A on the right in FIG. 74A corresponds to a configuration in which the gap G is narrowed and a fixation member disposed in the gap G will be securely clamped and unable to move relative to the platform 908. A rigid surface of the platform 908 opposite the pivoting compression member 972 along with the compression member holds the fixation member in place.

In one method, pins or other fixation members are placed in the fixation pin securement device 970A and the cannula coupling device 912. In the illustrated embodiment, these devices can employ similar clamping mechanisms. Thereafter, screws 982 are advanced to cause the compression member 972 to pivot about the pin or shaft 980 from a first position in which the gap G provided between a clamping surface of the compression member 972A and a rigid surface of the platform 908 is larger to a second position in which the gap G is smaller. The second position is a clamped position for the fixation member and will retain the platform in position until the screw 982 is withdrawn enlarging the gap G.

FIGS. 75-75B illustrate another approach to a fixation pin securement devices 970B in which the fixation pin securement device comprises a compression member 972B configured to clamp a plurality of segments of an outside surface of a fixation member. The platform 908 includes a plurality of projections 984 extending upward from an upper surface of the platform. The projections preferably are threaded. Each projection includes a collet 986 or similar device disposed therein having an inner lumen sized to receive a fixation member. A plurality of slots extends downward from an upper surface of the collet 986 and an angled surface 988 is disposed between top ends of each member defined between a pair of such slots. A corresponding angled surface 990 is provided on an inside of a cap 992. The cap 992 has internal threads that act on the threads of the projection 984 to advance the angled surfaces 990 onto the angled surfaces 988. Further advancement collapses the slots of the collet 986 causing compression about the outer surface of the fixation member. FIG. 75 shows that this approach can be used for the fixation pin securement devices 970B and/or for the cannula coupling device 912.

While the systems discussed above are well suited for specific approaches, the system 900 can be adapted for a posterior approach or for an anterior approach. This provides a great deal of flexibility to the surgeon and only adds minimal additional components to a universal kit. The orientation of the axis of rotation A (see FIGS. 70 and 72) enhances the sensitivity of a system that incorporates accelerometers and other sensor drift insensitive components. The home point features 968A, 968B enable the surgeon to obtain maximal accuracy by allowing the acquisition of position and orientation data for a number of anatomical landmarks at close range to the home point position. This allows the system to initialize the sensors near the points to be acquired to enhance accuracy.

II. Navigation Using Optical Components

Many of the foregoing systems advantageously use inertial sensors to aid in navigation of procedures. Certain embodiments discussed herein can advantageously use optical techniques alone or in combination with inertial sensor systems discussed herein to provide additional features and advantages.

A. Optical Tracking of System Components

Figure 65:
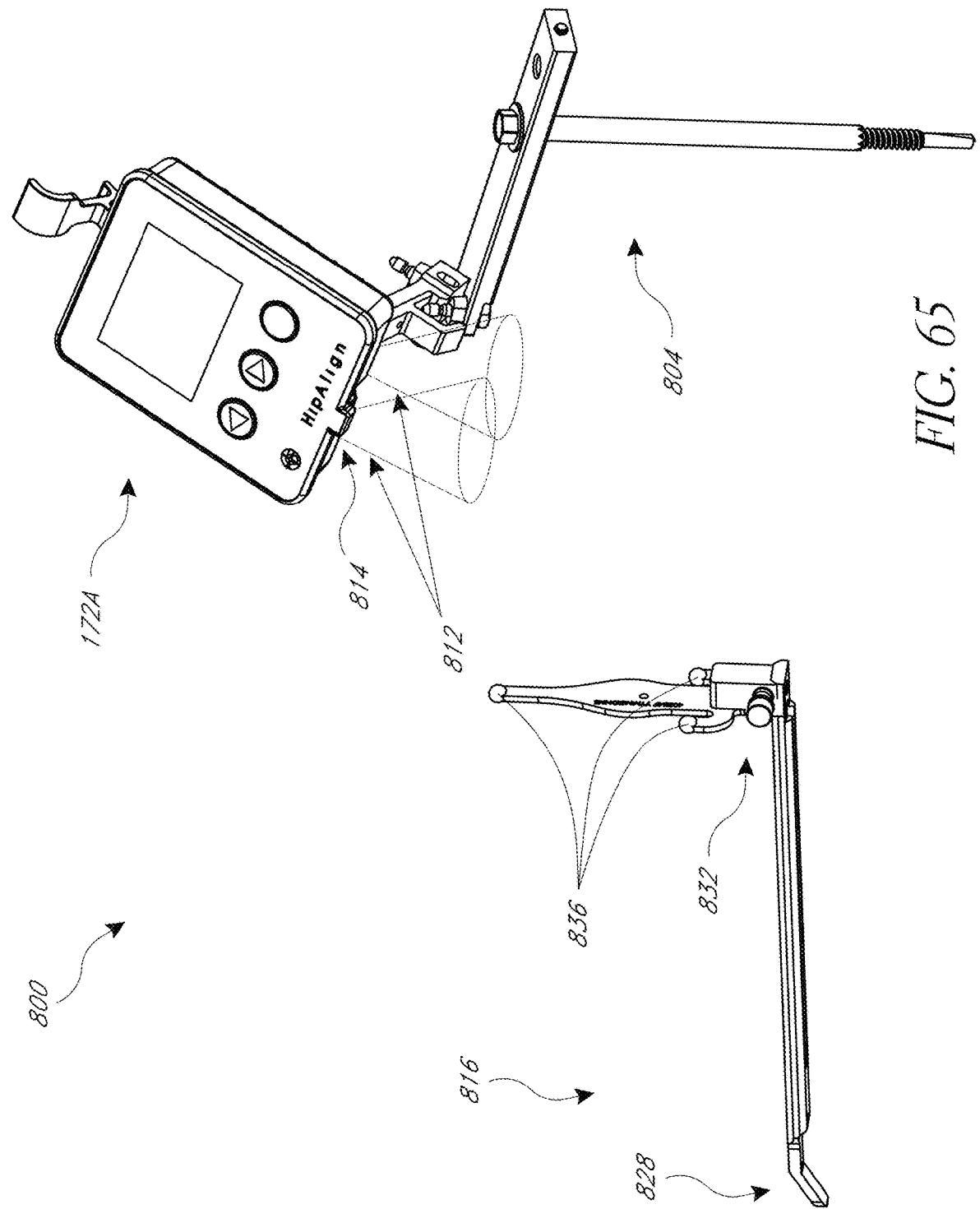
FIG. 65 is an embodiment of a system for close range optical tracking.

FIG. 65 illustrates one embodiment of a system 800 that includes close-range optical tracking capabilities. In this context "close range" is a broad term that means near the patient, such as any of in the surgical field, directly above the pelvis but below the surgeon's head, within the boundaries of the surgical table, etc. This term is intended to exclude systems where cameras are outside the surgical fields. Close range greatly reduces or eliminates "line of sight" problems that plague traditional optical navigation.

In the illustrated embodiment, a jig system 804 is provided for connecting to patient bone. The jig system 804 can include any of the features of any of the jig systems discussed herein. For simplicity, the jig system is illustrated with that of FIG. 1, e.g., including the cannula 124 and the platform 136. A surgical orientation device 172A is mounted to the platform 136. The orientation device 172A can be similar to those hereinbefore described, but also includes one or more cameras 812. Preferably the orientation device 172A includes two or more cameras 812 to enable capture of binocular data. The cameras preferably are small cameras, for example the Aptina MT9T111, which is discussed at http://www.aptina.com/products/soc/mt9t111d00stc/. The cones projecting from the lower side of the device 172A schematically represent the direction of the field of view of the cameras 812.

This data can at least be used to determine the heading of and in some cases six degrees of freedom of a stylus 816. The stylus has a distal end 828 configured to touch landmarks as part of a landmark acquisition maneuver, as discussed above. A proximal (or other) portion 832 of the stylus 816 has an array of trackers 836 that can be tracked by the cameras 812 to provide orientation, position, heading, attitude, or other combinations of spatial characteristics of portions of the stylus 816 or anatomy with which it is coupled.

The cameras 812 can operate without any additional sensor, such as inertial sensors. In some embodiments, the cameras 812 are used in concert with inertial sensors to confirm or to improve accuracy of the sensors. For example, drift in a rate sensor, e.g., accumulated errors, can be monitored by comparing the output of the rate sensor with the viewed position from the cameras. The system can intervene if the sensor output drifts too much, for example, telling the user to reset the rate sensors.

Another optical device such as a laser or an IR emitter 814 can be provided in the orientation device 172A. An IR emitter can be useful to illuminate the fiduciaries to make them more readily detectable by the cameras under the intense lighting in the surgical field.

B. Optical Component for Femur Tracking

Figure 76:
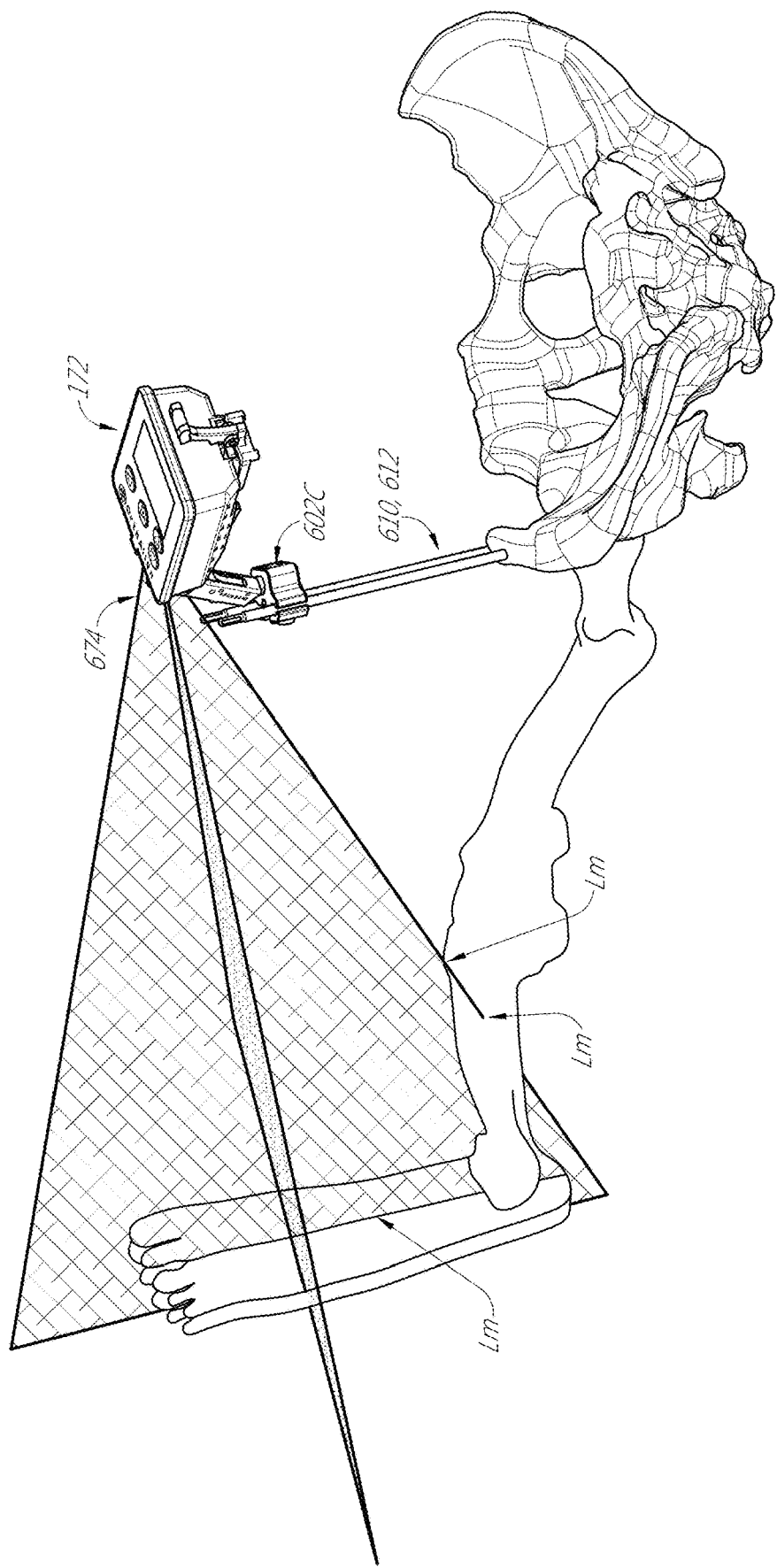
FIGS. 76-80 illustrate a modular system with an optical component.
Figure 77:
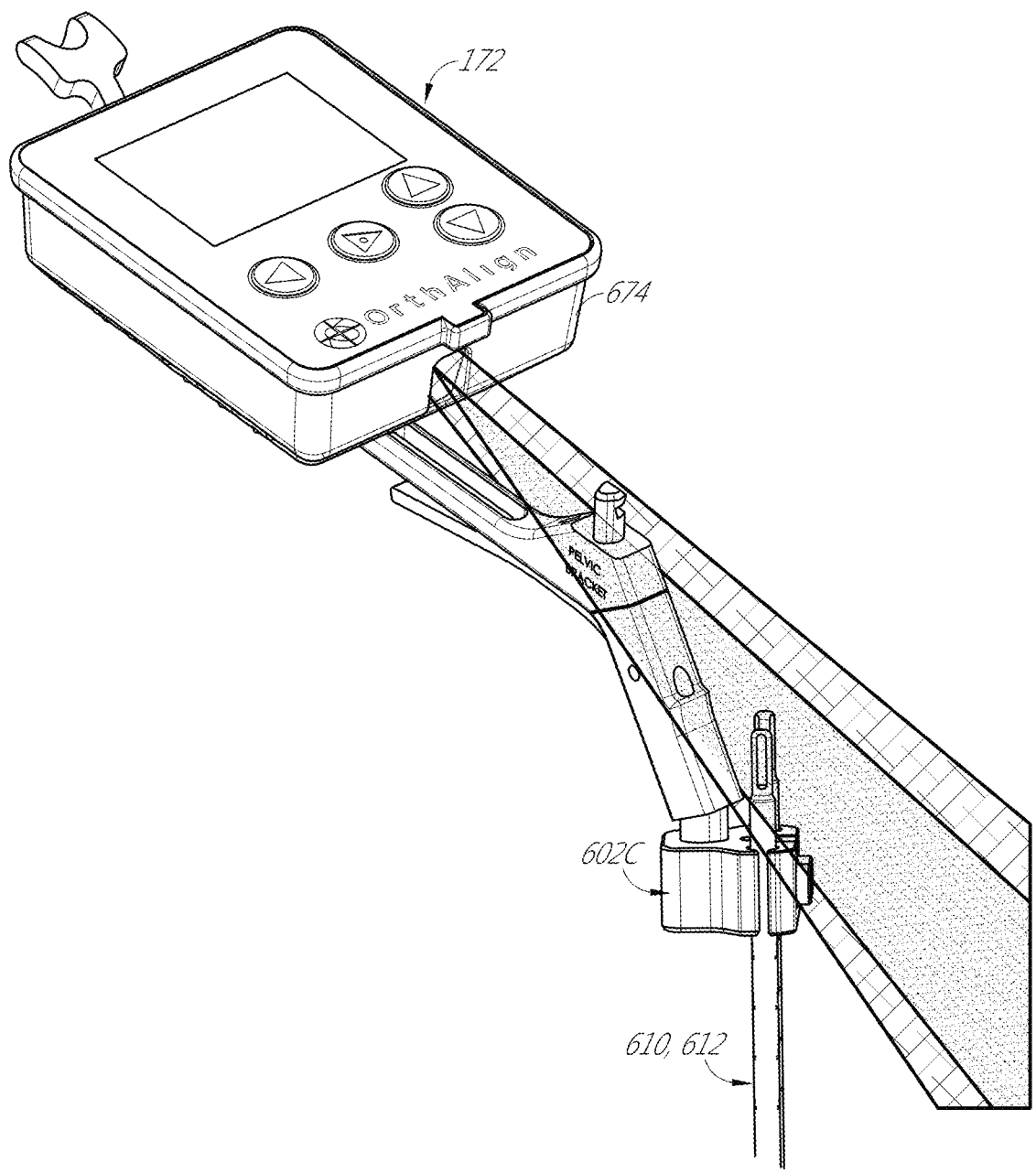
Figure 78:
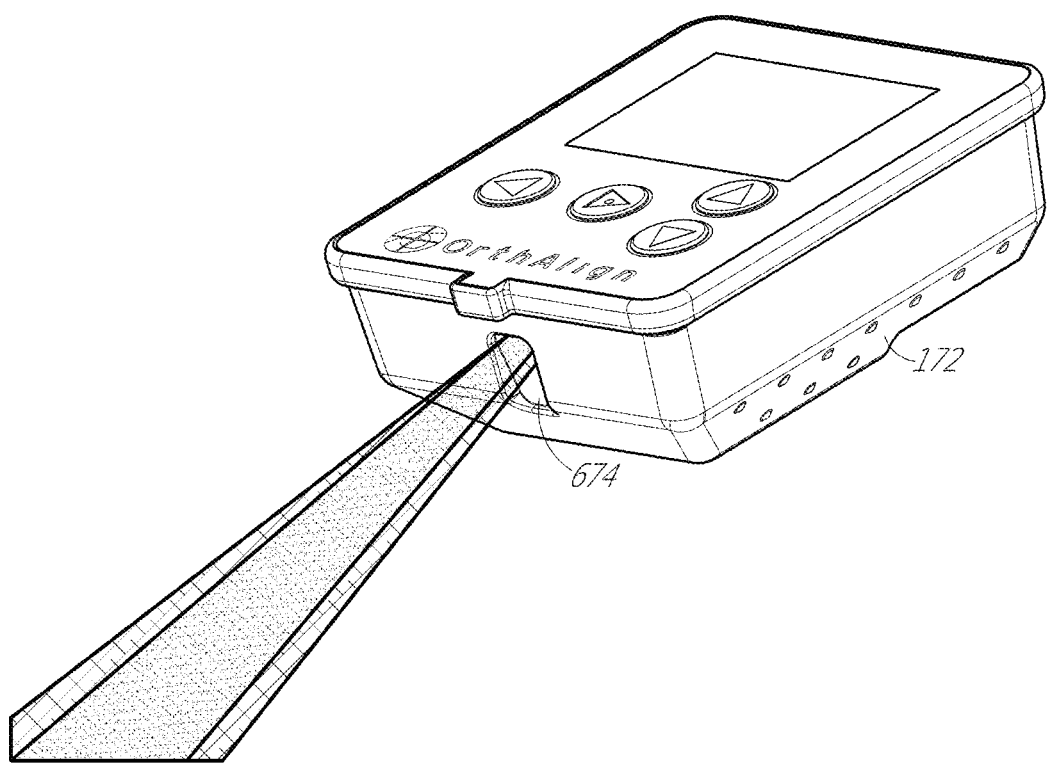

FIGS. 76-78 illustrate an embodiment of a system 600 that includes an optical component 674. In this context, optical component is a broad term. The surgical orientation device 172 can comprise optical component 674 that can be located on the top side, the bottom side, or sidewalls of the surgical orientation device 172. The optical component 674 can comprise transparent window integrated into the surgical orientation device 172. The windows can permit visible light (e.g. laser light) to emit from the optical component 674 of the surgical orientation device 172. The optical component 674 can provide a visual guide to replicate the original position of the femur relative to the pelvis.

With continued reference to FIG. 76, the optical component 674 can comprise one or more lasers, which can be configured to project laser light through the windows described above. For example, the optical component 674 can comprise a forward laser. The laser light can be used to project a point, a plane, and or a cross-hair onto a target or targets, including but not limited to an anatomical feature or landmark.

The optical component 674 can provide alternative or additional orientation information to a surgeon regarding the orientation of the surgical orientation device 172. For example, laser light can be used to project a plane on a portion of bone to indicate a resection line and a cross-hair laser pattern can be used to ensure alignment along two perpendicular axes. In certain embodiments, the optical component 674 can be used to determine an alignment of an anatomical feature or landmark. For example, the optical component 674 can project laser light to a target such as an anatomical feature. The surgeon can mark one or more points along the line of the projection of the optical component 674. The surgeon can complete any steps described herein. The surgeon, thereafter, can verify the one or more points are along the line of the projection of the optical component 674.

In the illustrated embodiment, the optical component 674 is a component of the surgical orientation device 172. Other configurations are contemplated. The optical component 674 can be a component of the fixation base 602. The optical component 674 can be a component of one or more fixation pins 610, 612. The optical component 674 can be an integral feature of any component of system 600. The optical component 674 can be a separate component from any component of system 600. The optical component 674 can be a stand-alone device which attaches to the pelvis.

Figure 79:
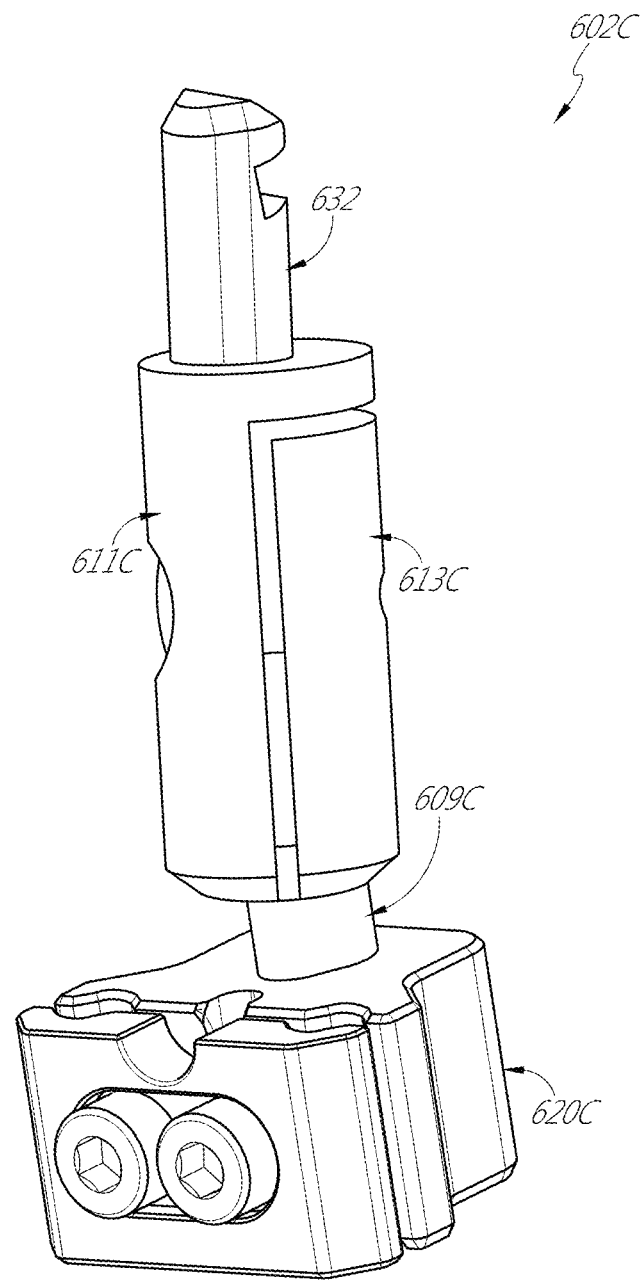
Figure 80:
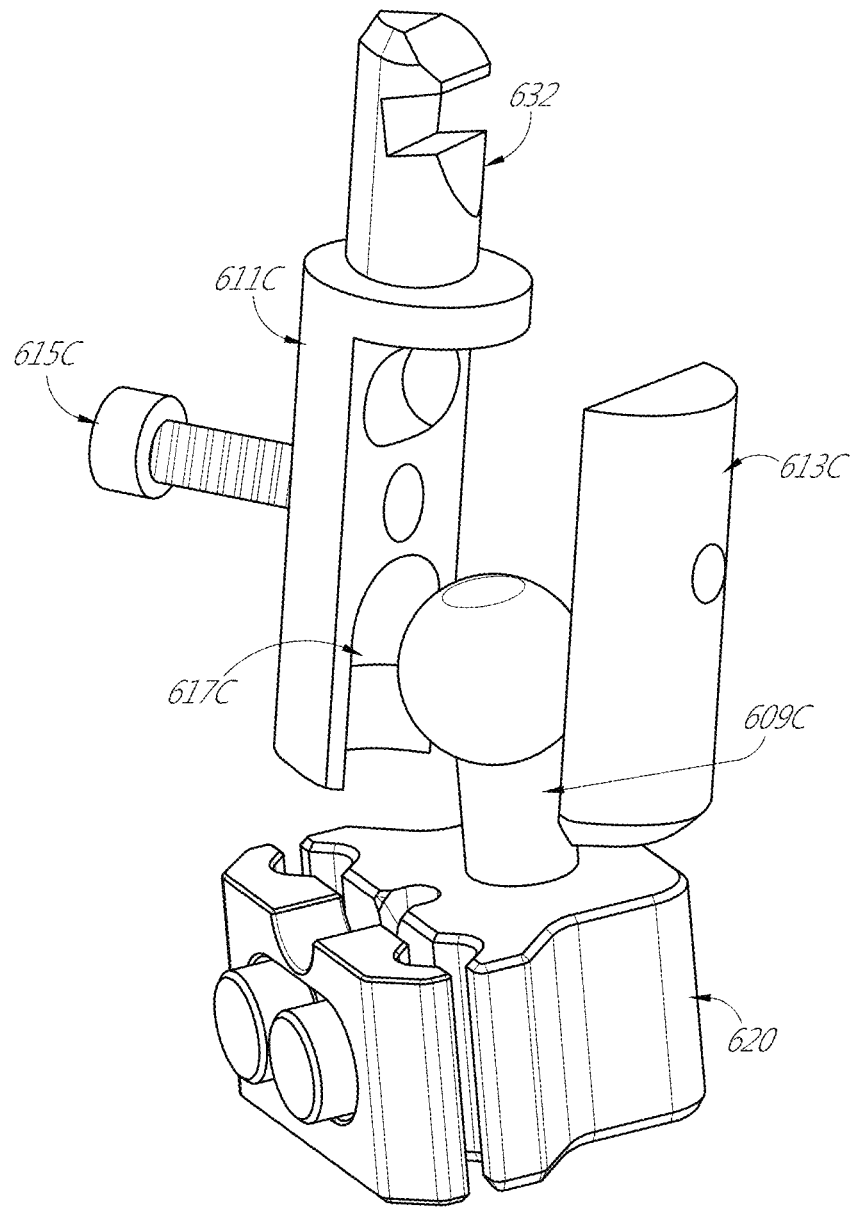

The system 600 can be modified to accommodate the optical component 674. The fixation base 602C can include a platform 620C as shown in FIGS. 79-80. The platform 620C can include a head 609C. The head 609C can be coupled to a platform 611C and a support 613C. The platform 611C and the support 613C can function as a clamp with the head 609C. FIG. 80 shows an exploded view of the fixation base 602C.

In the illustrated embodiment, the fixation base 602C can include one or more fixation devices 615C. In the illustrated embodiment, one fixation devices 615C is shown but other configurations are contemplated (e.g., two, three, four, etc.). The fixation device 615C can include one or more threaded sections. In the illustrate embodiment, the fixation device 615C is a screw with a head and a threaded shank. The platform 611C can include one or more holes. The support 613C can include one or more holes. The fixation device 615C can pass through or engage one or more holes in the support 613C. In some embodiments, each hole in the support 613C is threaded. The fixation devices 615C can pass through or engage one or more holes in the platform 611C. In some embodiments, each hole in the platform 611C is threaded. Rotation of the fixation device 615C can causes the support 613C to move toward the platform 611C and/or the platform 611C to move toward the support 613C. The platform 611C and the support 613C form a channel 617C. The channel 617C can be sized to accept the head 609C. When the platform 611C and the support 613C are separated, the head 608 can have pivotal or polyaxial movement. When the platform 611C and the support 613C are brought together by the fixation device 615C, the head 608C can be fixed in position.

The platform 611C can include the first coupler 632 described herein. The first coupler 632 can couple to the first assembly 604 as described herein. In FIG. 18, the first coupler 632 can be parallel to the pins 610, 612. In FIG. 76, the first coupler 632 can be angled relative to the pins 610, 612. In the anterior approach, the pins 610, 612 can be offset from vertical. The probe 678 (not shown) can be bent or curved as described herein. The shape of the probe 678 can facilitate the touching of points or anatomical landmarks in the anterior approach.

The assembly shown in FIG. 76 can permit the surgical orientation device to be moved relative to the anatomy of the patient. The clamping of the platform 611C and the support 613C can fix the position of the surgical orientation device 172 during surgery. The display of the surgical orientation device 172 can indicate whether the optical component 674 is on or off. The display of the surgical orientation device 172 can include an instructions related to the method of using the optical component 674.

In a preferred arrangement, the surgical orientation device 172 can be positioned and/or moved until the optical component 674 projects a beam on a portion of the anatomy. To achieve this centering, the optical component 674 can emit a laser beam or beams distally from the surgical orientation device 172. This laser beam or beams can illuminate a portion of the femur. This laser beam or beams can illuminate a portion of the knee joint. This laser beam or beams can illuminate a portion of the tibia. This laser beam or beams can illuminate a portion of the ankle. This laser beam or beams can illuminate a portion of the foot. This laser beam or beams can illuminate a portion of the foot constrained within a positioning boot. The surgical orientation device 172 can be moved until the laser beam is aligned with at least one anatomical region. In some methods, the laser beam is aligned with at least one anatomical region with little soft tissue. The soft tissue may move relative to the underlying bone. The surgeon can select locations to mark where the skin is close to the underlying bone.

The optical component 674 can be used in conjunction with the anterior and posterior approach described herein. When measuring changes in leg length and lateral joint offset, the apparent changes are sensitive to changes in the orientation of the femur relative to the pelvis. The changes are particularly sensitive to the abduction angle. The changes are moderately sensitive to the rotation about the mechanical axis of the femur. There may be two methods available to the surgeon. The first method is to reposition the femur prior to measuring the change such that the orientation of the femur relative to the pelvis is the same as that when the preoperative baseline measurement was made. Surgeons attempt to use the first method but this method is not very accurate. The method is not accurate primarily because the surgeon has poor visibility of the pelvis of the patient, which is hidden by soft tissue and surgical drapes.

The second method is to measure the orientation of the femur relative to pelvis during preoperative baseline and postoperatively and then correct for changes in orientation by doing a virtual rotation about the postoperative center of rotation of the femur. The second method is described herein with respect to the posterior approach and the anterior approach. The second method may require obtaining three points of the femur, such as points 690 shown in FIGS. 24A and 25C. The second method may require calculating the center of rotation (COR) of the hip using the set of points on the rim of the shell, as shown in FIG. 33. The second method is usually used in navigation systems but adds extra steps. In the case of the posterior approach described above, for example, three points 690 on the femur, femur tracker 686, 686A or femur base 687A must be registered to resolve for the femur orientation preoperatively and then postoperatively each time the leg length is to be measured. Also, the center of rotation must be determined which is done by registering three points on the acetabular cup after it has been inserted.

The optical component 674 can reduce the number of registrations. The optical component 674 can be mounted on the pelvis. The orientation of the optical component 674 can be fixed throughout the procedure. The optical component 674 can project a beam distally onto the leg. The surgeon can mark one or more points. These marks can guide the surgeon in replicating the orientation of the femur relative to the pelvis each time a leg length measurement is needed.

In some embodiments, the optical component 674 can be a "fan" style laser projection. The optical component 674 can project a line or pattern onto the leg. The method can, in variation, include any of the following steps. The following method is described in the context of an anterior approach in which the patient is supine as shown in FIG. 76. The method can include positioning the operative leg in a fully extended position to simulate a standing position. The method can include projecting the laser onto the anterior surface of the leg, running up the foot. The laser could be mounted on a lockable ball joint to facilitate adjustments to line up the laser and then lock it in place, as shown in FIG. 79. The method can include marking one or more marks Lm on the surface of the leg and foot coincident with the laser line. The method can include performing the baseline leg length measurement or registration on the exposed bone of the femur as close to the center of rotation as possible. This may minimize errors. This step can include placing a mark Fm on skin over the femur as described herein. For example, a mark placed at the distal femur may provide enhanced accuracy by eliminating error due to movement of the joints distal thereof. Such a location may also simplify an accurate procedure by eliminating the need to constrain the distal joints including the knee and ankle. The method can include performing the hip replacement. The method can include replicating the orientation of the femur by lining up the one or more marks Lm with the laser line again. The method can include performing the postoperative leg length measurement to determine changes in leg length and lateral offset. This step can include registering the mark Fm on the femur as described herein.

The method described herein can reduce the need to add a femur tracker 686, 686A or femur base 687A to the femur. The method described herein can reduce the need to drill holes in the femur to attach the femur tracker 686, 686A or femur base 687A. This can prevent fractures or further damage to the femur. In some methods, the optical component 674 is used in combination with a camera. The camera can be the camera 684 described herein. The camera can be camera 812 described herein. The camera can capture a photographic image of the laser or laser beam. The camera can capture a photographic image of the one or more marks Lm. The camera can capture a photographical image of the leg and/or foot. The surgical orientation device 172 and/or the orientation sensing device 204 as described herein can convert the photographic image to orientation and/or positional information of the anatomy of the patient.

C. Optical Component for Anatomical Tracking

Figure 81:
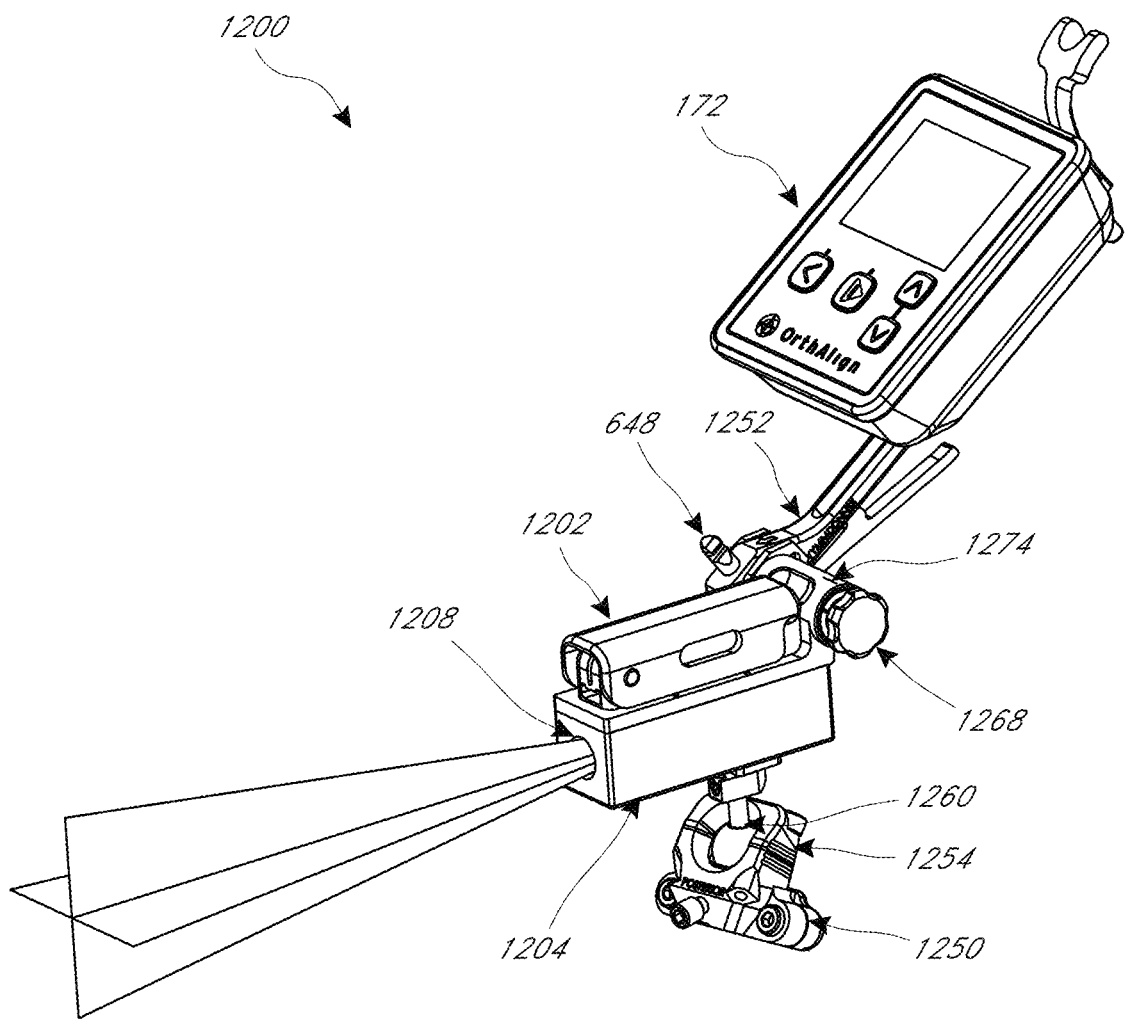
FIGS. 81-85 illustrate a modular system with an optical component.
Figure 82:
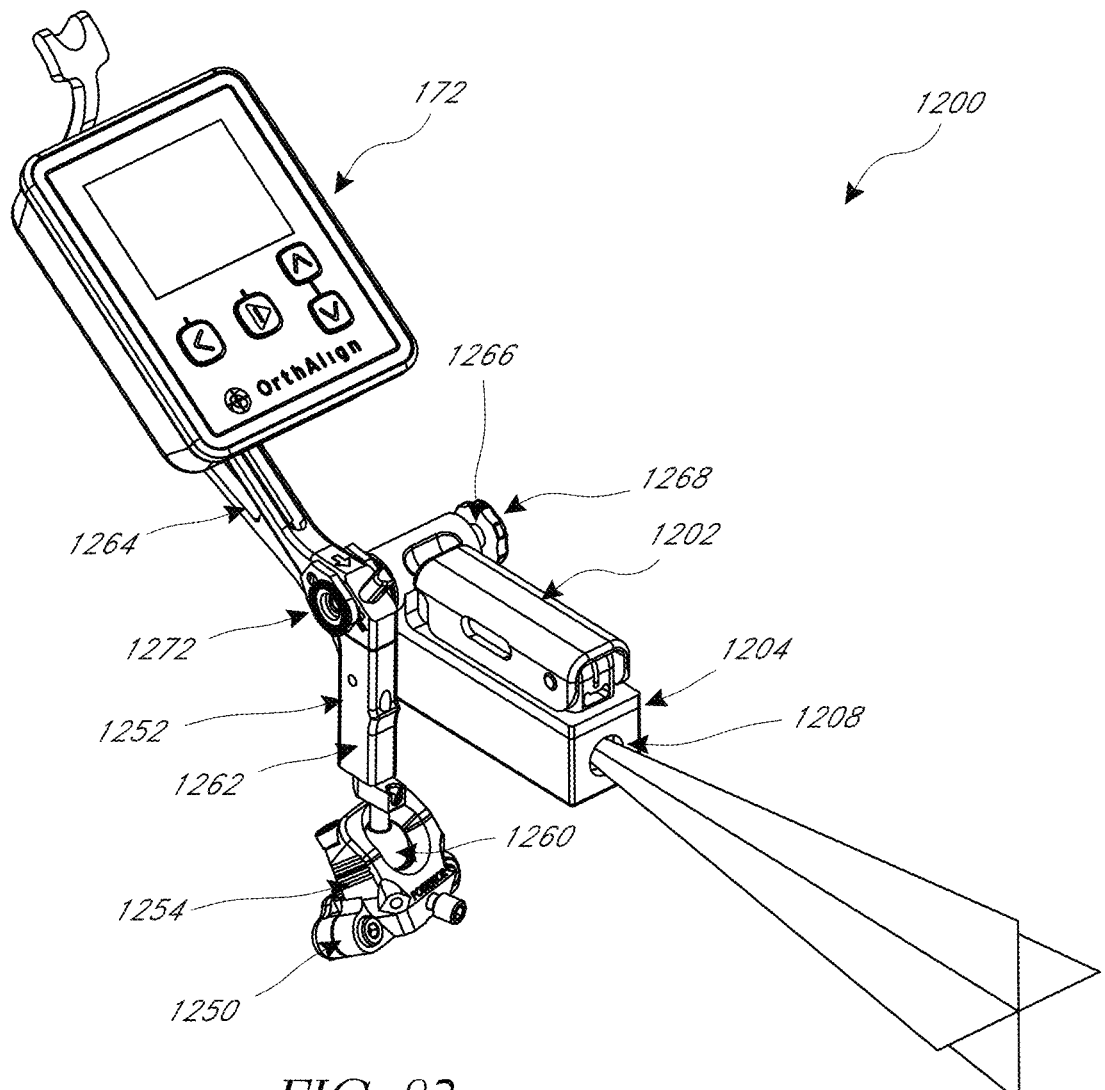

FIGS. 81-85 illustrate an embodiment of a system 1200 that includes an optical component 1202. In this context, optical component is a broad term. The optical component 1202 can be any device designed to project light including visible, ultraviolet, and infrared light. The optical component 1202 can be a laser which emits light with a very narrow spectrum, for instance a single color of light. The optical component 1202 can focus light on a single location, such as a tiny spot. The optical component 1202 can focus light along a line. The optical component 1202 can project one or more points, lines, planes, shapes, colors, and/or patterns. FIGS. 81-82 show the projection of light that when incident on a surface is visible as two intersecting lines, which pattern may be referred to herein as a cross-hair. The optical component 1202 can project light onto a target or targets, including but not limited to an anatomical feature or landmark. In some embodiments, the light can be projected onto a flat or substantially flat local area and when so projected forms a cross-hair. In some embodiments, the light can be projected onto a curved or substantially curved local area. In some methods of use, the shape of the surface does not alter the projection of light, for instance the intersection of the cross-hair. In some methods of use, the shape of the surface does not alter the utility of the approach, as described herein.

The system 1200 can include any additional component of the systems described herein. The system 1200 can include the surgical orientation device 172 as shown in FIGS. 81-82. The optical component 1202 can be a separate component from the surgical orientation device 172. The optical component 1202 can be located below the surgical orientation device 172 adjacent to a fixture to be coupled with a patient, e.g., closer to the pelvis of the patient. Other configurations are contemplated. The optical component 1202 can be located beside or adjacent to or above the surgical orientation device 172. The display of the surgical orientation device 172 can indicate whether power to the optical component 1202 is on or off. The display of the surgical orientation device 172 can include instructions related to the method of using the optical component 1202.

Figure 83:
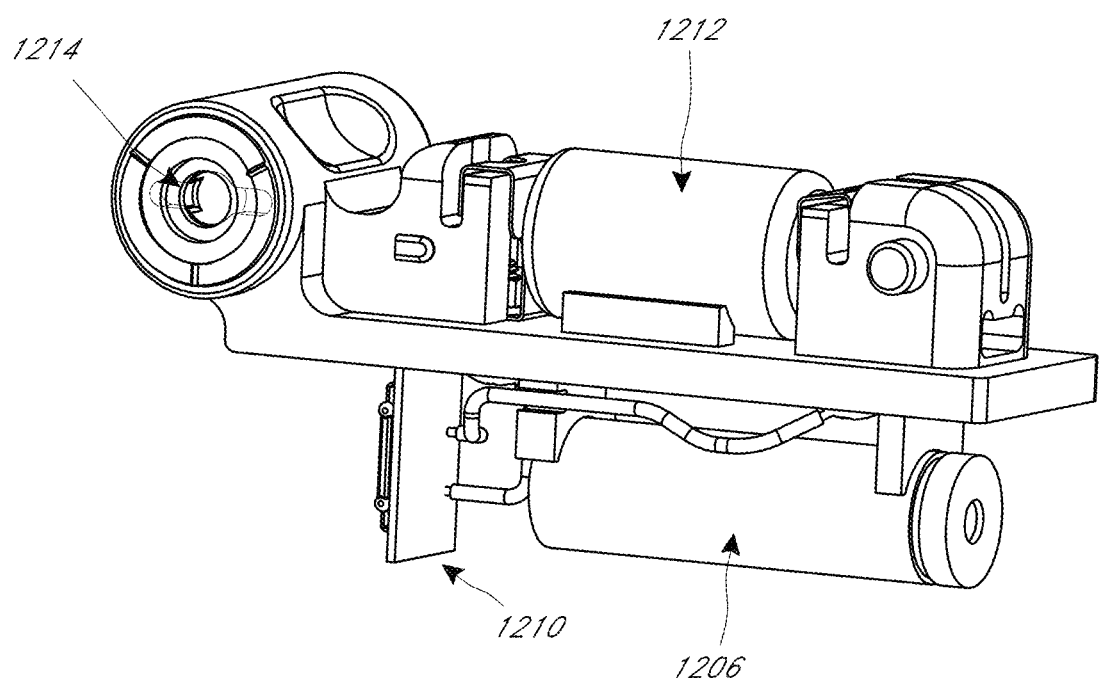

The optical component 1202 can include a housing 1204. The housing 1204 can protect a light source 1206 disposed within the housing 1204. FIG. 83 shows the optical component 1202 with the housing 1204 removed. Referring back to FIG. 81-82, the housing 1204 can include a window 1208. The window 1208 can allow the light source 1206 to project a light from the housing 1204. The window 1208 can be located on the top side, the bottom side, or sidewalls of the housing 1204. The window 1208 can be transparent. The optical component 1202 can include one or more windows 1208. The window 1208 can be integrally formed with the housing 1204 or a separate component coupled to the housing 1204. The window 1208 can permit visible light (e.g. laser light) to emit from the optical component 1202. In some embodiments, the housing 1204 can include one or more openings. For example, the window 1208 need not be present if an opening permits the visible light in another spectrum to be emitted from the housing 1204.

The optical component 1202 can include one or more light sources 1206, as shown in FIG. 83. The optical component 1202 can include one or more light sources and a corresponding number of one or more windows 1208 or openings in the housing 1204. One or more light sources 1206 can project light through a single window 1208 or a single opening in the housing 1204. In some embodiments, the housing 1204 and the light source 1206 move as a unit relative to the surgical orientation device 172 or to a fixture to which the housing 1204 is coupled to position the light toward the desired location. The light source 1206 can be a laser, as described herein. The light source 1206 can project light outward from the optical component 1202, as shown in FIGS. 81-82.

Referring to FIG. 83, the optical component 1202 can include one or more electronic components 1210. The electronic component 1210 can control the emission of light. In some embodiments, the electronic component 1210 can include a processor or microprocessor to control the emission of light. The electronic component 1210 can connect a power source to the light source 1206. The optical component 1202 can include an indicator of whether the optical component 1202 is on or off. The indicator can be an indicator light. The indicator can be an on/off switch that the surgeon moves or presses to activate the light source 1206. The optical component 1202 can include a power source 1212 to provide power to the light source 1206. The power source 1212 can be a battery. The battery can be disposed within the housing 1204 or within a separate housing of the optical component 1202. The optical component 1202 could be electrically connected to the surgical orientation device 172 to be powered or controlled thereby. The optical component 1202 or another component of the system 1200 can include an alignment guide 1274 to indicate the position of the optical component 1202 as shown in FIG. 81. The alignment guide 1274 is shown as a line, but other configurations are contemplated. The alignment guide 1274 can be one or more markings which visually indicates the position of the optical component. For instance, the alignment guide 1274 can indicate the rotation of the housing 1204 relative to a jig or other fixture, such as the first assembly, as described herein. The alignment guide 1274 can include a scale to indicate the degree of rotation.

The optical component 1202 can be positioned to project light toward a desired location. The optical component 1202 can provide a visual guide to replicate an original position of an anatomical feature relative to another anatomical feature, as described herein. In methods wherein the optical component 1202 is mounted to the pelvis, the optical component 1202 can provide a visual guide to replicate the original position of the leg or a portion thereof relative to the pelvis. The optical component 1202 can provide alternative or additional orientation information to a surgeon regarding the orientation on the pelvis relative to the leg. In some methods of use, the light provides information regarding the anatomy. The optical component 1202 can project anatomical axes or planes. The optical component 1202 can project a mechanical axis or a center of rotation. The optical component 1202 can project a line or plane of light on a portion of bone to indicate a resection line. The optical component 1202 can project a cross-hair shape of light to indicate two perpendicular axes.

In some methods of use, the optical component 1202 can be used to determine an alignment of an anatomical feature or landmark. The optical component 1202 can be mounted to an anatomical feature. As described herein, in some methods of use, the optical component 1202 is mounted to the pelvis of the patient. The optical component 1202 can be mounted to a jig or other fixture. The surgical orientation device 172 can be mounted to the jig. The optical component 1202 can be fixed in position during the surgical procedure. The optical component 1202 can project light from the same position during the surgical procedure. The optical component 1202 can project a line or a plane of light onto a portion of the anatomy. The surgeon can mark one or more points along the line or the plane of light. The surgeon can complete any method steps described herein. Thereafter, the optical component 1202 can project the same line or plane of light. The surgeon can verify the one or more points are aligned along the line or plane of light. The surgeon can reposition the anatomy to align one or more points along the line or plane of light. In some methods of use, the optical component 1202 is fixed relative to the pelvis. The surgeon can reposition the leg such as the femur, tibia, knee, ankle, and/or foot relative to the pelvis. The surgeon can align the femur, tibia, knee, ankle, and/or foot relative to the pelvis after one or more method steps.

Referring to FIGS. 81 and 82, the jig can include any features described herein, including features of the first assemblies described herein. The system 1200 can include a fixation base 1250 and a first assembly 1252. The fixation base 1250 and the first assembly 1252 can be rigidly connected to the hip of a patient in the illustrated configuration so that motion of the hip cause corresponding motion of sensor(s) in the first assembly 1252 as discussed herein. Sensing this motion enables the system 1200 to eliminate movement of the patient as a source of error in the navigation.

Figure 84:
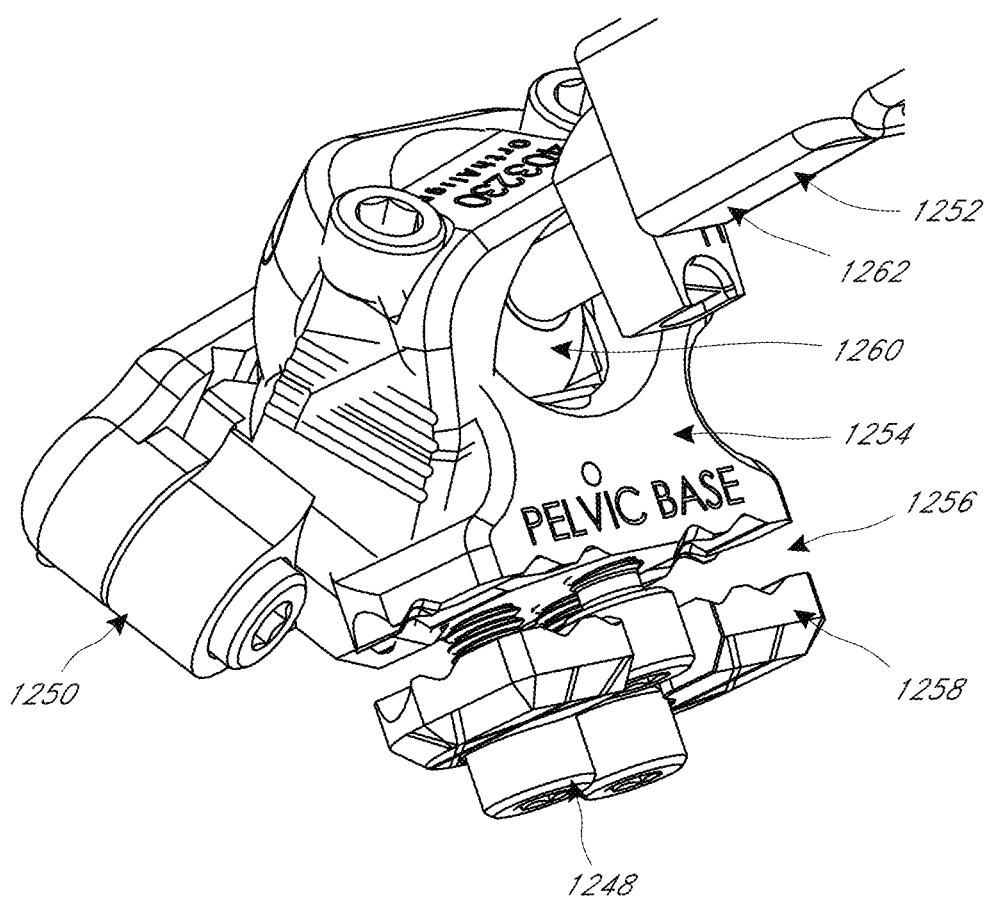

FIG. 84 shows the fixation base 1250 and the distal end of the system 1200. The fixation base 1250 can include a platform 1254. The platform 1254 can include one or more holes 1256. The holes 1256 can be sized to accept a fastener such as a mounting pin (not shown, but similar to the pin 610 shown in FIG. 39) to secure the fixation base 1250 to the bone. The fixation base 1250 can function as a clamp with the one or more mounting pins. The fixation base 1250 can include a support 1258. The platform 1254 can interact with the support 1258 to function as a clamp. Rotation of one or more fixation devices 1248 can cause the support 1258 to move toward the platform 1254 and/or the platform 1254 to move toward the support 1258. In some embodiments, the platform 1254 can include one or more spikes (not shown). The one or more spikes can secure the fixation base 1250 to the bone in addition to or as an alternative to the one or more mounting pins.

The platform 1254 can include an articulation 1260. The articulation 1260 can allow movement between the platform 1254 and a first segment 1262 of the first assembly 1252. The articulation 1260 can be a ball and socket joint. The articulation 1260 can include an axle, a sleeve, a bearing, a bushing, and/or a swivel. The articulation 1260 can be any joint or connection that allows motion about one or more planes or axes. The articulation 1260 can be sufficiently rigid to maintain the position of the first segment 1262 relative to the platform 1254 once moved into position. In the illustrated embodiment, the first segment 1262 of the first assembly 1252 includes a ball and the platform 1254 includes the socket. Other configurations are contemplated.

In some methods of use, the fixation base 1250 is mounted adjacent to the hip joint. The fixation base 1250 can be mounted to the pelvis, as described herein. The position of the first segment 1262 of the first assembly 1252 can be adjusted via the articulation 1260. The position of the second segment 1264 of the first assembly 1252 can be adjusted via the articulation 1260. The optical component 1202 can be coupled to the first assembly 1252 as described herein. The position of the optical component 1202 can be adjusted via the articulation 1260. In some embodiments, the position of the optical component 1202 is determined in part by the position of the articulation 1260. The system 1200 may have additional features to position of the optical component 1202, as described herein. In other embodiments, the position of the optical component 1202 is determined entirely by the position of the articulation 1260.

Referring back to FIG. 82, the first segment 1262 of the first assembly 1252 can extend above, e.g., vertically or generally vertically from the platform 1254 during use. The first segment 1262 can include any features described herein that pertain to segments of the fixture including features of the pelvic bracket 638. The first assembly 1252 can include a second segment 1264. The second segment 1264 can include any features described herein that pertain to segments of the fixture including features of the extension 644 and the mount 646. The second segment 1264 is designed to couple with the surgical orientation device 172. The surgical orientation device 172 can include features to mate with the second segment 1264 (not shown). The surgical orientation device 172 can be rigidly coupled to the first segment 1262 by way of the second segment 1264 during use. In some embodiments, the surgical orientation device 172 can be rigidly coupled to the first segment 1262 directly. The first segment 1262 and the second segment 1264 can be integrally formed or separate components.

The surgical orientation device 172 can be angled relative to a longitudinal axis of the first assembly 1252 and/or relative to a fixed reference, such as a horizontal plane, when coupled to the first assembly 1252. The surgical orientation device 172 can be angled approximately 35° from the horizontal plane. Other angles from the horizontal plane are contemplated, (e.g., 5°, 10°, 15°, 20°, 25°, 30°, 40°, 45°, 50°, 55°, 60°, 65°, 70°, 75°, 80°, or 85°, between 30°-40°, between 25°-45°). The articulation 1260 can adjust the angle of the surgical orientation device 172. In some embodiments, the angle of the surgical orientation device 172 improves visibility. The angle is a compromise between tilting the surgical orientation device 172 up toward the surgeon and allowing another surgeon or surgical assistant on the other side of the patient to still see the display. One reason for angling the surgical orientation device 172 is that in an anterior approach, the surgeon stands toward the patient's feet while impacting the acetabular implant and a horizontally oriented display would be difficult to see from this vantage point.

The system 1200 can include additional features to facilitate positioning of the optical component 1202. The additional features can allow the independent adjustment of the optical component 1202. The optical component 1202 can include an articulation 1266. The articulation 1266 can allow movement between the optical component 1202 and the first assembly 1252. The articulation 1266 can include a ball and socket joint (not shown). The articulation 1266 can include a sleeve, a bearing, a bushing, and/or a swivel. The articulation 1266 can be any joint that allows motion about one or more planes or axes. The articulation 1266 can be sufficiently rigid to maintain the position of the optical component 1202 relative to the first assembly 1252 once moved into position.

The articulation 1266 can include an axle. The axle can extend between the optical component 1202 and the first assembly 1252. The articulation 1266 can allow positioning of the optical component 1202 relative to the first assembly 1252. In the illustrated embodiment, the axle is disposed perpendicular or generally perpendicular to the first assembly 1252. In other embodiments, the axle is parallel, generally parallel, or any angle relative to the first assembly 1252.

The first segment 1262 and/or the second segment 1264 can include an engagement feature to engage the articulation 1266. The engagement feature can include an opening extending at least partially through the first segment 1262 and/or the second segment 1264 of the first assembly 1252. The second segment 1264 can include an opening configured to allow the articulation 1266 to pass through the second segment 1264. In some embodiments, the articulation 1266 can freely rotate relative to the second segment 1264. In some embodiments, the second segment 1264 can engage articulation 1266 on either side of the second segment 1264. In FIG. 82, the optical component 1202 is mounted laterally (e.g., to the right side from the vantage point of a target) of the second segment 1264. The articulation 1266 can be removed and the optical component 1202 can be mounted to the left side of the second segment 1264.

Figure 85:
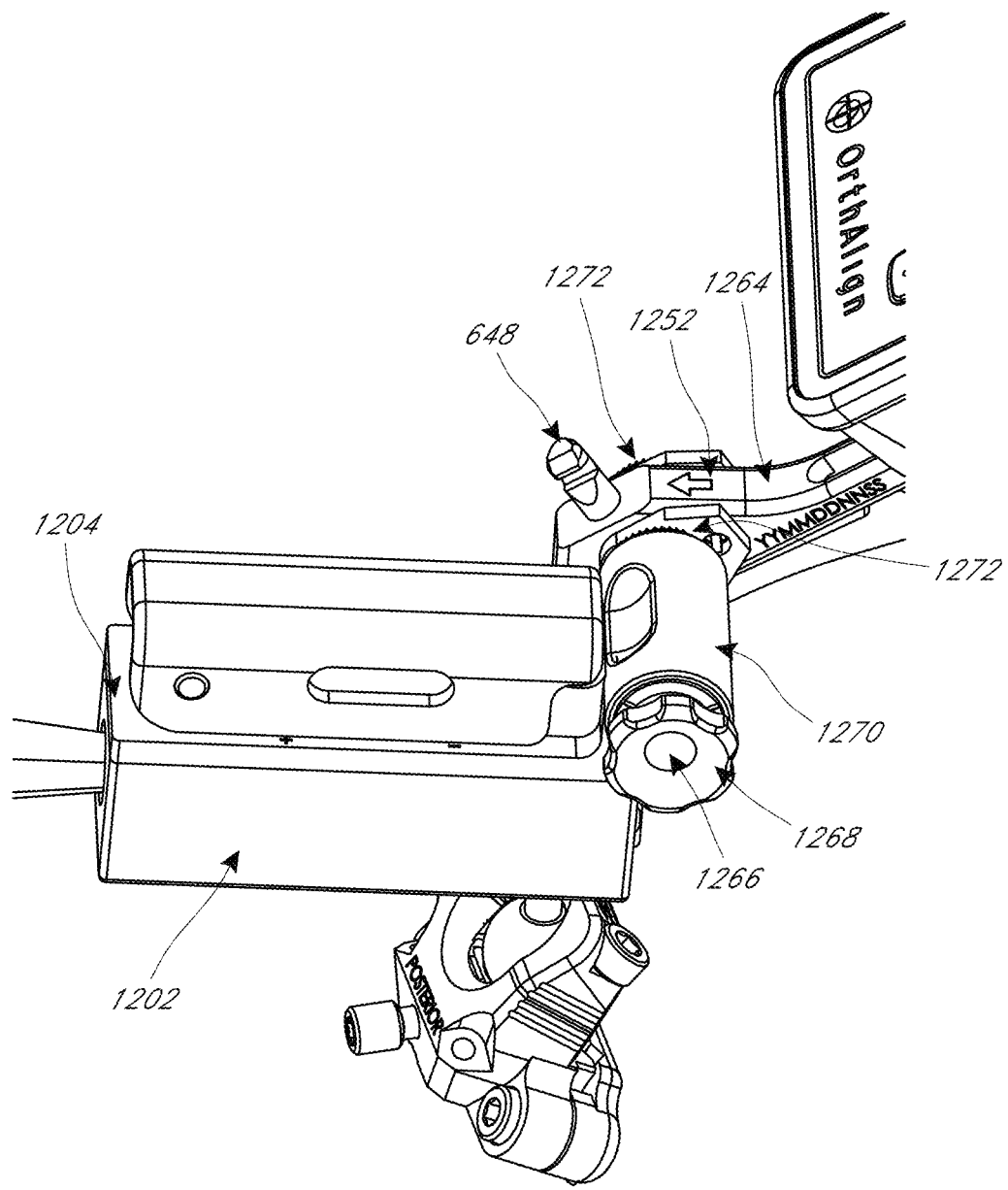

Referring to FIG. 85, the system 1200 can include an adjustment feature 1268. The adjustment feature 1268 can cause the rotation of the optical component 1202 relative to the first assembly 1252. The adjustment feature 1268 can be a knob. The adjustment feature 1268 can be coupled to the axle to cause rotation of the axle. The adjustment feature 1268 can be coupled to the housing 1204 to cause rotation of the housing 1204. The housing 1204 can include a sleeve or tubular portion 1270 designed to fit around the axle. The housing 1204 can include a mating configuration (not shown) to engage the axle and/or the adjustment feature 1268. The mating configuration allows rotation of the adjustment feature 1268 to cause rotation of the housing 1204 of the optical component 1202. The mating configuration can include a corresponding flange and slot. In some embodiments, the housing 1204 or a component coupled to the housing 1204 includes a slot 1214, as shown in FIG. 83. The axle and/or the adjustment feature 1268, or a component coupled thereto, can include a flange. The slot can accept the flange in one or more configurations (e.g., one orientation, two orientations, three orientations, etc.). The slot and the flange are designed to transmit torque between the axle and/or the adjustment feature 1268 and the housing 1204. Other mating configurations to transmit torque are contemplated.

In some embodiments, the optical component 1202 can be positioned at any one of a plurality of discrete positions relative to the first assembly 1252. For instance, the system 1200 can include a plurality of splines 1272 between the optical component 1202 and an adjacent structure. The plurality of splines 1272 can be a serrated plate. The adjacent structure can be coupled to the first assembly 1252. FIGS. 82 and 85 shows the splines 1272 on the left side of the second segment 1264. In some embodiments, a similar or identical set of splines 1272 is located on the right side of the second segment 1264 as shown in FIG. 85. This configuration can allow the optical component 1202 to be mounted on either the right or left side of the fixture. The plurality of splines 1272 can retain the position of the optical component 1202 relative to the first assembly 1252. In other embodiments, the optical component 1202 can be oriented at an infinite number of positions relative to the first assembly 1252 or at a select position along a continuum of motion. The connection between the optical component 1202 and the first assembly 1252 is sufficiently rigid to maintain the position of the optical component 1202 relative to the first assembly 1252 once moved into position.

The system 1200 can include a second assembly, which can have any of the features described herein including features of the second assembly 606 shown in FIG. 22A. The second assembly provides a full range of controlled motion and sensor(s) that are able to track the motion, in concert with sensor(s) in the first assembly 1252. The second segment 1264 of the first assembly 1252 can include a second coupler 648 as shown in FIG. 85. In some embodiments, the second coupler 648 is a universal coupler, as described herein.

The system 1200 can include a probe. The probe can have any of the features described herein including features of the probe 678 shown in FIGS. 22B-22C. The probe can be coupled to the second assembly (see, e.g., FIG. 22A) such that the probe is movable relative to the second assembly. This maneuverability enables the distal end of the probe to pivot or rotate to contact anatomical landmarks, as discussed herein. This maneuverability enables the distal end of the probe to pivot or rotate to contact points on a femur tracker such as femur tracker 686 described herein. The femur tracker can be used to track the position of the femur during the procedure. The femur tracker can include one or more points which are fixed relative to the femur. The second assembly permits a range of motion of a distal end of the probe to facilitate acquiring a plurality of landmarks or points that are different distances from the attachment location of the fixation base 1250. The position of the second assembly and/or the probe can be adjusted via the articulation 1260, as described herein.

The optical component 1202 can be mounted to allow independent articulation via the articulation 1266. The optical component 1202 can be positioned independently of the surgical navigation unit 172. The optical component 1202 can be positioned independently of the probe. The optical component 1202 can be positioned independently of any other component of system 1200. The optical component 1202 can be positioned independently to project light on the desired anatomical location, such as a portion of the leg.

The optical component 1202 can be adjusted in pitch such as by rotation about the articulation 1266. In some embodiments, the optical component 1202 can be adjusted to tilt forward and backward (pitch). In some embodiments, the optical component 1202 can be adjusted to swivel right and left (yaw). In some embodiments, the optical component 1202 can be adjusted to pivot side to side (roll). In some embodiments, the optical component 1202 can be adjusted to translate up and down. In some embodiments, the optical component 1202 can be adjusted to translate right and left. In some embodiments, the optical component 1202 can be adjusted to translate forward and backward.

Other configurations are contemplated. The optical component 1202 can be mounted to allow independent motion about one or more axes or planes. The optical component 1202 can be mounted to allow for polyaxial movement. The optical component 1202 can be mounted to include a ball and socket joint such as articulation 1260. The optical component 1202 can have one degree of freedom relative to the first assembly 1252. The optical component 1202 can have more than one degree of freedom relative to the first assembly 1252 (e.g., two, three, four, five, etc.).

Other configurations are contemplated. The optical component 1202 can be a component of the fixation base 1250. The optical component 1202 can be an integral feature of any component of system 1200. The optical component 1202 can be a stand-alone device which attaches to the pelvis.

The system 1200 can permit the optical component 1202 to be moved relative to the anatomy of the patient. In methods involving the fixation base 1250 coupled to the pelvis, the optical component 1202 can be moved relative to the pelvis. The rigidity of the system 1200 can fix the position of the optical component 1202 once moved into position during surgery.

In some methods of use, the optical component 1202 can be positioned and/or moved until the optical component 1202 projects light on a portion of the anatomy. The optical component 1202 can emit light such as a line, plane, or shape away from the surgical orientation device 172. The light can illuminate a portion of the femur. The light can illuminate a portion of the knee joint. The light can illuminate a portion of the tibia. The light can illuminate can illuminate a portion of the ankle. The light can illuminate a portion of the foot. The light can illuminate a portion of the foot constrained within a positioning boot. The optical component 1202 can be moved until the light is projected on at least one anatomical region. In some methods of use, the light is projected onto at least one anatomical region with little soft tissue. The soft tissue may move relative to the underlying bone. The surgeon can select locations to illuminate where the skin is close to the underlying bone.

The method of use can include the step of placing the patient in a position wherein the leg of the patient is extended. The method of use can include the step of placing the pelvis of a patient in a fixed position. The method of use can include the step of placing the femur of a patient in a fixed position. The method of use can include the step of placing the tibia of a patient in a fixed position. The method of use can include the step of placing the knee of a patient in a fixed position. The method of use can include the step of placing the foot of a patient in a fixed position.

The method of use can include a posterior approach. The method of use can include positioning the patient on his/her side. The method of use can include orienting the anterior pelvic plane vertically. The method of use can include orientating the anterior pelvic plane perpendicular to the plane of the table on which the patient is positioned.

The method of use can include an anterior approach. The method of use can include positioning the patient in a supine position. The method of use can include orienting the anterior pelvic plane horizontally. The method of use can include orientating the anterior pelvic plane parallel to the plane of the table on which the patient is positioned.

The method of use can include the step of securing of the fixation base 1250 to the pelvis. The method of use can include the step of adjusting the first assembly 1252 relative to the fixation base 1250. The method of use can include the step of adjusting a ball joint to adjust the first assembly 1252 relative to the fixation base 1250. The method of use can include the step of adjusting the optical component 1202 relative to the fixation base 1250. The method of use can include the step of adjusting a ball joint to adjust the optical component 1202 relative to the fixation base 1250. The method of use can include the step of adjusting the optical component 1202 relative to the first assembly 1252. The method of use can include the step of adjusting the pitch of the optical component 1202 relative to the fixation base 1250. The method of use can include the step of mounting the optical component 1202 to a pelvis of a patient adjacent to a hip joint. The method of use can include the step of adjusting the optical component 1202 relative to the pelvis in one or more degrees of freedom.

The method of use can include the step of projecting light from the optical component 1202. The method of use can include the step of projecting light onto the leg of the patient to illuminate a portion of the leg away from the hip joint. The method of use can include the step of projecting light onto the femur. The method of use can include the step of projecting light onto the femur just proximal to the knee. The method of use can include the step of projecting light onto the knee. The method of use can include the step of projecting light onto the tibia. The method of use can include projecting light onto the ankle. The method of use can include the step of projecting light onto the foot.

The method of use can include the step of recording the position of the light. The method of use can include the step of marking the position of the light. The method of use can include the step of marking two or more points along a line of light. The method of use can include the step of drawing a line along the line of light. The method of use can include the step of capturing an image of the incidence of light. The method of use can include the step of utilizing a camera to capture the incidence of light.

The method of use can include the step of registering a portion of the proximal femur adjacent to the hip joint. The method of use can include the step of touching a plurality of points with a probe. The method of use can include the step of recording the position of a probe as the probe touches one or more points. The method of use can include the step of affixing a femoral plate. The method of use can include the step of contacting two or more points on the femoral plate with a probe. The method of use can include the step of contacting three points on the femoral plate with a probe. The method of use can include the step of recording the position of a probe as the probe touches one or more points on a femoral plate.

The method of use can include the step replacing the hip joint or a portion thereof. The method of use can include the step of installing an artificial hip joint. The method of use can include the step of ensuring the optical component 1202 remains stationary relative to the pelvis during the step of replacing the hip joint. The method of use can include the step of ensuring the surgical orientation device 172 remains stationary relative to the pelvis during the step of replacing the hip joint.

The method of use can include the step of registering the portion of the proximal femur after replacing the hip joint. The method of use can include the step of touching a plurality of points with a probe after replacing the hip joint. The method of use can include the step of recording the position of a probe as the probe touches one or more points after replacing the hip joint. The method of use can include the step of comparing the position of a probe as the probe touches one or more points to the position recorded before replacing the hip joint. The method of use can include the step of contacting two or more points on the femoral plate with a probe after replacing the hip joint. The method of use can include the step of contacting three points on the femoral plate with a probe after replacing the hip joint. The method of use can include the step of recording the position of a probe as the probe touches one or more points on a femoral plate after replacing the hip joint. The method of use can include the step of comparing the position of a probe as the probe touches one or more points on a femoral plate to the position recorded before replacing the hip joint.

The method of use can include the step of confirming the leg length after replacing the hip joint. The method of use can include the step of confirming joint offset after replacing the hip joint. When measuring changes in leg length and/or lateral joint offset, the apparent changes are sensitive to changes in the orientation of the femur relative to the pelvis. The changes are particularly sensitive to the abduction angle. The changes are moderately sensitive to the rotation about the mechanical axis of the femur. The optical component 1202 can be used to verify the orientation of the leg relative to the pelvis before and after replacing the hip joint.

The step of confirming the leg length and/or joint offset can include the step of obtaining three points of the femur. The method of use can include the step of calculating the center of rotation (COR) of the hip using the set of points on the rim of the shell. The method of use can include the step of registering three points to resolve for the femur orientation preoperatively and then postoperatively each time the leg length is to be measured.

The method of use can include the step of projecting light after replacing the hip joint. The method of use can include the step of comparing the position of the light before and after replacing the hip joint. The method of use can include the step of comparing the incidence of light after replacing the hip joint with the one or more marks made before replacing the hip joint. The method of use can include the step of comparing the incidence of light after replacing the hip joint with the two or more marks made before replacing the hip joint. The method of use can include the step of comparing the incidence of light after replacing the hip joint with a line made before replacing the hip joint.

The method of use can include the step of confirming the position of the leg relative to the pelvis after replacing the hip joint. The method of use can include the step of confirming the position of the femur relative to the pelvis after replacing the hip joint. The method of use can include the step of confirming the position of the tibia relative to the pelvis after replacing the hip joint. The method of use can include the step of confirming the position of the knee relative to the pelvis after replacing the hip joint. The method of use can include the step of confirming the position of the ankle relative to the pelvis after replacing the hip joint. The method of use can include the step of confirming the position of the foot relative to the pelvis after replacing the hip joint.

The optical component 1202 can be useful to measure the orientation of the leg relative to pelvis during preoperative baseline and postoperatively. The surgeon can correct for changes in orientation by repositioning the leg based on the light. These marks can guide the surgeon in replicating the orientation of the leg relative to the pelvis each time a leg length measurement or joint offset measurement is needed. The optical component 1202 can be used in conjunction with the anterior and posterior approach described herein.

Although these inventions have been disclosed in the context of certain preferred embodiments and examples, it will be understood by those skilled in the art that this application extends beyond the specifically disclosed embodiments to other alternative embodiments and/or uses of the invention and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or sub-combinations of the specific features and aspects of the embodiments may be made and still fall within the scope of the application. For example, the application contemplates the connection hub alone or in combination with any of the other modules could comprise a separate aspect. Or, any one or a combination of the modules could be directly connected to an umbrella hub or overhead support to form another separate aspect. Accordingly, it should be understood that various features and aspects of the disclosed embodiments can be combined with or substituted for one another in order to form varying modes of the disclosed embodiments. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A hip procedure navigation system, comprising:
a first pin configured to be driven into a pelvic bone of a patient,
a second pin configured to be driven into the pelvic bone of the patient,
a fixation base comprising a first channel configured to receive the first pin and a second channel configured to receive the second pin, wherein the fixation base is configured to slide along the first pin received within the first channel and the second pin received within the second channel,
a threaded fixation device configured to be rotated to secure the fixation base to the first pin and the second pin, wherein the first channel and the second channel extend in a direction traverse to the direction of the threaded fixation device,
a navigation device configured to be removably coupled to the fixation base, wherein the navigation device comprises at least one inertial sensor,
wherein the at least one inertial sensor is configured to determine cup inclination and anteversion angles, wherein a display provides an indication of the cup inclination and anteversion angles.

2. The hip procedure navigation system of claim 1, further comprising an impactor.

3. The hip procedure navigation system of claim 1, wherein the cup inclination and anteversion angles are determined relative to a horizontal plane.

4. The hip procedure navigation system of claim 1, wherein the cup inclination and anteversion angles are determined relative to a vertical plane.

5. The hip procedure navigation system of claim 1, wherein the fixation base is configured to be rigidly connected to the pelvic bone of the patient so that motion of the pelvic bone cause corresponding motion of the at least one inertial sensor.

6. The hip procedure navigation system of claim 1, wherein the navigation device extends above the fixation base when coupled to the fixation base.

7. The hip procedure navigation system of claim 1, wherein the threaded fixation device is transverse to the first pin and the second pin.

8. A hip procedure navigation system, comprising:
a first pin configured to be driven into a pelvic bone of a patient,
a second pin configured to be driven into the pelvic bone of the patient,
a fixation base comprising a first channel configured to receive the first pin and a second channel configured to receive the second pin, wherein the fixation base is configured to slide along the first pin and the second pin,
a threaded fixation device configured to be rotated to decrease a transverse distance of the first channel and decrease a transverse distance of the second channel to secure the fixation base to the first pin and the second pin,
a navigation device configured to be removably coupled to the fixation base, wherein the navigation device comprises at least one inertial sensor, wherein the at least one inertial sensor is configured to determine cup inclination and anteversion angles,
wherein navigation device is configured to repeatedly moved between the fixation base and an impactor.

9. The hip procedure navigation system of claim 8, further comprising the impactor.

10. The hip procedure navigation system of claim 8, wherein the navigation system is configured to generate, in real time, the cup inclination and anteversion angles.

11. The hip procedure navigation system of claim 8, wherein the cup inclination and anteversion angles are determined relative to a horizontal plane.

12. The hip procedure navigation system of claim 8, wherein the cup inclination and anteversion angles are determined relative to a vertical plane.

13. The hip procedure navigation system of claim 8, wherein the navigation device is configured to remain on the impactor as the impactor is struck.

14. The hip procedure navigation system of claim 8, wherein the threaded fixation device is transverse to the first pin and the second pin.

15. A hip procedure navigation system, comprising:
a first pin configured to be driven into a pelvic bone of a patient,
a second pin configured to be driven into the pelvic bone of the patient,
a fixation base configured to slide along the first pin and the second pin,
a threaded fixation device configured to be rotated to secure the fixation base to the first pin and the second pin, wherein the threaded fixation device is transverse to the first pin and the second pin,
a navigation device configured to be removably coupled to the fixation base, wherein the navigation device comprises at least one inertial sensor,
wherein the at least one inertial sensor is configured to determine cup inclination and anteversion angles relative to a reference plane.

16. The hip procedure navigation system of claim 15, further comprising an impactor.

17. The hip procedure navigation system of claim 15, wherein the cup inclination and anteversion angles are determined relative to a horizontal plane.

18. The hip procedure navigation system of claim 15, wherein the cup inclination and anteversion angles are determined relative to a vertical plane.

19. The hip procedure navigation system of claim 15, wherein the fixation base comprises threaded hole to engage the threaded fixation device.

20. The hip procedure navigation system of claim 8, wherein the fixation base comprises threaded hole to engage the threaded fixation device.

* * * * *